United States Patent
Nonaka et al.

(10) Patent No.: US 7,335,776 B2
(45) Date of Patent: *Feb. 26, 2008

(54) REMEDIES FOR DEPRESSION CONTAINING EP1 ANTAGONIST AS THE ACTIVE INGREDIENT

(75) Inventors: Shigeyuki Nonaka, Mishima-gun (JP); Takayuki Maruyama, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 785 days.

This patent is subject to a terminal disclaimer.

(21) Appl. No.: 10/471,553

(22) PCT Filed: Mar. 13, 2002

(86) PCT No.: PCT/JP02/02359

§ 371 (c)(1),
(2), (4) Date: Sep. 12, 2003

(87) PCT Pub. No.: WO02/072145

PCT Pub. Date: Sep. 19, 2002

(65) Prior Publication Data

US 2004/0082653 A1    Apr. 29, 2004

(51) Int. Cl.
C07D 277/04    (2006.01)
C07D 277/08    (2006.01)
A61K 31/425    (2006.01)
A01N 43/78    (2006.01)

(52) U.S. Cl. ........................ 548/146; 514/365; 514/562

(58) Field of Classification Search ................ 514/602, 514/116, 471, 365, 562; 548/146
See application file for complete search history.

(56) References Cited

U.S. PATENT DOCUMENTS

| 5,308,866 A | 5/1994 | Lesieur et al. |
| 6,235,777 B1 | 5/2001 | Ohuchida et al. |
| 6,448,290 B1 | 9/2002 | Ohuchida et al. |

FOREIGN PATENT DOCUMENTS

| EP | 512400 A1 | 11/1992 |
| EP | 0 608 847 A1 | 8/1994 |
| EP | 778821 A1 | 6/1997 |
| EP | 835246 A1 | 4/1998 |
| EP | 0 878 465 A2 | 11/1998 |
| EP | 878465 A1 | 11/1998 |
| EP | 947500 A1 | 10/1999 |
| EP | 1071648 A1 | 1/2001 |
| JP | 11-322709 A | 11/1999 |
| WO | WO 89/01472 A1 | 2/1989 |
| WO | WO 92/19617 A2 | 11/1992 |
| WO | WO 96/06822 A1 | 3/1996 |
| WO | WO 97/00863 A1 | 1/1997 |
| WO | WO 99/47497 A2 | 9/1999 |
| WO | WO 00/20371 A1 | 4/2000 |
| WO | WO 00/69465 A1 | 11/2000 |
| WO | WO 01/19814 A2 | 3/2001 |
| WO | WO 01/19819 A2 | 3/2001 |

OTHER PUBLICATIONS

XP-002329964—(2000)—Derwent Publications Ltd., (WO 00/69465—Abstract).
XP-002330632—(1999)—Derwent Publications Ltd., (JP 11-322709—Abstract).
XP-002330633—(2002)—Derwent Publications Ltd., (WO 02/16311—Abstract).
Supplementary Partial European Search Report dated Jun. 16, 2005.
Tayo, Fola M., Tricyclic antidepressants antagonize prostaglandin (PG) E2-induced contractions of the houseguinea pig ileum and hypomotility in the mouse, Experientia, 1985, vol. 41, pp. 474 to 476.
Manku, M. S. et al., Chloroguine, quinine, procaine, quinidine, tricyclic antidepressants, and methyxanthines as prostaglandin agonists and antagonists, Lancet, 1976, vol. 2, No. 7995, pp. 1115 to 1117.

*Primary Examiner*—Sreeni Padmanabhan
*Assistant Examiner*—Umamaheswari Ramachandran
(74) *Attorney, Agent, or Firm*—Sughrue Mion, PLLC

(57) ABSTRACT

A pharmaceutical composition for the treatment and/or prevention of depression comprising a compound having an antagonistic activity for $EP_1$ receptor which a prostaglandin $E_2$ receptor subtype.

$EP_1$ antagonist is useful for the treatment of depression, for example, endogenous depression, reactive depression, weatherability depression, neurological depressed state, the depressed state of brain organic mental disorder.

2 Claims, No Drawings

REMEDIES FOR DEPRESSION CONTAINING EP1 ANTAGONIST AS THE ACTIVE INGREDIENT

TECHNICAL FIELD

The present invention relates to a pharmaceutical composition for the treatment of depression comprising the $EP_1$ antagonist as active ingredient.

BACKGROUND

Prostaglandin $E_2$ ($PGE_2$) has been known as a metabolite in the arachidonic acid cascade. It has been known that $PGE_2$ possesses cyto-protective activity, uterine contractile activity, a pain-inducing effect, a promoting effect on digestive peristalsis, an awaking effect, a suppressive effect on gastric acid secretion, hypotensive activity, and diuretic activity.

In the recent study, it was found that $PGE_2$ receptor was divided into some subtypes, which possesses different physical roles from each other. At present, four receptor subtypes are known and they are called $EP_1$, $EP_2$, $EP_3$ and $EP_4$ respectively [Negishi M. et al, J. Lipid Mediators Cell Signaling 12, 379-391 (1995)].

$PGE_2$ has a broad range of a physiologically active, therefore it has a fault that an activity other than a purpose will become a side effect. However, it has been studied to overcome the fault by a reserch of each subtype role and a synthesis of compounds having an effective action for one subtype only.

Among these subtypes, it is known that $EP_1$ subtype relates to pain, fever, diuresis [Br. J. Pharmacol., 112, 735-40 (1994); European J. Pharmacol., 152, 273-279 (1988); Gen Pharmacol., September 1992, 23(5), 805-809]. Therefor, it is believed that an antagonism for this receptor is useful as analgesics, antipyretic or a therapeutic agent of frequent urination.

Besides, it is known that $EP_1$ antagonists have an inhibitory activity of a formation of abnormal crypt in the lining of the large intestine and polyp in the intestine, and show an anticancer activity [see reference WO 00/69465].

Depression is led by various factors, and the pathological physiology is remained incompletely understood. Monoamine reuptake inhibitor and monoamine oxidase (MAO) inhibitor are showed an antidepressive activity, and it is consider that an abnormal mono-aminergic neuron system plays a role in the development of depression.

As an antidepressant, MAO inhibitors including hydrazine derivatives, emotion stimulators such as a reuptake inhibitor of noradrenaline (NA) and 5-hydroxytryptamine (5-HT), emotion regulators including benzodiazepine derivatives and psychostimulants including Meratoran are known. Then, MAO inhibitors are not used because of a serious hepatopathy and hypertensive crisis, and new type reuptake inhibitor of NA and 5-HT are used, that they are improved side effects such as dry mouth, drowsiness, dizziness, urinary disturbance that are side effects of tricyclic antidepressants as typified by imipramine.

On the other hand, it was not confirmed by an experiment that a relationship of $EP_1$ receptors and depression and antidepressive activity of $EP_1$ antagonist.

DISCLOSURE OF THE INVENTION

Energetic investigations about a role of $EP_1$ receptors in the brain by various experiments using $EP_1$ antagonists have been carried out. The present inventors have found that $EP_1$ antagonists have an antidepressive activity and accomplished the present invention. As mentioned above, it was known that an increase of dopamine in the brain on $EP_1$ receptor knockout mouse, however, it was not confirmed whether $EP_1$ antagonists have an antidepressive activity.

The present invention relates to a pharmaceutical composition for the treatment and/or prevention of depression, such as endogenous depression, reactive depression, weatherability depression, neurological depressed state, the depressed state of brain organic mental disorder, comprising an antagonist for $EP_1$ receptor, which is one subtype of $PGE_2$ receptor.

$EP_1$ antagonists of the present invention bond to $EP_1$ receptor, which is a subtype of $PGE_2$ receptor, and show an antagonistic action. More preferably $EP_1$ antagonists are specifically bond to $EP_1$ receptor and show an antagonistic action.

Known $EP_1$ antagonists and any $EP_1$ antagonists, which will be found in the future, are included in $EP_1$ antagonists of the present invention.

Any $EP_1$ antagonists are preferable and more preferable $EP_1$ antagonists are, for example, (1) in the specification of EP 878465, the compound of formula (IA)

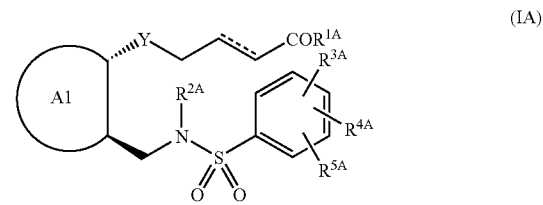

wherein

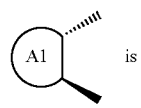 is (a)

, (b)

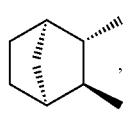, (c)

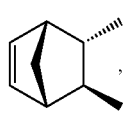, (d)

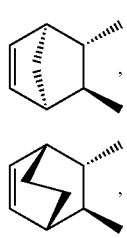

(e)

-continued

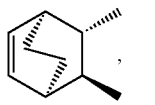
(f)

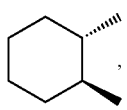
(g)

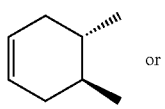 or
(h)

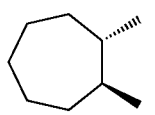
(i)

$R^{1A}$ is hydroxy, C1-4 alkoxy or a group of formula
$NR^{6A}R^{7A}$
in which $R^{6A}$ and $R^{7A}$ each independently, is hydrogen or C1-4 alkyl,
$R^{2A}$ is hydrogen or C1-4 alkyl,
$R^{3A}$ and $R^{4A}$ are C1-4 alkyl, halogen atom or trifluoromethyl,
$R^{5A}$ is hydrogen, C1-4 alkyl, halogen atom or trifluoromethyl,
Y is cis-vinylene or trans-vinylene

is a single bond or a double bond:
a non-toxic salt thereof or a cyclodextrin clathrate thereof,
(2) in the specification of WO 98/27053, the compound of formula (IB)

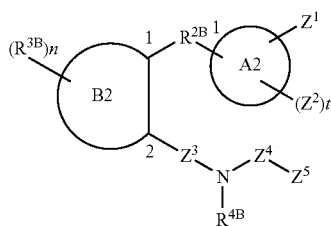
(IB)

wherein

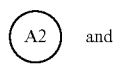 and

(A2 ring)

(B2 ring)

each independently, is C5-15 carbocyclic ring or 5-7 membered heterocyclic ring containing 1 or 2 of oxygens, sulfurs or nitrogens, $Z^1$ is
—$COR^{1B}$,
—C1-4 alkylene-$COR^{1B}$,
—CH=CH—$COR^{1B}$,
—C≡C—$COR^{1B}$,
—O—C1-3 alkylene-$COR^{1B}$,
in which $R^{1B}$ is hydroxy, C1-4 alkoxy or $NR^{6B}R^{7B}$ in which $R^{6B}$ and $R^{7B}$ each independently, is hydrogen or C1-4 alkyl; or
—C1-5 alkylene-OH, $Z^2$ is hydrogen, C1-4 alkyl, C1-4 alkoxy, nitro, halogen atom, trifluoromethyl, trifluoromethoxy, hydroxy or $COR^{1B}$ in which $R^{1B}$ as hereinafter defined;

$Z^3$ is a single bond or C1-4 alkylene, $Z^4$ is $SO_2$ or CO, $Z^5$ is (1) C1-8 alkyl, C2-8 alkenyl or C2-8 alkynyl, (2) phenyl, C3-7 cycloalkyl or 5-7 membered heterocyclic ring containing 1-2 of oxygens, sulfurs or nitrogens, (3) C1-4 alkyl, C2-4 alkenyl or C2-4 alkynyl substituted by phenyl or C3-7 cycloalkyl, in the above (2) and (3), phenyl, C3-7 cycloalkyl and 5-7 membered heterocyclic ring containing 1-2 of oxygens, sulfurs or nitrogens may be substituted by 1-5 of $R^{5B}$ in which multiple $R^{5B}$ each independently, is hydrogen, C1-6 alkyl, C1-6 alkoxy, C1-6 alkylthio, nitro, halogen atom, trifluoromethyl, trifluoromethoxy or hydroxy;

$R^{2B}$ is $CONR^{8B}$, $NR^{8B}CO$, $CONR^{8B}$—C1-4 alkylene, C1-4 alkylene-$CONR^{8B}$, $NR^{8B}CO$—C1-4 alkylene, C1-4 alkylene-$NR^{8B}CO$, C1-3 alkyleen-$CONR^{8B}$-C1-3 alkylene, C1-3 alkylene-$NR^{8B}CO$—C1-3 alkylene, in which $R^{8B}$ is hydrogen or C1-4 alkyl; oxygen, sulfur, $NZ^6$ in which $Z^6$ is hydrogen or C1-4 alkyl; -$Z^7$-C1-4 alkylene, C1-4 alkylene-$Z^7$, C1-3 alkylene-$Z^7$-C1-3 alkylene in which $Z^7$ is oxygen, sulfur or $NZ^6$ in which $Z^6$ is as hereinbefore defined; CO, CO—C1-4 alkylene, C1-4 alkylene-CO, C1-3 alkylene-CO—C1-3 alkylene, C2-4 alkylene, C2-4 alkenylene, C2-4 alkynylene, $R^{3B}$ is hydrogen, C1-6 alkyl, C1-6 alkoxy, C1-6 alkylthio, nitro, halogen atom, trifluoromethyl, trifluoromethoxy, hydroxy or hydroxymethyl, $R^{4B}$ is (1) hydrogen, (2) C1-8 alkyl, C2-8 alkenyl or C2-8 alkynyl, (3) C1-6 alkyl substituted by 1-2 of $COOZ^8$, $CONZ^9Z^{10}$, $OZ^8$ in which $Z^8$, $Z^9$ and $Z^{10}$ each independently is hydrogen or C1-4 alkyl; and C1-4 alkoxy-C1-4 alkoxy, (4) C3-7 cycloalkyl, (5) C1-4 alkyl, C2-4 alkenyl or C2-4 alkynyl substituted by phenyl or C3-7 cycloalkyl, in the above (4) and (5), phenyl, C3-7 cycloalkyl may be substituted by 1-5 of $R^{5B}$ in which $R^{5B}$ is as hereinbefore defined, n and t each independently, is 1-4, with the proviso that (1) $R^{2B}$ bond to atom of only 1-position in $B^2$ ring and $R^{3B}$ bond to atom of only 2-position in $B^2$ ring, (2) when $A^2$ ring is benzene and $(Z^2)_t$ is not $COR^{1B}$, then $Z^1$ bond only 3 or 4-position in benzene of $A^2$ ring;

(3) in the specification of WO 92/19617, the compound of formula (IC)

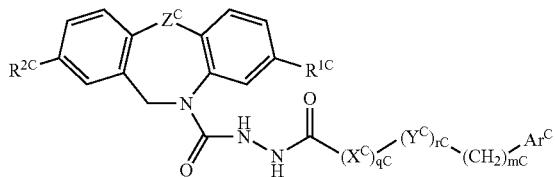

(IC)

wherein R$^{1C}$ is hydrogen, halogen atom or —CF$_3$,
R$^{2C}$ is hydrogen, halogen atom, —OH or —OCH$_3$,
Z$^C$ is oxygen, sulfur, —S(O)— or —S(O)$_2$—,
X$^C$ is —CH═CH—, —CF$_2$—, —CHF—, —(CH$_2$)$_{nc}$— or —(CH$_2$)$_{pc}$—CH═CH—,
Y$^C$ is —CH(OH)—, —NR$^{3C}$—, sulfur, —S(O)—, —S(O)$_2$— or oxygen,
q$^C$ is 0 or 1,
r$^C$ is 0 or 1, with the proviso that in the case of following (1), (2) or (3), r$^C$ is not 0:
  (1) X$^C$ is —CH═CH—, —(CH$_2$)$_{nc}$— or —(CH$_2$)$_{pc}$—CH═CH—, q$^C$ is 1 and Ar$^C$ is imidazole or phenyl,
  (2) X$^C$ is —(CH$_2$)$_{nc}$—, q$^C$ is 1, n$^C$ is 1 and Ar$^C$ is ethylphenyl substituted by halogen atom, methyl or alkoxy,
  (3) q$^C$ is 1, m$^C$ is 1, 2, 3, 4, 5 or 6 and Ar$^C$ is imidazole or phenyl,
m$^C$ is 0-6, with the proviso that when X$^C$ is —(CH$_2$)$_{nc}$—, q$^C$ is 1, Y$^C$ is oxygen, sulfur, —S(O)— or —S(O)$_2$— and Ar$^C$ is phenyl, and then m$^C$ is not 0,
n$^C$ is 1-6,
p$^C$ is 1-6
R$^{3C}$ is hydrogen or t-butyloxycarbonyl,
Ar$^C$ is aryl, alkyl-substituted aryl or aryl-substituted aryl;
(4) in the specification of WO 96/06822, the compound of formula (ID)

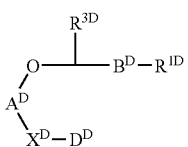

(ID)

wherein A$^D$ is an optionally substituted: 8-10 membered bicyclic heteroaryl, 5-6 membered heteroaryl, naphthyl or phenyl, with the proviso that —OCH(R$^{3D}$)— and —X$^D$- linking group are positioned in a 1, 2 relationship to one another on ring carbon atoms,
B$^D$ is an optionally substituted 5-6 membered heteroaryl ring system or optionally substituted phenyl,
D$^D$ is optionally substituted: pyridyl, pyrazinyl, pyrimidyl, pyridazyl, pyrrolyl, thienyl, furyl, pyrazolyl, thiazolyl, isothiazolyl, oxazolyl, isoxazolyl or phenyl,
X$^D$ is —(CHR$^{4D}$)$_{nD}$— or —(CHR$^{4D}$)$_{pD}$CR$^{4D}$═CR$^{4D}$(CHR$^{4D}$)$_{qD}$—, in which n$^D$ is 1-3, and p$^D$ and q$^D$ are either both 0 or one of p$^D$ and q$^D$ is 1 and the other is 0,
R$^{1D}$ is positioned on ring B$^D$ in a 1, 3 or 1,4 relationship with the —OCH(R$^{3D}$)-linking group in 6-membered rings and in a 1, 3 relationship with —OCH(R$^{3D}$)-linking group in 5-membered rings and carboxy, carboxy-C1-3 alkyl, tetrazolyl, tetrazolyl-C1-3 alkyl, tetronic acid, hydroxamic acid or sulphonic acid, or R$^{1D}$ is —CONR$^{aD}$R$^{a1D}$ in which R$^{aD}$ is hydrogen or C1-6 alkyl, R$^{a1D}$ is hydrogen, or optionally substituted C1-6 alkyl, C2-6 alkenyl, C2-6 alkynyl, C3-7 cycloalkyl, C3-7 cycloalkyl-C1-6 alkyl, C3-7 cycloalkyl-C2-6 alkenyl, C3-7 cycloalkyl-C2-6 alkynyl, C5-7 cycloalkenyl, C3-7 cycloalkenyl-C1-6 alkyl, C5-7 cycloalkenyl-C2-6 alkenyl, C5-7 cycloalkenyl-C2-6 alkynyl, C1-3 alkyl substituted by 5-6 membered saturated or partially saturated heterocyclic ring, 5-6 membered saturated or partially saturated heterocyclic ring or 5-6 membered heteroaryl, or R$^{aD}$ and R$^{a1D}$ together with the amide nitrogen to which they are attached (NR$^{aD}$R$^{a1D}$) form an amino acid residue or ester thereof, or
R$^{1D}$ is —CONHSO$_2$R$^{bD}$ in which R$^{bD}$ is optionally substituted C1-6 alkyl, C2-6 alkenyl, C2-6 alkynyl, C3-7 cycloalkyl-C1-6 alkyl, C3-7 cycloalkyl-C2-6 alkenyl, C3-7 cycloalkyl-C2-6 alkynyl, C3-7 cycloalkenyl-C1-6 alkyl, C3-7 cycloalkenyl-C2-6 alkenyl, C3-7 cycloalkenyl-C2-6 alkynyl, 5-6 membered heteroaryl, 5-6 membered heteroaryl-C1-6 alkyl, phenyl, phenyl-C1-6 alkyl, 5-6 membered saturated or partially saturated hetrocyclic ring or 5-6 membered saturated or partially saturated hetrocyclic ring-C1-6 alkyl,
R$^{3D}$ is hydrogen or C1-4 alkyl,
R$^{4D}$ is hydrogen or C1-4 alkyl,
with the proviso that 4-(2-benzyl-3-hydroxy-4-formylphenoxymethyl)-3-methoxybenzoic acid and 4-(2-(3-phenyl-prop-2-ene-1-yl)-3-hydroxy-4-formyophenoxymethyl-3-methoxybenzoic acid are excluded;
or N-oxide thereof, or S-oxide of sulfur containing rings, or a pharmaceutically acceptable salt thereof or in vivo hydrolyzable ester or amide thereof;
(5) in the specification of WO 97/00863, the compound of formula (IE)

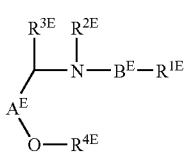

(IE)

wherein A$^E$ is optionally substituted: phenyl, naphthyl, pyridyl, pyrazinyl, pyridazinyl, pyrimidyl, thienyl, thiazolyl, oxazolyl or thiadiazolyl having at least two adjacent ring carbon atoms, with the proviso that —CH(R$^{3E}$)N(R$^{2E}$)B$^E$—R$^{1E}$ and —OR$^{4E}$ are positioned in a 1, 2 relationship to one another on ring carbon atom and the ring atom position ortho to the OR$^{4E}$ linking group (and therefor in the 3-position relative to the —CHR$^{3E}$NR$^{2E}$-linking group) is not substituted,
B$^E$ is optionally substituted: phenyl, pyridyl, thiazolyl, oxazolyl, thienyl, thiadiazolyl, imidazolyl, pyrazinyl, pyridazinyl or pyrimidyl,
R$^{1E}$ is positioned on ring B$^E$ in a 1, 3 or 1, 4 relationship with —CH(R$^{3E}$)N(R$^{2E}$)-linking group and is carboxy, carboxy-C1-3 alkyl, tetrazolyl, tetrazolyl-C1-3 alkyl, tetronic acid, hydroxamic acid, sulphonic acid, or
R$^{1E}$ is —CONR$^{aE}$R$^{a1E}$ in which R$^{aE}$ is hydrogen or C1-6 alkyl, R$^{a1E}$ is hydrogen, C1-6 alkyl (optionally substituted by halogen atom, amino, C1-4 alkylamino, di-C1-4 alkylamino, hydroxy, nitro, cyano, trifluoromethyl, C1-4 alkoxy or C1-4 alkoxycarbonyl), C2-6 alkenyl (the double bond is not in the 1-position), C2-6 alkynyl (the triple bond is not in the 1-position), carboxyphenyl, 5-6 membered heterocyclyl-C1-3 alkyl, 5-6 membered heteroaryl-C1-3 alkyl, 5-6 membered heterocyclyl or 5-6 membered heteroaryl, or $R^{aE}$ and $R^{a1E}$ together with the amide nitrogen to which they are attached ($NR^{aE}R^{a1E}$) form an amino acid residue or ester thereof, or $R^{1E}$ is —$CONHSO_2R^{bE}$ in which $R^{bE}$ is C1-6 alkyl (optionally substituted by halogen atom, hydroxy, nitro, cyano, trifluoromethyl, C1-4 alkoxy, amino, C1-4 alkylamino, di-C1-4 alkylamino or C1-4 alkoxycarbonyl), C2-6 alkenyl (the double bond is not in the 1-position), C2-6 alkynyl (the triple bond is not in the 1-position), 5-6 membered heterocyclyl-C1-3 alkyl, 5-6 membered heteroaryl-C1-3 alkyl, 5-6 membered heterocyclyl or 5-6 membered heteroaryl or phenyl, wherein any heterocyclyl or heteroaryl group in $R^{a1E}$ is optionally substituted by halogen atom, hydroxy, nitro, amino, cyano, C1-6 alkoxy, C1-6 alkyl-$S(O)_{pE}$—($p^E$ is 0, 1 or 2), C1-6 alkylcarbamoyl, C1-4 alkylcarbamoyl, di(C1-4 alkyl)carbamoyl, C2-6 alkenyl, C2-6 alkynyl, C1-4 alkoxycarbonylamino, C1-4 alkanoylamino, C1-4 alkanoyl(N-C1-4 alkyl)amino, C1-4 alkanesulfonamide, benzenesulfonamide, aminosulfonyl, C1-4 alkylaminosulfonyl, di(C1-4 alkyl)aminosulfonyl, C1-4 alkoxycarbonyl, C-4 alkanoyloxy, C1-6 alkanoyl, formylC1-4 alkyl, hydroxyimino-C1-6 alkyl, C1-4 alkoxyimino-C1-6 alkyl or C1-6 alkylcarbamoylamino, or $R^{1E}$ is —$SO_2N(R^{cE})R^{c1E}$ in which $R^{cE}$ is hydrogen or C1-4 alkyl and $R^{c1E}$ is hydrogen or C1-4 alkyl, or $R^{1E}$ is the formula ($E^A$), ($E^B$) or ($E^C$):

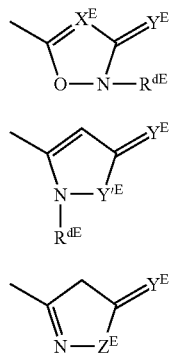

wherein $X^E$ is CH or nitrogen, $Y^E$ is oxygen or sulfur, $Y'^E$ is oxygen or $NR^{dE}$ and $Z^E$ is $CH_2$, $NR^{dE}$ or oxygen, with the proviso that there is no more than one ring oxygen and there are at least two ring heteroatoms and wherein $R^{dE}$ is hydrogen or C1-4 alkyl, $R^{2E}$ is hydrogen, C1-6 alkyl optionally substituted by hydroxy, cyano or trifluoromethyl, C2-6 alkynyl (the double bond is not in the 1-position), C2-6 alkynyl (the triple bond in not in the 1-position), phenyl-C1-3 alkyl or pyridyl-C1-3 alkyl, $R^{3E}$ is hydrogen, methyl or ethyl, $R^{4E}$ is optionally substituted: C1-6 alkyl, C3-7 cycloalkyl-C1-3 alkyl or C3-7 cycloalkyl, with the proviso that 2-[2-methoxybenzylamino]pyridine-5-carboxylic acid, 4-[2-methoxybenzylamino]benzoic acid, 5-[2,3-dimethoxybenzylamino]-2-chloro-3-aminosulfonylbenzoic acid and 5-[2,5-dimethoxybenzylamino]-2-hydroxybenzoic acid are excluded;

or N-oxide of —$NR^{2E}$-, or S-oxide of sulfur containing rings, or a pharmaceutically acceptable salt thereof or in vivo hydrolyzable ester or amide thereof (6) in the specification of WO 99/47497, the compound of formula (IF)

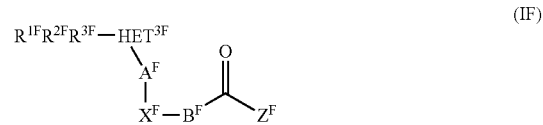

wherein $HET^F$ is 5-12 membered mono- or bi-cyclic aromatic ring containing 0-3 heteroatoms selected from oxygen, $S(O)_{nF}$ and $N(O)_{mF}$, in which $m^F$ is 0 or 1, $n^F$ is 0, 1 or 2, $A^F$ is —$W^F$—, —$C(O)$—, —$C(R^{7F})$—$W^F$—, —$W^F$—$C(R^{7F})_2$—, —$CR^{7F}(OR^{20F})$—, —$C(R^{7F})_2$—, —$C(R^{7F})_2$—$C(OR^{20F})R^{7F}$—, —$C(R^{7F})_2$—$C(R^{7F})_2$— or —$CR^{7F}$=$CR^{7F}$—, in which $W^F$ is oxygen, $S(O)_{nF}$ or $NR^{17F}$, $X^F$ is 5-10 membered mono- or bi-cyclic aryl or heteroaryl having 1-3 heteroatoms selected from oxygen, $S(O)_{nF}$ and $N(O)_{mF}$, and optionally substituted by $R^{14F}$ and $R^{15F}$, and $A^F$ and $B^F$ are attached to the aryl or heteroaryl ortho relative to each other, $Y^F$ is O, $S(O)_{nF}$, $NR^{17F}$, a bond or —$CR^{18F}$=$CR^{18F}$—;

$B^F$ is —$(C(R^{18F})_2)_{pF}$—$Y^F$—$(C(R^{18F})_2)_{qF}$—, in which $p^F$ and $q^F$ are independently 0-3, such that when $Y^F$ is O, $S(O)_{nF}$, $NR^{17F}$ or —$CR^{18F}$=$CR^{18F}$—, $p^F+q^F$ is 0-6, and when $Y^F$ is a bond, $p^F+q^F$ is 1-6;

$Z^F$ is OH, $NHSO_2R^{19F}$;

$R^{1F}$, $R^{2F}$ and $R^{3F}$ each independently, is hydrogen, halogen atom, lower alkyl, lower alkenyl, lower alkynyl, lower alkenyl-$HET^F(R^{aF})_{4-9}$, —$(C(CR^{4F})_2)_{pF})SR^{5F}$, —$(C(R^{4F})_2)_{pF}OR^{8F}$, —$(C(R^{4F})_2)_{pF}N(R^{6F})_2$, CN, $NO_2$, —$(C(R^{4F})_2)_{pF}C(R^{7F})_3$, —$COOR^{9F}$, —$CON(R^{6F})_2$ or —$(C(R^{4F})_2)_{pF}S(O)_{nF}R^{10F}$, each $R^{4F}$ is hydrogen, F, $CF_3$, lower alkyl or two $R^{4F}$, taken together, is a ring of up to six atoms, optionally containing one heteroatom selected from O, $S(O)_{nF}$ and $N(O)_{mF}$, each $R^{5F}$ is independently lower alkyl, lower alkenyl, lower alkynyl, $CF_3$, lower alkyl-$HET^F$, lower alkenyl-$HET^F$, —$(C(R^{18F})_2)_{pF}Ph(R^{11F})_{0-2}$, each $R^{6F}$ is independently hydrogen, lower alkyl, lower alkenyl, lower alkynyl, $CF_3$, Ph, Bn or two $R^{6F}$ together with N to which they are attached, is a ring of up to six atoms, optionally containing an additional heteroatom selected from O, $S(O)_{nF}$ and $N(O)_{mF}$, each $R^{7F}$ is independently hydrogen, F, $CF_3$, lower alkyl, or two $R^{7F}$ taken together, is 3-6 membered aromatic or aliphatic ring containing 0-2 heteroatom selected from O, $S(O)_{nF}$, and $N(O)_{mF}$, each $R^{8F}$ is hydrogen or $R^{5F}$, each $R^{9F}$ is independently hydrogen, lower alkyl, lower alkenyl, lower alkynyl, Ph or Bn, each $R^{10F}$ is independently lower alkyl, lower alkenyl, lower alkynyl, $CF_3$, $Ph(R^{11F})_{0-3}$, $CH_2Ph(R^{11F})_{0-3}$ or $N(R^{6F})_2$, each $R^{11F}$ is independently lower alkyl, $SR^{20F}$, $OR^{20F}$, $N(R^{6F})_2$, —$COOR^{12F}$, —$CON(R^{6F})_2$, —$COR^{12F}$, CN, $CF_3$, $NO_2$ or halogen atom, each $R^{12F}$ is independently hydrogen, lower alkyl or benzyl, each $R^{13F}$ is independently hydrogen, halogen atom, lower alkyl, O-lower alkenyl, S-lower alkyl, $N(R^{6F})_2$, $COOR^{12F}$, CN, $CF_3$ or $NO_2$, $R^{14F}$ and $R^{15F}$ are independently lower alkyl, halogen atom, $CF_3$, $OR^{16}F$, $S(O)_{nF}R^{16F}$ or $C(R^{16F})_2OR^{17F}$, each $R^{16F}$ is independently hydrogen, lower alkyl, lower alkenyl, Ph, Bn or $CF_3$, each $R^{17F}$ is independently hydrogen, lower alkyl or Bn, each $R^{18F}$ is independently hydrogen, F or lower alkyl, or two $R^{18F}$ taken together, is 3-6 membered ring optionally containing one heteroatom selected from oxygen, $S(O)_{nF}$ and nitrogen, each $R^{19F}$ is independently lower alkyl, lower alkenyl, lower alkynyl, $CF_3$, $HET(R^{aF})_{4-9}$, lower alkyl-$HET(R^{aF})_{4-9}$, lower alkenyl-$HET(R^{aF})_{4-9}$, each $R^{20F}$ is independently hydrogen, lower alkyl, lower alkenyl, lower alkynyl, $CF_3$ or $Ph(R^{13F})_2$, each $R^{aF}$ is independently selected from the following group:

hydrogen, hydroxy, halogen atom, CN, $NO_2$, amino, C1-6 alkyl, C2-6 alkenyl, C2-6 alkynyl, C1-6 alkoxy, C2-6 alkenyloxy, C2-6 alkynyloxy, C1-6 alkylamino, di(C1-6 alkyl)amino, $CF_3$, C(O)C1-6 alkyl, C(O)C2-6 alkenyl, C(O)C2-6 alkynyl, COOH, COO(C1-6)alkyl, COO(C2-6)alkenyl and COO(C2-6)alkynyl, said alkyl, alkenyl, alkynyl, and alkyl portions of alkylamino and dialkylamino being optionally substituted by 1-3 of hydroxy, halogen atom, aryl, C1-6 alkoxy, C2-6 alkenyloxy, C2-6 alkynyloxy, $CF_3$, CO(C1-6)alkyl, CO(C2-6)alkenyl, CO(C2-6)alkynyl, COOH, COO(C1-6)alkyl, COO(C2-6)alkenyl, COO(C2-6)alkynyl $NH_2$, NH(C1-6)alkyl and N(C1-6-alkyl)$_2$;

or a non-toxic salt thereof, (7) in the specification of WO 2000/20371, the compound of formula (IG)

$$Ar^{1G}-W^G-Ar^{2G}-X^G-W^G \qquad (IG)$$

wherein $Ar^{1G}$ is aryl or heteroaryl, optionally substituted by $R^{1G}$ or $R^{3G}$, $R^{1G}$ is $Y^G_{mG}-R^{2G}$, $Y^G_{mG}-Ar^{3G}$, halogen atom, $N(R^{5G})_2$, CN, $NO_2$, $C(R^{6G})_3$, $CON(R^{5G})_2$, $S(O)_{nG}R^{7G}$ or hydroxy, $Y^G$ is a linker between $R^{2G}$ or $Ar^{3G}$ and $Ar^{1G}$ containing 0-4 carbon atoms and not more than one heteroatom selected from oxygen, nitrogen and sulfur, said linker optionally containing CO, $S(O)_{nG}$, —C≡C— or acetylenic group, and said linker being optionally substituted by $R^{2G}$, $m^G$ is 0 or 1, $n^G$ is 0, 1 or 2, $R^{2G}$ is hydrogen, F, $CHF_2$, $CF_3$, lower alkyl or hydroxy(C1-6)alkyl, or two $R^{2G}$ taken together, is carbocyclic ring of up to six members, said ring containing not more than one heteroatom selected from oxygen, nitrogen or sulfur, $Ar^{3G}$ is aryl or heteroaryl, optionally substituted by $R^{3G}$, $R^{3G}$ is $R^{4G}$, halogen atom, halo(C1-6)alkyl, $N(R^{5G})_2$, CN, $NO_2$, $C(R^{6G})_3$, $CON(R^{5G})_2$, $OR^{4G}$, $SR^{4G}$ or $S(O)_{nG}R^{7G}$, $R^{4G}$ is hydrogen, lower alkyl, lower alkenyl, lower alkynyl, $CHF_2$ or $CF_3$, $R^{5G}$ is $R^{4G}$, Ph or Bn, or two $R^{5G}$ taken together, is a ring of up to six members containing carbon atoms and 0-2 heteroatoms selected from oxygen, nitrogen or sulfur, $R^{6G}$ is hydrogen, F, $CF_3$ or lower alkyl, or two $R^{6G}$ taken together, is a ring of up to six members containing carbon atoms and 0-2 heteroatoms selected from oxygen, nitrogen or sulfur, $R^{7G}$ is lower alkyl, lower alkenyl, lower alkynyl, $CHF_2$, $CF_3$, $N(R^{5G})_2$, $Ph(R^{8G})_2$ or $CH_2Ph(R^{8G})_2$, $R^{8G}$ is $R^{4G}$, $OR^{4G}$, $SR^{4G}$ or halogen atom, $W^G$ is a 3-6 membered linking group containing 0-2 heteroatoms selected from oxygen, nitrogen and sulfur, said linking group optionally containing CO, $S(O)^{mG}$, C≡C, acetylenic group, and optionally being substituted by $R^{9G}$, $R^{9G}$ is $R^{2G}$, lower alkyl, lower alkynyl, $OR^{4G}$ or $SR^{4G}$, $Ar^{2G}$ is aryl or heteroaryl, optionally substituted by $R^{3G}$, $R^{10G}$ is $R^{4G}$, halogen atom, $N(R^{5G})_2$, CN, $NO_2$, $C(R^{6G})_3$, $OR^{4G}$, $SR^{4G}$ or $S(O)_{nG}R^{7G}$, $X^G$ is a linker which is attached to $Ar^{2G}$ ortho to the attachment of $W^G$, said linker containing 0-4 carbon atoms and not more than one heteroatom selected from oxygen, nitrogen and sulfur, said linker further optionally containing CO, $S(O)_{nG}$, C≡C or acetylenic group, and said linker being optionally substituted by $R^{11G}$, $R^{11G}$ is $R^{9G}$, $Q^G$ is a member selected from the group consisting of COOH, tetrazole, $SO_3H$, hydroxamic acid, $CONHSO_2R^{12G}$ and $SO_2NHCOR^{12G}$, $R^{12G}$ is a member selected from the group consisting of $CF_3$, lower alkyl, lower alkenyl, lower alkynyl and $Z^GAr^{4G}$, $Z^G$ is a linker containing 0-4 carbon atom, optionally substituted by $R^{13G}$, $R^{13G}$ is $R^{9G}$, $Ar^{4G}$ is aryl or heteroaryl, optionally substituted by $R^{14G}$, $R^{14G}$ is $R^{10G}$ or NHCOMe;

or an non-toxic salt thereof, (8) in the specification of WO 2001/19814, the compound of formula (IH)

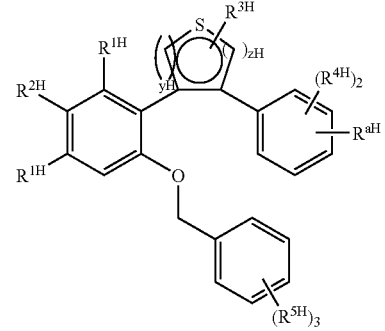

wherein $y^H$ and $z^H$ are independently 0-2, with the proviso that $y^H+z^H=2$, $R^{aH}$ is 1) heteroaryl, wherein heteroaryl is selected from the group (a)-(n):

(a) fury, (b) diazinyl, triazinyl or tetrazinyl, (c) imidazolyl, (d) isoxazolyl, (e) isothiazolyl, (f) oxadiazolyl, (g) oxazolyl, (h) pyrazolyl, (i) pyrrolyl, (j) thiadiazolyl, (k) thiazolyl, (l) thienyl, (m) triazolyl and (n) tetrazolyl, wherein heteroaryl is optionally substituted by one or more substituents independently selected from $R^{11H}$ and C1-4 alkyl;

2) —$COR^{6H}$,

3) —$NR^{7H}R^{8H}$,

4) —$SO_2R^{9H}$, 5) hydroxy,

6) C1-6 alkoxy, optionally substituted by one or more substituents independently selected from $R^{11H}$, and 7) C1-6 alkyl, C2-6 alkenyl or C3-6 cycloalkyl, optionally substituted by one or more substituents independently selected from $R^{11H}$, and further substituted by 1-3 substituents independently selected from the group of (a)-(h):

(a) —COR$^{6H}$, (b) —NR$^{7H}$R$^{8H}$, (c) —SO$_2$R$^{9H}$, (d) hydroxy, (e) C1-6 alkoxy or haloC1-6 alkoxy, and (f) heteroaryl;

R$^{aH}$ is positioned on the phenyl ring to which it is bonded in a 1, 3 or 1, 4 relationship relative to the thienyl group of formula (IH), R$^{1H}$, R$^{2H}$, R$^{3H}$, R$^{4H}$ and R$^{5H}$ are independently selected from the following group:

1) hydroxy, 2) halogen atom, 3) C1-6 alkyl, 4) C1-6 alkoxy, 5) C1-6 alkylthio, 6) nitro, 7) carboxy, and 8) CN, wherein groups of 3)-5) are optionally substituted by one or more substituents independently selected from R$^{11H}$, R$^{6H}$ is hydrogen, hydroxy, C1-6 alkyl, C1-6 alkoxy and NR$^{7H}$R$^{8H}$, wherein C1-6 alkyl and C1-6 alkoxy are optionally substituted by one or more substituents independently selected from R$^{11H}$, R$^{7H}$ and R$^{8H}$ are independently selected from the group: 1) hydrogen, 2) hydroxy, 3) SO$_2$R$^{9H}$, 4) C1-6 alkyl, 5) C1-6 alkoxy, 6) phenyl, 7) naphthyl, 8) furyl, 9) thienyl and 10) pyridyl, wherein groups of 4)-5) are optionally substituted by one or more substituents independently selected from R$^{11H}$, and groups of 6)-10) are optionally substituted by one or more substituents independently selected from R$^{11H}$ or C1-4 alkyl, R$^9$H is selected from the group:

1) hydroxy, 2) N(R$^{10H}$)$_2$, 3) C1-6 alkyl, optionally substituted by one or more substituents independently selected from R$^{11H}$, 4) phenyl, 5) naphthyl, 6) furyl, 7) thienyl, and 8) pyridyl, groups of 4)-8) are optionally substituted by one or more substituents independently selected from R$^{11H}$ and C1-4 alkyl, R$^{10H}$ is hydrogen or C1-6 alkyl, R$^{11H}$ is halogen atom, hydroxy, C1-3 alkoxy, nitro, N(R$^{10}$H)$_2$, and pyridyl;

or a pharmaceutically acceptable salt, hydrate or ester thereof;

(9) in the specification of WO 2001/19819, the compound of formula (IJ)

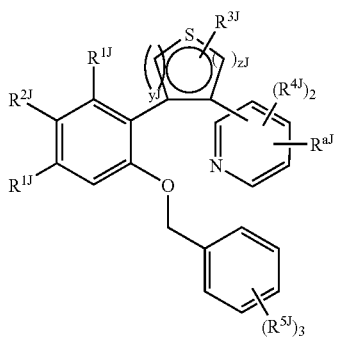

(IJ)

wherein y$^J$ and z$^J$ are independently 0-2, with the proviso that y$^J$+z$^J$=2, R$^{aJ}$ is 1) heteroaryl, wherein heteroaryl is selected from the group (a)-(n):
(a) fury, (b) diazinyl, triazinyl or tetrazinyl, (c) imidazolyl, (d) isoxazolyl, (e) isothiazolyl, (f) oxadiazolyl, (g)oxazolyl, (h) pyrazolyl, (i) pyrrolyl, (j) thiadiazolyl, (k) thiazolyl, (l) thienyl, (m) triazolyl and (n) tetrazolyl, wherein heteroaryl is optionally substituted by one or more substituents independently selected from R$^{11J}$ and C1-4 alkyl;

2) —COR$^{6J}$,
3) —NR$^{7J}$R$^{8J}$,
4) —SO$_2$R$^{9J}$,
5) hydroxy,
6) C1-6 alkoxy, optionally substituted by one or more substituents independently selected from R$^{11J}$, and
7) C1-6 alkyl, C2-6 alkenyl or C3-6 cycloalkyl, optionally substituted by one or more substituents independently selected from R$^{11J}$, and further substituted by 1-3 substituents independently selected from the group of (a)-(f):

(a) —COR$^{6J}$, (b) —NR$^{7J}$R$^{8J}$, (c) —SO$_2$R$^{9J}$, (d) hydroxy, (e) C1-6 alkoxy or haloC1-6 alkoxy, and (f) heteroaryl, R$^{aJ}$ is positioned on the pyridyl ring to which it is bonded in a 1, 3 or 1, 4 relationship relative to the thienyl group of formula (IJ), R$^{1J}$, R$^{2J}$, R$^{3J}$, R$^{4J}$ and R$^{5J}$ are independently selected from the following group:

1) hydroxy, 2) halogen atom, 3) C1-6 alkyl, 4) C1-6 alkoxy, 5) C1-6 alkylthio, 6) nitro, 7) carboxy, and 8) CN, wherein groups of 3)-5) are optionally substituted by one or more substituents independently selected from R$^{11J}$, R$^{6J}$ is hydrogen, hydroxy, C1-6 alkyl, C1-6 alkoxy and NR$^{7J}$R$^{8J}$, wherein C1-6 alkyl and C1-6 alkoxy are optionally substituted by one or more substituents independently selected from R$^{11J}$, R$^{7J}$ and R$^{8J}$ are independently selected from the group: 1) hydrogen, 2) hydroxy, 3) SO$_2$R$^{9J}$, 4) C1-6 alkyl, 5) C1-6 alkoxy, 6) phenyl, 7) naphthyl, 8) furyl, 9) thienyl and 10) pyridyl, wherein groups of 4)-5) are optionally substituted by one or more substituents independently selected from R$^{11J}$, and groups of 6)-10) are optionally substituted by one or more substituents independently selected from R$^{11J}$ or C1-4 alkyl, R$^{9J}$ is selected from the group:

1) hydroxy, 2) N(R$^{10J}$)$_2$, 3) C1-6 alkyl, optionally substituted by one or more substituents independently selected from R$^{11J}$, 4) phenyl, 5) naphthyl, 6) furyl, 7) thienyl, and 8) pyridyl, groups of 4)-8) are optionally substituted by one or more substituents independently selected from R$^{11J}$ and C1-4 alkyl, R$^{10J}$ is hydrogen or C1-6 alkyl, R$^{11J}$ is halogen atom, hydroxy, C1-3 alkoxy, nitro, N(R$^{10J}$)$_2$, and pyridyl;

or a pharmaceutically acceptable salt, hydrate or ester thereof

(10) N-phenyl-aryl-sulfonamide compound of formula (IK)

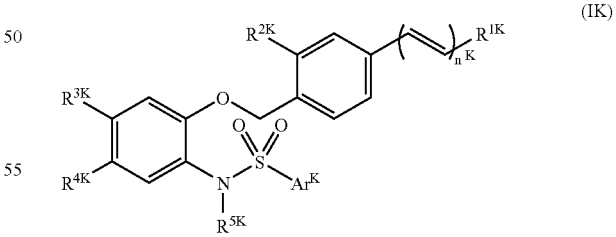

(IK)

wherein R$^{1K}$ is COOH, hydroxymethyl, 5-tetrazolyl, 5-oxo-1,2,4-oxadiazolyl or 5-oxo-1,2,4-thiadiazolyl, R$^{2K}$ is hydrogen, methyl, methoxy or chloro, R$^{3K}$ and R$^{4K}$ are a combination of (1) methyl and methyl, (2) methyl and chloro, (3) chloro and methyl, or (4) trifluoromethyl and hydrogen; or R$^3$ and R$^4$ are taken together with the carbon to which R$^3$ and R$^4$ are attached to form (5) cyclopentene, (6) cyclohexene or (7) benzene ring, $R^{5K}$ is isopropyl, isobutyl, 2-methyl-2-propenyl, cyclopropylmethyl, methyl, ethyl, propyl, 2-propenyl or 2-hydroxy-2-methylpropyl, $Ar^K$ is thiazolyl optionally substituted with methyl, pyridyl or 5-methyl-2-furyl, $n^K$ is 0 or 1, with the proviso that when $R^{1K}$ is 5-tetrazolyl, 5-oxo-1,2,4-oxadiazolyl or 5-oxo-1,2,4-thiadiazolyl, and then n is 0, an alkyl ester thereof or a non-toxic salt thereof.

The above compound of formula (IA)-(IK) may be converted into a corresponding pharmaceutically acceptable salt by known methods. Non-toxic salts and water-soluble salts are preferred.

Appropriate salts are salts of alkali metals (e.g. potassium, sodium), salts of alkaline-earth metals (e.g. calcium, magnesium), ammonium salts (e.g. tetramethylammonium), salts of pharmaceutically acceptable organic amines (e.g. triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine).

Non-toxic and water-soluble acid addition salts are preferable. Appropriate acid addition salts are, salts of inorganic acids, such as hydrochloride, hydrobromide, sulfate, phosphate, nitrate; salts of organic acid, such as acetate, trifluoroacetate, lactate, tartrate, oxalate, fumarate, maleate, citrate, benzoate, methanesulphonate, ethanesulphonate, benzenesulphonate, toluenesulphonate, isethionate, glucuronate, gluconate.

The compound of the present invention and a non-toxic salt thereof may be converted into the corresponding a hydrate thereof by conventional means.

The compound of the present invention, a non-toxic salt thereof or a hydrate thereof may be converted into the corresponding a cyclodextrin clathrate thereof by conventional means.

As the concretely compound of formula (IA)-(IJ) in the present invention, compounds described in the specification in WO 98/27053, EP 878465, WO 92/19617, WO 96/06822, WO 97/00863, WO 99/47497, WO 00/20371, WO 2001/19814, WO 2001/19819, for example, compounds described in Examples are preferable.

As the concretely compound of formula (IK), the compound described in Examples of this specification are preferable.

In the compounds described in the above specification, compounds which bond to $EP_1$ receptor and show an antagonistic action are preferable. More preferably, compounds which specifically bond to $EP_1$ receptor and show an antagonistic action.

The compound of formula (IA)-(IK) may be prepared by method described in each corresponding published International application, published European patent application or the specification of Japanese application.

In the present invention, $EP_1$ antagonists are not limited in order to achieve the object that is treatment and/or prevention depression. Especially, following compounds are preferable.

In the compound of formula (IA)-(IK), the compound of formula (IA), (IB) and (IK) are preferable.

1) In the compound of formula (IA), the compound in which

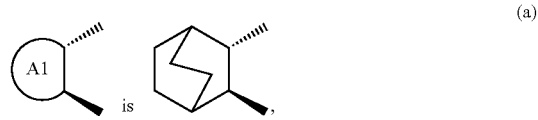
(a)

is preferable.

2) In the compound of formula (IB), the compound in which

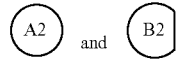

are C5-15 carbocyclic ring, $Z^5$ is 5-7 membered heterocyclic ring containing 1 or 2 oxygens, sulfurs or nitrogens, which ring may be substituted by 1-5 of $R^{5B}$ in which multiple $R^{5B}$ each, independently, is hydrogen, C1-6 alkyl, C1-6 alkoxy, C1-6 alkylthio, nitro, halogen atom, trifluoromethyl, trifluoromethoxy or hydroxy;

is preferable.

3) In the compound of formula (IK), all compounds are preferable, especially, the compound in which $Ar^k$ is 5-methyl-2-furyl, 2-thiazolyl, 5-methyl-2-thiazolyl, 2-pyridyl, 3-pyridyl is preferable. Concretely, following compounds are preferable.

(1) 4-[2-[N-isobutyl-N-(5-methyl-2-furylsulfonyl)amino]-5-trifluoromethylphenoxymethyl]cinnamic acid, (2) 4-[2-[N-isopropyl-N-(5-methyl-2-furylsulfonyl)amino]-5-trifluoromethylphenoxymethyl]benzoic acid, (3) 4-[2-[N-isobutyl-N-(5-methyl-2-furylsulfonyl)amino]-5-trifluoromethylphenoxymethyl]benzoic acid, (4) 4-[2-[N-isobutyl-N-(5-methyl-2-furylsulfonyl)amino]-4-chloro-5-methylphenoxymethyl]benzoic acid, (5) 4-[2-[N-isopropyl-N-(5-methyl-2-furylsulfonyl)amino]-4,5-dimethylphenoxymethyl]benzoic acid, (6) 4-[2-[N-isobutyl-N-(5-methyl-2-furylsulfonyl)amino]-4,5-dimethylphenoxymethyl]benzoic acid, (7) 3-methyl-4-[2-[N-isobutyl-N-(5-methyl-2-furylsulfonyl)amino]-4-methyl-5-chloro phenoxymethyl]benzoic acid, (8) 3 methyl-4-[2-[N-isobutyl-N-(5-methyl-2-furylsulfonyl)amino]-4-chloro-5-methylphenoxymethyl]benzoic acid, (9) 3-chloro-4-[2-[N-isobutyl-N-(5-methyl-2-furylsulfonyl)amino]-4-methyl-5-chlorophenoxymethyl]benzoic acid,

(10) 3-chloro-4-[2-[N-isopropyl-N-(5-methyl-2-furylsulfonyl)amino]-4-methyl-5-chlorophenoxymethyl]benzoic acid,

(11) 3-methoxy-4-[2-[N-isopropyl-N-(5-methyl-2-furylsulfonyl)amino]-4-methyl-5-chlorophenoxymethyl benzoic acid,

(12) 3-methyl-4-[2-[N-isobutyl-N-(5-methyl-2-furylsulfonyl)amino]-4,5-dimethylphenoxymethyl]benzoic acid,

(13) 3-methoxy-4-[2-[N-isopropyl-N-(5-methyl-2-furylsulfonyl)amino]-4,5-dimethylphenoxymethyl]benzoic acid,

(14) 3-methoxy-4-[2-[N-isobutyl-N-(5-methyl-2-furylsulfonyl)amino]-4,5-dimethylphenoxymethyl]benzoic acid,

(15) 3-methoxy-4-[2-[N-isopropyl-N-(5-methyl-2-furylsulfonyl)amino]-4-chloro-5-methylphenoxymethyl]benzoic acid,

(16) 3-chloro-4-[2-[N-isobutyl-N-(5-methyl-2-furylsulfonyl)amino]-4,5-dimethylphenoxymethyl]benzoic acid,

(17) 3-chloro-4-[2-[N-isopropyl-N-(5-methyl-2-furylsulfonyl)amino]-4,5-dimethylphenoxymethyl]benzoic acid,

(18) 3-methyl-4-[2-[N-isobutyl-N-(5-methyl-2-furylsulfonyl)amino]-4-chloro-5-methylphenoxymethyl]cinnamic acid,
(19) 4-[2-[N-isopropyl-N-(5-methyl-2-furylsulfonyl)amino]-4-methyl-5-chlorophenoxymethyl]cinnamic acid,
(20) 4-[2-[N-isobutyl-N-(5-methyl-2-furylsulfonyl)amino]-4-methyl-5-chlorophenoxymethyl]cinnamic acid,
(21) 4-[2-[N-isopropyl-N-(5-methyl-2-furylsulfonyl)amino]-4,5-dimethylphenoxymethyl]cinnamic acid,
(22) 3-methyl-4-[2-[N-isopropyl-N-(5-methyl-2-furylsulfonyl)amino]-5-trifluoromethylphenoxymethyl]cinnamic acid,
(23) 3-methyl-4-[2-[N-isopropyl-N-(5-methyl-2-furylsulfonyl)amino]-4,5-dimethylphenoxymethyl]benzoic acid,
(24) 3-methyl-4-[2-[N-isopropyl-N-(5-methyl-2-furylsulfonyl)amino]-4,5-dimethylphenoxymethyl]cinnamic acid,
(25) 3-methyl-4-[2-[N-isobutyl-N-(5-methyl-2-furylsulfonyl)amino]-4,5-dimethylphenoxymethyl]cinnamic acid,
(26) 4-[2-[N-isobutyl-N-(5-methyl-2-furylsulfonyl)amino]-4,5-dimethyl phenoxymethyl]cinnamic acid,
(27) N-[4-chloro-5-methyl-2-[2-methyl-4-(5-tetrazolyl)phenylmethyloxy]phenyl]-N-isobutyl-(5-methyl-2-furyl)sulfonylamide,
(28) 3-methoxy-4-[2-[N-isobutyl-N-(5-methyl-2-furylsulfonyl)amino]-4-methyl-5-chlorophenoxymethyl]cinnamic acid,
(29) N-[4,5-dimethyl-2-[2-methyl-4-(5-tetrazolyl)phenylmethyloxy]phenyl]-N-isobutyl-(5-methyl-2-furyl)sulfonylamide,
(30) N-[4,5-dimethyl-2-[2-methyl-4-(5-tetrazolyl)phenylmethyloxy]phenyl]-N-isopropyl-(5-methyl-2-furyl)sulfonylamide,
(31) N-[4-chloro-5-methyl-2-[4-(5-tetrazolyl)phenylmethyloxy]phenyl]-N-isobutyl-(5-methyl-2-furyl)sulfonylamide,
(32) N-[4-chloro-5-methyl-2-[4-(5-oxo-1,2,4-oxadiazol-3-yl)phenylmethyloxy]phenyl]-N-isopropyl-(5-methyl-2-furyl)sulfonylamide,
(33) N-[4-chloro-5-methyl-2-[4-(5-oxo-1,2,4-oxadiazol-3-yl)phenylmethyloxy]phenyl]-N-isobutyl-(5-methyl-2-furyl)sulfonylamide,
(34) 4-[6-[N-isobutyl-N-(5-methyl-2-furylsulfonyl)amino]indan-5-yloxymethyl]benzoic acid,
(35) 4-[6-[N-isopropyl-N-(5-methyl-2-furylsulfonyl)amino]indan-5-yloxymethyl]benzoic acid,
(36) 4-[7-[N-isobutyl-N-(5-methyl-2-furylsulfonyl)amino]-1,2,3,4-tetrahydronaphtharen-6-yloxymethyl]benzoic acid,
(37) 4-[7-[N-isopropyl-N-(5-methyl-2-furylsulfonyl)amino]-1,2,3,4-tetrahydronaphtharen-6-yloxymethyl]benzoic acid,
(38) N-[4,5-dimethyl-2-[2-methyl-4-(5-oxo-1,2,4-oxadiazol-3-yl)phenylmethyloxy]phenyl]-N-isopropyl-(5-methyl-2-furyl)sulfonylamide,
(39) N-[4,5-dimethyl-2-[2-methyl-4-(5-oxo-1,2,4-oxadiazol-3-yl)phenylmethyloxy]phenyl]-N-isobutyl-(5-methyl-2-furyl)sulfonylamide,
(40) N-[4,5-dimethyl-2-[4-(5-tetrazolyl)phenylmethyloxy]phenyl]-N-isopropyl-(5-methyl-2-furyl)sulfonylamide,
(41) N-[4,5-dimethyl-2-[4-(5-tetrazolyl)phenylmethyloxy]phenyl]-N-isobutyl-(5-methyl-2-furyl)sulfonylamide,
(42) N-[4,5-dimethyl-2-[4-(5-oxo-1,2,4-oxadiazol-3-yl)phenylmethyloxy]phenyl]-N-isobutyl-(5-methyl-2-furyl)sulfonylamide,
(43) 3-methyl-4-[2-[N-isobutyl-N-(5-methyl-2-furylsulfonyl)amino]-4-methyl-5-chlorophenoxymethyl]cinnamic acid,
(44) N-[4,5-dimethyl-2-[2-methoxy-4-(5-oxo-1,2,4-oxadiazol-3-yl) phenylmethyloxy]phenyl]-N-isobutyl-(5-methyl-2-furyl)sulfonylamide,
(45) N-[4,5-dimethyl-2-[2-methoxy-4-(5-oxo-1,2,4-oxadiazol-3-yl) phenylmethyloxy]phenyl]-N-isopropyl-(5-methyl-2-furyl)sulfonylamide,
(46) 4-[6-[N-isobutyl-N-(5-methyl-2-furylsulfonyl)amino]indan-5-yloxymethyl]cinnamic acid,
(47) 3-methyl-4-[6-[N-isobutyl-N-(5-methyl-2-furylsulfonyl)amino]indan-5-yloxymethyl]benzoic acid,
(48) 3-methyl-4-[6-[N-isobutyl-N-(5-methyl-2-furylsulfonyl)amino]indan-5-yloxymethyl]cinnamic acid,
(49) 4-[2-[N-(2-methyl-2-propenyl)-N-(5-methyl-2-furylsulfonyl)amino]-4,5-dimethylphenoxymethyl]benzoic acid,
(50) 3-methyl-4-[6-[N-isopropyl-N-(5-methyl-2-furylsulfonyl)amino]indan-5-yloxymethyl]benzoic acid,
(51) 3-methyl-4-[6-[N-isopropyl-N-(5-methyl-2-furylsulfonyl)amino]indan-5-yloxymethyl]cinnamic acid,
(52) 4-[6-[N-isopropyl-N-(5-methyl-2-furylsulfonyl)amino]indan-5-yloxymethyl]cinnamic acid,
(53) 4-[3-[N-isobutyl-N-(5-methyl-2-furylsulfonyl)amino]-2-naphthyloxymethyl]benzoic acid,
(54) 3,5-dimethyl-4-[2-[N-isobutyl-N-(5-methyl-2-furylsulfonyl)amino]-5-trifluoromethylphenoxymethyl]benzoic acid,
(55) 3-methyl-4-[6-[N-(2-methyl-2-propenyl)-N-(5-methyl-2-furylsulfonyl)amino]indan-5-yloxymethyl]benzoic acid,
(56) 4-[6-[N-cyclopropylmethyl-N-(5-methyl-2-furylsulfonyl)amino]indan-5-yloxymethyl]-3-methylbenzoic acid,
(57) 4-[6-[N-isobutyl-N-(5-methyl-2-furylsulfonyl)amino]indan-5-yloxymethyl]-3-methylbenzylalcohol,
(58) 3-methyl-4-[6-[N-methyl-N-(5-methyl-2-furylsulfonyl)amino]indan-5-yloxymethyl]benzoic acid,
(59) 4-[6-[N-ethyl-N-(5-methyl-2-furylsulfonyl)amino]indan-5-yloxymethyl]-3-methylbenzoic acid,
(60) 4-[6-[N-methyl-N-(5-methyl-2-furylsulfonyl)amino]indan-5-yloxymethyl]cinnamic acid,
(61) 4-[6-[N-ethyl-N-(5-methyl-2-furylsulfonyl)amino]indan-5-yloxymethyl]cinnamic acid,
(62) 4-[6-[N-propyl-N-(5-methyl-2-furylsulfonyl)amino]indan-5-yloxymethyl]cinnamic acid,
(63) 4-[4,5-dimethyl-2-[N-(2-methyl-2-propenyl)-N-(5-methyl-2-furylsulfonyl)amino]phenoxymethyl]-3-methylbenzoic acid,
(64) 4-[6-[N-(2-methyl-2-propenyl)-N-(5-methyl-2-furylsulfonyl)amino]indan-5-yloxymethyl]cinnamic acid,
(65) 4-[6-[N-cyclopropylmethyl-N-(5-methyl-2-furylsulfonyl)amino] indan-5-yloxymethyl]cinnamic acid,
(66) 4-[6-[N-(2-propenyl)-N-(5-methyl-2-furylsulfonyl)amino]indan-5-yloxymethyl]cinnamic acid,
(67) 3-methyl-4-[6-[N-propyl-N-(5-methyl-2-furylsulfonyl)amino] indan-5-yloxymethyl]benzoic acid,
(68) 3-methyl-4-[6-[N-(2-propenyl)-N-(5-methyl-2-furylsulfonyl)amino]indan-5-yloxymethyl]benzoic acid,
(69) 4-[4,5-dimethyl-2-[N-methyl-N-(5-methyl-2-furylsulfonyl)amino]phenoxy methyl]benzoic acid,
(70) 4-[4,5-dimethyl-2-[N-ethyl-N-(5-methyl-2-furylsulfonyl)amino]phenoxy methyl]benzoic acid,
(71) 4-[4,5-dimethyl-2-[N-(5-methyl-2-furylsulfonyl)-N-propylamino]phenoxy methyl]benzoic acid,
(72) 4-[3-[N-isopropyl-N-(5-methyl-2-furylsulfonyl)amino] naphtharen-2-yloxymethyl]-3-methylbenzoic acid,
(73) 4-[3-[N-isobutyl-N-(5-methyl-2-furylsulfonyl)amino] naphtharen-2-yloxymethyl]-3-methylbenzoic acid,

(74) 4-[3-[N-isopropyl-N-(5-methyl-2-furylsulfonyl)amino]naphtharen-2-yloxymethyl]cinnamic acid,
(75) 4-[3-[N-isobutyl-N-(5-methyl-2-furylsulfonyl)amino]naphtharen-2-yloxymethyl]cinnamic acid,
(76) 3-methyl-4-[3-[N-isopropyl-N-(5-methyl-2-furylsulfonyl)amino]naphtharen-2-yloxymethyl]cinnamic acid,
(77) 3-methyl-4-[3-[N-isobutyl-N-(5-methyl-2-furylsulfonyl)amino]naphtharen-2-yloxymethyl]cinnamic acid
(78) 4-[4,5-dimethyl-2-[N-[(5-methyl-2-furyl)sulfonyl]-N-2-propenylamino]phenoxymethyl]benzoic acid,
(79) 4-[4,5-dimethyl-2-[N— methyl-N-(5-methyl-2-furylsulfonyl)amino]phenoxymethyl]-3-methylbenzoic acid,
(80) 4-[4,5-dimethyl-2-[N-ethyl-N-(5-methyl-2-furylsulfonyl)amino]phenoxymethyl]-3-methylbenzoic acid,
(81) 4-[4,5-dimethyl-2-[N-(5-methyl-2-furylsulfonyl)-N-propylamino]phenoxymethyl]-3-methylbenzoic acid,
(82) 4-[4,5-dimethyl-2-[N-(5-methyl-2-furylsulfonyl)-N-(2-propenyl)amino]phenoxymethyl]-3-methylbenzoic acid,
(83) 4-[4,5-dimethyl-2-[N-(2-hydroxy-2-methylpropyl)-N-(5-methyl-2-furylsulfonyl)amino]phenoxymethyl]-3-methylbenzoic acid,
(84) 4-[6-[N-(2-hydroxy-2-methylpropyl)-N-(5-methyl-2-furylsulfonyl)amino]indan-5-yloxymethyl]-3-methylbenzoic acid,
(85) 4-[4,5-dimethyl-2-[N-cyclopropylmethyl-N-(5-methyl-2-furylsulfonyl)amino]phenoxymethyl]benzoic acid,
(86) 4-[4,5-dimethyl-2-[N-(2-hydroxy-2-methylpropyl)-N-(5-methyl-2-furylsulfonyl)amino]phenoxymethyl]benzoic acid,
(87) 4-[6-[N-(2-hydroxy-2-methylpropyl)-N-(5-methyl-2-furylsulfonyl)amino]indan-5-yloxymethyl]cinnamic acid,
(88) 4-[4,5-dimethyl-2-[N-cyclopropylmethyl-N-(5-methyl-2-furylsulfonyl)amino]phenoxymethyl]-3-methylbenzoic acid.
(89) 4-[2-[N-isopropyl-N-(2-thiazolylsulfonyl)amino]-5-trifluoromethylphenoxymethyl]benzoic acid,
(90) 4-[2-[N-isobutyl-N-(2-thiazolylsulfonyl)amino]-5-trifluoromethylphenoxymethyl]benzoic acid,
(91) 4-[2-[N-isopropyl-N-(2-thiazolylsulfonyl)amino]-5-trifluoromethylphenoxymethyl]cinnamic acid,
(92) 4-[2-[N-isobutyl-N-(2-thiazolylsulfonyl)amino]-5-trifluoromethylphenoxymethyl]cinnamic acid,
(93) 4-[2-[N-isobutyl-N-(4-methyl-2-thiazolylsulfonyl)amino]-5-trifluoromethylphenoxymethyl]benzoic acid,
(94) 4-[2-[N-isobutyl-N-(4-methyl-2-thiazolylsulfonyl)amino]-5-trifluoromethylphenoxymethyl]cinnamic acid,
(95) 4-[2-[N-isopropyl-N-(2-thiazolylsulfonyl)amino]-4-chloro-5-methylphenoxy methyl]benzoic acid,
(96) N-[4-trifluoromethyl-2-[4-(5-tetrazolyl)phenylmethyloxy]phenyl]-N-isobutyl-2-thiazolylsulfonylamide,
(97) N-[4-trifluoromethyl-2-[4-(5-tetrazolyl)phenylmethyloxy]phenyl]-N-isopropyl-2-thiazolylsulfonylamide,
(98) N-[4-trifluoromethyl-2-[4-(5-oxo-1,2,4-oxadiazol-3-yl)phenylmethyloxy]phenyl]-N-isopropyl-2-thiazolylsulfonylamide,
(99) N-[4-trifluoromethyl-2-[4-(5-oxo-1,2,4-thiadiazol-3-yl)phenylmethyloxy]phenyl]-N-isopropyl-2-thiazolylsulfonylamide,
(100) 4-[2-[N-isopropyl-N-(4-methyl-2-thiazolylsulfonyl)amino]-4-chloro-5-methylphenoxymethyl]benzoic acid,
(101) 4-[2-[N-isobutyl-N-(4-methyl-2-thiazolylsulfonyl)amino]-4-chloro-5-methylphenoxymethyl]benzoic acid,
(102) 3-chloro-4-[2-[N-isopropyl-N-(4-methyl-2-thiazolylsulfonyl)amino]-4-chloro-5-methylphenoxymethyl]benzoic acid,
(103) 3-methyl-4-[2-[N-isobutyl-N-(4-methyl-2-thiazolylsulfonyl)amino]-5-trifluoromethylphenoxymethyl]benzoic acid,
(104) 3-methyl-4-[2-[N-isobutyl-N-(4-methyl-2-thiazolylsulfonyl)amino]-4-chloro-5-methylphenoxymethyl]benzoic acid,
(105) 3-methoxy-4-[2-[N-isobutyl-N-(4-methyl-2-thiazolylsulfonyl)amino]-4-chloro-5-methylphenoxymethyl]benzoic acid,
(106) 3-methoxy-4-[2-[N-isobutyl-N-(4-methyl-2-thiazolylsulfonyl)amino]-5-trifluoromethylphenoxymethyl]benzoic acid,
(107) N-[4-trifluoromethyl-2-[4-(5-tetrazolyl)phenylmethyloxy]phenyl]-N-isobutyl-(4-methyl-2-thiazolyl)sulfonylamide,
(108) N-[4-trifluoromethyl-2-[4-(5-oxo-1,2,4-oxadiazol-3-yl)phenylmethyloxy]phenyl]-N-isopropyl-(4-methyl-2-thiazolyl)sulfonylamide,
(109) N-[4-trifluoromethyl-2-[4-(5-oxo-1,2,4-oxadiazol-3-yl)phenylmethyloxy]phenyl]-N-isobutyl-(4-methyl-2-thiazolyl)sulfonylamide,
(110) 4-[2-[N-isobutyl-N-(4-methyl-2-thiazolylsulfonyl)amino]-4-methyl-5-chlorophenoxymethyl]benzoic acid,
(111) 3-chloro-4-[2-[N-isobutyl-N-(4-methyl-2-thiazolylsulfonyl)amino]-4-methyl-5-chlorophenoxymethyl]benzoic acid,
(112) 3-methoxy-4-[2-[N-isobutyl-N-(4-methyl-2-thiazolylsulfonyl)amino]-4-methyl-5-chlorophenoxymethyl]benzoic acid,
(113) N-[4-trifluoromethyl-2-[4-(5-tetrazolyl)phenylmethyloxy]phenyl]-N-isopropyl-(4-methyl-2-thiazolyl)sulfonylamide,
(114) 3-methyl-4-[2-[N-isobutyl-N-(4-methyl-2-thiazolylsulfonyl)amino]-4,5-dimethylphenoxymethyl]benzoic acid,
(115) 3-methyl-4-[2-[N-isopropyl-N-(4-methyl-2-thiazolylsulfonyl)amino]-4,5-dimethylphenoxymethyl]benzoic acid,
(116) 3-methoxy-4-[2-[N-isobutyl-N-(4-methyl-2-thiazolylsulfonyl)amino]-4,5-dimethylphenoxymethyl]benzoic acid,
(117) 3-chloro-4-[2-[N-isobutyl-N-(4-methyl-2-thiazolylsulfonyl)amino]-4,5-dimethylphenoxymethyl]benzoic acid,
(118) 3-chloro-4-[2-[N-isopropyl-N-(4-methyl-2-thiazolylsulfonyl)amino]-4,5-dimethylphenoxymethyl]benzoic acid,
(119) 4-[2-[N-isopropyl-N-(4-methyl-2-thiazolylsulfonyl)amino]-4,5-dimethylphenoxymethyl]benzoic acid,
(120) 4-[2-[N-isobutyl-N-(4-methyl-2-thiazolylsulfonyl)amino]-4,5-dimethylphenoxymethyl]benzoic acid,
(121) 4-[2-[N-isobutyl-N-(4-methyl-2-thiazolylsulfonyl)amino]-4-chloro-5-methylphenoxymethyl]cinnamic acid,
(122) 3-methyl-4-[2-[N-isobutyl-N-(4-methyl-2-thiazolylsulfonyl)amino]-5-trifluoromethylphenoxymethyl]cinnamic acid,
(123) 3-chloro-4-[2-[N-isobutyl-N-(4-methyl-2-thiazolylsulfonyl)amino]-5-trifluoromethylphenoxymethyl]cinnamic acid,
(124) 3-methyl-4-[2-[N-isopropyl-N-(4-methyl-2-thiazolylsulfonyl)amino]-4,5-dimethylphenoxymethyl]cinnamic acid,
(125) 3-methyl-4-[2-[N-isobutyl-N-(4-methyl-2-thiazolylsulfonyl)amino]-4,5-dimethylphenoxymethyl]cinnamic acid,
(126) 4-[2-[N-isobutyl-N-(4-methyl-2-thiazolylsulfonyl)amino]-4-methyl-5-chlorophenoxymethyl]cinnamic acid, (127) 3-methyl-4-[2-[N-isobutyl-N-(4-methyl-2-thiazolylsulfonyl)amino]-4-methyl-5-chlorophenoxymethyl]cinnamic acid,
(128) 3-methyl-4-[2-[N-isobutyl-N-(4-methyl-2-thiazolylsulfonyl)amino]-4-chloro-5-methylphenoxymethyl]cinnamic acid,
(129) N-[4-chloro-5-methyl-2-[2-methyl-4-(5-tetrazolyl)phenylmethyloxy]phenyl]-N-isobutyl-(4-methyl-thiazolyl)sulfonylamide,
(130) N-[4-chloro-5-methyl-2-[4-(5-tetrazolyl)phenylmethyloxy]phenyl]-N-isopropyl-(4-methyl-2-thiazolyl)sulfonylamide,
(131) 4-[2-[N-isobutyl-N-(4-methyl-2-thiazolylsulfonyl)amino]-4,5-dimethylphenoxymethyl]cinnamic acid,
(132) N-[4-trifluoromethyl-2-[2-methyl-4-(5-tetrazolyl)phenylmethyloxy]phenyl]-N-isopropyl-(4-methyl-2-thiazolyl)sulfonylamide,
(133) N-[4-trifluoromethyl-2-[2-methyl-4-(5-tetrazolyl)phenylmethyloxy]phenyl]-N-isobutyl-(4-methyl-2-thiazolyl)sulfonylamide,
(134) 3-chloro-4-[2-[N-isobutyl-N-(4-methyl-2-thiazolylsulfonyl)amino]-4,5-dimethylphenoxymethyl]cinnamic acid,
(135) N-[4,5-dimethyl-2-[2-methyl-4-(5-tetrazolyl)phenylmethyloxy]phenyl]-N-isobutyl-(4-methyl-2-thiazolyl)sulfonylamide,
(136) N-[4,5-dimethyl-2-[2-methyl-4-(5-tetrazolyl)phenylmethyloxy]phenyl]-N-isopropyl-(4-methyl-2-thiazolyl)sulfonylamide,
(137) N-[4,5-dimethyl-2-[4-(5-tetrazolyl)phenylmethyloxy]phenyl]-N-isopropyl-(4-methyl-2-thiazolyl)sulfonylamide,
(138) N-[4,5-dimethyl-2-[4-(5-tetrazolyl)phenylmethyloxy]phenyl]-N-isobutyl-(4-methyl-2-thiazolyl)sulfonylamide,
(139) N-[4-chloro-5-methyl-2-[4-(5-tetrazolyl)phenylmethyloxy]phenyl]-N-isopropyl-(4-methyl-2-thiazolyl)sulfonylamide,
(140) N-[4-chloro-5-methyl-2-[4-(5-tetrazolyl)phenylmethyloxy]phenyl]-N-isobutyl-(4-methyl-2-thiazolyl)sulfonylamide,
(141) N-[4-chloro-5-methyl-2-[4-(5-oxo-1,2,4-oxadiazol-3-yl)phenylmethyloxy]phenyl]-N-isobutyl-(4-methyl-2-thiazolyl)sulfonylamide,
(142) N-[4-chloro-5-methyl-2-[2-methyl-4-(5-oxo-1,2,4-oxadiazol-3-yl)phenylmethyloxy]phenyl]-N-isobutyl-(4-methyl-2-thiazolyl)sulfonylamide,
(143) 3-methoxy-4-[2-[N-isobutyl-N-(4-methyl-2-thiazolylsulfonyl)amino]-4,5-dimethylphenoxymethyl]cinnamic acid,
(144) N-[4,5-dimethyl-2-[2-methyl-4-(5-oxo-1,2,4-oxadiazol-3-yl)phenyl methyloxy]phenyl]-N-isopropyl-(4-methyl-2-thiazolyl)sulfonylamide,
(145) N-[4,5-dimethyl-2-[2-methyl-4-(5-oxo-1,2,4-oxadiazol-3-yl)phenylmethyloxy]phenyl]-N-isobutyl-(4-methyl-2-thiazolyl)sulfonylamide,
(146) N-[4,5-dimethyl-2-[4-(5-oxo-1,2,4-oxadiazol-3-yl)phenylmethyloxy]phenyl]-N-isopropyl-(4-methyl-2-thiazolyl)sulfonylamide,
(147) N-[4,5-dimethyl-2-[4-(5-oxo-1,2,4-oxadiazol-3-yl)phenylmethyloxy]phenyl]-N-isobutyl-(4-methyl-2-thiazolyl)sulfonylamide,
(148) N-[4,5-dimethyl-2-[2-methoxy-4-(5-oxo-1,2,4-oxadiazol-3-yl)phenylmethyloxy]phenyl]-N-isopropyl-(4-methyl-2-thiazolyl)sulfonylamide,
(149) N-[4,5-dimethyl-2-[2-methoxy-4-(5-tetrazolyl)phenylmethyloxy]-phenyl]-N-isopropyl-(4-methyl-2-thiazolyl)sulfonylamide,
(150) 4-[6-[N-isobutyl-N-(4-methyl-2-thiazolylsulfonyl)amino]indan-5-yloxymethyl]benzoic acid,
(151) 4-[6-[N-isobutyl-N-(4-methyl-2-thiazolylsulfonyl)amino]indan-5-yloxymethyl]cinnamic acid,
(152) 3-methyl-4-[6-[N-isobutyl-N-(4-methyl-2-thiazolylsulfonyl)amino]-indan-5 -yloxymethyl]benzoic acid,
(153) 3-methyl-4-[6-[N-isobutyl-N-(4-methyl-2-thiazolylsulfonyl)amino]indan-5-yloxymethyl]cinnamic acid,
(154) 3-methyl-4-[2-[N-(2-methyl-2-propenyl)-N-(4-methyl-2-thiazolylsulfonyl)amino]-4-chloro-5-methylphenoxymethyl]benzoic acid,
(155) 4-[2-[N-(2-methyl-2-propenyl)-N-(4-methyl-2-thiazolylsulfonyl)amino]-5-trifluoromethylphenoxymethyl]cinnamic acid,
(156) 3-methyl-4-[2-[N-(2-methyl-2-propenyl)-N-(4-methyl-2-thiazolylsulfonyl)amino]-4,5-dimethylphenoxymethyl]benzoic acid,
(157) 3-methyl-4-[6-[N-isopropyl-N-(2-thiazolylsulfonyl)amino]-indan-5-yloxymethyl]benzoic acid,
(158) 3-methyl-4-[6-[N-isobutyl-N-(2-thiazolylsulfonyl)amino]indan-5-yloxymethyl]benzoic acid,
(159) 3-methyl-4-[6-[N-isopropyl-N-(4-methyl-2-thiazolylsulfonyl)amino]indan-5-yloxymethyl]benzoic acid,
(160) 4-[6-[N-isopropyl-N-(2-thiazolylsulfonyl)amino]indan-5-yloxymethyl]benzoic acid,
(161) 4-[6-[N-isobutyl-N-(2-thiazolylsulfonyl)amino]indan-5-yloxymethyl]benzoic acid,
(162) 4-[6-[N-isopropyl-N-(4-methyl-2-thiazolylsulfonyl)amino]indan-5-yloxymethyl]benzoic acid,
(163) 4-[6-[N-isopropyl-N-(4-methyl-2-thiazolylsulfonyl)amino]-indan-5-yloxymethyl]cinnamic acid,
(164) 3-methyl-4-[6-[N-isopropyl-N-(4-methyl-2-thiazolylsulfonyl)amino]indan-5-yloxymethyl]cinnamic acid,
(165) 4-[2-[N-isopropyl-N-(2-thiazolylsulfonyl)amino]-4,5-dimethylphenoxymethyl]benzoic acid,
(166) 4-[2-[N-isobutyl-N-(2-thiazolylsulfonyl)amino]-4,5-dimethylphenoxymethyl]benzoic acid,
(167) 4-[2-[N-isopropyl-N-(2-thiazolylsulfonyl)amino]-4,5-dimethylphenoxymethyl]cinnamic acid,
(168) 4-[2-[N-isobutyl-N-(2-thiazolylsulfonyl)amino]-4,5-dimethylphenoxymethyl]cinnamic acid,
(169) 4-[6-[N-isopropyl-N-(2-thiazolylsulfonyl)amino]-indan-5-yloxymethyl]cinnamic acid,
(170) 4-[6-[N-isobutyl-N-(2-thiazolylsulfonyl)amino]indan-5-yloxymethyl]cinnamic acid,
(171) 3-methyl-4-[2-[N-isopropyl-N-(2-thiazolylsulfonyl)amino]-4,5-dimethylphenoxymethyl]benzoic acid,
(172) 3-methyl-4-[2-[N-isobutyl-N-(2-thiazolylsulfonyl)amino]-4,5-dimethylphenoxymethyl]benzoic acid,
(173) 3-methyl-4-[2-[N-isopropyl-N-(2-thiazolylsulfonyl)amino]-4,5-dimethylphenoxymethyl]cinnamic acid,
(174) 3-methyl-4-[2-[N-isobutyl-N-(2-thiazolylsulfonyl)amino]-4,5-dimethylphenoxymethyl]cinnamic acid,
(175) 3-methyl-4-[6-[N-isopropyl-N-(2-thiazolylsulfonyl)amino]-indan-5-yloxymethyl]cinnamic acid,
(176) 3-methyl-4-[6-[N-isobutyl-N-(2-thiazolylsulfonyl)amino]indan-5-yloxymethyl]cinnamic acid,
(177) 4-[3-[N-isobutyl-N-(4-methyl-2-thiazolylsulfonyl)amino]naphtharen-2-yloxymethyl]benzoic acid,
(178) 4-[3-[N-isopropyl-N-(4-methyl-2-thiazolylsulfonyl)amino]-naphtharen-2-yloxymethyl]benzoic acid,
(179) 4-[3-[N-isobutyl-N-(4-methyl-2-thiazolylsulfonyl)amino]naphtharen-2-yloxymethyl]-3-methylbenzoic acid,
(180) 4-[3-[N-isopropyl-N-[2-(4-methylthiazolyl)sulfonyl]amino]naphtharen-2-yloxymethyl]-3-methylbenzoic acid,
(181) 4-[3-[N-isobutyl-N-(4-methyl-2-thiazolylsulfonyl)amino]naphtharen-2-yloxymethyl]cinnamic acid, (182) 4-[3-[N-isopropyl-N-(4-methyl-2-thiazolylsulfonyl)amino]naphtharen-2-yloxymethyl]cinnamic acid,
(183) 4-[4,5-dimethyl-2-[N-methyl-N-(4-methyl-2-thiazolylsulfonyl)amino]phenoxymethyl]-3-methylbenzoic acid,
(184) 4-[4,5-dimethyl-2-[N-ethyl-N-(4-methyl-2-thiazolylsulfonyl)amino]phenoxymethyl]-3-methylbenzoic acid,
(185) 4-[4,5-dimethyl-2-[N-propyl-N-(4-methyl-2-thiazolylsulfonyl)amino]phenoxymethyl]-3-methylbenzoic acid,
(186) 4-[4,5-dimethyl-2-[N-(2-propenyl)-N-(4-methyl-2-thiazolylsulfonyl)amino]phenoxymethyl]-3-methylbenzoic acid,
(187) 4-[4,5-dimethyl-2-[N-cyclopropylmethyl-N-(4-methyl-2-thiazolylsulfonyl)amino]phenoxymethyl]-3-methylbenzoic acid,
(188) 4-[4,5-dimethyl-2-[N-(2-hydroxy-2-methylpropyl)-N-(4-methyl-2-thiazolyl sulfonyl)amino]phenoxymethyl]-3-methylbenzoic acid,
(189) 4-[6-[N-(2-methyl-2-propenyl)-N-(4-methyl-2-thiazolylsulfonyl)amino]indan-5-yloxymethyl]benzoic acid,
(190) 4-[6-[N-(4-methyl-2-thiazolylsulfonyl)-N-(2-propenyl)amino]indan-5-yloxymethyl]benzoic acid,
(191) 4-[6-[N-cyclopropylmethyl-N-(4-methyl-2-thiazolylsulfonyl)amino]indan-5-yloxymethyl]benzoic acid,
(192) 4-[3-[N-isobutyl-N-[2-(4-methylthiazolyl)sulfonyl]amino]naphtharen-2-yloxymethyl]benzoic acid,
(193) 4-[3-[N-isopropyl-N-(4-methyl-2-thiazolylsulfonyl)amino]naphtharen-2-yloxymethyl]-3-methylbenzoic acid,
(194) 4-[6-[N-ethyl-N-(4-methyl-2-thiazolylsulfonyl)amino]indan-5-yloxymethyl]benzoic acid,
(195) 4-[6-[N-(4-methyl-2-thiazolylsulfonyl)-N-propylamino]indan-5-yloxymethyl]benzoic acid,
(196) 4-[6-[N-methyl-N-(4-methyl-2-thiazolylsulfonyl)amino]indan-5-yloxymethyl]benzoic acid,
(197) 3-methyl-4-[6-[N-methyl-N-(4-methyl-2-thiazolylsulfonyl)amino]indan-5-yloxymethyl]cinnamic acid,
(198) 4-[6-[N-ethyl-N-(4-methyl-2-thiazolylsulfonyl)amino]indan-5-yloxymethyl]-3-methylcinnamic acid,
(199) 3-methyl-4-[6-[N-(2-methyl-2-propenyl)-N-(4-methyl-2-thiazolylsulfonyl)amino]indan-5-yloxymethyl]cinnamic acid,
(200) 4-[6-[N-cyclopropylmethyl-N-(4-methyl-2-thiazolylsulfonyl)amino]indan-5-yloxymethyl]-3-methylcinnamic acid,
(201) 3-methyl-4-[6-[N-(4-methyl-2-thiazolylsulfonyl)-N-(2-propenyl)amino]indan-5-yloxymethyl]cinnamic acid,
(202) 4-[6-[N-(2-hydroxy-2-methylpropyl)-N-(4-methyl-2-thiazolylsulfonyl)amino]indan-5-yloxymethyl]-3-methylcinnamic acid,
(203) 3-methyl-4-[6-[N-(4-methyl-2-thiazolylsulfonyl)-N-propylamino]indan-5-yloxymethyl]cinnamic acid,
(204) 4-[6-[N-(2-hydroxy-2-methylpropyl)-N-(4-methyl-2-thiazolylsulfonyl)amino]indan-5-yloxymethyl]benzoic acid,
(205) 4-[2-[N-isobutyl-N-(2-pyridylsulfonyl)amino]-5-trifluoromethylphenoxymethyl]cinnamic acid,
(206) 4-[2-[N-isobutyl-N-(3-pyridylsulfonyl)amino]-5-trifluoromethylphenoxymethyl]benzoic acid,
(207) 3-chloro-4-[2-[N-isopropyl-N-(2-pyridylsulfonyl)amino]-4-chloro-5-methylphenoxymethyl]benzoic acid,
(208) 3-methyl-4-[2-[N-isobutyl-N-(2-pyridylsulfonyl)amino]-4-chloro-5-methylphenoxymethyl]benzoic acid,
(209) 3-methyl-4-[2-[N-isobutyl-N-(3-pyridylsulfonyl)amino]-4-chloro-5-methylphenoxymethyl]benzoic acid,
(210) 3-methyl-4-[2-[N-isobutyl-N-(2-pyridylsulfonyl)amino]-4-methyl-5-chlorophenoxymethyl]benzoic acid,
(211) N-[4-trifluoromethyl-2-[4-(5-tetrazolyl)phenylmethyloxy]phenyl]-N-isopropyl-3-pyridylsulfonylamide,
(212) N-[4-trifluoromethyl-2-[4-(5-tetrazolyl)phenylmethyloxy]phenyl]-N-isobutyl-3-pyridylsulfonylamide,
(213) 4-[2-[N-isobutyl-N-(3-pyridylsulfonyl)amino]-4-methyl-5-chlorophenoxymethyl]benzoic acid,
(214) 3-chloro-4-[2-[N-isobutyl-N-(3-pyridylsulfonyl)amino]-4-methyl-5-chlorophenoxymethyl]benzoic acid,
(215) 3-methyl-4-[2-[N-isobutyl-N-(2-pyridylsulfonyl)amino]-5-trifluoromethylphenoxymethyl]cinnamic acid,
(216) 3-methoxy-4-[2-[N-isobutyl-N-(2-pyridylsulfonyl)amino]-4,5-dimethyl phenoxymethyl]benzoic acid,
(217) 3-methoxy-4-[2-[N-isobutyl-N-(3-pyridylsulfonyl)amino]-4,5-dimethyl phenoxymethyl]benzoic acid,
(218) 3-methyl-4-[2-[N-isobutyl-N-(3-pyridylsulfonyl)amino]-4,5-dimethyl phenoxymethyl]benzoic acid,
(219) 3-methyl-4-[2-[N-isobutyl-N-(2-pyridylsulfonyl)amino]-4,5-dimethyl phenoxymethyl]benzoic acid,
(220) N-[4-trifluoromethyl-2-[4-(5-tetrazolyl)phenylmethyloxy]phenyl]-N-isopropyl-2-pyridylsulfonylamide,
(221) N-[4-trifluoromethyl-2-[4-(5-tetrazolyl)phenylmethyloxy]phenyl]-N-isobutyl-2-pyridylsulfonylamide,
(222) 3-methyl-4-[2-[N-isobutyl-N-(3-pyridylsulfonyl)amino]-4-methyl-5-chlorophenoxymethyl]benzoic acid,
(223) 4-[2-[N-isobutyl-N-(2-pyridylsulfonyl)amino]-4,5-dimethylphenoxymethyl]benzoic acid,
(224) N-[4-trifluoromethyl-2-[4-(5-oxo-1,2,4-oxadiazol-3-yl)phenylmethyloxy]phenyl]-N-isobutyl-2-pyridylsulfonylamide,
(225) 4-[2-[N-isopropyl-N-(2-pyridylsulfonyl)amino]-4-methyl-5-chlorophenoxymethyl]cinnamic acid,
(226) 3-methyl-4-[2-[N-isobutyl-N-(2-pyridylsulfonyl)amino]-4-methyl-5-chlorophenoxymethyl]cinnamic acid,
(227) 3-methyl-4-[2-[N-isobutyl-N-(2-pyridylsulfonyl)amino]-4,5-dimethylphenoxymethyl]cinnamic acid,
(228) 4-[2-[N-isobutyl-N-(3-pyridylsulfonyl)amino]-4,5-dimethylphenoxymethyl]cinnamic acid,
(229) 3-methyl-4-[2-[N-isobutyl-N-(3-pyridylsulfonyl)amino]-4,5-dimethylphenoxymethyl]cinnamic acid,
(230) N-[4-trifluoromethyl-2-[2-methyl-4-(5-tetrazolyl)phenylmethyloxy]phenyl]-N-isopropyl-2-pyridylsulfonylamide,
(231) 3-chloro-4-[2-[N-isobutyl-N-(3-pyridylsulfonyl)amino]-4,5-dimethylphenoxymethyl]cinnamic acid,
(232) N-[4,5-dimethyl-2-[2-methyl-4-(5-tetrazolyl)phenylmethyloxy]phenyl]-N-isobutyl-2-pyridylsulfonylamide,
(233) N-[4,5-dimethyl-2-[2-methyl-4-(5-tetrazolyl)phenylmethyloxy]phenyl]-N-isobutyl-3-pyridylsulfonylamide,
(234) N-[4-chloro-5-methyl-2-[4-(5-tetrazolyl)phenylmethyloxy]phenyl]-N-isobutyl-3-pyridylsulfonylamide,
(235) N-[4,5-dimethyl-2-[2-chloro-4-(5-tetrazolyl)phenylmethyloxy]phenyl]-N-isobutyl-2-pyridylsulfonylamide,
(236) N-[4,5-dimethyl-2-[2-chloro-4-(5-tetrazolyl)phenylmethyloxy]phenyl]-N-isopropyl-3-pyridylsulfonylamide,
(237) N-[4,5-dimethyl-2-[2-chloro-4-(5-tetrazolyl)phenylmethyloxy]phenyl]-N-isobutyl-3-pyridylsulfonylamide,
(238) 3-methyl-4-[2-[N-isobutyl-N-(3-pyridylsulfonyl)amino]-4-chloro-5-methylphenoxymethyl]cinnamic acid,
(239) N-[4,5-dimethyl-2-[4-(5-tetrazolyl)phenylmethyloxy]phenyl]-N-isopropyl-2-pyridylsulfonylamide,
(240) N-[4,5-dimethyl-2-[4-(5-tetrazolyl)phenylmethyloxy]phenyl]-N-isobutyl-2-pyridylsulfonylamide,
(241) N-[4,5-dimethyl-2-[4-(5-tetrazolyl)phenylmethyloxy]phenyl]-N-isobutyl-3-pyridylsulfonylamide,
(242) 3-chloro-4-[2-[N-isobutyl-N-(3-pyridylsulfonyl)amino]-5-trifluoromethylphenoxymethyl]cinnamic acid, (243) N-[4-chloro-5-methyl-2-[2-methyl-4-(5-tetrazolyl)phenylmethyloxy]phenyl]-N-isopropyl-2-pyridylsulfonylamide,
(244) N-[4-chloro-5-methyl-2-[2-methyl-4-(5-tetrazolyl)phenylmethyloxy]phenyl]-N-isobutyl-2-pyridylsulfonylamide,
(245) N-[4,5-dimethyl-2-[2-methyl-4-(5-oxo-1,2,4-oxadiazol-3-yl)phenylmethyloxy]phenyl]-N-isopropyl-2-pyridylsulfonylamide,
(246) N-[4,5-dimethyl-2-[2-methyl-4-(5-oxo-1,2,4-oxadiazol-3-yl)phenylmethyloxy]phenyl]-N-isobutyl-3-pyridylsulfonylamide,
(247) N-[4,5-dimethyl-2-[2-methoxy-4-(5-tetrazolyl)phenylmethyloxy]phenyl]-N-isobutyl-2-pyridylsulfonylamide,
(248) N-[4,5-dimethyl-2-[2-methoxy-4-(5-tetrazolyl)phenylmethyloxy]phenyl]-N-isopropyl-2-pyridylsulfonylamide,
(249) N-[4,5-dimethyl-2-[2-methoxy-4-(5-oxo-1,2,4-oxadiazol-3-yl)phenylmethyloxy]phenyl]-N-isobutyl-2-pyridylsulfonylamide, and
(250) N-[4,5-dimethyl-2-[2-methoxy-4-(5-oxo-1,2,4-oxadiazol-3-yl)phenylmethyloxy]phenyl]-N-isopropyl-2-pyridylsulfonylamide.

In the compound of formula (IA)-(IK), most preferable $EP_1$ antagonists are following compounds.
1) 6-[(2S, 3S)-3-(4-chloro-2-methylphenylsulfonylaminomethyl)-bicyclo[2.2.2]octan-2-yl]-5Z-hexenoic acid (the compound A),
2) 4-[2-[N-isopropyl-N-(5-methyl-2-furylsulfonyl)amino]-5-trifluoromethylphenoxymethyl]benzoic acid (the compound B),
3) 4-[2-(N-isobutyl-2-furanylsulfonylamino)-5-trifluoromethylphenoxymethyl]cinnamic acid (the compound C),
4) 4 [2-[N-isobutyl-N-(5-methyl-2-furylsulfonyl)amino]-4,5-dimethylphenoxymethyl]benzoic acid (the compound D),
5) 3-methyl-4-[2-[N-isobutyl-N-(5-methyl-2-furylsulfonyl)amino]4,5-dimethylphenoxymethyl]benzoic acid (the compound E),
6) 4-[6-[N-isobutyl-N-(5-methyl-2-furylsulfonyl)amino]indan-5-yloxymethyl]cinnamic acid (the compound F),
7) 3-methyl-4-[6-[N-isobutyl-N-(4-methyl-2-thiaolylsulfonyl)amino]indan-5-yloxymethyl]cinnamic acid (the compound G),
8) 4-[4,5-dimethyl-2-[N-(5-methyl-2-furylsulfonyl)-N-propylamino]phenoxymethyl]benzoic acid (the compound H),
9) 4-[5-trifluoromethyl-2-[N-(5-methyl-2-furylcarbonyl)-N-isopropylamino]phenoxymethyl]cinnamic acid (the compound J) and
10) 4-[6-[N-isobutyl-N-(4-methyl-2-thizolylsulfonyl)amino]indan-5-yloxymethyl]benzoic acid (the compound K).

The compound A was described in the specification of EP 878465 as Example 2c.

The compound C was described in the specification of WO 98/27053 as Example 18(9).

The compounds B, D, E, F, G, H, J and K are contained in the compound of formula (IK). These compounds were also contained in the compound of formula (IB), but they were not specifically described in the specification of WO 98/27053.

Although the chemical structures of all compounds were different each other, these compounds had this activity in common, and so, it became clear that an antagonism for $EP_1$ receptor lead to the treatment and/or prevention of depression.

It have been known that $EP_1$ antagonist could be used as an analgesic, an antipyretic, a therapeutic agent of frequent urination, and an anticancer agent by antagonizing $EP_1$, however it have not been known that $EP_1$ antagonists have an antidepressive activity, and it was firstly demonstrated by this invention.

The depression in this invention is contained depression and a depressed state, for example, endogenous depression, reactive depression, weatherability depression, and neurological depressed state, the depressed state of brain organic mental disorder.

[Process for the Preparation of the Present Invention]

The compound of formula (IA), (IB), (IC), (ID), (IE), (IF), (IG), (IH) and (IJ) may be prepared by each method described in the specification of WO98/27053, EP878465, WO92/19617, WO96/06822, WO97/00863, WO99/47497, WO00/20371, WO2001/19814 and WO2001/19819.

The compound of formula (IK) may be prepared by a method described in the specification of WO98/27053, or by a following method. A detailed process for the preparation is described hereinafter.

In the scheme, R is C1-4 alkyl, Tf is trifluoromethanesulfonyl, the other symbols are as hereinbefore defined.
R: C1-4 alkyl,
Ms: mesyl,
$Tf_2O$: trifluoromethanesulfonic acid anhydrous,
Et: ethyl,
TCDI: 1,1'-thiocarbonyldiimidazole.

Scheme (A)

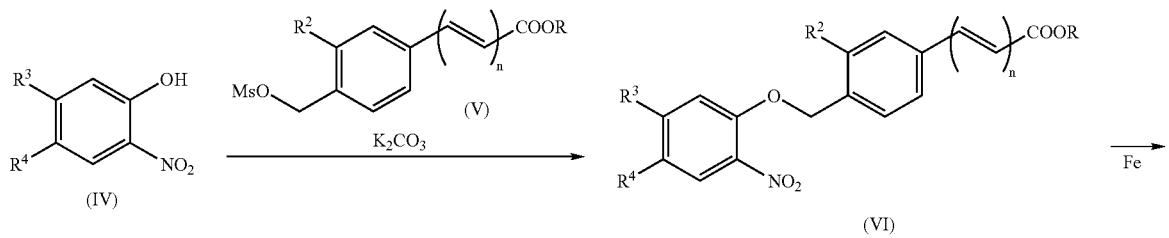

-continued
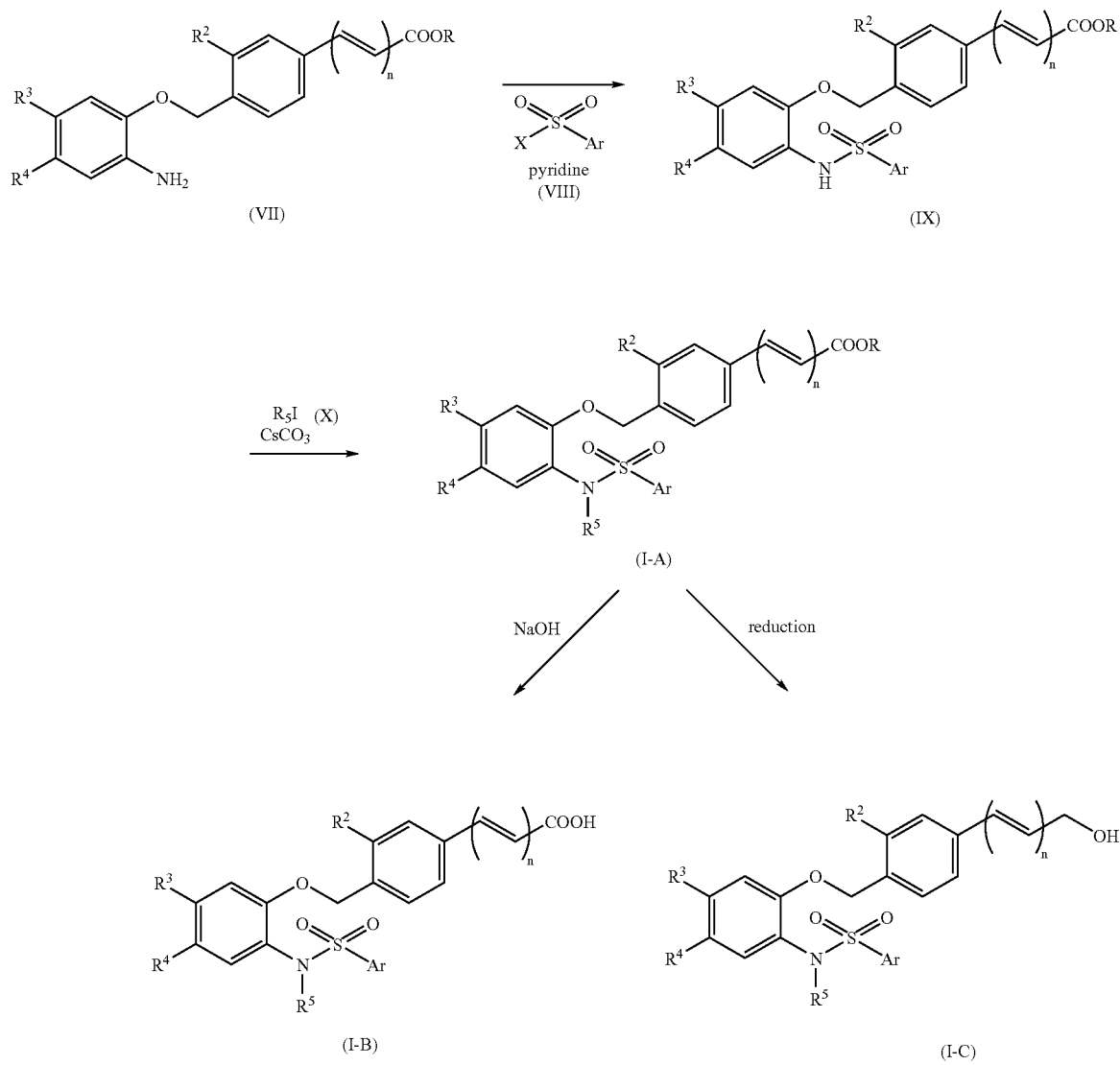
Scheme (B)
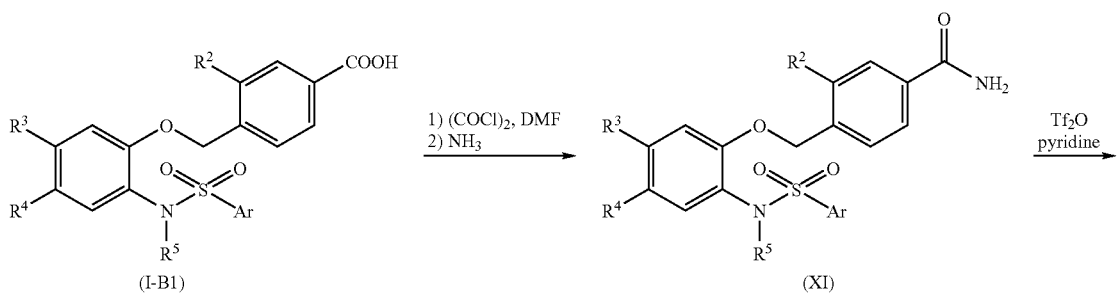

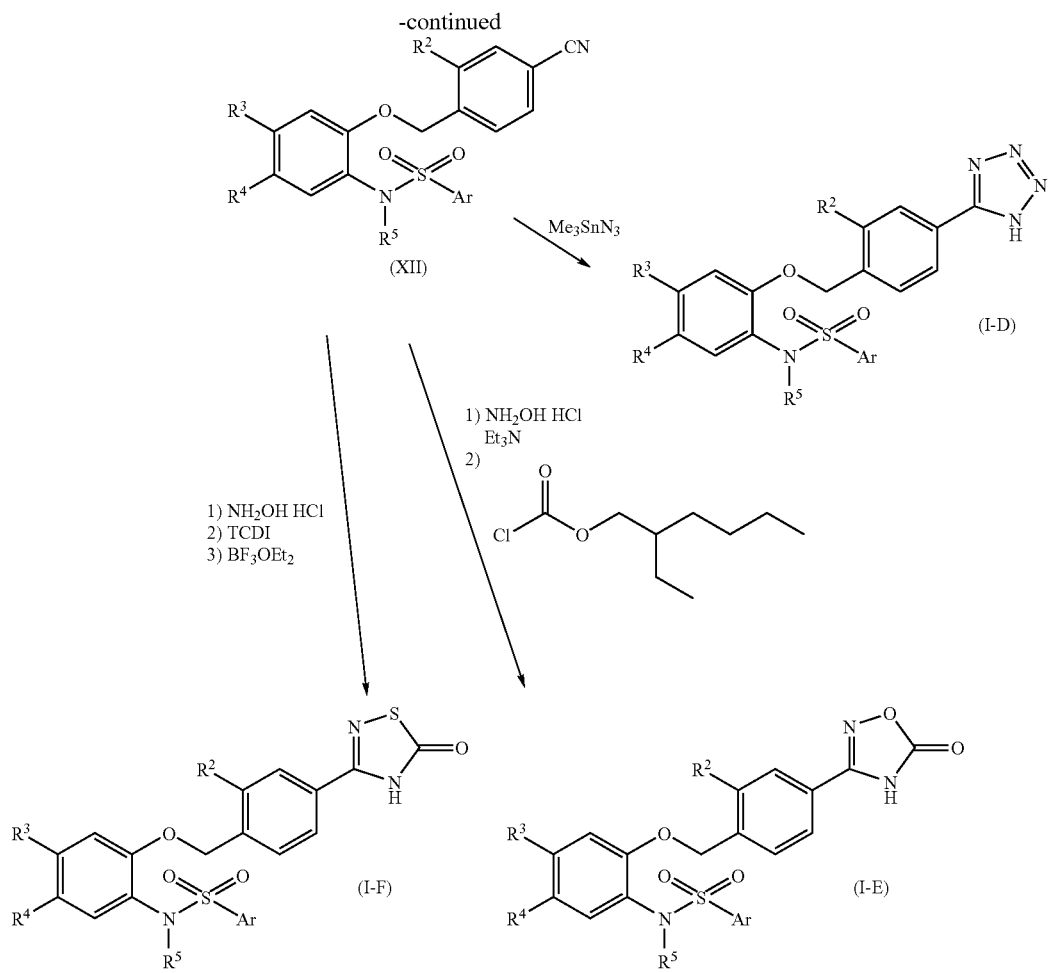

Concretely, the compound B, the compound D, the compound E, the compound F, the compound G, the compound H, the compound J and the compound K were prepared by a method described in following Example.

The compound B: Example 2(2), the compound D: Example 2(6), the compound E: Example 2, the compound F: Example 2(32), the compound G: Example 2(74), the compound H: Example 5(30), the compound J: Example 7, the compound K: Example 2(71).

[Pharmacological Activities]

It was confirmed by the following experiments that the compounds of formula of (IA)-(IK) could be useful for the treatment of depression. The following paper can be referred to about a tail-suspension test and its testing system in mice.
1) Psychopharmacology (1985) 85: 367-370
2) Prog. Neuro-Psychopharmacol. & Biol. Psychiat. 1987 Vol. 11, 659-671

(1) Tail-Suspension Test in Mice

The test compound (10 mg/kg animal body weight) was administered orally to male ddy mice weighing around 30 g 1 hour before the beginning of measurement. The mice were suspended by their tail on the hook of Tail Suspension TEST System (Neuroscience, Inc., Model NS-TST01-SS2) using adhesive tape. The subsequent immobility time for 10 minutes was measured. If the mice have none of administration, they get about 300 seconds as an immobility time in this experiment. Generally, the medicine having an anti-depressive action shortens this immobility time.

The result was as follows. In addition, in any case, ten animals were used for each group.

TABLE 1

| Compounds | Immobility time (sec.) | Inhibition (%) |
| --- | --- | --- |
| Vehicle | 290 ± 33 | 0.0 |
| Compound A | 202 ± 20 | 30 ± 7* |
| Compound B | 194 ± 23 | 35 ± 8** |
| Compound C | 212 ± 20 | 23 ± 7* |
| Compound D | 217 ± 24 | 27 ± 8* |
| Compound E | 185 ± 36 | 38 ± 12* |
| Compound F | 160 ± 26 | 47 ± 9** |
| Compound G | 206 ± 35 | 31 ± 12* |

(*: $p < 0.05$, : $p < 0.01$, *: $p < 0.001$ vs. vehicle/Student's t test)

(Discussion)

Immobility time in compounds A, B, C, D, E, F and G were shortened as compared with that in the vehicle treated group, and each rate of inhibition was statistically significant. Although the chemical structures of these compounds were different structure each other, all of them had $EP_1$ receptor antagonistic activity, and shortened the immobility state induced by tail-suspension, and these results clearly indicate that compounds having $EP_1$ antagonistic activity have an action increasing mobility, namely an anti-depressive action.

(2) Forced Swim Test in Rats

The seven-week old male SD (IGS) rat freely fed was solely put into the forced swimming equipment (the cylinder (Neuroscience, Inc.) of diameter of inner 19 cm, and height 40 cm, depth-sounding 17 cm, water temperature of 23±1° C.) manufactured with the transparent acrylics board, and let it swim for 15 minutes. The rat was immediately dried after the end of trial and was returned to the home cage. At the same time of the next day the rats were exposed to the same conditions, and behavior of rats were observed for 5 minutes. In this time, the behavior of rat is distinguished by immobile state, struggling, submerging and swimming. The immobility time, period that rats were floating on the water by taking their head outside of the water without stroking by both legs, were measured. In addition, the water in equipment was exchanged for every trial. Moreover, one trial was conducted for each animal.

The test compound was administered orally by 5 mL/kg dosage immediately after the end of the examination on the 1st, and 1 hour before the examination on the 2nd. And, the positive control compound (desipramine; selective serotonin reuptake inhibitor) was similarly administered intraperitoneally by 2 mL/kg dosage immediately after the end of the examination on the 1st, and 1 hour before the examination on the 2nd.

The result was as follows. In addition, in any case, twelve animals were used for each group.

TABLE 2

| Compounds | Immobility time (sec.) | Inhibition (%) |
| --- | --- | --- |
| Vehicle | 236 ± 14 | 0 ± 6 |
| Desipramine | 112 ± 15 | 53 ± 6*** |
| Compound B | 163 ± 21 | 31 ± 9*** |
| Compound G | 193 ± 13 | 18 ± 5* |
| Compound H | 156 ± 21 | 35 ± 9** |
| Compound J | 194 ± 16 | 20 ± 7* |
| Compound K | 172 ± 17 | 29 ± 7** |

(*: $p < 0.05$, : $p < 0.01$, *: $p < 0.001$ vs. vehicle/Student's t test)

(Discussion)

Immobility time in compounds B, G, H, J and K group were shortened as compared with that in the vehicle treated group, and each rate of inhibition was statistically significant. Although the chemical structures of these compounds were different structure each other, all of them had $EP_1$ receptor antagonistic activity, and so, it became clear that these compounds shortened the immobility state induced by forced swim by antagonizing to $EP_1$ receptor, and showed the action to increase the mobility, namely an anti-depressive action.

[Toxicity]

The toxicity of the compounds of the present invention is very low and therefore, it is confirmed that these compounds are safe for use as medicine. For example, $LD_{50}$ values of the compound A and B of the present invention by oral administration to mouse are 2000 mg/kg and over.

INDUSTRIAL APPLICABILITY

[Application for Pharmaceuticals]

The compounds of the formula (IA)-(IK) or a non-toxic salt thereof have $EP_1$ receptor antagonistic activity, therefor, they are useful as antidepressant.

For the purpose described above, the compounds of formula (IA)-(IK) of the present invention or a non-toxic salt thereof may be normally administered systemically or topically, usually by oral or parenteral administration.

The compound of formula (IA)-(IK) or a non-toxic salt thereof may be administered in combination with other medicaments for the purpose of 1) complement and/or enhancement of preventing and/or treating effect,
2) improvement of dynamics and absorption of the compound, and lowering of dose, and/or
3) alleviation of side effect of the compound.

The compound of formula (IA)-(IK) may be administered in combination with other medicaments as a composition in one drug product comprising these components, or may be administered separately. When they are administered independently, they may be administered simultaneously or with time lag. Administering with time lag includes the method of administering the compound of formula (IA)-(IK) before other medicaments and vice versa, and they may be administered in the same route or not.

The above combination takes effects on whichever disease treating and/or preventing effect of the compound of formula (IA)-(IK) is complemented and/or enhanced.

As other medicaments to complement and/or to enhance the preventing and/or treating effect of an $EP_1$ antagonist of formula (IA)-(IK) for depression, for example, antianxiety agent such as series of benzodiazepine, thienodiazepine or nonbenzodiazepine; antidepressant such as monoamine releasing agent, monoamine oxidase inhibitor, monoamine reuptake inhibitor (e.g. SNRI (Serotonin-Noradrenaline Reuptake Inhibitor), SSRI (Selective Serotonin Reuptake Inhibitor)), dopamine ($D_2$) antagonist, CRF antagonist, $\beta_3$ agonist, neurotensin antagonist, $NK_1$ antagonist, tricyclic antidepressant, tetracyclic antidepressant; anticholinergic agent, affinity polyacryl resin, obstipant, mucosal paralyzant, bulk cathartic, saline purgative, fibrillose preparation, drug for controlling intestinal function, automatic nervous regulator, calcium antagonist, phosphodiesterase inhibitor, serotonin antagonist (e.g. $5\text{-}HT_3$ antagonist, $5\text{-}HT_4$ antagonist), serotonin agonist (e.g. $5\text{-}HT_4$ agonist, $5\text{-}HT_{1A}$ agonist), gastrointestinal regulator (e.g. CCK-A antagonist, $\beta_3$ agonist, neurotensin antagonist, opioid agonist, $NK_1$ antagonist, $NK_2$ antagonist, $5\text{-}HT_{1A}$ agonist, muscarine agonist, 5-lipoxygenase inhibitor, CRF antagonist) are given.

As antianxiety agent, for example, alprazolam, oxazepam, oxazolam, tandospirone citrate, cloxazolam, clotiazepam, clorazepate dipotassium, chlordiazepoxide, diazepam, tofisopam, prazepam, fludiazepam, flutazolam, flutoprazepam, bromazepam, mexazolam, medazepam, ethyl loflazepate, lorazepam are given.

As antidepressant, for example, dosulepin hydrochloride, ethyl loflazepate, progabide, etizolam, setiptiline maleate, minaprine dihydrochloride, amoxapine, lofepramine hydrochloride, maprotiline hydrochloride, mianserin hydrochloride, G-34586, MD-690276, FCE-20124, modafinil, RV-12309, S-1574, bupropion, venlafaxine hydrochloride, tandospirone citrate, paroxetine hydrochloride, trazodone hydrochloride, risperidone, milnacipran hydrochloride, citalopram hydrobromide, fluvoxamine maleate, mirtazapine, topiramate, nefazodone hydrochloride, moclobemide, sertraline hydrochloride, OR-611, lamotrigine, olanzapine, pramipexole hydrochloride, fluoxetine hydrochroride, LU-26-054, tomoxetine hydrochloride, BMY-13805-1, duloxetine hydrochloride, MD-370503, BIMT-17, CP-93393, L-759274, LAX-101c are given.

As SSRI (Selective Serotonin Reuptake Inhibitor), for example, minaprine dihydrochloride, sibutramine hydrochloride, tramadol hydrochloride, venlafaxine hydrochloride, WY-45030, paroxetine hydrochloride, milnacipran hydrochloride, citalopram hydrobromide, fluvoxamine maleate, nefazodone hydrochloride, sertraline hydrochloride, fluoxetine hydrochroride, LU-26-054, duloxetine hydrochloride are given.

As dopamine antagonist, for example, amoxapine, etizolam, spiperone, sulpiride, timiperone, domperidone, nemonapride, haloperidol, fluphenazine, prochlorperazine, propericiazine, bromperidol, risperidone, clebopride malate, itopride hydrochloride, sultopride hydrochloride, tiapride hydrochloride, mosapramine hydrochloride, oxypertine, zotepine, pimozide, mazindol, indeloxazine hydrochloride, dosulepine hydrochloride, mazaticol hydrochloride are given.

As CRF antagonist, for example, DPC-368, NBI-34041, NBI-37582 are given.

As $\beta_3$ agonist, for example, SR-58611A, AJ-9677, KUL-7211, SB-418790, GW427353, N-5984 are given.

As $NK_1$ antagonist, for example, ezlopitant, MK-869, CP-122721, DNK-333, L758298, NKP-608, SR-140333, TAK-637, CS-003 are given.

As $NK_2$ antagonist, for example, saredutant, nepadutant, DNK-333, CS-003 are given.

As tricyclic antidepressant, for example, amoxapine, setiptiline maleate, trimipramine maleate, amitriptyline hydrochloride, imipramine hydrochloride, clomipramine hydrochloride, desipramine hydrochloride, dosulepine hydrochloride, nortriptyline hydrochloride, mianserin hydrochloride, lofepramine hydrochloride are given.

As tetracyclic antidepressant, for example, mianserin hydrochloride, setiptiline maleate, maprotiline hydrochloride are given.

As anticholinergic agent, for example, aniracetam, etomidoline, tofisopam, dimetotiazine mesylate, scopolamine butylbromide, oxapium iodide, diphenylpiperidinomethyldioxolane iodide, tiemonium iodide, scopolia extract, trospium chloride, oxyphencyclimine hydrochloride, cyclopentolate hydrochloride, dicycloverine hydrochloride, trihexyphenidyl hydrochloride, pirenzepine hydrochloride, piroheptine hydrochloride, propiverine hydrochloride, mazaticol hydrochloride, metixene hydrochloride, ipratropium bromide, pipethanate ethobromide, oxitropium bromide, glycopyrronium bromide, tiquizium bromide, timepidium bromide, scopolamine butylbromide, butropium bromide, prifinium bromide, flutropium bromide, propantheline bromide, anisotropine methylbromide, methylbenactyzium bromide, mepenzolate bromide, scopolamine hydrobromide, homatropine hydrobromide, N-methylscopolamine sulfate, atropine sulfate are given.

As obstipant, for example, albumin tannate, bismuth subnitrate, bismuth subgallate are given.

As mucosal paralyzant, for example, oxethazaine, strocain, topicain are given.

As bulk cathartic, for example, carmellose sodium (carboxy methylcellulose sodium) is given.

As saline purgative, magnesium oxide, magnesium sulfate, magnesium carbonate are given.

As calcium antagonist, for example, verapamil, nifedipine, diltiazem, nicardipine, nilvadipine are given.

As phosphodiesterase inhibitor, for example, cilostazol, amrinone, anagrelide hydrochloride, enoxymon, olprinone hydrochloride, pimobendan, milrinone, doxofyline, sildenafil citrate, mopidamol, toborinone, tadalafil, vardenafil, MCI-154, cilomilast, roflumilast are given.

As serotonin antagonist, for example, ketanserin tartarate, mosapramine hydrochloride, zotepine, ondansetron hydrochloride, tropisetron hydrochloride, risperidone, granisetron hydrochloride, sarpogrelate hydrochloride, perospirone hydrochloride hydrate, mirtazapine, ramosetron hydrochloride, azasetron hydrochloride, nefazodone hydrochloride, olanzapine, quetiapine fumarate, ziprasidone hydrochloride hydrate, dolasetron mesylate, clozapine, alosetron hydrochloride, indisetron hydrochloride, RS-25259-197, HP-873, EGIS-3886, itasetron hydrochloride, KC-9946, F0930-RS, blonanserin, BIMT-17 are given.

As serotonin agonist, for example, buspirone hydrochloride, tandospirone citrate, sumatriptan succinate, mosapride citrate, naftopidil, LAS-17177, mirtazapine, naratriptan hydrochloride, zolmitriptan, rizatriptan benzoate, eletriptan hydrobromide, LAS-31416, tegaserod maleate, VML-251, BMY-13805-1, xaliproden hydrochloride, repinotan hydrochloride are given.

As CCK-A antagonist, for example, loxiglumide, dexloxiglumide, lintitript, devacard, Z-203 are given.

As 5-lipoxygenase inhibitor, for example, oxatomide, diruton, ML-3000, darbufelone mesylate, DUP-654, LDP-977 are given.

Weight ratio of the compound of formula (IA)-(IK) and other medicaments is not limited.

A combination of any two or more of other medicaments may be administered.

A combination of any two or more of the compound of formula (IA)-(IK) may be administered.

In other medicaments to complement and/or to enhance the preventing and/or treating effect of the compound of formula (IA)-(IK), medicaments that not only exist now but also may be found in the future on the basis of above mechanisms are included.

For the purpose described above, the compound of formula (IA)-(IK) or a salt thereof of the present invention or a concomitant drug combined the compound of formula (IA)-(IK) with other medicaments may be normally administered systemically or topically, usually by oral or parenteral administration.

The doses to be administered are determined depending upon, for example, age, body weight, symptom, the desired therapeutic effect, the route of administration, and the duration of the treatment, etc. In the human adult, the doses per person at a time are generally from 1 mg to 1000 mg, by oral administration, up to several times per day, and from 1 mg to 100 mg, by parenteral administration (preferably intravenous administration), up to several times per day, or continuous administration between 1 and 24 hours per day into vein.

As mentioned above, the doses to be used depend upon various conditions. Therefore, there are cases wherein doses lower than or greater than the ranges specified above may be used.

The compound of formula (IA)-(IK) or a salt thereof or concomitant drug combined the compound of formula (IA)-(IK) with other medicaments may be administered in the composition of, for example, solid compositions, liquid compositions or other compositions each for oral administration, or injections, liniments or suppositories, each for parenteral administration.

Solid compositions for oral administration include compressed tablets, pills, capsules, dispersible powders and granules.

Capsules include hard capsules and soft capsules.

In such solid forms, one or more of the active compounds may be admixed with vehicles such as lactose, mannitol, glucose, hydroxypropyl cellulose, microcrystalline cellulose, starch, polyvinylpyrrolidone or magnesium aluminometasilicate. The compositions may comprise, in accordance with the conventional process, additives other than the inert diluent, for example, lubricants such as magnesium stearate; disintegrants such as cellulose calcium glycolate;

stabilizer such as lactose; and solubilizing agent such as glutamic acid or aspartic acid. Tablets or pills may be coated with a film of a gastric soluble or enteric substance such as sucrose, gelatin, hydroxypropyl cellulose or hydroxypropyl methylcellulose phthalate, or with two or more layers, if necessary. Furthermore, capsules made of a substance which can be absorbed in the body, for example, gelatin, are included.

Liquid forms for oral administration include pharmaceutically acceptable solutions, suspensions and emulsions, syrups and elixirs. In such forms, one or more of the active compounds may be dissolved, suspended or emulsified into diluents commonly used in the art (such as purified water, ethanol). Besides such liquid forms may also comprise some additives, such as wetting agents, suspending agents, sweetening agents, flavoring agents, aroma or preservative.

The other compositions for oral administration include sprays which comprise one or more active compounds and are formulated in a manner known per se in the art. The compositions may comprise, in addition to an inert diluent, a stabilizer such as sodium bisulfite and a tonicity agent such as sodium chloride, sodium citrate or citric acid. The preparation process of sprays is described in detail in, for example, U.S. Pat. Nos. 2,868,691 and 3,095,355.

In the present invention, injections for parenteral administration include sterile aqueous and/or non-aqueous solutions, suspensions and emulsions. The aqueous solutions or suspensions include, for example, distilled water for injection and saline. The non-aqueous solutions or suspensions include propylene glycol, polyethylene glycol, vegetable oils such as olive oil, alcohol such as ethanol and Polysorbate 80 (trade mark). Furthermore, sterile aqueous and non-aqueous solutions, suspensions, and emulsions may be used in combination. Such compositions may additionally comprise adjuvants such as antiseptic, humectant, emulsifier, dispersant, stabilizer (such as lactose) and solubilizing agent (such as glutamic acid and aspartic acid). They are sterilized by filtration through a bacteria retaining filter, the addition of a fungicide, or irradiation. Also, a sterile solid composition is prepared and then, for example, a freeze-dried product may be dissolved in sterilized or sterile distilled water for injection or another sterile solvent before use.

The other compositions for parenteral administration include liquids for external use, ointments, endermic liniments, suppositories for intrarectal administration and pessaries for vaginal administration which comprise one or more of the active substances and may be prepared by methods known per se.

The compounds of the present invention may be administered in the form of, for example, solid compositions, liquid compositions or other compositions for oral administration, injections, liniments or suppositories for parenteral administration.

Solid compositions for oral administration include compressed tablets, pills, capsules, dispersible powders and granules. Capsules include hard capsules and soft capsules.

In such solid forms, one or more of the active compound(s) may be admixed with vehicles (such as lactose, mannitol, mannit, glucose, hydroxypropyl cellulose, microcrystalline cellulose, starch, polyvinylpyrrolidone or magnesium aluminometasilicate). The compositions may comprise, in accordance with the conventional process, additives other than the inert diluent, for example, lubricants such as magnesium stearate, disintegrants such as cellulose calcium glycolate, and solubilizing agent such as glutamic acid or aspartic acid. Tablets or pills may be coated with a film of a gastric soluble or enteric substance such as sucrose, gelatin, hydroxypropyl cellulose or hydroxypropyl cellulose phthalate, or with two or more layers, if necessary. Furthermore, capsules made of a substance which can be absorbed in the body, for example, gelatin, are included.

Liquid compositions for oral administration include pharmaceutically acceptable emulsions, solutions, syrups and elixirs. Such liquid compositions comprise one or more of the active substance(s) and an ordinarily employed inert diluent(s) (such as purified water or ethanol) dissolving the substance(s) therein. The compositions may comprise, in addition to the inert diluent, an adjuvant such as humectants or suspending agents, sweetening agents, flavoring agents, aromatic agents and antiseptics.

The other compositions for oral administration include sprays which comprise one or more active substances and are formulated in a manner known per se in the art. The compositions may comprise, in addition to an inert diluent, a stabilizer such as sodium bisulfite and a tonicity agent such as sodium chloride, sodium citrate or citric acid. The preparation process of sprays is described in detail in, for example, U.S. Pat. Nos. 2,868,691 and 3,095,355.

In the present invention, injections for parenteral administration include sterile aqueous and/or non-aqueous solutions, suspensions and emulsions. The aqueous solutions or suspensions include, for example, distilled water for injection and saline. The non-aqueous solutions or suspensions include propylene glycol, polyethylene glycol, vegetable oils such as olive oil, alcohol such as ethanol and Polysorbate 80 (trade mark). Furthermore, sterile aqueous and non-aqueous solutions, suspensions, and emulsions may be used in combination. Such compositions may additionally comprise adjuvants such as antiseptic, humectant, emulsifier, dispersant, stabilizer and solubilizing agent (such as glutamic acid and aspartic acid). They are sterilized by filtration through a bacteria retaining filter, the addition of a fungicide, or irradiation. Also, a sterile solid composition is prepared and then, for example, a freeze-dried product may be dissolved in sterilized or sterile distilled water for injection or another sterile solvent before use.

The other compositions for parenteral administration include liquids for external use, ointments, endermic liniments, suppositories for intrarectal administration and pessaries for vaginal administration which comprise one or more of the active substances and may be prepared by methods known per se.

BEST MODE FOR CARRYING OUT THE INVENTION

The following Reference examples and Examples are intend to illustrate, but not to limit the present invention.

The solvents in parentheses at chromatographic separations section show the developing or eluting solvents and the ratios of the solvents used are indicated by volume. Without special explanation, NMR data was determined in CDCl$_3$ solution. And the solvents in parentheses at NMR data section show solvents used in determination.

REFERENCE EXAMPLE 1

4-(2-nitro-4,5-dimethylphenoxymethyl)-3-methyl-benzoic acid methyl ester

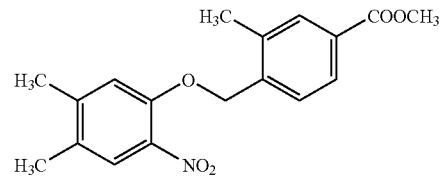

Under atmosphere of argon, a mixture of 2-nitro-4,5-dimethylphenol (4 g), DMF (100 ml), potassium carbonate (6.6 g) and 4-mesyloxymethyl-3-methylbenzoic acid methyl ester (6.8 g) were stirred for 15 minutes at 60° C. After the termination of reaction, the mixture was cooled and poured into iced water. The mixture was extracted with ethyl acetate-hexane. The organic layer was washed, dried, concentrated under reduced pressure to give the title compound (7.22 g) having the following physical data.

TLC: Rf 0.24 (n-hexane:ethyl acetate=4:1).

REFERENCE EXAMPLE 2

4-(2-amino-4,5-dimethylphenoxymethyl)-3-methyl-benzoic acid methyl ester

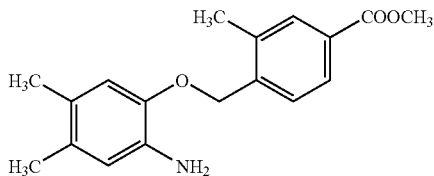

A mixture of 4-(2-nitro-4,5-dimethylphenoxymethyl)-3-methylbenzoic acid methyl ester prepared in reference example 1 (7.21 g), acetic acid (88 ml) and water (8.8 ml) was stirred at 50° C. To the reaction solution, iron powder (6.11 g) was gradually added, and the mixture was stirred for 1 hour at 50° C. After cooling, the mixture was filtered and the filtrate was concentrated and azeotroped with toluene. To the residue, ethyl acetate-water (100 ml-100 ml) was added and the mixture was filtrated over Celite (registered trademark). The organic layer was washed, dried, concentrated under reduced pressure to give the title compound (4.66 g) having the following physical data.

TLC: Rf 0.51 (n-hexane:ethyl acetate=2:1).

REFERENCE EXAMPLE 3

3-methyl-4-[2-[N-(5-methyl-2-furylsulfonyl)amino]-4,5-dimethylphenoxymethyl]benzoic acid methyl ester

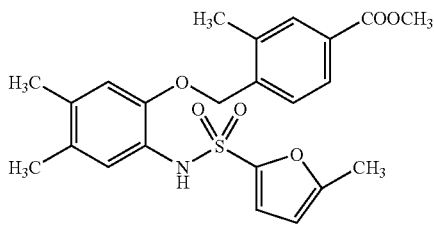

A solution of 4-(2-amino-4,5-dimethylphenoxymethyl)-3-methylbenzoic acid methyl ester prepared in reference example 2 (632 mg) in pyridine (4 ml) was cooled to 0° C., then 5-methylfuran-2-sulfonyl chloride (490 mg) was added dropwise thereto. After the solution was stirred for 1 hour at room temperature, the reaction mixture was diluted by ethyl acetate, and poured into water. The organic layer was washed, dried, concentrated under reduced pressure. The residue was washed by mixed solvent of diisopropylether and hexane to give the title compound (875 mg) having the following physical data.

TLC: Rf 0.42 (n-hexane:ethyl acetate=2:1).

EXAMPLE 1

3-methyl-4-[2-[N-isobutyl-N-(5-methyl-2-furylsulfonyl)amino]-4,5-dimethylphenoxymethyl]benzoic acid methyl ester

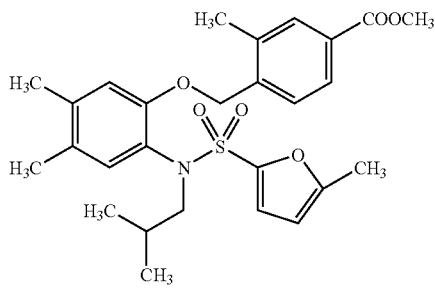

To a solution of 3-methyl-4-[2-[N-(5-methyl-2-furylsulfonyl)amino]-4,5-dimethylphenoxymethyl]benzoic acid methyl ester prepared in reference example 3 (870 mg) in N,N-dimethylacetamide (2 ml), cesium carbonate (1.37 g) and isobutyl iodide (0.36 ml) were added and the mixture was stirred for 1 hour at 100° C. The reaction mixture was allowed to cool and poured into ethyl acetate-water (40 ml-40 ml). The organic layer was washed, dried and concentrated under reduced pressure. The residue was purified by column chromatography on silica gel (toluene-ethyl acetate) to give the title compound (855 mg) having the following physical data.

TLC: Rf 0.51 (n-hexane:ethyl acetate=2:1); NMR: δ 7.87 (d, J=8.4 Hz, 1H), 7.86 (s, 1H), 7.38 (d, J=8.4 Hz, 1H), 7.04 (s, 1H), 6.70 (m, 2H), 5.93 (m, 1H), 4.91 (brs, 2H), 3.92 (s, 3H), 3.48 (m, 2H), 2.34 (s, 3H), 2.23 (s, 3H), 2.18 (s, 3H), 2.09 (s, 3H), 0.90 (brs, 6H).

EXAMPLE 2

3-methyl-4-[2-[N-isobutyl-N-(5-methyl-2-furylsulfonyl)amino]-4,5-dimethylphenoxymethyl]benzoic acid

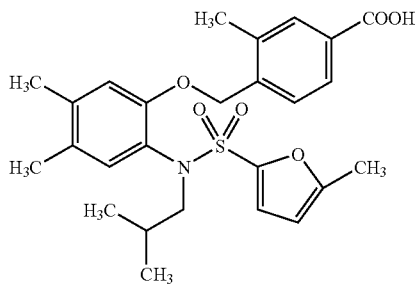

To a solution of 3-methyl-4-[2-[N-isobutyl-N-(5-methyl-2-furylsulfonyl)amino]4,5-dimethylphenoxymethyl]benzoic acid methyl ester prepared in example 1 (850 mg) in dioxane (10 ml), 2N aqueous sodium hydroxide (2.5 ml) and methanol (4 ml) were added, and the mixture was stirred for 30 hours at room temperature. To the mixture, 2N hydrochloric acid was added, then ethyl acetate-water (30 ml-15 ml) was also added. The organic layer was washed, dried and concentrated under reduced pressure. The residue was dissolved in hot ethanol (40 ml) and added by hot water (40 ml), then allowed to cool. Precipitation was filtrated, and dried to give the title compound (755 mg) having the following physical data.

TLC: Rf 0.78 (chloroform:methanol:water=8:2:0.2); NMR: δ 7.94 (d, J=7.8 Hz, 1H), 7.93 (s, 1H), 7.44 (d, J=7.8 Hz, 1H), 7.04 (s, 1H), 6.74-6.70 (m, 2H), 5.94 (dd, J=3.3, 0.9 Hz, 1H), 4.94 (br, 2H), 3.48 (d, J=6.6 Hz, 2H), 2.37 (s, 3H), 2.24 (s, 3H), 2.19 (s, 3H), 2.11 (s, 3H), 1.68 (sep, J=6.6 Hz, 1H), 0.91 (d, J=6.6 Hz, 6H).

EXAMPLE 2(1)~EXAMPLE 2(124)

By the same procedures as described in reference example 1→reference example 2→reference example 3→example 1→example 2 using corresponding compounds, the title compounds having the following physical data were obtained.

EXAMPLE 2(1)

4-[2-[N-isobutyl-N-(5-methyl-2-furylsulfonyl)amino]-5-trifluoromethylphenoxymethyl]cinnamic acid

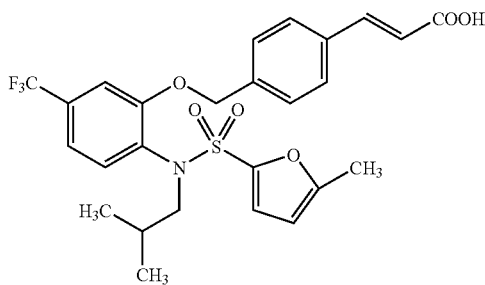

TLC: Rf 0.51 (n-hexane:ethyl acetate:acetic acid=1:1:0.02); NMR: δ 7.80 (d, J=16.2 Hz, 1H), 7.59 (d, J=8.0 Hz, 2H), 7.45-7.36 (m, 3H), 7.26 (dd, J=8.2, 1.8 Hz, 1H), 7.18 (d, J=1.8 Hz, 1H), 7.00-5.00 (br, 1H), 6.75 (d, J=3.4 Hz, 1H), 6.49 (d, J=16.2 Hz, 1H), 5.98 (dq, J=3.4, 0.8 Hz, 1H), 5.05 (brs, 2H), 3.51 (d, J=7.4 Hz, 2H), 2.16 (s, 3H), 1.75-1.50 (m, 1H), 0.88 (d, J=6.8 Hz, 6H).

EXAMPLE 2(2)

4-[2-[N-isopropyl-N-(5-methyl-2-furylsulfonyl)amino]-5-trifluoromethylphenoxymethyl]benzoic acid

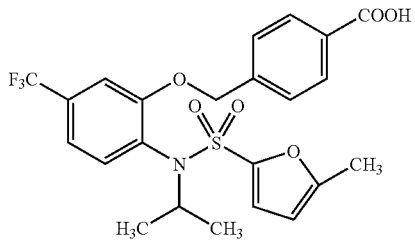

TLC: Rf 0.44 (chloroform:methanol=9:1); NMR: δ 8.16 (d, J=8.4 Hz, 2H), 7.60 (d, J=8.4 Hz, 2H), 7.21-7.26 (m, 3H), 6.84 (d, J=3.2 Hz, 1H), 6.05 (m, 1H), 5.21 (m, 2H), 4.49 (m, 1H), 2.33 (s, 3H), 1.10 (d, J=6.6 Hz, 6H).

EXAMPLE 2(3)

4-[2-[N-isobutyl-N-(5-methyl-2-furylsulfonyl)amino]-5-trifluoromethylphenoxymethyl]benzoic acid

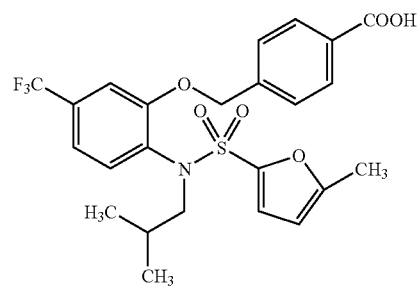

TLC: Rf 0.46 (chloroform:methanol=9:1); NMR: δ 8.15 (d, J=8.6 Hz, 2H), 7.46 (d, J=8.6 Hz, 2H), 7.41 (m, 1H), 7.29 (m, 1H), 7.18 (m, 1H), 6.76 (d, J=3.4 Hz, 1H), 5.98 (m, 1H), 5.10 (s, 2H), 3.51 (d, J=6.2 Hz, 2H), 2.16 (s, 3H), 1.64 (m, 1H), 0.90 (d, J=6.8 Hz, 6H).

EXAMPLE 2(4)

4-[2-[N-isobutyl-N-(5-methyl-2-furylsulfonyl)amino]-4-chloro-5-methylphenoxymethyl]benzoic acid

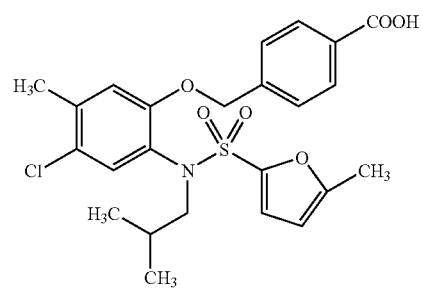

TLC: Rf 0.30 (chloroform:methanol=9:1); NMR: δ 8.12 and 7.46 (each d, J=8.1 Hz, each 2H), 7.20 (s, 1H), 6.81-6.75 (m, 2H), 6.01-5.98 (m, 1H), 5.12-4.98 (m, 2H), 3.45 (d, J=7.5 Hz, 2H), 2.34 and 2.19 (each s, each 3H), 1.75-1.59 (m, 1H), 0.91 (d, J=6.9 Hz, 6H).

EXAMPLE 2(5)

4-[2-[N-isopropyl-N-(5-methyl-2-furylsulfonyl)amino]-4,5-dimethylphenoxymethyl]benzoic acid

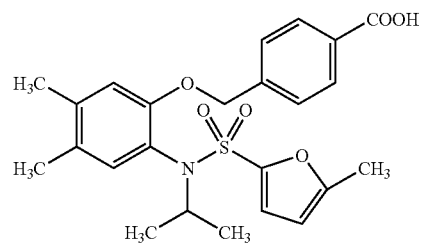

TLC: Rf 0.38 (chloroform:methanol=10:1); NMR: δ 8.12-8.09 (m, 2H), 7.56 (d, J=8.4 Hz, 2H), 6.81 (s, 1H), 6.79 (d, J=3.3 Hz, 1H), 6.75 (s, 1H), 6.02 (dd, J=3.3, 1.2 Hz, 1H), 5.10 (s, 2H), 4.48 (m, 1H), 2.30 (s, 3H), 2.23 (s, 3H), 2.17 (s, 3H), 1.11 (d, J=6.6 Hz, 6H).

EXAMPLE 2(6)

4-[2-[N-isobutyl-N-(5-methyl-2-furylsulfonyl)amino]-4,5-dimethylphenoxymethyl]benzoic acid

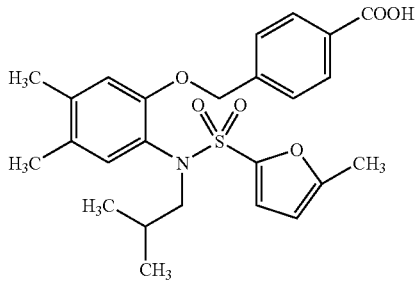

TLC: Rf 0.38 (chloroform:methanol=10:1); NMR: δ 8.12-8.08 (m, 2H), 7.42 (d, J=8.4 Hz, 2H), 7.03 (s, 1H), 6.71 (d, J=3.3 Hz, 1H), 6.68 (s, 1H), 5.92 (dd, J=3.3, 0.9 Hz, 1H), 5.00 (brs, 2H), 3.52-3.46 (m, 2H), 2.22 (s, 3H), 2.18 (s, 3H), 2.13 (s, 3H), 1.68 (m, 1H), 0.91 (d, J=6.6 Hz, 6H).

EXAMPLE 2(7)

3-methyl-4-[2-[N-isobutyl-N-(5-methyl-2-fuiylsulfonyl)amino]-4-methyl-5-chlorophenoxymethyl]benzoic acid

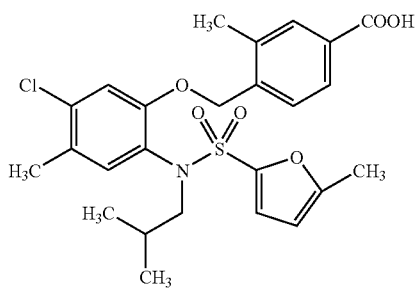

TLC: Rf 0.42 (chloroform:methanol=9:1); NMR: δ 8.00-7.89 (m, 2H), 7.41 (d, J=8.4 Hz, 1H), 7.16 (s, 1H), 6.95 (s, 1H), 6.74 (d, J=3.3 Hz, 1H), 5.96 (m, 1H), 4.94 (s, 2H), 3.47 (d, J=6.3 Hz, 2H), 2.37 (s, 3H), 2.30 (s, 3H), 2.11 (s, 3H), 1.64 (m, 1H), 0.90 (d, J=6.6 Hz, 6H).

EXAMPLE 2(8)

3-methyl-4-[2-[N-isobutyl-N-(5-methyl-2-furylsulfonyl)amino]-4-chloro-5-methylphenoxymethyl]benzoic acid

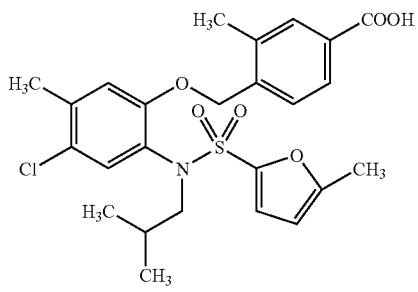

TLC: Rf 0.58 (chloroform:methanol=9:1); NMR: δ 7.96 (d, J=7.5 Hz, 1H), 7.94 (s, 1H), 7.47 (d, J=7.5 Hz, 1H), 7.20 (s, 1H), 6.81 (s, 1H), 6.77 (d, J=3.3 Hz, 1H), 6.03-5.97 (m, 1H), 4.99 (brs, 2H), 3.44 (d, J=7.5 Hz, 2H), 2.39 (s, 3H), 2.36 (s, 3H), 2.17 (s, 3H), 1.75-1.60 (m, 1H), 0.89 (d, J=6.6 Hz, 6H).

EXAMPLE 2(9)

3-chloro-4-[2-[N-isobutyl-N-(5-methyl-2-furylsulfonyl)amino]-4-methyl-5-chlorophenoxymethyl]benzoic acid

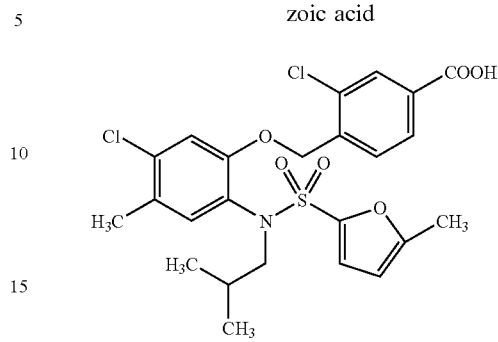

TLC: Rf 0.38 (chloroform:methanol=9:1); NMR: δ 8.13 (d, J=1.5 Hz, 1H), 8.02 (dd, J=8.4, 1.5 Hz, 1H), 7.58 (d, J=8.4 Hz, 1H), 7.15 (s, 1H), 6.94 (s, 1H), 6.76 (d, J=3.3 Hz, 1H), 5.98 (m, 1H), 5.25-4.90 (br, 2H), 3.48 (d, J=6.6 Hz, 2H), 2.31 (s, 3H), 2.16 (s, 3H), 1.64 (m, 1H), 0.92 (d, J=6.6 Hz, 6H).

EXAMPLE 2(10)

3-chloro-4-[2-[N-isopropyl-N-(5-methyl-2-furylsulfonyl)amino]-4-methyl-5-chlorophenoxymethyl] benzoic acid

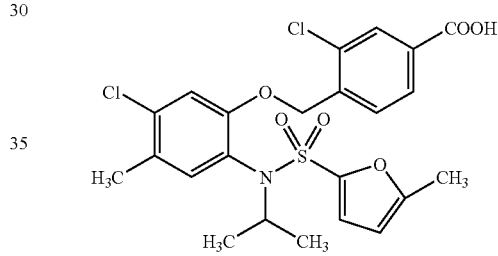

TLC: Rf 0.38 (chloroform:methanol=9:1); NMR: δ 8.12 (d, J=1.5 Hz, 1H), 8.07 (dd, J=8.4, 1.5 Hz, 1H), 7.88 (d, J=8.4 Hz, 1H), 6.99 (s, 1H), 6.95 (s, 1H), 6.85 (d, J=3.3 Hz, 1H), 6.06 (m, 1H), 5.20 (d, J=14.4 Hz, 1H), 5.15 (d, J=14.4 Hz, 1H), 4.48 (m, 1H), 2.33 (s, 3H), 2.30 (s, 3H), 1.11 (d, J=6.3 Hz, 3H), 1.09 (d, J=6.3 Hz, 3H).

EXAMPLE 2(11)

3-methoxy-4-[2-[N-isopropyl-N-(5-methyl-2-furylsulfonyl)amino]-4-methyl-5-chlorophenoxymethyl] benzoic acid

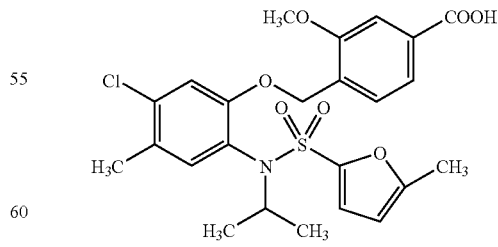

TLC: Rf 0.49 (chloroform:methanol=9:1); NMR: δ 7.78 (dd, J=8.1, 1.5 Hz, 1H), 7.76 (d, J=1.5 Hz, 1H), 7.59 (d, J=1.5 Hz 1H), 7.01 (s, 1H), 6.96 (s, 1H), 6.83 (d, J=3.3 Hz, 1H), 6.05-6.00 (m, 1H), 5.11 (d, J=14.1 Hz, 1H), 5.07 (d, J=14.1 Hz, 1H), 4.55-4.40 (m, 1H), 3.94 (s, 3H), 2.30 (s, 3H), 2.29 (s, 3H), 1.12 (d, J=6.9 Hz, 6H).

EXAMPLE 2(12)

3-methoxy-4-[2-[N-isopropyl-N-(5-methyl-2-furyl-sulfonyl)amino]-4,5-dimethylphenoxymethyl]benzoic acid

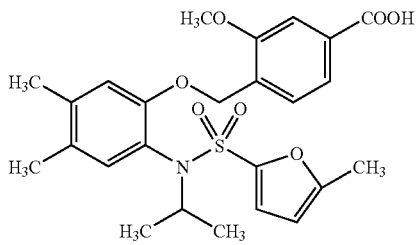

TLC: Rf 0.44 (chloroform:methanol=9:1); NMR: δ 7.77 (dd, J=8.1, 1.2 Hz, 1H), 7.74 (d, J=8.1 Hz, 1H), 7.58 (d, J=1.2 Hz, 1H), 6.84 (s, 1H), 6.81 (d, J=3.3 Hz, 1H), 6.78 (s, 1H), 6.05-6.00 (m, 1H), 5.09 (s, 2H), 4.60-4.40 (m, 1H), 3.94 (s, 3H), 2.29 (s, 3H), 2.24 (s, 3H), 2.17 (s, 3H), 1.12 (d, J=6.9 Hz, 6H).

EXAMPLE 2(13)

3-methoxy-4-[2-[N-isobutyl-N-(5-methyl-2-furylsulfonyl)amino]-4,5-dimethylphenoxymethyl]benzoic acid

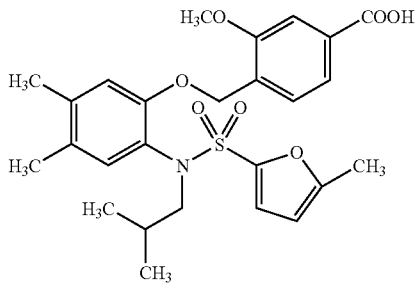

TLC: Rf 0.45 (chloroform:methanol=9:1); NMR: δ 7.73 (dd, J=8.1, 1.2 Hz, 1H), 7.58 (d, J=1.2 Hz, 1H), 7.40 (d, J=8.1 Hz, 1H), 7.07 (s, 1H), 6.75-6.70 (m, 2H), 5.95-5.90 (m, 1H), 5.15-4.85 (m, 2H), 3.94 (s, 3H), 3.51 (br, 2H), 2.23 (s, 3H), 2.19 (s, 3H), 2.11 (s, 3H), 1.80-1.60 (m, 1H), 0.94 (br, 6H).

EXAMPLE 2(14)

3-methoxy-4-[2-[N-isopropyl-N-(5-methyl-2-furyl-sulfonyl)amino]-4-chloro-5-methylphenoxymethyl]benzoic acid

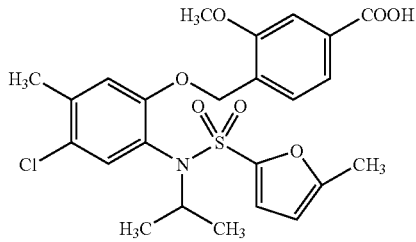

TLC: Rf 0.46 (chloroform:methanol=9:1); NMR(DMSO-d₆): δ 13.02 (s, 1H), 7.58-7.50 (m, 3H), 7.24 (s, 1H), 6.98 (s, 1H), 6.94 (d, J=3.3 Hz, 1H), 6.25 (m, 1H), 5.10 (d, J=13.5 Hz, 1H), 5.04 (d, J=13.5 Hz, 1H), 4.24 (m, 1H), 3.87 (s, 3H), 2.34 (s, 3H), 2.27 (s, 3H), 0.99 (d, J=6.6 Hz, 3H), 0.98 (d, J=6.6 Hz, 3H).

EXAMPLE 2(15)

3-chloro-4-[2-[N-isobutyl-N-(5-methyl-2-furylsulfonyl)amino]-4,5-dimethylphenoxymethyl]benzoic acid

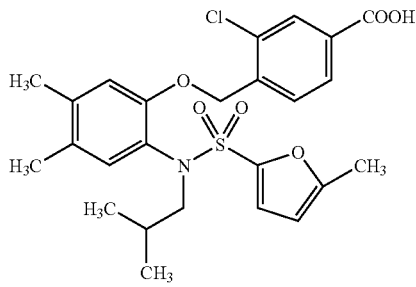

TLC: Rf 0.40 (chloroform:methanol=9:1); NMR: δ 8.12 (d, J=1.8 Hz, 1H), 8.02 (dd, J=8.1, 1.8 Hz, 1H), 7.61 (d, J=8.1 Hz, 1H), 7.03 (s, 1H), 6.75 (d, J=3.3 Hz, 1H), 6.70 (s, 1H), 5.96 (m, 1H), 5.25-4.85 (br, 2H), 3.50 (d, J=6.6 Hz, 2H), 2.24 (s, 3H), 2.19 (s, 3H), 2.16 (s, 3H), 1.79 (m, 1H), 0.93 (d, J=6.6 Hz, 6H).

EXAMPLE 2(16)

3-chloro-4-[2-[N-isopropyl-N-(5-methyl-2-furylsulfonyl)amino]-4,5-dimethylphenoxymethyl]benzoic acid

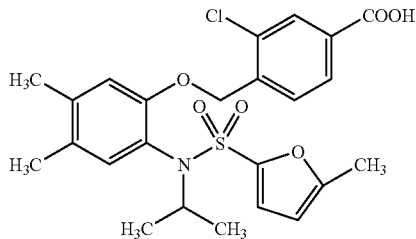

TLC: Rf 0.39 (chloroform:methanol=9:1); NMR: δ 8.11 (d, J=1.8 Hz, 1H), 8.06 (dd, J=8.1, 1.8 Hz, 1H), 7.90 (d, J=8.1 Hz, 1H), 6.86-6.80 (m, 2H), 6.75 (s, 1H), 6.05 (m, 1H), 5.17 (s, 2H), 4.51 (m, 1H), 2.32 (s, 3H), 2.25 (s, 3H), 2.18 (s, 3H), 1.12 (d, J=6.6 Hz, 3H), 1.11 (d, J=6.6 Hz, 3H).

EXAMPLE 2(17)

3-methyl-4-[2-[N-isobutyl-N-(5-methyl-2-furylsulfonyl)amino]-4-chloro-5-methylphenoxymethyl]cinnamic acid

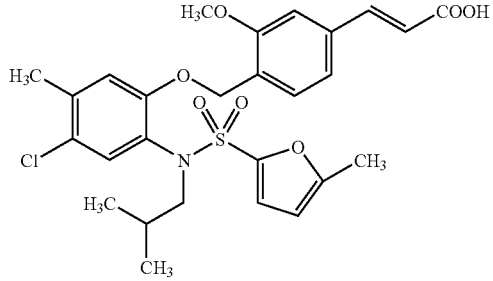

TLC: Rf 0.37 (chloroform:methanol=9:1); NMR (CD₃OD): δ 7.63 (d, J=16.2 Hz, 1H), 7.45 (s) and 7.44 (d, J=8.1 Hz) total 2H, 7.34 (d, J=8.1 Hz, 1H), 7.17 (s, 1H), 7.10 (s, 1H), 6.72 (d, J=3.3 Hz, 1H), 6.50 (d, J=16.2 Hz, 1H), 6.08 (dd, J=3.3, 1.2 Hz, 1H), 4.98 (brs, 2H), 3.44 (d, J=6.9 Hz, 2H), 2.37 (s, 3H), 2.35 (s, 3H), 2.10 (s, 3H), 1.60 (m, 1H), 0.87 (d, J=6.6 Hz, 6H).

EXAMPLE 2(18)

4-[2-[N-isopropyl-N-(5-methyl-2-furylsulfonyl)amino]-4-methyl-5-chlorophenoxymethyl]cinnamic acid

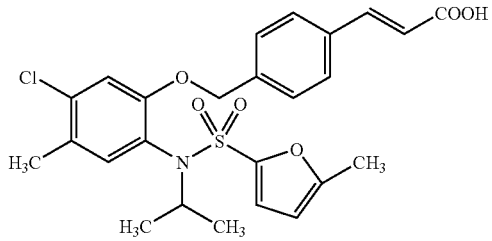

TLC: Rf 0.31 (chloroform:methanol=9:1); NMR: δ 7.73 (d, J=15.9 Hz, 1H), 7.57 and 7.49 (each d, J=8.1 Hz, each 2H), 6.98 and 6.92 (each s, each 1H), 6.81 (d, J=3.3 Hz, 1H), 6.46 (d, J=15.9 Hz, 1H), 6.03 (d, J=3.3 Hz, 1H), 5.05 (s, 2H), 4.50-4.38 (m, 1H), 2.30 and 2.28 (each s, each 3H), 1.10 and 1.09 (each d, J=6.6 Hz, each 3H).

EXAMPLE 2(19)

4-[2-[N-isobutyl-N-(5-methyl-2-furylsulfonyl)amino]-4-methyl-5-chlorophenoxymethyl]cinnamic acid

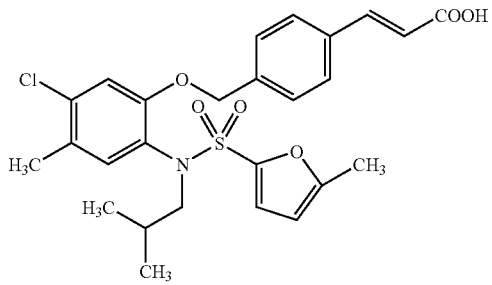

TLC: Rf 0.31 (chloroform:methanol=9:1); NMR: δ 7.77 (d, J=15.9 Hz, 1H), 7.56 and 7.35 (each d, J=7.8 Hz, each 2H), 7.14 and 6.92 (each s, each 1H), 6.72 (d, J=3.6 Hz, 1H), 6.47 (d, J=15.9 Hz, 1H), 5.95 (d, J=3.6 Hz, 1H), 5.00-4.88 (m, 2H), 3.52-3.42 (m, 2H), 2.29 and 2.13 (each s, each 3H), 1.72-1.60 (m, 1H), 0.90 (d, J=6.3 Hz, 6H).

EXAMPLE 2(20)

4-[2-[N-isopropyl-N-(5-methyl-2-furylsulfonyl)amino]-4,5-dimethylphenoxymethyl]cinnamic acid

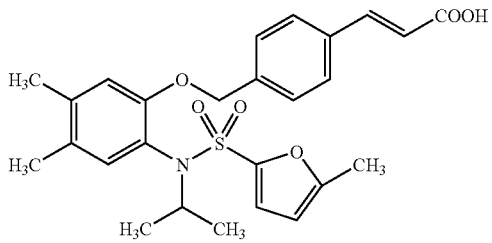

TLC: Rf 0.39 (chloroform:methanol=9:1); NMR: δ 7.78 (d, J=15.9 Hz, 1H), 7.57 (d, J=8.4 Hz, 2H), 7.50 (d, J=8.4 Hz, 2H), 6.80 (s, 1H), 6.79 (d, J=3.3 Hz, 1H), 6.76 (s, 1H), 6.46 (d, J=15.9 Hz, 1H), 6.01 (m, 1H), 5.06 (s, 2H), 4.47 (sept, J=6.6 Hz, 1H), 2.30 (s, 3H), 2.23 (s, 3H), 2.16 (s, 3H), 1.11 and 1.10 (each d, J=6.6 Hz, each 3H).

EXAMPLE 2(21)

3-methyl-4-[2-[N-isopropyl-N-(5-methyl-2-furylsulfonyl)amino]-5-trifluoromethylphenoxymethyl]cinnamic acid

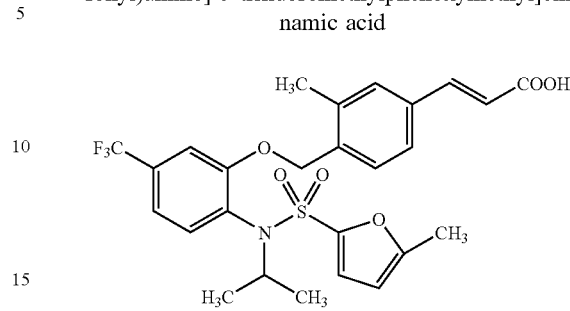

TLC: Rf 0.42 (chloroform:methanol=9:1); NMR(DMSO-$d_6$): δ 12.36 (br s, 1H), 7.61-7.52 (m, 5H), 7.38 (d, J=8.0 Hz, 1H), 7.24 (d, J=8.0 Hz, 1H), 6.96 (d, J=3.5 Hz, 1H), 6.54 (d, J=16.0 Hz, 1H), 6.28 (d, J=3.5 Hz, 1H), 5.24 (d, J=13.0 Hz, 1H), 5.18 (d, J=13.0 Hz, 1H), 4.26 (septet, J=6.5 Hz, 1H), 2.35 (s, 3H), 2.30 (s, 3H), 0.97 (d, J=6.5 Hz, 6H).

EXAMPLE 2(22)

3-methyl-4-[2-[N-isopropyl-N-(5-methyl-2-furylsulfonyl)amino]-4,5-dimethylphenoxymethyl]benzoic acid

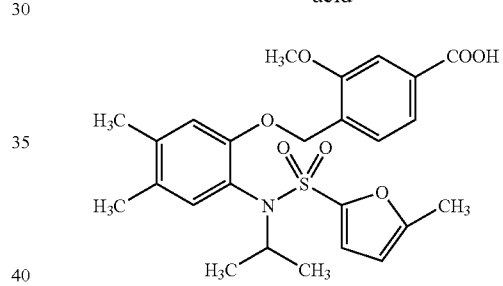

TLC: Rf 0.28 (n-hexane:ethyl acetate=1:1); NMR: δ 7.97 (d, J=7.8 Hz, 1H), 7.93 (s, 1H), 7.65 (d, J=7.8 Hz, 1H), 6.82 (s, 1H), 6.79 (d, J=3.3 Hz, 1H), 6.77 (s, 1H), 6.01 (dd, J=3.3, 1.2 Hz, 1H), 5.08 (d, J=13.2 Hz, 1H), 5.02 (d, J=13.2 Hz, 1H), 4.47 (quint, J=6.6 Hz, 1H), 2.40 (s, 3H), 2.29 (s, 3H), 2.25 (s, 3H), 2.17 (s, 3H), 1.11 (d, J=6.6 Hz, 6H).

EXAMPLE 2(23)

3-methyl-4-[2-[N-isopropyl-N-(5-methyl-2-furylsulfonyl)amino]-4,5-dimethylphenoxymethyl]cinnamic acid

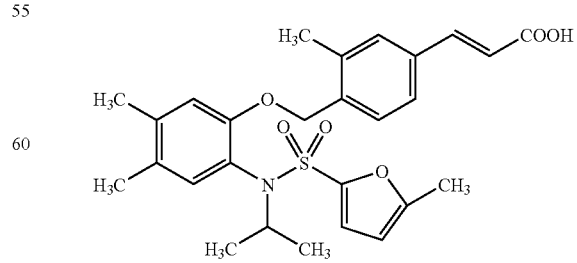

TLC: Rf 0.30 (n-hexane:ethyl acetate=1:2); MS (FAB, Pos.): 498 (M+H)$^+$.

EXAMPLE 2(24)

3-methyl-4-[2-[N-isobutyl-N-(5-methyl-2-furylsulfonyl)amino]-4,5-dimethylphenoxymethyl]cinnamic acid

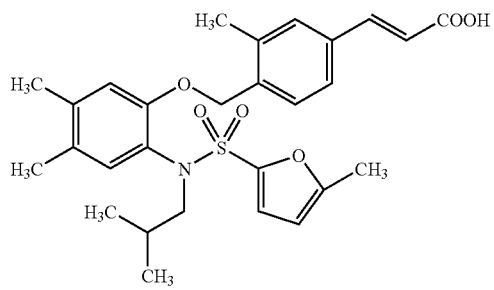

TLC: Rf 0.26 (n-hexane:ethyl acetate=1:2); MS (FAB, Pos.): 512 (M+H)$^+$.

EXAMPLE 2(25)

4-[2-[N-isobutyl-N-(5-methyl-2-furylsulfonyl)amino]-4,5-dimethylphenoxymethyl]cinnamic acid

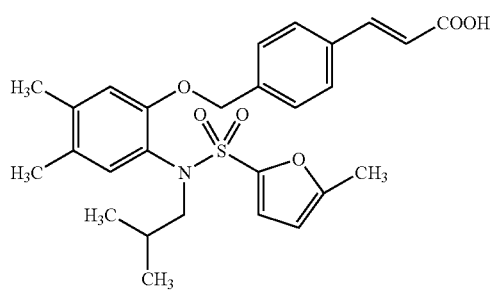

TLC: Rf 0.47 (chloroform:methanol=9:1); NMR(DMSO-d$_6$): 7.69 (d, J=8.1 Hz, 2H), 7.58 (d, J=16.2 Hz, 1H), 7.34 (d, J=8.1 Hz, 2H), 6.93 (s, 1H), 6.90 (s, 1H), 6.79 (d, J=3.3 Hz, 1H), 6.54 (d, J=16.2 Hz, 1H), 6.13 (m, 1H), 5.10-4.80 (m, 2H), 3.40-3.20 (m, 2H, covered with H$_2$O in DMSO-d$_6$), 2.18 (s, 3H), 2.11 (s, 3H), 2.10 (s, 3H), 1.58-1.42 (m, 1H), 0.82 (d, J=6.6 Hz, 6H).

EXAMPLE 2(26)

3-methoxy-4-[2-[N-isobutyl-N-(5-methyl-2-furylsulfonyl)amino]-4-methyl-5-chlorophenoxymethyl]cinnamic acid

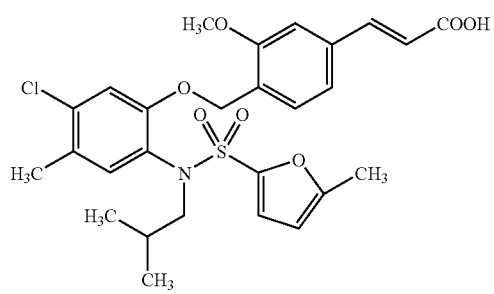

TLC: Rf 0.30 (chloroform:methanol=9:1); NMR: δ 7.76 (d, J=15.9 Hz, 1H), 7.30 (d, J=8.1 Hz, 1H), 7.26 (s, 1H), 7.20 (d, J=8.1 Hz, 1H), 7.04 (s, 1H), 6.96 (s, 1H), 6.72 (d, J=3.3 Hz, 1H), 6.46 (d, J=15.9 Hz, 1H), 6.00-5.90 (m, 1H), 4.95 (brs, 2H), 3.91 (s, 3H), 3.48 (brs, 2H), 2.29 (s, 3H), 2.13 (s, 3H), 1.75-1.60 (m, 1H), 0.91 (brd, J=6.6 Hz, 6H).

EXAMPLE 2(27)

4-[6-[N-isobutyl-N-(5-methyl-2-furylsulfonyl)amino]indan-5-yloxymethyl]benzoic acid

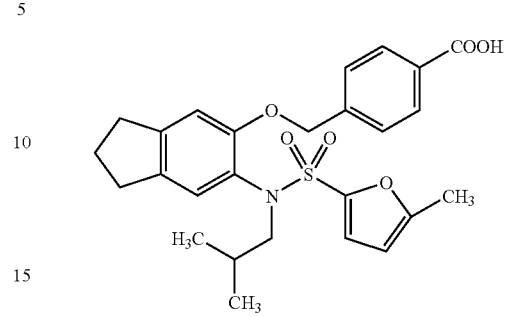

TLC: Rf 0.45 (chloroform:methanol=9:1); NMR: δ 8.11 (d, J=8.1 Hz, 2H), 7.43 (d, J=8.1 Hz, 2H), 7.12 (s, 1H), 6.77 (s, 1H), 6.73 (d, J=3.3 Hz, 1H), 5.94 (m, 1H), 5.15-4.85 (br, 2H), 3.60-3.40 (br, 2H), 2.86 (t, J=7.2 Hz, 4H), 2.14 (s, 3H), 2.13-2.00 (m, 2H), 1.68 (m, 1H), 1.02-0.82 (br, 6H).

EXAMPLE 2(28)

4-[6-[N-isopropyl-N-(5-methyl-2-furylsulfonyl)amino]indan-5-yloxymethyl]benzoic acid

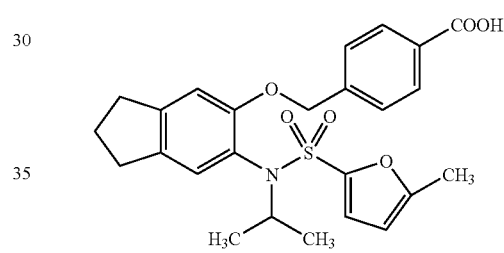

TLC: Rf 0.45 (chloroform:methanol=9:1); NMR: δ 8.12 (d, J=8.4 Hz, 2H), 7.57 (d, J=8.4 Hz, 2H), 6.90 (s, 1H), 6.83 (s, 1H), 6.81 (d, J=3.3 Hz, 1H), 6.02 (m, 1H), 5.17-5.05 (m, 2H), 4.49 (m, 1H), 2.93-2.79 (m 4H), 2.31 (s, 3H), 2.15-2.00 (m, 2H), 1.12 (d, J=6.6 Hz, 3H), 1.11 (d, J=6.6 Hz, 3H).

EXAMPLE 2(29)

4-[7-[N-isobutyl-N-(5-methyl-2-furylsulfonyl)amino]-1,2,3,4-tetrahydronaphthalen-6-yloxymethyl]benzoic acid

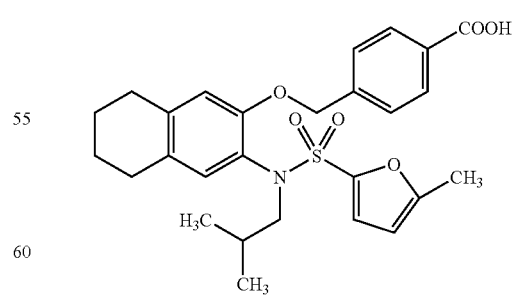

TLC: Rf 0.45 (chloroform:methanol 9:1); NMR: δ 8.10 (d, J=8.1 Hz, 2H), 7.42 (d, J=8.1 Hz, 2H), 6.95 (s, 1H), 6.73 (d, J=3.3 Hz, 1H), 6.57 (s, 1H), 5.93 (m, 1H), 5.15-4.82 (br, 2H), 3.48 (d, J=7.2 Hz, 2H), 2.77-2.60 (m, 4H), 2.13 (s, 3H), 1.82-1.60 (m, 5H), 0.92 (d, J=6.6 Hz, 6H).

EXAMPLE 2(30)

4-[7-[N-isopropyl-N-(5-methyl-2-furylsulfonyl)amino]-1,2,3,4-tetrahydronaphthalen-6-yloxymethyl]benzoic acid

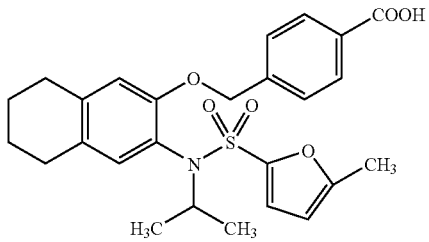

TLC: Rf 0.45 (chloroform:methanol=9:1); NMR: δ 8.12 (d, J=8.4 Hz, 2H), 7.56 (d, J=8.4 Hz, 2H), 6.80 (d, J=3.3 Hz, 1H), 6.74 (s, 1H), 6.64 (s, 1H), 6.02 (m, 1H), 5.16-5.04 (m, 2H), 4.48 (m, 1H), 2.77-2.58 (m, 4H), 2.30 (s, 3H), 1.82-1.69 (m, 4H), 1.12 (d, J=6.6 Hz, 3H), 1.11 (d, J=6.6 Hz, 3H).

EXAMPLE 2(31)

3-methyl-4-[2-[N-isobutyl-N-(5-methyl-2-furylsulfonyl)amino]-4-methyl-5-chlorophenoxymethyl]cinnamic acid

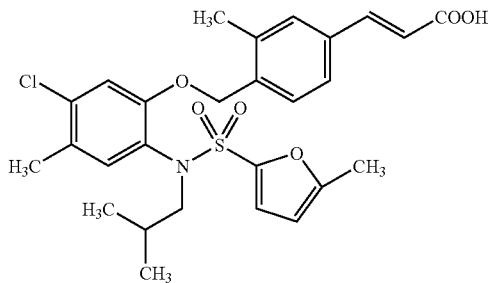

TLC: Rf 0.30 (chloroform:methanol=9:1); NMR (CD$_3$OD): δ 7.65 (d, J=15.9 Hz, 1H), 7.46 (s) and 7.44 (d, J=7.8 Hz) total 2H, 7.34 (d, J=7.8 Hz, 1H), 7.18 (s, 1H), 7.14 (s, 1H), 6.71 (d, J=3.3 Hz, 1H), 6.50 (d, J=15.9 Hz, 1H), 6.07 (dd, J=3.3, 0.9 Hz, 1H), 4.95 (m, 2H), 3.44 (d, J=7.5 Hz, 2H), 2.35 (s, 3H), 2.28 (s, 3H), 2.09 (s, 3H), 1.61 (m, 1H), 0.87 (d, J=6.6 Hz, 6H).

EXAMPLE 2(32)

4-[6-[N-isobutyl-N-(5-methyl-2-furylsulfonyl)amino]indan-5-yloxymethyl]cinnamic acid

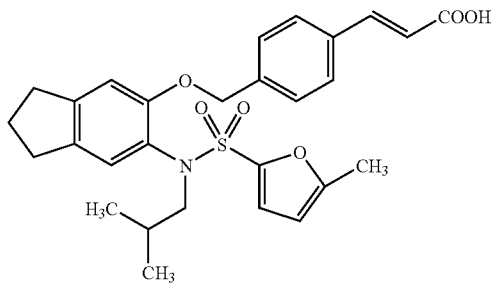

TLC: Rf 0.42 (chloroform:methanol=9:1); NMR: δ 7.79 (d, J=15.9 Hz, 1H), 7.55 (d, J=8.1 Hz, 2H), 7.37 (d, J=8.1 Hz, 2H), 7.11 (s, 1H), 6.78 (s, 1H), 6.71 (d, J=3.3 Hz, 1H), 6.47 (d, J=15.9 Hz, 1H), 5.93 (m, 1H), 5.10-4.80 (br, 2H), 3.60-3.40 (br, 2H), 2.86 (t, J=7.5 Hz, 4H), 2.14 (s, 3H), 2.08 (m, 2H), 1.68 (m, 1H), 1.00-0.82 (br, 6H).

EXAMPLE 2(33)

3-methyl-4-[6-[N-isobutyl-N-(5-methyl-2-furylsulfonyl)amino]indan-5-yloxymethyl]benzoic acid

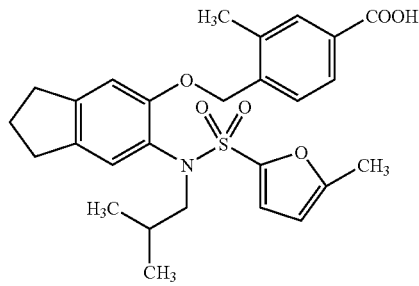

TLC: Rf 0.33 (chloroform:methanol=10:1); NMR (CDCl$_3$+1 drop of CD$_3$OD): δ 7.89 (d, J=8.4 Hz, 1H), 7.88 (s, 1H), 7.39 (d, J=8.4 Hz, 1H), 7.12 (s, 1H), 6.79 (s, 1H), 6.71 (d, J=3.3 Hz, 1H), 5.94 (m, 1H), 5.06-4.74 (m, 2H), 3.60-3.37 (m, 2H), 2.92-2.82 (m, 4H), 2.34 (s, 3H), 2.17-2.03 (m, 2H), 2.10 (s, 3H), 1.69 (m, 1H), 1.01-0.80 (m, 6H).

EXAMPLE 2(34)

3-methyl-4-[6-[N-isobutyl-N-(5-methyl-2-furylsulfonyl)amino]indan-5-yloxymethyl]cinnamic acid

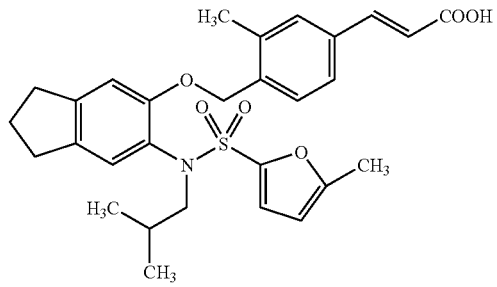

TLC: Rf 0.30 (chloroform:methanol=10:1); NMR: δ 7.78 (d, J=15.9 Hz, 1H), 7.42-7.36 (m, 3H), 7.10 (s, 1H), 6.80 (s, 1H), 6.72 (d, J=3.3 Hz, 1H), 6.46 (d, J=15.9 Hz, 1H), 5.94 (m, 1H), 5.04-4.77 (m, 2H), 3.59-3.37 (m, 2H), 2.91-2.82 (m, 4H), 2.34 (s, 3H), 2.14-2.05 (m, 2H), 2.12 (s, 3H), 1.68 (m, 1H), 1.00-0.82 (m, 6H).

EXAMPLE 2(35)

4-[2-[N-(2-methyl-2-propenyl)-N-(5-methyl-2-furylsulfonyl)amino]-4,5-dimethylphenoxymethyl]benzoic acid

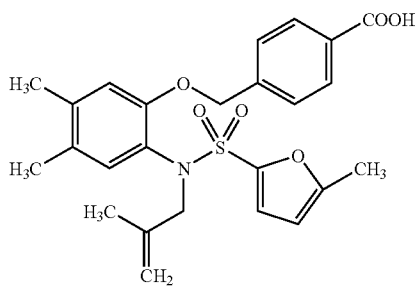

TLC: Rf 0.42(chloroform:methanol=10:1); NMR: δ 8.11 (d, J=8.1 Hz, 2H), 7.42 (d, J=8.1 Hz, 2H), 7.02 (s, 1H), 6.74 (d, J=3.3 Hz, 1H), 6.67 (s, 1H), 6.00-5.95 (m, 1H), 5.00 (brs, 2H), 4.77 (s, 2H), 4.26 (brs, 2H), 2.21 (s, 3H), 2.17 (s, 3H), 2.13 (s, 3H), 1.78 (s, 3H).

EXAMPLE 2(36)

4-[2-[N-isopropyl-N-(2-thiazolylsulfonyl)amino]-5-trifluoromethylphenoxymethyl]benzoic acid

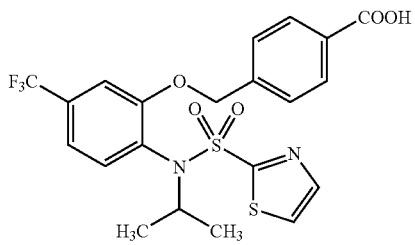

TLC: Rf 0.58 (ethyl acetate); NMR(CD$_3$OD): δ 8.03 (d, J=8.7 Hz, 2H), 7.92 (d, J=3.3 Hz, 1H), 7.82 (d, J=3.3 Hz, 1H), 7.54 (d, J=8.4 Hz, 2H), 7.43 (brs, 1H), 7.37 (d, J=8.1 Hz, 1H), 7.30 (brd, J=8.1 Hz, 1H), 5.23 (ABd, J=12.6 Hz) and 5.14 (ABd, J=12.6 Hz) total 2H, 4.64 (sept, J=6.9 Hz, 1H), 1.15 (d, J=6.9 Hz) and 1.14 (d, J=6.9 Hz) total 6H.

EXAMPLE 2(37)

4-[2-[N-isobutyl-N-(2-thiazolylsulfonyl)amino]-5-trifluoromethylphenoxymethyl]benzoic acid

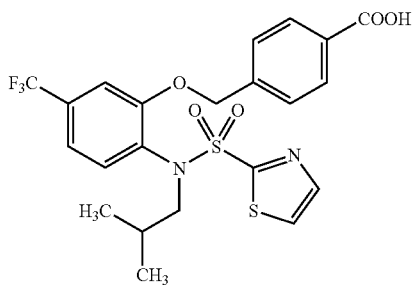

TLC: Rf 0.60 (ethyl acetate); NMR(CD$_3$OD): δ 8.02 (d, J=8.7 Hz, 2H), 7.74 (m, 2H), 7.52 (d, J=7.2 Hz, 1H), 7.38 (d, J=8.7 Hz) and 7.37 (s) total 3H, 7.32 (brd, J=7.2 Hz, 1H), 5.02 (br, 2H), 3.60 (brd, J=7.5 Hz, 2H), 1.70-1.58 (m, 1H), 0.92 (d, J=6.9 Hz, 6H).

EXAMPLE 2(38)

4-[2-[N-isopropyl-N-(2-thiazolylsulfonyl)amino]-5-trifluoromethylphenoxymethyl]cinnamic acid

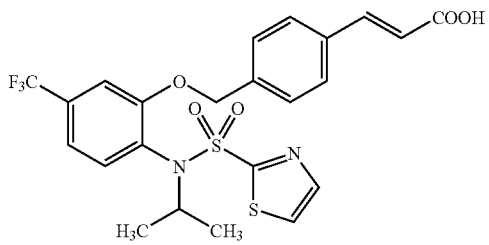

TLC: Rf 0.42 (chloroform:methanol=9:1); NMR (CD$_3$OD): δ 7.91 (d, J=3 Hz, 1H), 7.81 (d, J=3 Hz, 1H), 7.69 (d, J=15.9 Hz, 1H), 7.63 (d, J=8.4 Hz, 2H), 7.48 (d, J=8.4 Hz, 2H), 7.42 (s, 1H), 7.36 (d, J=8.1 Hz, 1H), 7.29 (brd, J=8.1 Hz, 1H), 6.52 (d, J=15.9 Hz, 1H), 5.18 (ABd, J=12.3 Hz) and 5.09 (ABd, J=12.3 Hz) total 2H, 4.63 (sept, J=6.6 Hz, 1H), 1.15 (d, J=6.6 Hz) and 1.13 (d, J=6.6 Hz) total 6H.

EXAMPLE 2(39)

4-[2-[N-isobutyl-N-(2-thiazolylsulfonyl)amino]-5-trifluoromethylphenoxymethyl]cinnamic acid

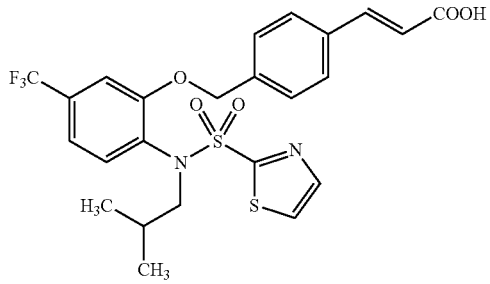

TLC: Rf 0.42 (chloroform:methanol=9:1); NMR (CD$_3$OD): δ 7.76-7.70 (m, 2H), 7.64 (s) and 7.63 (d, J=15.9 Hz) total 3H, 7.52 (d, J=8.1 Hz, 1H), 7.38-7.28 (m, 4H), 6.53 (d, J=15.9 Hz, 1H), 5.04-4.90 (m, 2H), 3.60 (brd, J=6.9 Hz, 2H), 1.72-1.56 (m, 1H), 0.92 (d, J=6.6 Hz, 6H).

EXAMPLE 2(40)

4-[2-[N-isobutyl-N-(4-methyl-2-thiazolylsulfonyl)amino]-5-trifluoromethylphenoxymethyl]benzoic acid

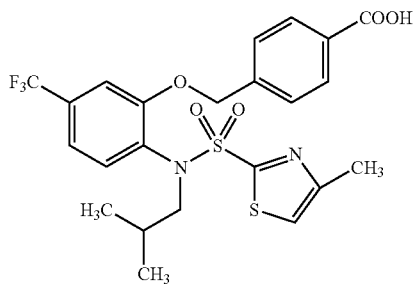

TLC: Rf 0.42 (chloroform:methanol=9:1); NMR (CD$_3$OD): δ 8.03 (d, J=8.4 Hz, 2H), 7.53 (d, J=8.1 Hz, 1H), 7.42-7.30 (m) and 7.27 (s) total 5H, 5.18-4.90 (m, 2H), 3.63-3.58 (m, 2H), 2.23 (d, J=0.9 Hz, 3H), 1.66 (m, 1H), 0.93 (d, J=6.6 Hz, 6H).

EXAMPLE 2(41)

4-[2-[N-isobutyl-N-(4-methyl-2-thiazolylsulfonyl)amino]-5-trifluoromethylphenoxymethyl]cinnamic acid

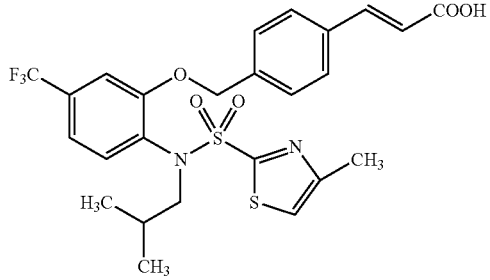

TLC: Rf 0.32 (chloroform:methanol=9:1); NMR(DMSO-d$_6$): δ 7.70 (d, J=8.1 Hz, 2H), 7.60 (d, J=15.9 Hz, 1H), 7.56-7.46 (m, 3H), 7.38 (d, J=8.7 Hz, 1H), 7.29 (d, J=8.1 Hz, 2H), 6.56 (d, J=15.9 Hz, 1H), 5.20-4.85 (m, 2H), 3.49 (d, J=6.9 Hz, 2H), 2.21 (s, 3H), 1.53 (m, 1H), 0.84 (d, J=6.6 Hz, 6H).

EXAMPLE 2(42)

4-[2-[N-isopropyl-N-(2-thiazolylsulfonyl)amino]-4-chloro-5-methylphenoxymethyl]benzoic acid

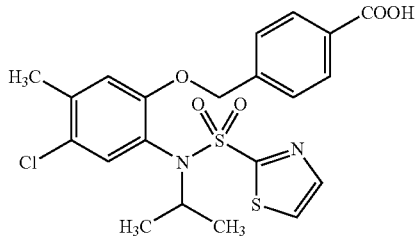

TLC: Rf 0.39 (chloroform:methanol=9:1); NMR: δ 8.13 (d, J=8.1 Hz, 2H), 7.91 (d, J=3.0 Hz, 1H), 7.52 (d, J=8.1 Hz, 2H), 7.50 (d, J=3.0 Hz, 1H), 7.10 (s, 1H), 6.85 (s, 1H), 5.09 (s, 2H), 4.67 (m, 1H), 2.36 (s, 3H), 1.16 (d, J=6.6 Hz, 3H), 1.15 (d, J=6.6 Hz, 3H).

EXAMPLE 2(43)

4-[2-[N-isopropyl-N-(4-methyl-2-thiazolylsulfonyl)amino]-4-chloro-5-methylphenoxymethyl]benzoic acid

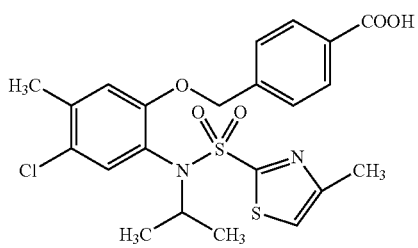

TLC: Rf 0.39 (chloroform:methanol=10:1); NMR: δ 8.13 (d, J=8.1 Hz, 2H), 7.52 (d, J=8.1 Hz, 2H), 7.09 (s, 1H), 7.04 (m, 1H), 6.85 (s, 1H), 5.10 (s, 2H), 4.68 (m, 1H), 2.49 (d, J=0.6 Hz, 3H), 2.36 (s, 3H), 1.15 (d, J=6.6 Hz, 3H), 1.14 (d, J=6.6 Hz, 3H).

EXAMPLE 2(44)

4-[2-[N-isobutyl-N-(4-methyl-2-thiazolylsulfonyl)amino]-4-chloro-5-methylphenoxymethyl]benzoic acid

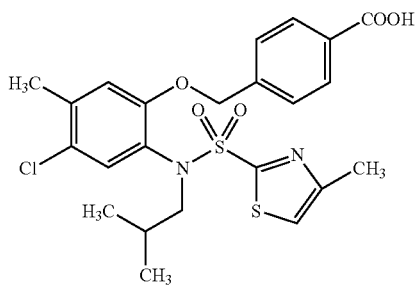

TLC: Rf 0.40 (chloroform:methanol=10:1); NMR: δ 8.12 (d, J=7.5 Hz, 2H), 7.37 (d, J=7.5 Hz, 2H), 7.27 (d, J=1.2 Hz, 1H), 6.96 (m, 1H), 6.78 (s, 1H), 5.10-4.78 (m, 2H), 3.57 (brs, 2H), 2.35 (s, 3H), 2.34 (s, 3H), 1.70 (m, 1H), 0.94 (d, J=6.6 Hz, 6H).

EXAMPLE 2(45)

3-chloro-4-[2-[N-isopropyl-N-(4-methyl-2-thiazolylsulfonyl)amino]-4-chloro-5-methylphenoxymethyl]benzoic acid

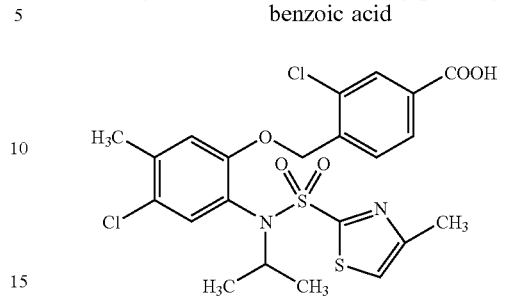

TLC: Rf 0.69 (chloroform:methanol:water=8:2:0.2); NMR: δ 8.12 (d, J=1.5 Hz, 1H), 8.06 (dd, J=8.1, 1.5 Hz, 1H), 7.83 (d, J=8.1 Hz, 1H), 7.11-7.10 (m, 2H), 6.86 (s, 1H), 5.23 (d, J=14.4 Hz, 1H), 5.15 (d, J=14.4 Hz, 1H), 4.71 (quint, J=6.6 Hz, 1H), 2.52 (d, J=1.2 Hz, 3H), 2.38 (s, 3H), 1.56 (d, J=6.6 Hz, 3H), 1.34 (d, J=6.6 Hz, 3H).

EXAMPLE 2(46)

3-methyl-4-[2-[N-isobutyl-N-(4-methyl-2-thiazolylsulfonyl)amino]-5-trifluoromethylphenoxymethyl]benzoic acid

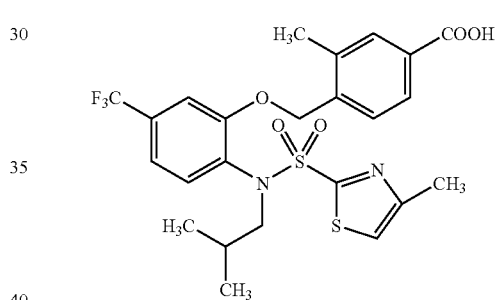

TLC: Rf 0.44 (chloroform:methanol=9:1); NMR: δ 7.96 (d, J=8.4 Hz, 1H), 7.95 (s, 1H), 7.48 (d, J=8.1 Hz, 1H), 7.35 (d, J=8.4 Hz, 1H), 7.32-7.24 (m, 1H), 7.20 (s, 1H), 6.98 (s, 1H), 5.06-4.85 (m, 2H), 3.70-3.50 (m, 2H), 2.39 (s, 3H), 2.34 (s, 3H), 1.75-1.59 (m, 1H), 0.91 (d, J=6.6 Hz, 6H).

EXAMPLE 2(47)

3-methyl-4-[2-[N-isobutyl-N-(4-methyl-2-thiazolylsulfonyl)amino]-4-chloro-5-methylphenoxymethyl]benzoic acid

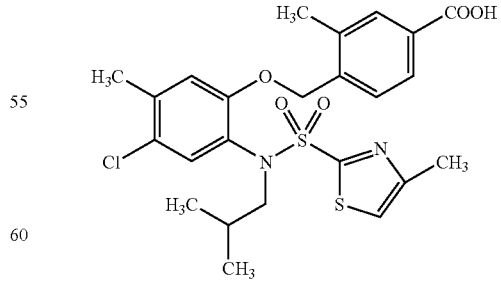

TLC: Rf 0.44 (chloroform:methanol=9:1); NMR(DMSO-$d_6$): δ 7.79 (s, 1H), 7.76 (d, J=8.1 Hz, 1H), 7.56 (s, 1H), 7.29 (s, 1H), 7.27 (d, J=8.1 Hz, 1H), 7.23 (s, 1H), 5.20-4.65 (m, 2H), 3.55-3.35 (m, 2H), 2.36 (s, 3H), 2.31 (s, 3H), 2.21 (s, 3H), 1.65-1.47 (m, 1H), 0.84 (d, J=6.6 Hz, 6H).

EXAMPLE 2(48)

3-methoxy-4-[2-[N-isobutyl-N-(4-methyl-2-thiazolylsulfonyl)amino]-4-chloro-5-methylphenoxymethyl]benzoic acid

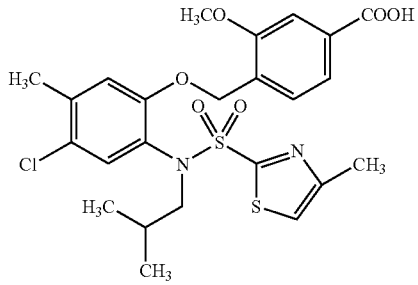

TLC: Rf 0.48 (chloroform:methanol=9:1); NMR: δ 7.74 (dd, J=7.8, 1.2 Hz, 1H), 7.59 (d, J=1.2 Hz, 1H), 7.31 (d, J=7.8 Hz, 1H), 7.30 (s, 1H), 6.94 (s, 1H), 6.81 (s, 1H), 5.10-4.70 (m, 2H), 3.94 (s, 3H), 3.59 (br, 2H), 2.35 (s, 3H), 2.34 (s, 3H), 1.80-1.60 (m, 1H), 1.12 (d, J=6.9 Hz, 6H).

EXAMPLE 2(49)

3-methoxy-4-[2-[N-isobutyl-N-(4-methyl-2-thiazolylsulfonyl)amino]-5-trifluoromethylphenoxymethyl]benzoic acid

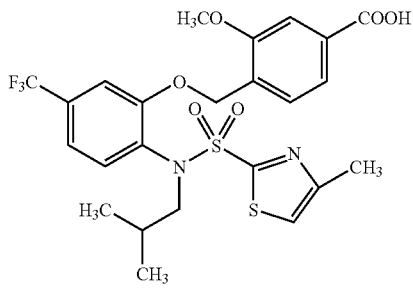

TLC: Rf 0.40 (chloroform:methanol=9:1); NMR: δ 7.73 (dd, J=8.1, 1.5 Hz, 1H), 7.60 (d, J=1.5 Hz, 1H), 7.50 (d, J=8.1 Hz, 1H), 7.34-7.19 (m, 3H), 6.95 (m, 1H), 5.12-4.80 (m, 2H), 3.95 (s, 3H), 3.77-3.48 (m, 2H), 2.34 (s, 3H), 1.77-1.60 (m, 1H), 0.94 (d, J=6.6 Hz, 6H).

EXAMPLE 2(50)

4-[2-[N-isobutyl-N-(4-methyl-2-thiazolylsulfonyl)amino]-4-methyl-5-chlorophenoxymethyl]benzoic acid

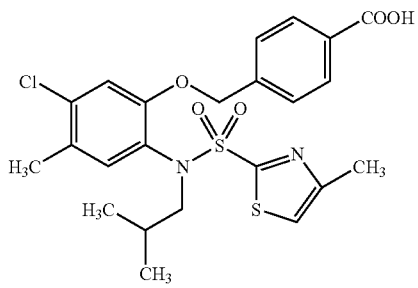

TLC: Rf 0.38 (chloroform:methanol=9:1); NMR: δ 8.11 and 7.33 (each d, J=8.4 Hz, each 2H), 7.22 (s, 1H), 6.92 and 6.91 (each s, each 1H), 5.10-4.70 (m, 2H), 3.74-3.42 (m, 2H), 2.31 and 2.30 (each s, each 3H), 1.78-1.62 (m, 1H), 1.05-0.83 (m, 6H).

EXAMPLE 2(51)

3-chloro-4-[2-[N-isobutyl-N-(4-methyl-2-thiazolylsulfonyl)amino]-4-methyl-5-chlorophenoxymethyl]benzoic acid

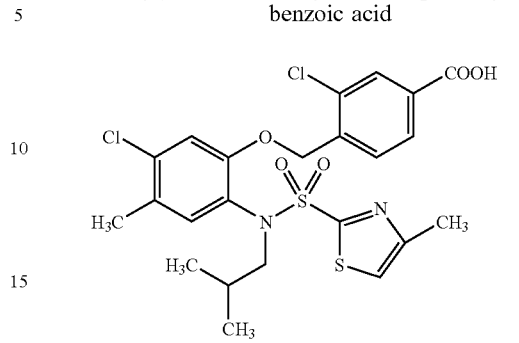

TLC: Rf 0.28 (chloroform:methanol=9:1); NMR: δ 8.11 (s, 1H), 8.02 and 7.45 (each d, J=8.1 Hz, each 1H), 7.21 (s, 1H), 6.97 (s, 1H), 6.94 (s, 1H), 5.12-4.74 (m, 2H), 3.75-3.45 (m, 2H), 2.32 and 2.31 (each s, each 3H), 1.80-1.62 (m, 1H), 1.05-0.82 (m, 6H).

EXAMPLE 2(52)

3-methoxy-4-[2-[N-isobutyl-N-(4-methyl-2-thiazolylsulfonyl)amino]-4-methyl-5-chlorophenoxymethyl]benzoic acid

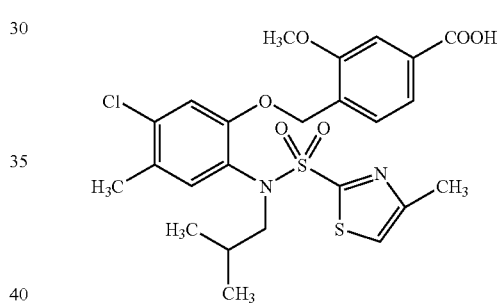

TLC: Rf 0.35 (chloroform:methanol=9:1); NMR: δ 7.73 (d, J=7.8 Hz, 1H), 7.59 (s, 1H), 7.30-7.20 (m, 2H), 6.95 (s, 1H), 6.91 (s, 1H), 5.09-4.62 (m, 2H), 3.94 (s, 3H), 3.78-3.45 (m, 2H), 2.31 (s, 6H), 1.79-1.63 (m, 1H), 1.08-0.85 (m, 6H).

EXAMPLE 2(53)

3-methyl-4-[2-[N-isobutyl-N-(4-methyl-2-thiazolylsulfonyl)amino]-4,5-dimethylphenoxymethyl]benzoic acid

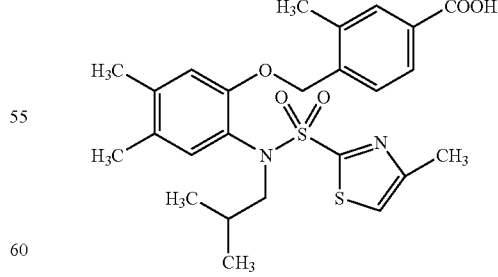

TLC: Rf 0.76 (chloroform:methanol:water=8:2:0.2); NMR: δ 7.93 (d, J=8.1 Hz, 1H), 7.92 (s, 1H), 7.30 (d, J=8.1 Hz, 1H), 7.08 (s, 1H), 6.90 (d, J=0.9 Hz, 1H), 6.71 (s, 1H), 4.91 (br, 1H), 4.79 (br, 1H), 3.65 (br, 1H), 3.56 (br, 1H), 2.35 (s, 3H), 2.30 (d, J=0.9 Hz, 3H), 2.24 (s, 3H), 2.19 (s, 3H), 1.71 (sep, J=6.9 Hz, 1H), 1.03-0.92 (br, 6H).

EXAMPLE 2(54)

3-methyl-4-[2-[N-isopropyl-N-(4-methyl-2-thiaz-olylsulfonyl)amino]-4,5-dimethylphenoxymethyl]benzoic acid

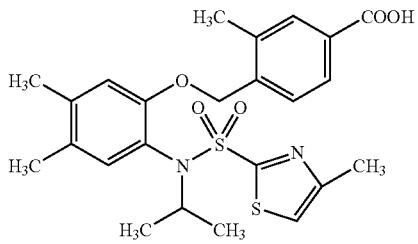

TLC: Rf 0.78 (chloroform:methanol:water=8:2:0.2); NMR: δ 7.95 (d, J=8.1 Hz, 1H), 7.93 (s, 1H), 7.54 (d, J=8.1 Hz, 1H), 6.98 (d, J=0.9 Hz, 1H), 6.86 (s, 1H), 6.78 (s, 1H), 5.03 (d, J=13.2 Hz, 1H), 4.98 (d, J=13.2 Hz, 1H), 4.69 (quint, J=6.6 Hz, 1H), 2.46 (d, J=0.9 Hz, 3H), 2.39 (s, 3H), 2.25 (s, 3H), 2.16 (s, 3H), 1.17 (d, J=6.6 Hz, 3H), 1.13 (d, J=6.6 Hz, 3H).

EXAMPLE 2(55)

3-methoxy-4-[2-[N-isobutyl-N-(4-methyl-2-thiaz-olylsulfonyl)amino]-4,5-dimethylphenoxymethyl]benzoic acid

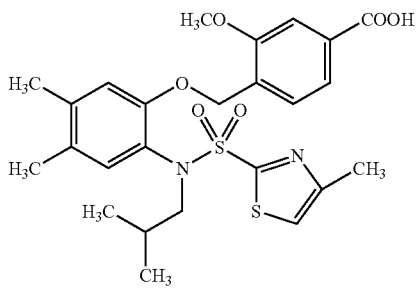

TLC: Rf 0.39 (chloroform:methanol=9:1); NMR: δ 7.72 (dd, J=8.1, 1.2 Hz, 1H), 7.57 (d, J=1.2 Hz, 1H), 7.26 (d, J=8.1 Hz, 1H), 7.11 (s, 1H), 6.87 (s, 1H), 6.71 (s, 1H), 4.95 (br, 1H), 4.75 (br, 1H), 3.93 (s, 3H), 3.69 (br, 1H), 3.56 (br, 1H), 2.29 (s, 3H), 2.23 (s, 3H), 2.19 (s, 3H), 1.80-1.65 (m, 1H), 0.97 (br, 6H).

EXAMPLE 2(56)

3-chloro-4-[2-[N-isobutyl-N-(4-methyl-2-thiazolyl-sulfonyl)amino]-4,5-dimethylphenoxymethyl]benzoic acid

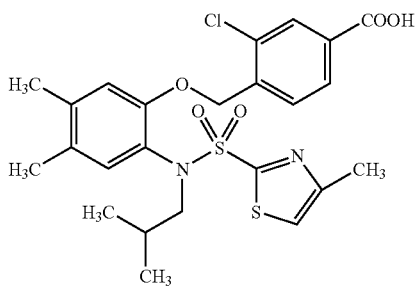

TLC: Rf 0.36 (chloroform:methanol=9:1); NMR: δ 8.11 (d, J=1.8 Hz, 1H), 8.01 (dd, J=8.1, 1.8 Hz, 1H), 7.49 (d, J=8.1 Hz, 1H), 7.08 (s, 1H), 6.95 (d, J=0.6 Hz, 1H), 6.69 (s, 1H), 5.20-4.70 (br, 2H), 3.80-3.45 (br, 2H), 2.32 (d, J=0.6 Hz, 3H), 2.24 (s, 3H), 2.19 (s, 3H), 1.75 (m, 1H), 1.07-0.85 (br, 6H).

EXAMPLE 2(57)

3-chloro-4-[2-[N-isopropyl-N-(4-methyl-2-thiazolyl-sulfonyl)amino]-4,5-dimethylphenoxymethyl]benzoic acid

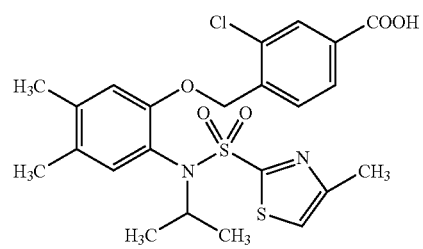

TLC: Rf 0.36 (chloroform:methanol=9:1); NMR(CDCl$_3$+CD$_3$OD): δ 8.06 (d, J=1.8 Hz, 1H), 7.98 (dd, J=8.1, 1.8 Hz, 1H), 7.70 (d, J=8.1 Hz, 1H), 7.05 (d, J=0.6 Hz, 1H), 6.86 (s, 1H), 6.76 (s, 1H), 5.14 (d, J=14.1 Hz, 1H), 5.08 (d, J=14.1 Hz, 1H), 4.70 (m, 1H), 2.47 (d, J=0.6 Hz, 3H), 2.25 (s, 3H), 2.17 (s, 3H), 1.17 (d, J=6.6 Hz, 3H), 1.15 (d, J=6.6 Hz, 3H).

EXAMPLE 2(58)

4-[2-[N-isopropyl-N-(4-methyl-2-thiazolylsulfonyl)amino]-4,5-dimethylphenoxymethyl]benzoic acid

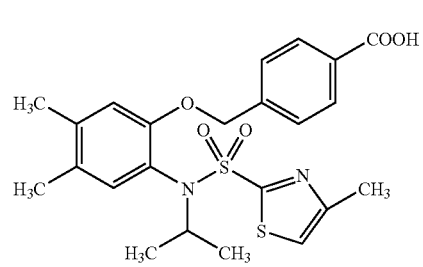

TLC: Rf 0.45 (chloroform:methanol=10:1); NMR: δ 8.11-8.08 (m, 2H), 7.49 (d, J=8.4 Hz, 2H), 6.97 (d, J=0.9 Hz, 1H), 6.86 (s, 1H), 6.75 (s, 1H), 5.06 (d, J=12.9 Hz, 1H), 5.04 (d, J=12.9 Hz, 1H), 4.71 (m, 1H), 2.46 (d, J=0.9 Hz, 3H), 2.23 (s, 3H), 2.16 (s, 3H), 1.18 (d, J=6.6 Hz, 3H), 1.15 (d, J=6.6 Hz, 3H).

EXAMPLE 2(59)

4-[2-[N-isobutyl-N-(4-methyl-2-thiazolylsulfonyl)amino]-4,5-dimethylphenoxymethyl]benzoic acid

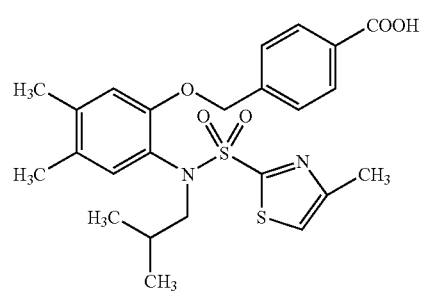

TLC: Rf 0.43 (chloroform:methanol=10:1); NMR: δ 8.09 (d, J=8.1 Hz, 2H), 7.33 (d, J=8.1 Hz, 2H), 7.08 (s, 1H), 6.89 (d, J=0.9 Hz, 1H), 6.68 (s, 1H), 5.08-4.68 (m, 2H), 3.75-3.45 (m, 2H), 2.30 (s, 3H), 2.23 (s, 3H), 2.18 (s, 3H), 1.71 (m, 1H), 1.04-0.83 (m, 6H).

EXAMPLE 2(60)

4-[2-[N-isobutyl-N-(4-methyl-2-thiazolylsulfonyl)amino]-4-chloro-5-methylphenoxymethyl]cinnamic acid

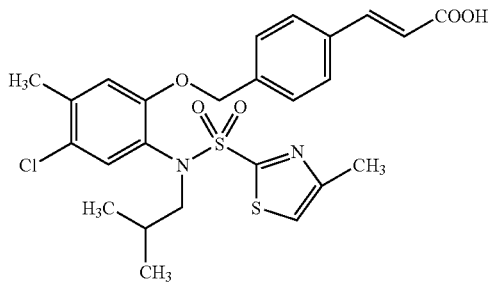

TLC: Rf 0.22 (chloroform:methanol=9:1); NMR (CD$_3$OD): δ 7.69 (d, J=16.2 Hz, 1H), 7.61 (d, J=8.1 Hz, 2H), 7.32-7.24 (m) and 7.29 (d, J=8.1 Hz) total 4H, 7.05 (s, 1H), 6.52 (d, J=16.2 Hz, 1H), 5.05-4.70 (m, 2H, covered with H$_2$O in CD$_3$OD), 3.63-3.50 (m, 2H), 2.37 (s, 3H), 2.22 (d, J=0.9 Hz, 3H), 1.65 (m, 1H), 0.93 (d, J=6.3 Hz, 6H).

EXAMPLE 2(61)

3-methyl-4-[2-[N-isobutyl-N-(4-methyl-2-thiazolyl-sulfonyl)amino]-5-trifluoromethylphenoxymethyl]cinnamic acid

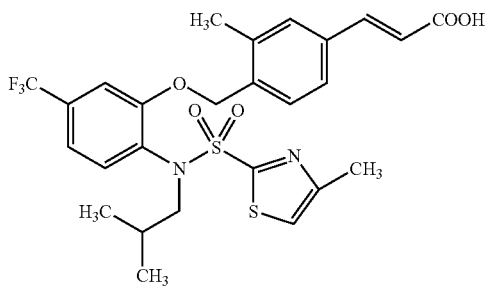

TLC: Rf 0.37 (chloroform:methanol=9:1); NMR: δ 7.76 (d, J=16.2 Hz, 1H), 7.47 (d, J=7.8 Hz, 1H), 7.45-7.35 (m, 2H), 7.32-7.23 (m, 2H), 7.20 (m, 1H), 6.98 (s, 1H), 6.48 (d, J=16.2 Hz, 1H), 5.03-4.82 (m, 2H), 3.70-3.50 (m, 2H), 2.36 (s, 3H), 2.34 (s, 3H), 1.74-1.58 (m, 1H), 0.91 (d, J=6.9 Hz, 6H).

EXAMPLE 2(62)

3-chloro-4-[2-[N-isobutyl-N-(4-methyl-2-thiazolyl-sulfonyl)amino]-5-trifluoromethylphenoxymethyl]cinnamic acid

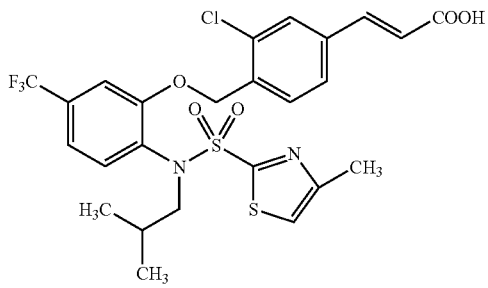

TLC: Rf 0.28 (n-hexane:ethyl acetate=1:2); NMR: δ 7.71 (d, J=16.2 Hz, 1H), 7.58 (s, 1H), 7.52-7.44 (m, 3H), 7.29 (d, J=8.1 Hz, 1H) 7.19 (s, 1H), 7.01 (d, J=0.9 Hz, 1H), 6.50 (d, J=16.2 Hz, 1H), 5.02 (br, 2H), 3.62 (d, J=6.6 Hz, 2H), 2.35 (s, 3H), 1.68 (sep, J=6.6 Hz, 1H), 0.93 (d, J=6.6 Hz, 6H).

EXAMPLE 2(63)

3-methyl-4-[2-[N-isopropyl-N-(4-methyl-2-thiazolylsulfonyl)amino]-4,5-dimethylphenoxymethyl]cinnamic acid

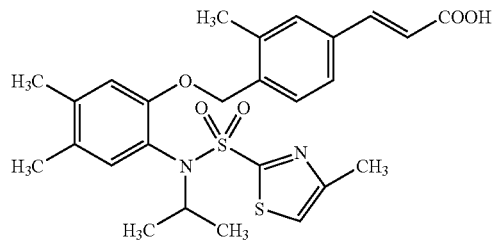

TLC: Rf 0.20 (n-hexane:ethyl acetate=1:2); MS (FAB, Pos.): 515(M+H)$^+$.

EXAMPLE 2(64)

3-methyl-4-[2-[N-isobutyl-N-(4-methyl-2-thiazolylsulfonyl)amino]-4,5-dimethylphenoxymethyl]cinnamic acid

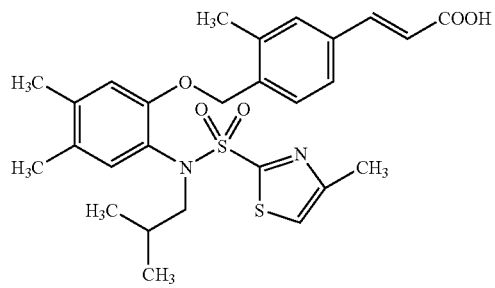

TLC: Rf 0.22 (n-hexane:ethyl acetate=1:2); MS (FAB, Pos.): 529(M+H)$^+$.

EXAMPLE 2(65)

4-[2-[N-isobutyl-N-(4-methyl-2-thiazolylsulfonyl)amino]-4-methyl-5-chlorophenoxymethyl]cinnamic acid

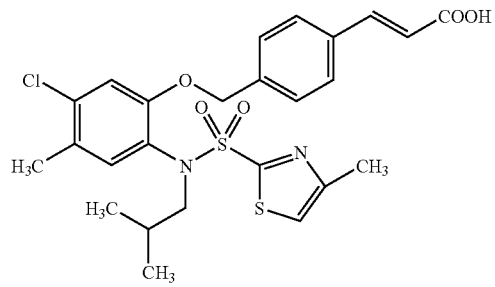

TLC: Rf 0.31 (chloroform:methanol=9:1); NMR: δ 7.79 (d, J=15.9 Hz, 1H), 7.56 and 7.27 (each d, J=8.1 Hz, each 2H), 7.21 (s, 1H), 6.95-6.88 (m, 2H), 6.48 (d, J=15.9 Hz, 1H), 5.00-4.65 (m, 2H), 3.72-3.42 (m, 2H), 2.33-2.22 (m, 6H), 1.78-1.60 (m, 1H), 1.05-0.83 (m, 6H).

EXAMPLE 2(66)

3-methyl-4-[2-[N-isobutyl-N-(4-methyl-2-thiazolyl-sulfonyl)amino]-4-methyl-5-chlorophenoxymethyl]cinnamic acid

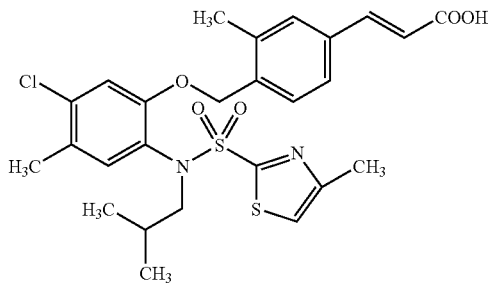

TLC: Rf 0.30 (chloroform:methanol=9:1); NMR: δ 7.76 (d, J=16.2 Hz, 1H), 7.42-7.37 (m, 2H), 7.30-7.15 (m, 2H), 6.98-6.89 (m, 2H), 6.47 (d, J=16.2 Hz, 1H), 4.95-4.67 (m, 2H), 3.72-3.40 (m, 2H), 2.38-2.22 (m, 9H), 1.77-1.61 (m, 1H), 1.05-0.82 (m, 6H).

EXAMPLE 2(67)

3-methyl-4-[2-[N-isobutyl-N-(4-methyl-2-thiazolyl-sulfonyl)amino]-4-chloro-5-methylphenoxymethyl]cinnamic acid

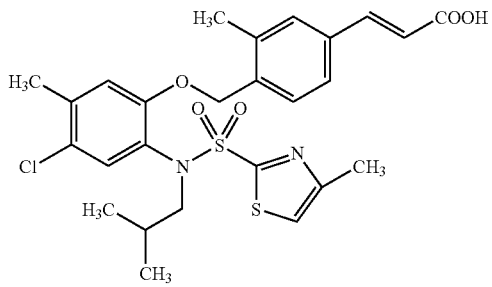

TLC: Rf 0.41 (chloroform:methanol=9:1); NMR: δ 7.76 (d, J=16.2 Hz, 1H), 7.39 (d, J=8.4 Hz, 1H), 7.38 (s, 1H), 7.27 (d, J=8.4 Hz, 1H), 7.23 (s, 1H), 6.97 (s, 1H), 6.81 (s, 1H), 6.47 (d, J=16.2 Hz, 1H), 5.04-4.66 (m, 2H), 3.65-3.39 (m, 2H), 2.36 (s, 3H), 2.35 (s, 3H), 2.33 (s, 3H), 1.75-1.61 (m, 1H), 0.92 (d, J=6.6 Hz, 6H).

EXAMPLE 2(68)

4-[2-[N-isobutyl-N-(4-methyl-2-thiazolylsulfonyl)amino]-4,5-dimethylphenoxymethyl]cinnamic acid

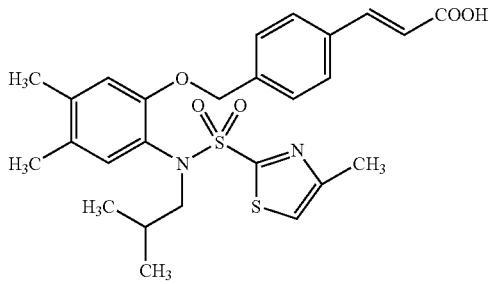

TLC: Rf 0.33 (chloroform:methanol=10:1); MS (APCI, Neg. 20V): 513 (M−H)−.

EXAMPLE 2(69)

3-chloro-4-[2-[N-isobutyl-N-(4-methyl-2-thiazolyl-sulfonyl)amino]-4,5-dimethylphenoxymethyl]cinnamic acid

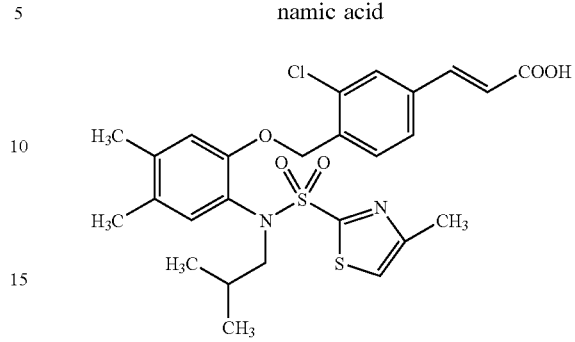

TLC: Rf 0.17 (chloroform:methanol=9:1); NMR (CD$_3$OD): δ 7.69 (d, J=1.8 Hz, 1H), 7.65 (d, J=15.9 Hz, 1H), 7.59 (dd, J=8.1, 1.5 Hz, 1H), 7.35 (d, J=8.1 Hz, 1H), 7.29 (d, J=1.2 Hz, 1H), 7.04 (s, 1H), 6.88 (s, 1H), 6.57 (d, J=15.9 Hz, 1H), 5.10-4.60 (m, 2H), 3.63-3.50 (m, 2H), 2.28 (s, 3H), 2.21 (d, J=1.2 Hz) and 2.20 (s) total 6H, 1.66 (m, 1H), 1.03-0.85 (m, 6H).

EXAMPLE 2(70)

3-methoxy-4-[2-[N-isobutyl-N-(4-methyl-2-thiazolylsulfonyl)amino]-4,5-dimethylphenoxymethyl]cinnamic acid

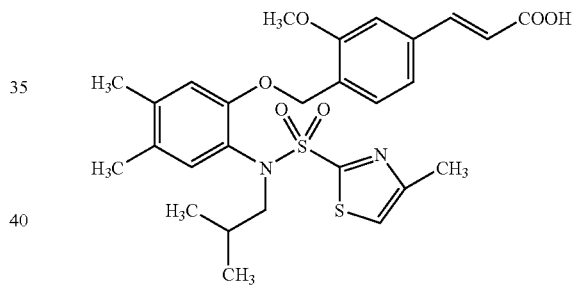

TLC: Rf 0.40 (dichloromethane:methanol=10:1); MS (FAB, Pos.): 545 (M+H)+.

EXAMPLE 2(71)

4-[6-[N-isobutyl-N-(4-methyl-2-thiazolylsulfonyl)amino]indan-5-yloxymethyl]benzoic acid

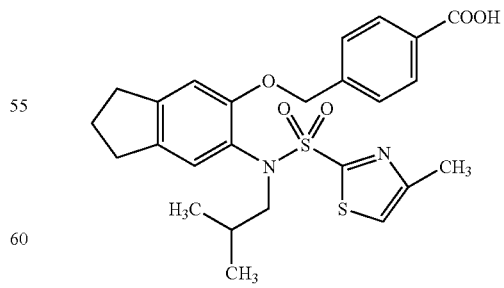

TLC: Rf 0.43 (chloroform:methanol=9:1); NMR: δ 8.10 (d, J=8.4 Hz, 2H), 7.34 (d, J=8.4 Hz, 2H), 7.16 (s, 1H), 6.89 (d, J=0.9 Hz, 1H), 6.76 (s, 1H), 5.06-4.70 (br, 2H), 3.78-3.45 (br, 2H), 2.87 (t, J=7.5 Hz, 4H), 2.31 (d, J=0.9 Hz, 3H), 2.09 (m, 2H), 1.74 (m, 1H), 1.04-0.86 (br, 6H).

EXAMPLE 2(72)

4-[6-[N-isobutyl-N-(4-methyl-2-thiazolylsulfonyl)amino]indan-5-yloxymethyl]cinnamic acid

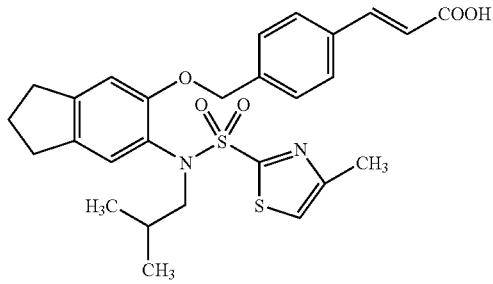

TLC: Rf 0.42 (chloroform:methanol=9:1); NMR: δ 7.79 (d, J=15.9 Hz, 1H), 7.55 (d, J=8.1 Hz, 2H), 7.28 (d, J=8.1 Hz, 2H), 7.15 (s, 1H), 6.89 (d, J=0.9 Hz, 1H), 6.77 (s, 1H), 6.47 (d, J=15.9 Hz, 1H), 5.05-4.60 (br, 2H), 3.78-3.45 (br, 2H), 2.86 (t, J=7.8 Hz, 4H), 2.30 (d, J=0.9 Hz, 3H), 2.08 (m, 2H), 1.73 (m, 1H), 1.06-0.83 (br, 6H).

EXAMPLE 2(73)

3-methyl-4-[6-[N-isobutyl-N-(4-methyl-2-thiazolylsulfonyl)amino]indan-5-yloxymethyl]benzoic acid

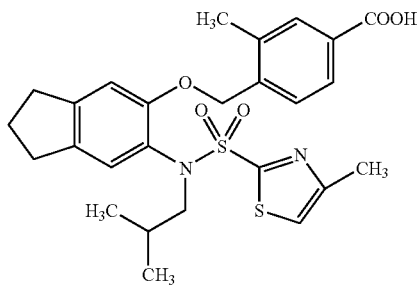

TLC: Rf 0.34 (dichloromethane:methanol=19:1); NMR: δ 7.95-7.92 (m, 2H), 7.31 (d, J=7.8 Hz, 1H), 7.16 (s, 1H), 6.91 (brs, 1H), 6.79 (s, 1H), 4.93 (brs, 1H), 4.73 (brs, 1H), 3.75-3.45 (m, 2H), 2.92-2.84 (m, 4H), 2.34 (s, 3H), 2.31 (d, J=0.6 Hz, 3H), 2.10 (m, 2H), 1.74 (m, 1H), 1.08-0.80 (brs, 6H).

EXAMPLE 2(74)

3-methyl-4-[6-[N-isobutyl-N-(4-methyl-2-thiazolylsulfonyl)amino]indan-5-yloxymethyl]cinnamic acid

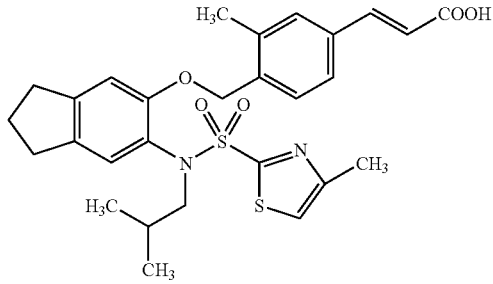

TLC: Rf 0.32 (dichloromethane:methanol=19:1); NMR: δ 7.76 (d, J=15.9 Hz, 1H), 7.40-7.36 (m, 2H), 7.25 (m, 1H), 7.14 (s, 1H), 6.91 (brs, 1H), 6.80 (s, 1H), 6.46 (d, J=15.9 Hz, 1H), 4.90 (brs, 1H), 4.69 (brs, 1H), 3.75-3.43 (m, 2H), 2.95-2.80 (m, 4H), 2.31 (s, 6H), 2.09 (m, 2H), 1.72 (m, 1H), 1.05-0.85 (brs, 6H).

EXAMPLE 2(75)

4-[2-[N-isobutyl-N-(2-pyridylsulfonyl)amino]-5-trifluoromethylphenoxymethyl]cinnamic acid

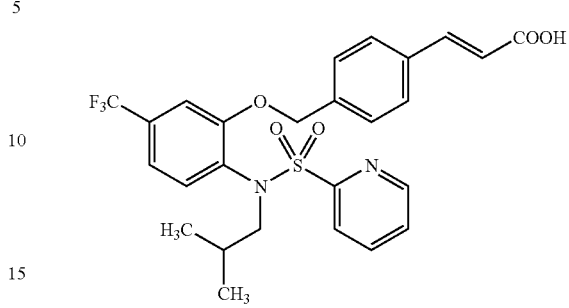

TLC: Rf 0.37 (chloroform:methanol=9:1); NMR (CD$_3$OD): δ 8.39 (ddd, J=4.5, 1.5, 0.9 Hz, 1H), 7.82 (dt, J=7.5, 1.5 Hz, 1H), 7.72-7.64 (m, 2H), 7.60 (d, J=8.1 Hz, 2H), 7.53 (d, J=7.5 Hz, 1H), 7.38 (ddd, J=7.5, 4.5, 0.9 Hz, 1H), 7.34-7.22 (m, 4H), 6.54 (d, J=15.9 Hz, 1H), 4.95-4.78 (m, 2H), 3.61 (d, J=6.6 Hz, 2H), 1.60 (m, 1H), 0.91 (d, J=6.9 Hz, 6H).

EXAMPLE 2(76)

4-[2-[N-isobutyl-N-(3-pyridylsulfonyl)amino]-5-trifluoromethylphenoxymethyl]benzoic acid

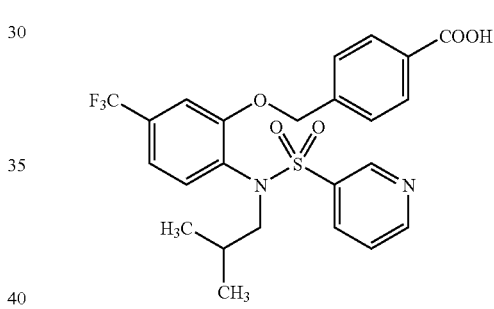

TLC: Rf 0.27 (chloroform:methanol=9:1); NMR (CD$_3$OD): δ 8.63 (m, 1H), 8.53 (dd, J=5.1, 1.8 Hz, 1H), 7.99 (d, J=8.4 Hz) and 7.94 (m) total 3H, 7.56 (d, J=7.5 Hz, 1H), 7.40-7.29 (m, 3H), 7.23 (d, J=8.4 Hz, 2H), 5.10-4.80 (m, 2H), 3.58-3.40 (m, 2H), 1.61 (m, 1H), 0.92 (brd, J=6 Hz, 6H).

EXAMPLE 2(77)

3-chloro-4-[2-[N-isopropyl-N-(2-pyridylsulfonyl)amino]-4-chloro-5-methylphenoxymethyl]benzoic acid

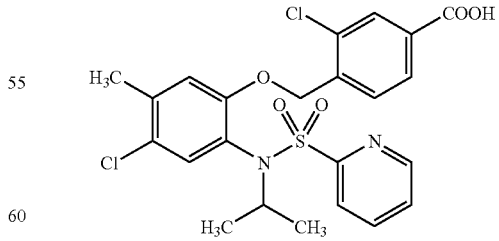

TLC: Rf 0.43 (chloroform:methanol=9:1); NMR (CD$_3$OD): δ 8.63 (m, 1H), 8.02 (d, J=1.8 Hz, 1H), 7.98-7.84 (m, 3H), 7.70 (d, J=8.1 Hz, 1H), 7.50 (m, 1H), 7.11 (s, 1H), 7.09 (s, 1H), 5.16 (ABd, J=13.5 Hz) and 5.08 (ABd, J=13.5 Hz) total 2H, 4.61 (sept, J=6.6 Hz, 1H), 2.39 (3, 3H), 1.12 (d, J=6.6 Hz) and 1.10 (d, J=6.6 Hz) total 6H.

EXAMPLE 2(78)

3-methyl-4-[2-[N-isobutyl-N-(2-pyridylsulfonyl)amino]-4-chloro-5-methylphenoxymethyl]benzoic acid

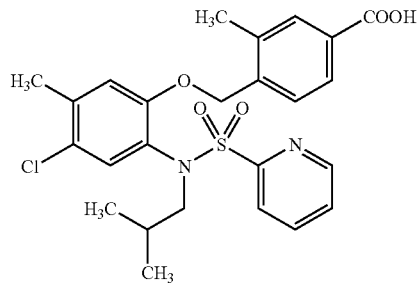

TLC: Rf 0.37 (chloroform:methanol=10:1); NMR: δ 8.52 (m, 1H), 7.94-7.92 (m, 2H), 7.77-7.68 (m, 2H), 7.31-7.24 (m, 3H), 6.76 (s, 1H), 4.83 (brs, 2H), 3.65-3.50 (m, 2H), 2.34 (s, 6H), 1.66 (m, 1H), 0.91 (d, J=6.6 Hz, 6H).

EXAMPLE 2(79)

3-methyl-4-[2-[N-isobutyl-N-(3-pyridylsulfonyl)amino]-4-chloro-5-methylphenoxymethyl]benzoic acid

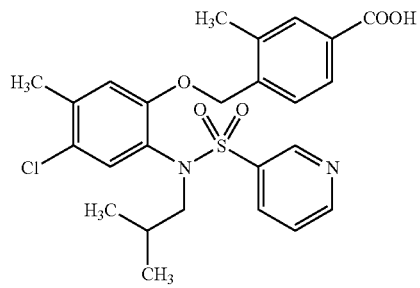

TLC: Rf 0.16 (dichloromethane:methanol=20:1); NMR: δ 12.90 (s, 1H), 8.67 (d, J=1.8 Hz, 1H), 8.62 (dd, J=4.8, 1.8 Hz, 1H), 7.94 (dt, J=8.1, 1.8 Hz, 1H), 7.74 (s, 1H), 7.68 (d, J=8.1 Hz, 1H), 7.37 (dd, J=8.1, 4.8 Hz, 1H), 7.27 (s, 1H), 7.24 (s, 1H), 7.01 (d, J=8.1 Hz, 1H), 4.95 (br, 1H), 4.76 (br, 1H), 3.45-3.30 (m, 2H), 2.34 (s, 3H), 2.24 (s, 3H), 1.49 (sept, J=6.6 Hz, 1H), 0.90-0.70 (br, 6H).

EXAMPLE 2(80)

3-methyl-4-[2-[N-isobutyl-N-(2-pyridylsulfonyl)amino]-4-methyl-5-chlorophenoxymethyl]benzoic acid

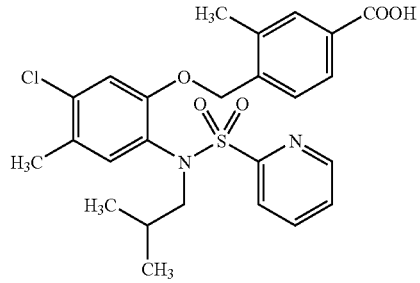

TLC: Rf 0.40 (chloroform:methanol=9:1); NMR: δ 8.50-8.40 (m, 1H), 7.95-7.85 (m, 2H), 7.75-7.60 (m, 2H), 7.30-7.20 (m, 3H), 6.89 (s, 1H), 4.76 (br, 2H), 3.61 (br, 2H), 2.31 (s, 3H), 2.29 (s, 3H), 1.75-1.55 (m, 1H), 1.00-0.80 (m, 6H).

EXAMPLE 2(81)

4-[2-[N-isobutyl-N-(3-pyridylsulfonyl)amino]-4-methyl-5-chlorophenoxymethyl]benzoic acid

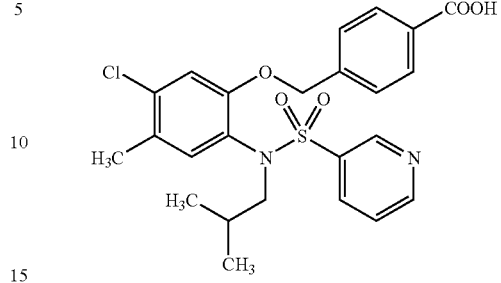

TLC: Rf 0.31 (chloroform:methanol=9:1); NMR: δ 8.83 (d, J=2.4, 0.6 Hz, 1H), 8.61 (dd, J=5.1, 1.8 Hz, 1H), 8.10 (d, J=8.4 Hz, 2H), 7.78-7.71 (m, 1H), 7.36 (s, 1H), 7.29-7.22 (m, 1H), 7.08 (d, J=8.4 Hz, 2H), 6.90 (s, 1H), 4.94-4.72 and 4.50-4.25 (each m, each 1H), 3.75-3.56 and 3.45-3.24 (each m, each 1H), 2.36 (s, 3H), 1.79-1.63 (m, 1H), 1.16-0.80 (m, 6H).

EXAMPLE 2(82)

3-chloro-4-[2-[N-isobutyl-N-(3-pyridylsulfonyl)amino]-4-methyl-5-chlorophenoxymethyl]benzoic acid

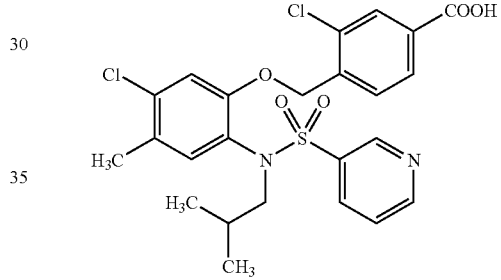

TLC: Rf 0.29 (chloroform:methanol=9:1); NMR: δ 8.87 (d, J=1.8 Hz, 1H), 8.63 (dd, J=5.1, 1.8 Hz, 1H), 8.13 (d, J=1.8 Hz 1H), 8.03 (dd, J=8.1, 1.8 Hz, 1H), 7.73-7.66 (m, 1H), 7.40 (s, 1H), 7.36 (dd, J=8.1, 5.1 Hz, 1H), 7.05 (d, J=8.1 Hz, 1H), 6.96 (s, 1H), 4.92-4.74 and 4.54-4.34 (each m, each 1H), 3.72-3.63 and 3.50-3.33 (each m, each 1H), 2.39 (s, 3H), 1.84-1.68 (m, 1H), 1.20-0.92 (m, 6H).

EXAMPLE 2(83)

3-methyl-4-[2-[N-isobutyl-N-(2-pyridylsulfonyl)amino]-5-trifluoromethylphenoxymethyl]cinnamic acid

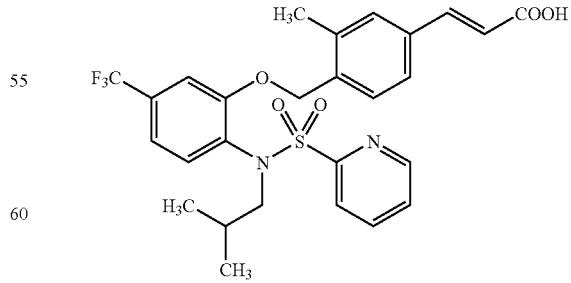

TLC: Rf 0.32 (chloroform:methanol=9:1); NMR(DMSO-$d_6$): δ 12.39 (br s, 1H), 8.51 (d, J=4.5 Hz, 1H), 7.90 (dd, J=7.5, 7.5 Hz, 1H), 7.70 (d, J=7.5 Hz, 1H), 7.55 (d, J=16.0 Hz, 1H), 7.53-7.46 (m, 5H), 7.35 (d, J=8.0 Hz, 1H), 7.14 (d, J=8.0 Hz, 1H), 6.55 (d, J=16.0 Hz, 1H), 5.00 (br s, 2H), 3.49 (d, J=7.0 Hz, 2H), 2.25 (s, 3H), 1.45 (triple septet, J=7.0, 7.0 Hz, 1H), 0.78 (d, J=7.0 Hz, 6H).

EXAMPLE 2(84)

3-methoxy-4-[2-[N-isobutyl-N-(2-pyridylsulfonyl)amino]-4,5-dimethylphenoxymethyl]benzoic acid

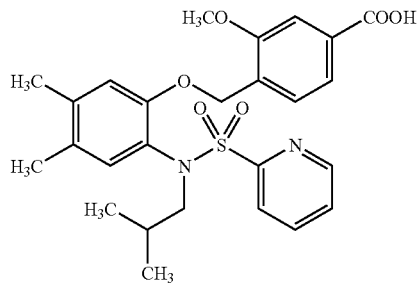

TLC: Rf 0.38 (chloroform:methanol=9:1); NMR: δ 8.47 (d, J=4.8 Hz, 1H), 7.75-7.60 (m, 3H), 7.56 (d, J=1.5 Hz, 1H), 7.20-7.15 (m, 2H), 7.12 (s, 1H), 6.65 (s, 1H), 4.84 (br, 1H), 4.66 (br, 1H), 3.92 (s, 3H), 3.61 (br, 2H), 2.22 (s, 3H), 2.18 (s, 3H), 1.80-1.60 (m, 1H), 0.96 (br, 6H).

EXAMPLE 2(85)

3-methoxy-4-[2-[N-isobutyl-N-(3-pyridylsulfonyl)amino]-4,5-dimethylphenoxymethyl]benzoic acid

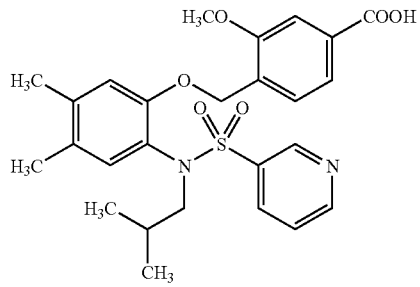

TLC: Rf 0.35 (chloroform:methanol=9:1); NMR: δ 8.86 (dd, J=2.1, 0.9 Hz, 1H), 8.57 (dd, J=5.1, 1.5 Hz, 1H), 7.75-7.65 (m, 2H), 7.61 (d, J=1.5 Hz, 1H), 7.30-7.20 (m, 2H), 6.92 (d, J=7.8 Hz, 1H), 6.72 (s, 1H), 4.75 (d, J=12.3 Hz, 1H), 4.43 (d, J=12.3 Hz, 1H), 3.93 (s, 3H), 3.75-3.60 (m, 1H), 3.45-3.35 (m, 1H), 2.29 (s, 3H), 2.25 (s, 3H), 1.85-1.65 (m, 1H), 1.09 (d, J=6.3 Hz, 3H), 0.92 (d, J=6.3 Hz, 3H).

EXAMPLE 2(86)

3-methyl-4-[2-[N-isobutyl-N-(3-pyridylsulfonyl)amino]-4,5-dimethylphenoxymethyl]benzoic acid

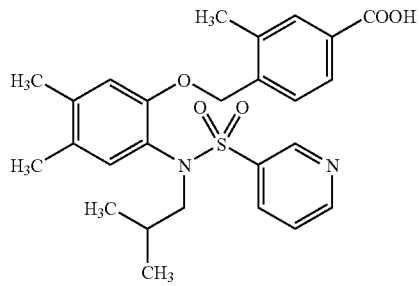

TLC: Rf 0.61 (chloroform:methanol:water=8:2:0.2); NMR(DMSO-d$_6$): δ 12.87 (brs, 1H), 8.64 (d, J=1.8 Hz, 1H), 8.59 (dd, J=4.8, 1.8 Hz, 1H), 7.91 (dt, J=8.1, 1.8 Hz, 1H), 7.73 (s, 1H), 7.67 (d, J=8.1 Hz, 1H), 7.35 (dd, J=8.1, 4.8 Hz, 1H), 7.04-6.96 (m, 3H), 4.92 (br, 1H), 4.66 (br, 1H), 3.48-3.22 (br, 2H), 2.23 (s, 3H), 2.22 (s, 3H), 2.15 (s, 3H), 1.49 (sep, J=6.9 Hz, 1H), 0.98-0.75 (m, 6H).

EXAMPLE 2(87)

3-methyl-4-[2-[N-isobutyl-N-(2-pyridylsulfonyl)amino]-4,5-dimethylphenoxymethyl]benzoic acid

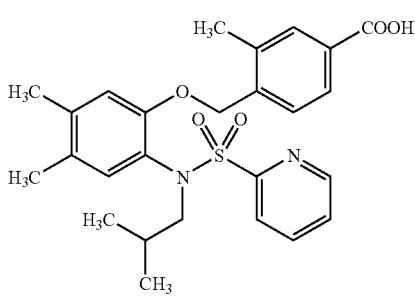

TLC: Rf 0.66 (chloroform:methanol:water=8:2:0.2); NMR(DMSO-d$_6$): δ 12.88 (s, 1H), 8.47 (d, J=4.5 Hz, 1H), 7.87 (dt, J=1.5, 7.8 Hz, 1H), 7.75 (s, 1H), 7.71 (d, J=7.8 Hz, 1H), 7.63 (d, J=7.8 Hz, 1H), 7.42 (ddd, J=7.8, 4.5, 1.5 Hz, 1H), 7.16 (d, J=7.8 Hz, 1H), 6.93 (s, 1H), 6.91 (s, 1H), 4.80 (br, 2H), 3.57 (d, J=6.6 Hz, 2H), 2.25 (s, 3H), 2.18 (s, 3H), 2.09 (s, 3H), 1.49 (sept, J=6.6 Hz, 1H), 0.81 (d, J=6.6 Hz, 6H).

EXAMPLE 2(88)

3-methyl-4-[2-[N-isobutyl-N-(3-pyridylsulfonyl)amino]-4-methyl-5-chlorophenoxymethyl]benzoic acid

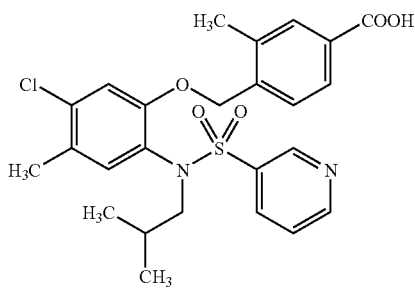

TLC: Rf 0.31 (chloroform:methanol=9:1); NMR: δ 8.83 (d, J=1.8 Hz, 1H), 8.61 (dd, J=5.4, 1.8 Hz, 1H), 7.93 (d, J=8.1 Hz 1H), 7.92 (s, 1H), 7.78 (dt, J=8.1, 1.8 Hz 1H), 7.34 (s, 1H), 7.23 (dd, J=8.1, 5.4 Hz, 1H), 6.95 (d, J=8.1 Hz, 1H), 6.94 (s, 1H), 4.88-4.65 and 4.54-4.34 (each m, each 1H), 3.71-3.53 and 3.43-3.24 (each m, each 1H), 2.36 (s, 3H), 2.27 (s, 3H), 1.78-1.63 (m, 1H), 1.08-0.79 (m, 6H).

EXAMPLE 2(89)

4-[2-[N-isobutyl-N-(2-pyridylsulfonyl)amino]-4,5-dimethylphenoxymethyl]benzoic acid

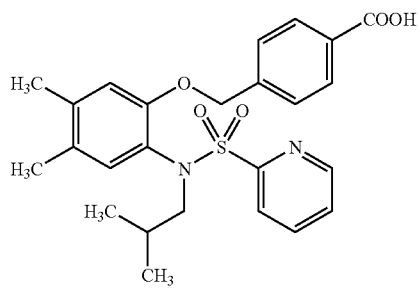

TLC: Rf 0.33 (chloroform:methanol=10:1); NMR: δ 8.46 (m, 1H), 8.09-8.05 (m, 2H), 7.71-7.60 (m, 2H), 7.28-7.25 (m, 2H), 7.20 (m, 1H), 7.09 (s, 1H), 6.62 (s, 1H), 5.02-4.50 (m, 2H), 3.83-3.43 (m, 2H), 2.21 (s, 3H), 2.17 (s, 3H), 1.67 (m, 1H), 1.04-0.82 (m, 6H).

EXAMPLE 2(90)

4-[2-[N-isopropyl-N-(2-pyridylsulfonyl)amino]-4-methyl-5-chlorophenoxymethyl]cinnamic acid

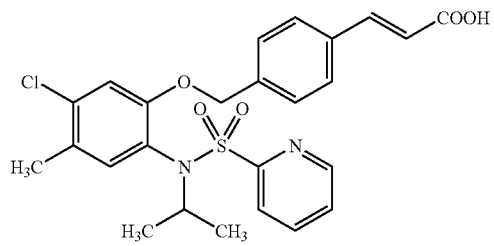

TLC: Rf 0.44 (chloroform:methanol=9:1); NMR: δ 8.70-8.60 (m, 1H), 7.84 (d, J=7.5 Hz, 1H), 7.79 (d, J=15.9 Hz, 1H), 7.71 (dt, J=1.8, 7.5 Hz, 1H), 7.55 (d, J=8.4 Hz, 2H), 7.39 (d, J=8.4 Hz, 2H), 7.35-7.25 (m, 1H), 6.99 (s, 1H), 6.96 (s, 1H), 6.48 (d, J=15.9 Hz, 1H), 4.96 (d, J=12.3 Hz, 1H), 4.92 (d, J=12.3 Hz, 1H), 4.75-4.60 (m, 1H), 2.26 (s, 3H), 1.14 (d, J=6.9 Hz, 3H), 1.11 (d, J=6.9 Hz, 3H).

EXAMPLE 2(91)

3-methyl-4-[2-[N-isobutyl-N-(2-pyridylsulfonyl)amino]-4-methyl-5-chlorophenoxymethyl]cinnamic acid

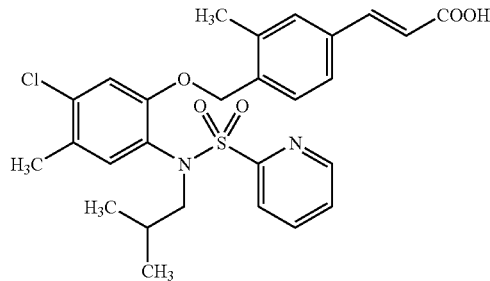

TLC: Rf 0.37 (chloroform:methanol=9:1); NMR: δ 8.50-8.40 (m, 1H), 7.77 (d, J=15.9 Hz, 1H), 7.75-7.60 (m, 2H), 7.40-7.35 (m, 2H), 7.25-7.20 (m, 2H), 7.15 (d, J=8.4 Hz, 1H), 6.90 (s, 1H), 6.49 (d, J=15.9 Hz, 1H), 4.73 (br, 2H), 3.60 (br, 2H), 2.29 (s, 3H), 2.28 (s, 3H), 1.70-1.55 (m, 1H), 0.91 (d, J=6.6 Hz, 6H).

EXAMPLE 2(92)

3-methyl-4-[2-[N-isobutyl-N-(2-pyridylsulfonyl)amino]-4,5-dimethylphenoxymethyl]cinnamic acid

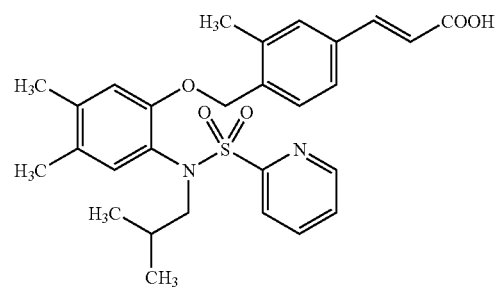

TLC: Rf 0.36 (dichloromethane:methanol 20:1); MS (FAB, Pos.): 509 (M+H)$^+$.

EXAMPLE 2(93)

4-[2-[N-isobutyl-N-(3-pyridylsulfonyl)amino]-4,5-dimethylphenoxymethyl]cinnamic acid

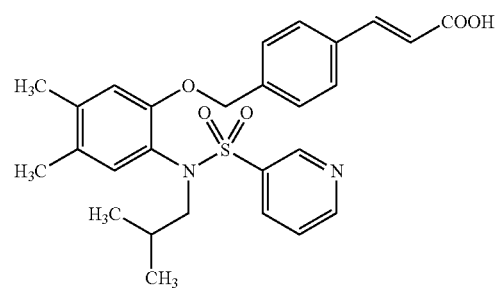

TLC: Rf 0.27 (chloroform:methanol=10:1); MS (APCI, Neg. 20V): 493 (M−H)$^-$.

EXAMPLE 2(94)

3-methyl-4-[2-[N-isobutyl-N-(3-pyridylsulfonyl)amino]-4,5-dimethylphenoxymethyl]cinnamic acid

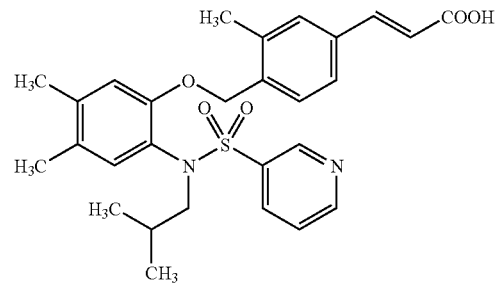

TLC: Rf 0.33 (dichloromethane:methanol=20:1); MS (FAB, Pos.): 509 (M+H)$^+$.

EXAMPLE 2(95)

3-chloro-4-[2-[N-isobutyl-N-(3-pyridylsulfonyl)amino]-4,5-dimethylphenoxymethyl]cinnamic acid

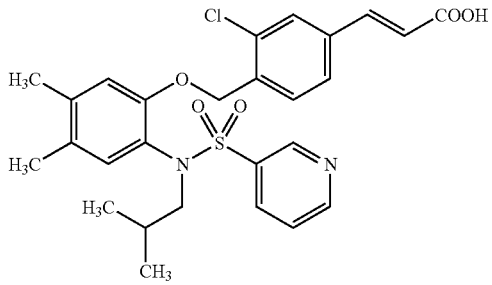

TLC: Rf 0.43 (chloroform:methanol=3:1); NMR: δ 8.88-8.82 (m, 1H), 8.61-8.52 (m, 1H), 7.75-7.68 (m, 1H), 7.61 (d, J=15.9 Hz, 1H), 7.52 (d, J=1.5 Hz, 1H), 7.47 (d, J=8.1 Hz, 1H), 7.32-7.20 (m, 2H), 6.97 (d, J=8.1 Hz, 1H), 6.70 (s, 1H), 6.50 (d, J=15.9 Hz, 1H), 4.88-4.75 and 4.53-4.41 (each m, each 1H), 3.74-3.58 and 3.48-3.32 (each m, each 1H), 2.29 and 2.25 (each s, each 3H), 1.82-1.63 (m, 1H), 1.15-0.82 (m, 6H).

EXAMPLE 2(96)

3-methyl-4-[2-[N-isobutyl-N-(3-pyridylsulfonyl)amino]-4-chloro-5-methylphenoxymethyl]cinnamic acid

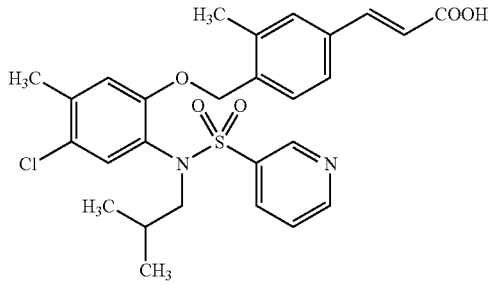

TLC: Rf 0.36 (chloroform:methanol=9:1); NMR(DMSO-$d_6$): δ 8.65 (m, 2H), 7.94 (m, 1H), 7.54 (d, J=16.2 Hz) and 7.51 (s) total 2H, 7.43 (d, J=8.1 Hz, 1H), 7.38 (dd, J=8.1, 4.8 Hz, 1H), 7.26 (s, 1H), 7.22 (s, 1H), 6.98 (d, J=8.1 Hz, 1H), 6.53 (d, J=16.2 Hz, 1H), 5.00-4.85 (m, 2H), 3.48-3.10 (m, 2H, covered with $H_2O$ in DMSO-$d_6$), 2.34 (s, 3H), 2.21 (s, 3H), 1.48 (m, 1H), 0.93 (m, 6H).

EXAMPLE 2(97)

3-chloro-4-[2-[N-isobutyl-N-(3-pyridylsulfonyl)amino]-5-trifluoromethylphenoxymethyl]cinnamic acid

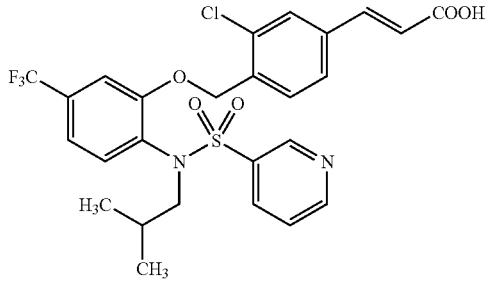

TLC: Rf 0.25 (chloroform:methanol=10:1); MS (APCI, Neg. 20V): 567 (M–H)⁻.

EXAMPLE 2(98)

3-methyl-4-[6-[N-isopropyl-N-(5-methyl-2-furylsulfonyl)amino]indan-5-yloxymethyl]benzoic acid

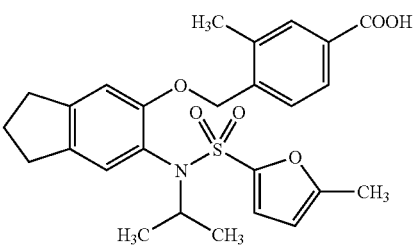

TLC: Rf 0.45 (chloroform:methanol=9:1); NMR(DMSO-$d_6$): δ 7.79 (s, 1H), 7.75 (d, J=8.0 Hz, 1H), 7.59 (d, J=8.0 Hz, 1H), 7.11 (s, 1H), 6.90 (d, J=3.3 Hz, 1H), 6.82 (s, 1H), 6.30-6.20 (m, 1H), 5.08 (s, 2H), 4.30-4.20 (m, 1H), 2.87 (t, J=7.5 Hz, 2H), 2.79 (t, J=7.5 Hz, 2H), 2.35 (s, 3H), 2.28 (s, 3H), 2.10-1.95 (m, 2H), 0.97 (d, J=6.6 Hz, 6H).

EXAMPLE 2(99)

3-methyl-4-[6-[N-isopropyl-N-(5-methyl-2-furylsulfonyl)amino]indan-5-yloxymethyl]cinnamic acid

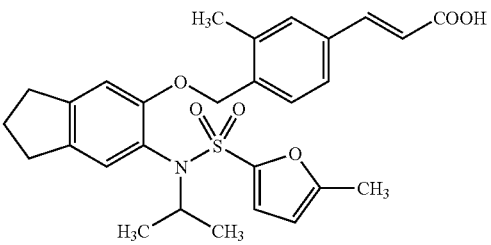

TLC: Rf 0.50 (chloroform:methanol=9:1); NMR(DMSO-$d_6$): δ 7.60-7.50 (m, 4H), 7.11 (s, 1H), 6.89 (d, J=3.3 Hz, 1H), 6.80 (s, 1H), 6.52 (d, J=16.2 Hz, 1H), 6.30-6.20 (m, 1H), 5.04 (d, J=13.5 Hz, 1H), 5.01 (d, J=13.5 Hz, 1H), 4.30-4.20 (m, 1H), 2.87 (t, J=7.2 Hz, 2H), 2.78 (t, J=7.2 Hz, 2H), 2.32 (s, 3H), 2.28 (s, 3H), 2.10-1.95 (m, 2H), 0.97 (d, J=6.6 Hz, 6H).

EXAMPLE 2(100)

4-[6-[N-isopropyl-N-(5-methyl-2-furylsulfonyl)amino]indan-5-yloxymethyl]cinnamic acid

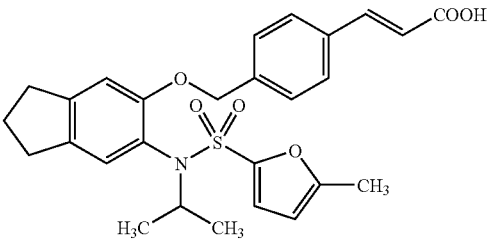

TLC: Rf 0.42 (chloroform:methanol=9:1); NMR: δ 7.79 (d, J=16.2 Hz, 1H), 7.57 (d, J=8.4 Hz, 2H), 7.51 (d, J=8.4 Hz, 2H), 6.89 (s, 1H), 6.84 (s, 1H), 6.80 (d, J=3.3 Hz, 1H), 6.46 (d, J=16.2 Hz, 1H), 6.02 (m, 1H), 5.14-5.00 (m, 2H), 4.46 (m, 1H), 2.91-2.80 (m, 4H), 2.31 (s, 3H), 2.14-2.02 (m, 2H), 1.11 (d, J=6.6 Hz, 3H), 1.10 (d, J=6.6 Hz, 3H).

EXAMPLE 2(101)

3-methyl-4-[2-[N-(2-methyl-2-propenyl)-N-(4-methyl-2-thiazolylsulfonyl)amino]-4-chloro-5-methylphenoxymethyl]benzoic acid

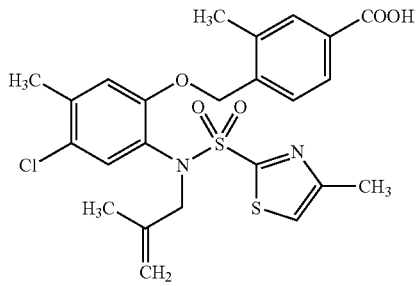

TLC: Rf 0.44 (chloroform:methanol=9:1); NMR(DMSO-$d_6$): δ 7.79 (s, 1H), 7.77 (d, J=8.4 Hz, 1H), 7.57 (s, 1H), 7.28 (d, J=8.4 Hz, 1H), 7.27 (s, 1H), 7.23 (s, 1H), 4.97 (m, 2H), 4.77 (m, 1H), 4.72 (m, 1H), 4.21 (m, 2H), 2.34 (s, 3H), 2.32 (s, 3H), 2.22 (s, 3H), 1.68 (s, 3H).

EXAMPLE 2(102)

4-[2-[N-(2-methyl-2-propenyl)-N-(4-methyl-2-thiazolylsulfonyl)amino]-5-trifluoromethyl phenoxymethyl]cinnamic acid

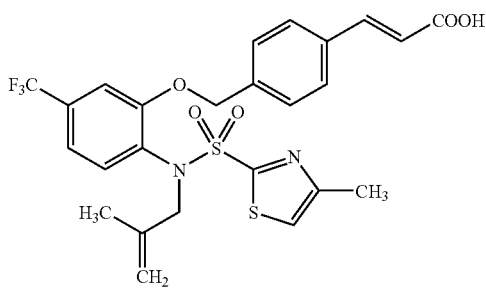

TLC: Rf 0.43 (chloroform:methanol=9:1); NMR: δ 7.80 (d, J=15.9 Hz, 1H), 7.58 (d, J=8.4 Hz, 2H), 7.45 (d, J=8.1 Hz, 1H), 7.33 (d, J=8.4 Hz, 2H), 7.30-7.20 (m, 1H), 7.15 (s, 1H), 6.99 (s, 1H), 6.50 (d, J=15.9 Hz, 1H), 4.97 (s, 2H), 4.77 (s, 1H), 4.72 (s, 1H), 4.37 (s, 2H), 2.35 (s, 3H), 1.77 (s, 3H)

EXAMPLE 2(103)

3-methyl-4-[2-[N-(2-methyl-2-propenyl)-N-(4-methyl-2-thiazolylsulfonyl)amino]-4,5-dimethylphenoxymethyl]benzoic acid

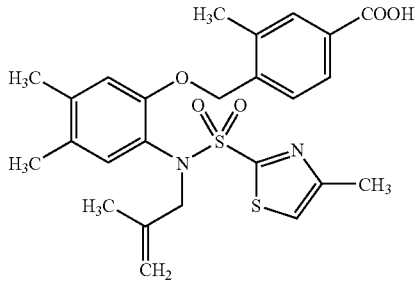

TLC: Rf 0.24 (dichloromethane:methanol=19:1); NMR (DMSO-$d_6$): δ 7.77-7.73 (m, 2H), 7.50 (brs, 1H), 7.23 (d, J=6.9 Hz, 1H), 6.99 (s, 1H), 6.96 (s, 1H), 4.87 (brs, 2H), 4.74 (brs, 1H), 4.71 (brs, 1H), 4.20 (brs, 2H), 2.28 (s, 3H), 2.19 (s, 3H), 2.16 (d, J=0.6 Hz, 3H), 2.11 (s, 3H), 1.68 (s, 3H).

EXAMPLE 2(104)

3-methyl-4-[6-[N-isopropyl-N-(2-thiazolylsulfonyl)amino]indan-5-yloxymethyl]benzoic acid

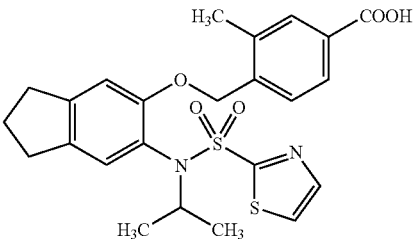

TLC: Rf 0.43 (chloroform:methanol=9:1); NMR: δ 7.96 (d, J=8.1 Hz, 1H), 7.93 (s, 1H), 7.89 (d, J=3.0 Hz, 1H), 7.58 (d, J=8.1 Hz, 1H), 7.46 (d, J=3.0 Hz, 1H), 6.95 (s, 1H), 6.86 (s, 1H), 5.05 and 4.99 (each d, J=13.5 Hz, each 1H), 4.69 (sept, J=6.6 Hz, 1H), 2.94-2.79 (m, 4H), 2.39 (s, 3H), 2.16-2.02 (m, 2H), 1.18 and 1.15 (each d, J=6.6 Hz, each 3H).

EXAMPLE 2(105)

3-methyl-4-[6-[N-isobutyl-N-(2-thiazolylsulfonyl)amino]indan-5-yloxymethyl]benzoic acid

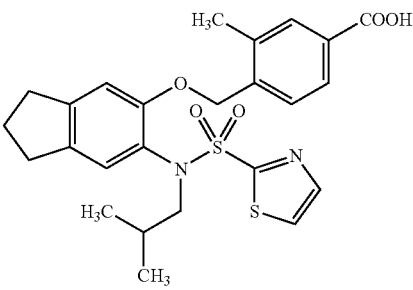

TLC: Rf 0.41 (chloroform:methanol=9:1); NMR: δ 7.93 (d, J=8.4 Hz, 1H), 7.92 (s, 1H), 7.71 (d, J=3.0 Hz, 1H), 7.35 (d, J=3.0 Hz, 1H), 7.31 (d, J=8.4 Hz, 1H), 7.15 (s, 1H), 6.77 (s, 1H), 5.02-4.64 (m, 2H), 3.81-3.43 (m, 2H), 2.95-2.76 (m, 4H), 2.34 (s, 3H), 2.17-2.01 (m, 2H), 1.82-1.64 (m, 1H), 1.08-0.83 (m, 6H).

EXAMPLE 2(106)

3-methyl-4-[6-[N-isopropyl-N-(4-methyl-2-thiazolylsulfonyl)amino]indan-5-yloxymethyl]benzoic acid

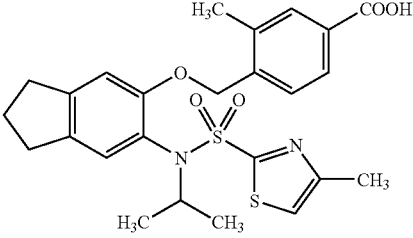

TLC: Rf 0.34 (dichloromethane:methanol=19:1); NMR: δ 7.97 (d, J=8.1 Hz, 1H), 7.94 (s, 1H), 7.57 (d, J=8.1 Hz, 1H), 7.00 (brs, 1H), 6.94 (s, 1H), 6.86 (s, 1H), 5.05 (d, J=13.5 Hz, 1H), 4.99 (d, J=13.5 Hz, 1H), 4.70 (m, 1H), 2.92-2.81 (m, 4H), 2.47 (s, 3H), 2.39 (s, 3H), 2.09 (m, 2H), 1.18 (d, J=6.6 Hz, 3H), 1.15 (d, J=6.6 Hz, 3H).

EXAMPLE 2(107)

4-[6-[N-isopropyl-N-(2-thiazolylsulfonyl)amino]indan-5-yloxymethyl]benzoic acid

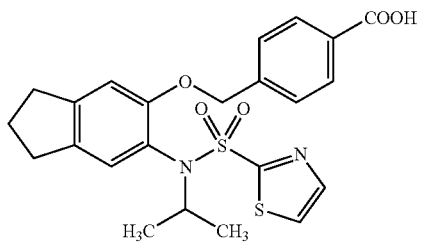

TLC: Rf 0.37 (chloroform:methanol=10:1); NMR: δ 8.13 (d, J=8.1 Hz, 2H), 7.88 (d, J=3.3 Hz, 1H), 7.51 (d, J=8.1 Hz, 2H), 7.44 (d, J=3.3 Hz, 1H), 6.95 (s, 1H), 6.84 (s, 1H), 5.06 (d, J=13.5 Hz, 1H), 5.05 (d, J=13.5 Hz, 1H), 4.71 (m, 1H), 2.92-2.78 (m, 4H), 2.14-2.02 (m, 2H), 1.18 (d, J=6.6 Hz 3H), 1.16 (d, J=6.6 Hz, 3H).

EXAMPLE 2(108)

4-[6-[N-isobutyl-N-(2-thiazolylsulfonyl)amino]indan-5-yloxymethyl]benzoic acid

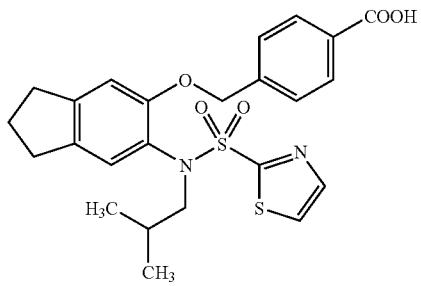

TLC: Rf 0.35 (chloroform:methanol=10:1); NMR: δ 8.11 (d, J=8.1 Hz, 2H), 7.71 (d, J=3.3 Hz, 1H), 7.35 (d, J=3.3 Hz, 1H), 7.34 (d, J=8.1 Hz, 2H), 7.15 (s, 1H), 6.75 (s, 1H), 4.97 (m, 1H), 4.77 (m, 1H), 3.80-3.47 (m, 2H), 2.89-2.82 (m, 4H), 2.15-2.01 (m, 2H), 1.73 (m, 1H), 1.05-0.85 (m, 6H).

EXAMPLE 2(109)

4-[6-[N-isopropyl-N-(4-methyl-2-thiazolylsulfonyl)amino]indan-5-yloxymethyl]benzoic acid

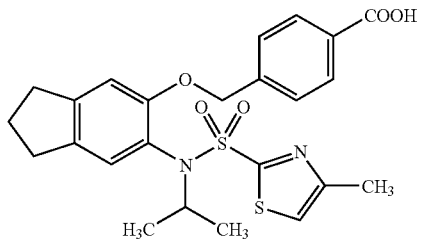

TLC: Rf 0.41 (chloroform:methanol=9:1); NMR: δ 8.11 (d, J=8.4 Hz, 2H), 7.50 (d, J=8.4 Hz, 2H), 6.98 (d, J=0.9 Hz, 1H), 6.94 (s, 1H), 6.84 (s, 1H), 5.11-5.00 (m, 2H), 4.71 (m, 1H), 2.91-2.79 (m, 4H), 2.47 (d, J=0.9 Hz, 3H), 2.15-2.03 (m, 2H), 1.18 (d, J=6.6 Hz, 3H), 1.15 (d, J=6.6 Hz, 3H).

EXAMPLE 2(110)

4-[6-[N-isopropyl-N-(4-methyl-2-thiazolylsulfonyl)amino]indan-5-yloxymethyl]cinnamic acid

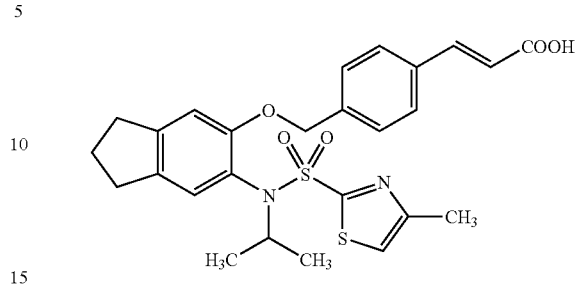

TLC: Rf 0.40 (chloroform:methanol=9:1); NMR: δ 7.79 (d, J=15.9 Hz, 1H), 7.56 (d, J=8.4 Hz, 2H), 7.45 (d, J=8.4 Hz, 2H), 6.98 (d, J=0.6 Hz, 1H), 6.92 (s, 1H), 6.85 (s, 1H), 6.47 (d, J=15.9 Hz, 1H), 5.06-4.95 (m, 2H), 4.70 (m, 1H), 2.92-2.78 (m, 4H), 2.46 (d, J=0.6 Hz, 3H), 2.16-2.01 (m, 2H), 1.17 (d, J=6.6 Hz, 3H), 1.14 (d, J=6.6 Hz, 3H).

EXAMPLE 2(111)

3-methyl-4-[6-[N-isopropyl-N-(4-methyl-2-thiazolylsulfonyl)amino]indan-5-yloxymethyl]cinnamic acid

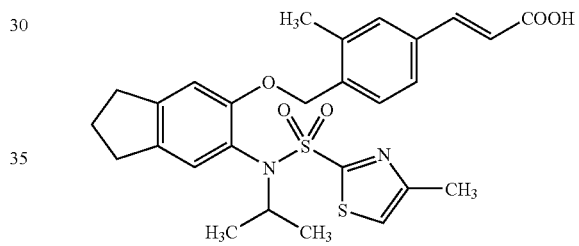

TLC: Rf 0.30 (dichloromethane:methanol=19:1); NMR (DMSO-d$_6$): δ 12.38 (brs, 1H), 7.57 (brs, 1H), 7.56 (d, J=15.9 Hz, 1H), 7.53 (s, 1H), 7.49 (brd, J=8.1 Hz, 1H), 7.39 (d, J=8.1 Hz, 1H), 7.13 (s, 1H), 6.83 (s, 1H), 6.53 (d, J=15.9 Hz, 1H), 4.99 (brs, 2H), 4.47 (m, 1H), 2.87 (m, 2H), 2.77 (m, 2H), 2.37 (d, J=0.9 Hz, 3H), 2.30 (s, 3H), 2.02 (m, 2H), 1.04 (d, J=6.6 Hz, 3H), 1.00 (d, J=6.6 Hz, 3H).

EXAMPLE 2(112)

4-[2-[N-isopropyl-N-(2-thiazolylsulfonyl)amino]-4,5-dimethylphenoxymethyl]benzoic acid

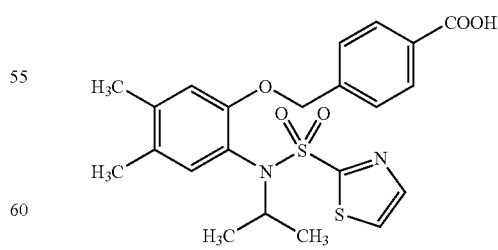

TLC: Rf 0.57 (chloroform:methanol=9:1); NMR: δ 8.10 (d, J=8.1 Hz, 2H), 7.86 (d, J=3.0 Hz, 1H), 7.49 (d, J=8.1 Hz, 2H), 7.43 (d, J=3.0 Hz, 1H), 6.85 (s, 1H), 6.75 (s, 1H), 5.04 (s, 2H), 4.72 (sept, J=6.9 Hz, 1H), 2.23 (s, 3H), 2.15 (s, 3H), 1.19 (d, J=6.9 Hz, 3H), 1.15 (d, J=6.9 Hz, 3H).

EXAMPLE 2(113)

4-[2-[N-isobutyl-N-(2-thiazolylsulfonyl)amino]-4,5-dimethylphenoxymethyl]benzoic acid

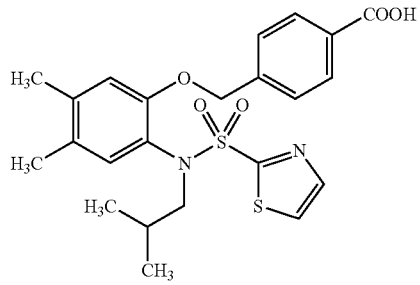

TLC: Rf 0.56 (chloroform:methanol=9:1); NMR: δ 8.11 (d, J=8.4 Hz, 2H), 7.70 (d, J=3.0 Hz, 1H), 7.36-7.32 (m, 3H), 7.07 (s, 1H), 6.66 (s, 1H), 5.10-4.65 (m, 2H), 3.80-3.45 (m, 2H), 2.22 (s, 3H), 2.18 (s, 3H), 1.71 (sept, J=6.9 Hz, 1H), 1.15-0.95 (m, 6H).

EXAMPLE 2(114)

4-[2-[N-isopropyl-N-(2-thiazolylsulfonyl)amino]-4,5-dimethylphenoxymethyl]cinnamic acid

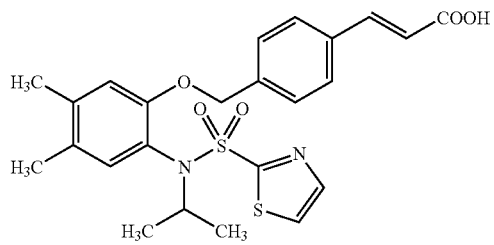

TLC: Rf 0.56 (chloroform:methanol=9:1); NMR: δ 7.86 (d, J=3.0 Hz, 1H), 7.79 (d, J=15.9 Hz, 1H), 7.56 (d, J=8.4 Hz, 2H), 7.42 (d, J=8.4 Hz, 2H), 7.42 (d, J=3.0 Hz, 1H), 6.84 (s, 1H), 6.76 (s, 1H), 6.46 (d, J=15.9 Hz, 1H), 5.04 (d, J=11.7 Hz, 1H), 4.98 (d, J=11.7 Hz, 1H), 4.71 (sept, J=6.6 Hz, 1H), 2.23 (s, 3H), 2.13 (s, 3H), 1.18 (d, J=6.6 Hz, 3H), 1.15 (d, J=6.6 Hz, 3H).

EXAMPLE 2(115)

4-[2-[N-isobutyl-N-(2-thiazolylsulfonyl)amino]-4,5-dimethylphenoxymethyl]cinnamic acid

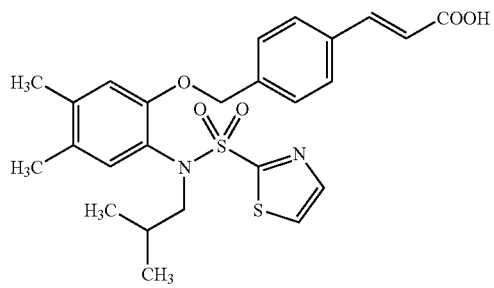

TLC: Rf 0.58 (chloroform:methanol=9:1); NMR: δ 7.79 (d, J=15.9 Hz, 1H), 7.67 (d, J=3.0 Hz, 1H), 7.55 (d, J=8.4 Hz, 2H), 7.34 (d, J=3.0 Hz, 1H), 7.27 (d, J=8.4 Hz, 2H), 7.05 (s, 1H), 6.67 (s, 1H), 6.47 (d, J=15.9 Hz, 1H), 5.00-4.62 (m, 2H), 3.80-3.45 (m, 2H), 2.22 (s, 3H), 2.17 (s, 3H), 1.70 (sept, J=6.6 Hz, 1H), 1.10-0.96 (m, 6H).

EXAMPLE 2(116)

4-[6-[N-isopropyl-N-(2-thiazolylsulfonyl)amino]indan-5-yloxymethyl]cinnamic acid

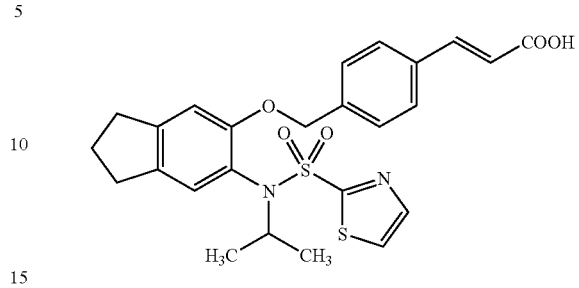

TLC: Rf 0.39 (chloroform:methanol=10:1); NMR: δ 7.87 (d, J=3.3 Hz, 1H), 7.80 (d, J=15.9 Hz, 1H), 7.56 (d, J=7.8 Hz, 2H), 7.45 (d, J=7.8 Hz, 2H), 7.44 (d, J=3.3 Hz, 1H), 6.94 (s, 1H), 6.85 (s, 1H), 6.48 (d, J=15.9 Hz, 1H), 5.01 (d, J=13.2 Hz, 1H), 5.00 (d, J=13.2 Hz, 1H), 4.70 (m, 1H), 2.91-2.79 (m, 4H), 2.14-2.01 (m, 2H), 1.17 (d, J=6.6 Hz, 3H), 1.15 (d, J=6.6 Hz, 3H).

EXAMPLE 2(117)

4-[6-[N-isobutyl-N-(2-thiazolylsulfonyl)amino]indan-5-yloxymethyl]cinnamic acid

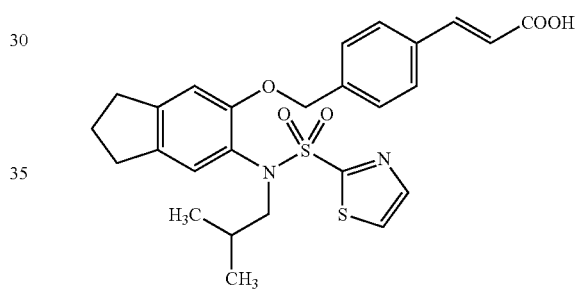

TLC: Rf 0.40 (chloroform:methanol=10:1); NMR: δ 7.80 (d, J=15.9 Hz, 1H), 7.69 (d, J=3.3 Hz, 1H), 7.55 (d, J=8.4 Hz, 2H), 7.34 (d, J=3.3 Hz, 1H), 7.27 (d, J=8.4 Hz, 2H), 7.14 (s, 1H), 6.75 (s, 1H), 6.48 (d, J=15.9 Hz, 1H), 4.92 (m, 1H), 4.70 (m, 1H), 3.78-3.46 (m, 2H), 2.90-2.80 (m, 4H), 2.14-2.01 (m, 2H), 1.72 (m, 1H), 1.02-0.83 (m, 6H).

EXAMPLE 2(118)

3-methyl-4-[2-[N-isopropyl-N-(2-thiazolylsulfonyl)amino]-4,5-dimethylphenoxymethyl]benzoic acid

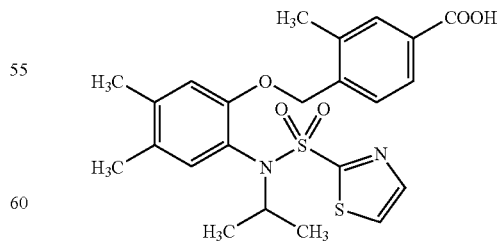

TLC: Rf 0.27 (chloroform:methanol=9:1); NMR: δ 8.00-7.90 (m, 2H), 7.87 (d, J=3.0 Hz, 1H), 7.55 (d, J=7.8 Hz, 1H), 7.44 (d, J=3.0 Hz, 1H), 6.85 and 6.77 (each s, each 1H), 5.09-4.92 (m, 2H), 4.78-4.62 (m, 1H), 2.39 (s, 3H), 2.25 (s, 3H), 2.16 (s, 3H), 1.19 and 1.15 (each d, J=6.6 Hz, each 3H).

EXAMPLE 2(119)

3-methyl-4-[2-[N-isobutyl-N-(2-thiazolylsulfonyl)amino]-4,5-dimethylphenoxymethyl]benzoic acid

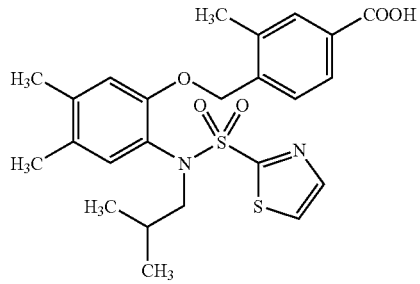

TLC: Rf 0.27 (chloroform:methanol=9:1); NMR: δ 7.95-7.89 (m, 2H), 7.70 and 7.34 (each d, J=3.3 Hz, each 1H), 7.32-7.29 (m, 1H), 7.06 and 6.69 (each s, each 1H), 5.00-4.68 (m, 2H), 3.78-3.48 (m, 2H), 2.34 (s, 3H), 2.23 (s, 3H), 2.18 (s, 3H), 1.80-1.65 (m, 1H), 1.08-0.82 (m, 6H).

EXAMPLE 2(120)

3-methyl-4-[2-[N-isopropyl-N-(2-thiazolylsulfonyl)amino]-4,5-dimethylphenoxymethyl]cinnamic acid

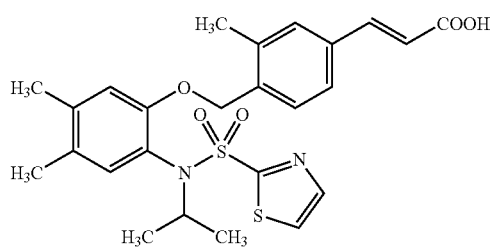

TLC: Rf 0.25 (chloroform:methanol=9:1); NMR: δ 7.87 (d, J=3.0 Hz, 1H), 7.77 (d, J=16.2 Hz, 1H), 7.52-7.32 (m, 4H), 6.83 and 6.79 (each s, each 1H), 6.46 (d, J=16.2 Hz, 1H), 5.05-4.87 (m, 2H), 4.75-4.62 (m, 1H), 2.36 (s, 3H), 2.25 (s, 3H), 2.15 (s, 3H), 1.17 and 1.13 (each d, J=6.6 Hz, each 3H).

EXAMPLE 2(121)

3-methyl-4-[2-[N-isobutyl-N-(2-thiazolylsulfonyl)amino]-4,5-dimethylphenoxymethyl]cinnamic acid

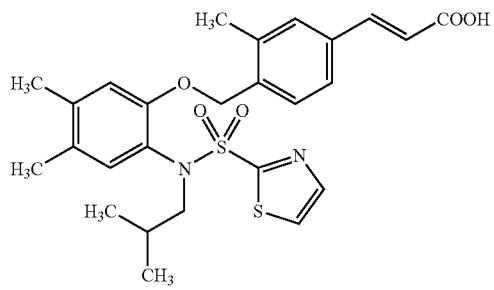

TLC: Rf 0.25 (chloroform:methanol=9:1); NMR: δ 7.76 (d, J=16.2 Hz, 1H), 7.69 (d, J=3.0 Hz, 1H), 7.42-7.35 (m, 2H), 7.34 (d, J=3.0 Hz, 1H), 7.25-7.19 (m, 1H), 7.05 and 6.70 (each s, each 1H), 6.47 (d, J=16.2 Hz, 1H), 4.95-4.62 (m, 2H), 3.75-3.48 (m, 2H), 2.31 (s, 3H), 2.24 (s, 3H), 2.18 (s, 3H), 1.78-1.62 (m, 1H), 1.78-1.62 (m, 6H).

EXAMPLE 2(122)

3-methyl-4-[6-[N-isopropyl-N-(2-thiazolylsulfonyl)amino]indan-5-yloxymethyl]cinnamic acid

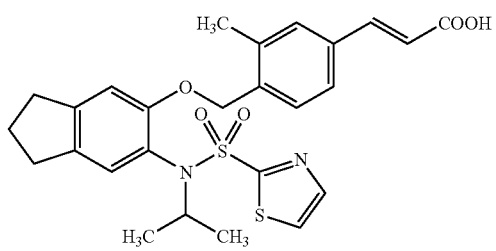

TLC: Rf 0.44 (chloroform:methanol=9:1); NMR: δ 7.88 (d, J=3.0 Hz, 1H), 7.77 (d, J=16.2 Hz, 1H), 7.51 (d, J=8.1 Hz, 1H), 7.45 (d, J=3.0 Hz, 1H), 7.42 (d, J=8.1 Hz, 1H), 7.38 (s, 1H), 6.93 (s, 1H), 6.87 (s, 1H), 6.46 (d, J=16.2 Hz, 1H), 5.02 and 4.95 (each d, J=12.9 Hz, each 1H), 4.68 (sept, J=6.6 Hz, 1H) 2.94-2.78 (m, 4H), 2.36 (s, 3H), 2.16-2.02 (m, 2H), 1.17 and 1.14 (each d, J=6.6 Hz, each 3H).

EXAMPLE 2(123)

3-methyl-4-[6-[N-isobutyl-N-(2-thiazolylsulfonyl)amino]indan-5-yloxymethyl]cinnamic acid

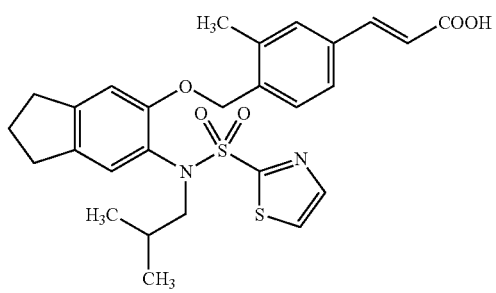

TLC: Rf 0.39 (chloroform:methanol=9:1); NMR(DMSO-$d_6$): δ 7.98 (d, J=3.0 Hz, 1H), 7.87 (d, J=3.0 Hz, 1H), 7.56 (d, J=16.2 Hz, 1H), 7.52 (s, 1H), 7.50 (d, J=8.1 Hz, 1H), 7.18 (d, J=8.1 Hz, 1H), 7.06 (s, 1H), 7.00 (s, 1H), 6.54 (d, J=16.2 Hz, 1H), 5.04-4.66 (m, 2H), 3.57-3.37 (m, 2H), 2.93-2.68 (m, 4H), 2.27 (s, 3H), 2.11-1.93 (m, 2H), 1.64-1.46 (m, 1H), 0.94-0.74 (m, 6H).

EXAMPLE 2(124)

4-[3-[N-isobutyl-N-(5-methyl-2-furylsulfonyl)amino]-2-naphthyloxymethyl]benzoic acid

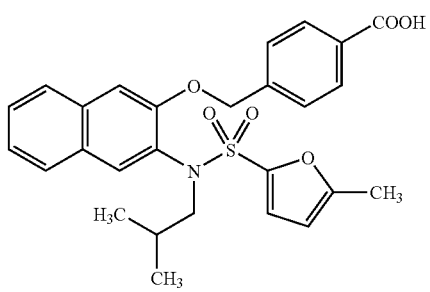

TLC: Rf 0.33 (chloroform:methanol=9:1); NMR (CD$_3$OD): δ 8.05 (d, J=8.4 Hz, 2H), 7.82-7.75 (m, 3H), 7.53 (d, J=8.4 Hz, 2H), 7.51-7.35 (m, 3H), 6.71 (d, J=3.3 Hz, 1H), 6.05 (m, 1H), 5.42-4.95 (br, 2H), 3.62 (d, J=7.5 Hz, 2H), 2.13 (s, 3H), 1.79-1.61 (m, 1H), 0.94 (d, J=6.3 Hz, 6H).

REFERENCE EXAMPLE 4

N-[4,5-dimethyl-2-(2-methyl-4-cyanophenylmethyloxy)phenyl]-N-isobutyl-(5-methyl-2-furyl)sulfonylamide

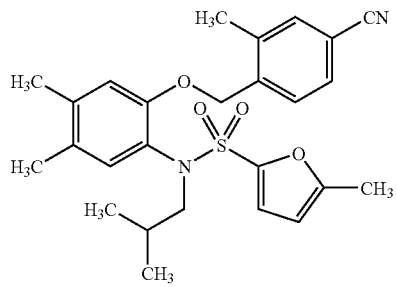

Under atmosphere of argon, a solution of 3-methyl-4-[2-[N-isobutyl-N-(5-methyl2-furylsulfonyl)amino]-4,5-dimethylphenoxymethyl]benzoic acid prepared in example 2 (178 mg) in dichloromethane (1.5 ml) was cooled to 0° C., then oxalyl chloride (48 µl) and a catalytic amount of N,N-dimethylformamide was added thereto. After the solution was stirred for 1 hour at room temperature, the reaction mixture was concentrated under reduced pressure, and azeotroped with toluene. Under atmosphere of argon, the residue was dissolved in dichloromethane (1.5 ml), and cooled to 0° C. The solution was added by 28% aqueous ammonia (1 ml) and stirred for 5 minutes. The solution was added by water and ethyl acetate. The organic layer was washed, dried and concentrated under reduced pressure. Under atmosphere of argon, the residue was dissolved in dichloromethane (1.5 ml), and cooled to 0° C. The solution was added by pyridine (0.18 ml) and trifluoromethanesulfonic acid anhydride (0.12 ml) and stirred for 50 minutes. The reaction mixture was poured into water, then it was added by ethyl acetate. The organic layer was washed, dried and concentrated under reduced pressure. The residue was purified by column chromatography on silica gel (hexane-ethyl acetate) to give the title compound (149 mg) having the following physical data.

TLC: Rf 0.74 (n-hexane:ethyl acetate=1:1).

EXAMPLE 3

N-[4,5-dimethyl-2-[2-methyl-4-(5-tetrazolyl)phenylmethyloxy]phenyl]-N-isobutyl-(5-methyl-2-furyl)sulfonylamide

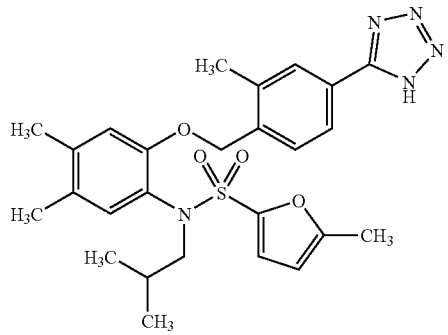

To N-[4,5-dimethyl-2-(2-methyl-4-cyanophenylmethyloxy)phenyl]-N-isobutyl-(5-methyl-2-furyl)sulfonylamide prepared in reference example 4 (79 mg), trimethyltin azide (43 mg) was added, and mixture was refluxed for 7 hours, then stirred for 1 day at room temperature. The reaction mixture was added by methanol (3 ml) and 2N hydrochloric acid (2 ml), then stirred for 2 hours. The solution was added by water and ethyl acetate. The organic layer was washed, dried and concentrated under reduced pressure. The residue was washed by hexane-ethyl acetate to give the title compound (81 mg) having the following physical data.

TLC: Rf 0.52 (chloroform:methanol:water=8:2:0.2); MS (FAB, Pos.): 510 (M+H)+.

EXAMPLE 3(1)~EXAMPLE 3(38)

By the same procedures as described in reference examples 1-3 and example 3, the title compounds having the following physical data were obtained.

EXAMPLE 3(1)

N-[4-chloro-5-methyl-2-[2-methyl-4-(5-tetrazolyl)phenylmethyloxy]phenyl]-N-isobutyl-(5-methyl-2-furyl)sulfonylamide

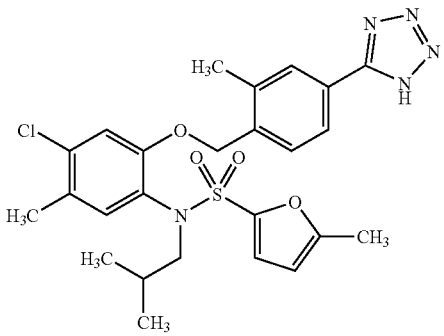

TLC: Rf 0.40 (dichloromethane:methanol=10:1); MS (FAB, Pos.): 530 (M)+.

EXAMPLE 3(2)

N-[4,5-dimethyl-2-[2-methyl-4-(5-tetrazolyl)phenylmethyloxy]phenyl]-N-isopropyl-(5-methyl-2-furyl)sulfonylamide

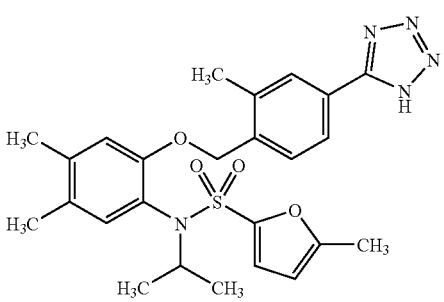

TLC: Rf 0.52 (chloroform:methanol:water=8:2:0.2); MS (FAB, Pos.): 496 (M+H)+.

EXAMPLE 3(3)

N-[4-chloro-5-methyl-2-[4-(5-tetrazolyl)phenylmethyloxy]phenyl]-N-isobutyl-(5-methyl-2-furyl)sulfonylamide

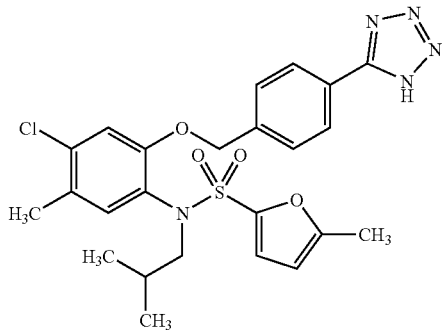

TLC: Rf 0.39 (chloroform:methanol:water=8:2:0.2); NMR: δ 8.05 (d, J=8.1 Hz, 2H), 7.47 (d, J=8.1 Hz, 2H), 7.08 (s, 1H), 6.93 (s, 1H), 6.80 (d, J=3.3 Hz, 1H), 6.01 (m, 1H), 5.15-4.80 (br, 2H), 3.46 (d, J=7.2 Hz, 2H), 2.27 (s, 3H), 2.19 (s, 3H), 1.64 (m, 1H), 0.88 (d, J=6.9 Hz, 6H).

EXAMPLE 3(4)

N-[4,5-dimethyl-2-[4-(5-tetrazolyl)phenylmethyloxy]phenyl]-N-isopropyl-(5-methyl-2-furyl)sulfonylamide

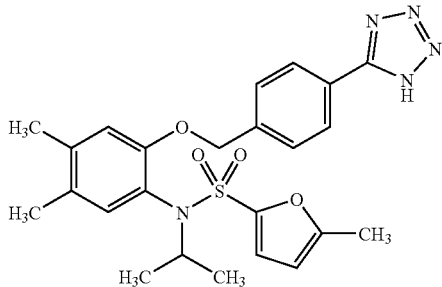

TLC: Rf 0.41 (chloroform:methanol water=8:2:0.2); NMR(DMSO-$d_6$): δ 8.04 (d, J=8.1 Hz, 2H), 7.66 (d, J=8.1 Hz, 2H), 7.01 (s, 1H), 6.91 (d, J=3.3 Hz, 1H), 6.76 (s, 1H), 6.29-6.23 (m, 1H), 5.18 and 5.12 (each d, J=13.5 Hz, each 1H), 4.30 (sept, J=6.6 Hz, 1H), 2.30 (s, 3H), 2.23 (s, 3H), 2.14 (s, 3H), 1.02 and 1.00 (each d, J=6.6 Hz, each 3H).

EXAMPLE 3(5)

N-[4,5-dimethyl-2-[4-(5-tetrazolyl)phenylmethyloxy]phenyl]-N-isobutyl-(5-methyl-2-furyl)sulfonylamide

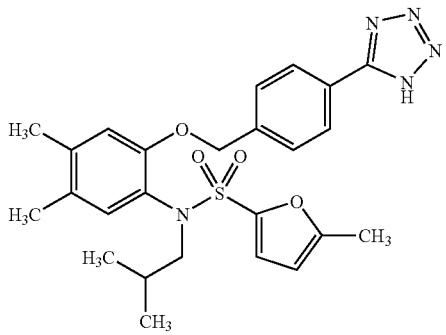

TLC: Rf 0.37 (chloroform:methanol water=8:2:0.2); NMR(DMSO-$d_6$): δ 8.04 (d, J=8.4 Hz, 2H), 7.53 (d, J=8.4 Hz, 2H), 6.96 (s, 1H), 6.92 (s, 1H), 6.82 (d, J=3.3 Hz, 1H), 6.19-6.13 (m, 1H), 5.28-4.82 (m, 2H), 3.38 (d, J=6.9 Hz, 2H), 2.21 (s, 3H), 2.14 (s, 6H), 1.64-1.44 (m, 1H), 0.85 (d, J=6.6 Hz, 6H).

EXAMPLE 3(6)

N-[4-trifluoromethyl-2-[4-(5-tetrazolyl)phenylmethyloxy]phenyl]-N-isobutyl-2-thiazolylsulfonylamide

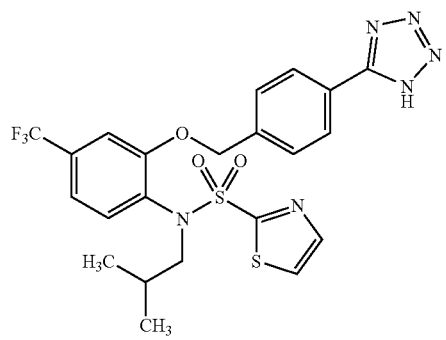

TLC: Rf 0.46 (chloroform:methanol:water=8:2:0.2); NMR: δ 8.09 (d, J=8.4 Hz, 2H), 7.76 (d, J=2.7 Hz, 1H), 7.49-7.44 (m, 4H), 7.27 (m, 1H), 7.19 (s, 1H), 5.01 (br, 2H), 3.63 (d, J=7.2 Hz, 2H), 1.67 (m, 1H), 0.97 (d, J=7.2 Hz, 6H).

EXAMPLE 3(7)

N-[4-trifluoromethyl-2-[4-(5-tetrazolyl)phenylmethyloxy]phenyl]-N-isopropyl-2-thiazolylsulfonylamide

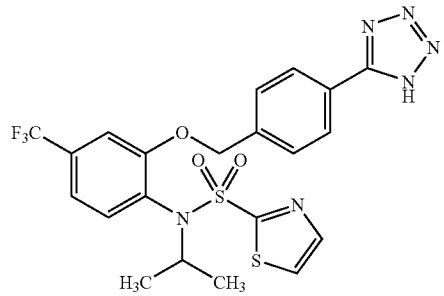

TLC: Rf 0.31 (chloroform:methanol:water=8:2:0.2); NMR: 8.07 (d, J=8.1 Hz, 2H), 7.94 (d, J=3.3 Hz, 1H), 7.60 (d, J=8.1 Hz, 2H), 7.56 (d, J=3.3 Hz, 1H), 7.36-7.20 (m, 3H), 5.17 and 5.13 (each d, J=12.0 Hz, each 1H), 4.68 (sept, J=6.6 Hz, 1H), 1.15 and 1.14 (each d, J=6.6 Hz, each 3H).

EXAMPLE 3(8)

N-[4-trifluoromethyl-2-[4-(5-tetrazolyl)phenylmethyloxy]phenyl]-N-isobutyl-(4-methyl-2-thiazolyl)sulfonylamide

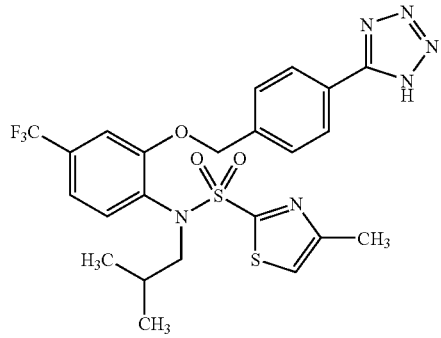

TLC: Rf 0.31 (chloroform:methanol:water=8:2:0.2); NMR: δ 8.04 (d, J=8.1 Hz, 2H), 7.42 (d, J=8.1 Hz, 1H), 7.37 (d, J=8.1 Hz, 2H), 7.23 (m, 1H), 7.16 (s, 1H), 6.99 (s, 1H), 4.95 (br, 2H), 3.56 (d, J=6.6 Hz, 2H), 2.26 (s, 3H), 1.59 (sept, J=6.6 Hz, 1H), 0.84 (d, J=6.6 Hz, 6H).

EXAMPLE 3(9)

N-[4-trifluoromethyl-2-[4-(5-tetrazolyl)phenylmethyloxy]phenyl]-N-isopropyl-(4-methyl-2-thiazolyl)sulfonylamide

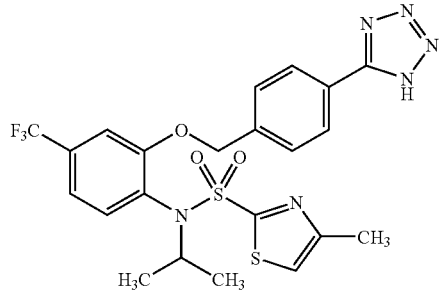

TLC: Rf 0.42 (chloroform:methanol:water=8:2:0.2); NMR: δ 7.93 (d, J=8.1 Hz, 2H), 7.41 (d, J=8.1 Hz, 2H), 7.24-7.16 (m, 3H), 7.02 (s, 1H), 5.10-4.92 (m, 2H), 4.57 (quint, J=6.6 Hz, 1H), 2.39 (s, 3H), 1.04 (d, J=6.6 Hz, 3H), 1.02 (d, J=6.6 Hz, 3H).

EXAMPLE 3(10)

N-[4-chloro-5-methyl-2-[2-methyl-4-(5-tetrazolyl)phenylmethyloxy]phenyl]-N-isobutyl-(4-methyl-2-thiazolyl)sulfonylamide

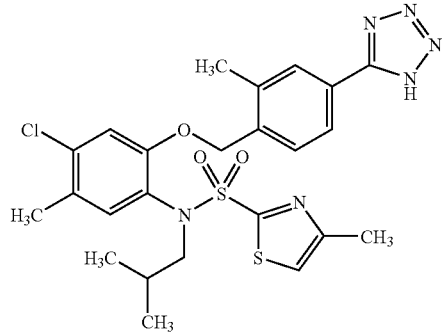

TLC: Rf 0.24 (dichloromethane:methanol=10:1); MS (FAB, Pos.): 547 (M)+.

EXAMPLE 3(11)

N-[4-chloro-5-methyl-2-[4-(5-tetrazolyl)phenylmethyloxy]phenyl]-N-isopropyl-(4-methyl-2-thiazolyl)sulfonylamide

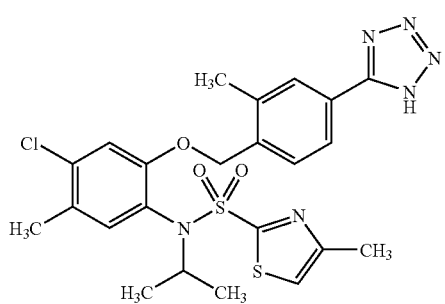

TLC: Rf 0.24 (dichloromethane:methanol=10:1); MS (FAB, Pos.): 533 (M)+.

EXAMPLE 3(12)

N-[4-trifluoromethyl-2-[2-methyl-4-(5-tetrazolyl)phenylmethyloxy]phenyl]-N-isopropyl-(4-methyl-2-thiazolyl)sulfonylamide

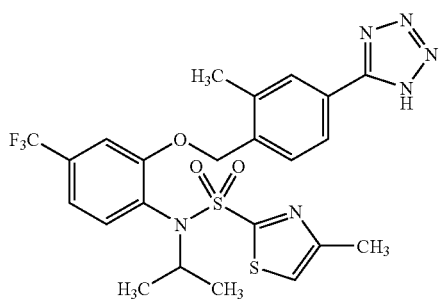

TLC: Rf 0.38 (chloroform:methanol:water=8:2:0.2); NMR: δ 7.91 (s, 1H), 7.82 (d, J=7.8 Hz, 1H), 7.64 (d, J=7.8 Hz, 1H), 7.33-7.20 (m, 3H), 7.12 (s, 1H), 5.11 (s, 2H), 4.65 (sept, J=6.6 Hz, 1H), 2.49 (s, 3H), 2.43 (s, 3H), 1.12 (d, J=6.6 Hz, 6H).

EXAMPLE 3(13)

N-[4-trifluoromethyl-2-[2-methyl-4-(5-tetrazolyl)phenylmethyloxy]phenyl]-N-isobutyl-(4-methyl-2-thiazolyl)sulfonylamide

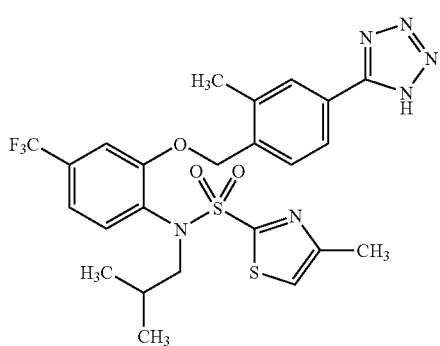

TLC: Rf 0.34 (chloroform:methanol:water=8:2:0.2); NMR: δ 7.97 (s, 1H), 7.89 (d, J=8.1 Hz, 1H), 7.48-7.38 (m, 2H), 7.34-7.18 (m, 2H), 7.05 (s, 1H), 5.12-4.84 (m, 2H), 3.59 (d, J=7.2 Hz, 2H), 2.41 (s, 3H), 2.34 (s, 3H), 1.74-1.58 (m, 1H), 0.89 (d, J=6.6 Hz, 6H).

EXAMPLE 3(14)

N-[4,5-dimethyl-2-[2-methyl-4-(5-tetrazolyl)phenylmethyloxy]phenyl]-N-isobutyl-(4-methyl-2-thiazolyl)sulfonylamide

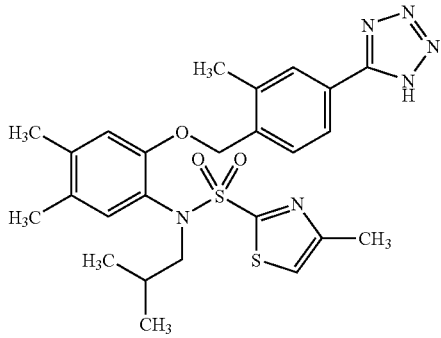

TLC: Rf 0.46 (chloroform:methanol:water=8:2:0.2); MS (FAB, Pos.): 527 (M+H)+.

EXAMPLE 3(15)

N-[4,5-dimethyl-2-[2-methyl-4-(5-tetrazolyl)phenylmethyloxy]phenyl]-N-isopropyl-(4-methyl-2-thiazolyl)sulfonylamide

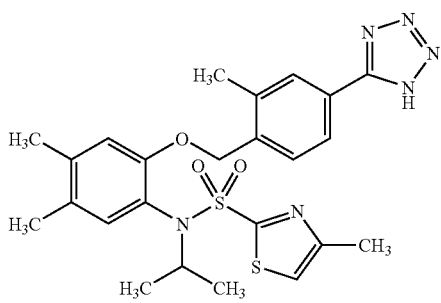

TLC: Rf 0.52 (chloroform:methanol:water=8:2:0.2); MS (FAB, Pos.): 513 (M+H)+.

EXAMPLE 3(16)

N-[4,5-dimethyl-2-[4-(5-tetrazolyl)phenylmethyloxy]phenyl]-N-isopropyl-(4-methyl-2-thiazolyl)sulfonylamide

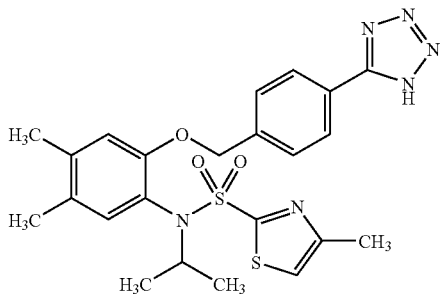

TLC: Rf 0.29 (chloroform:methanol=5:1); MS (APCI, Neg. 20V): 497 (M−H)−.

EXAMPLE 3(17)

N-[4,5-dimethyl-2-[4-(5-tetrazolyl)phenylmethyloxy]phenyl]-N-isobutyl-(4-methyl-2-thiazolyl)sulfonylamide

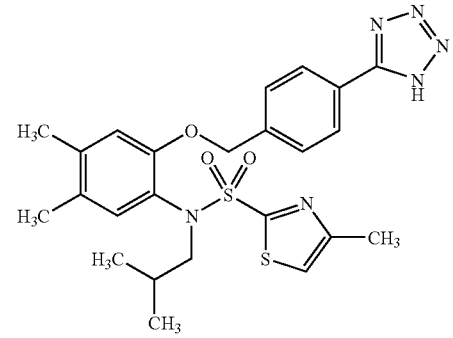

TLC: Rf 0.26 (chloroform:methanol=5:1); MS (APCI, Neg. 20V): 511 (M−H)−.

EXAMPLE 3(18)

N-[4-chloro-5-methyl-2-[4-(5-tetrazolyl)phenylmethyloxy]phenyl]-N-isopropyl-(4-methyl-2-thiazolyl)sulfonylamide

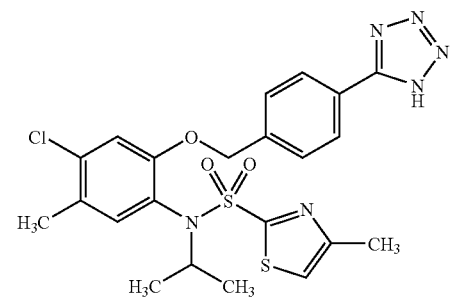

TLC: Rf 0.31 (chloroform:methanol:water=8:2:0.2); NMR: δ 8.02 (d, J=8.4 Hz, 2H), 7.51 (d, J=8.4 Hz, 2H), 7.10 (s, 1H), 6.98 (s, 2H), 5.03 and 4.95 (each d, J=12.6 Hz, each 1H), 4.65 (sept, J=6.6 Hz, 1H), 2.46 (s, 3H), 2.26 (s, 3H), 1.13 and 1.12 (each d, J=6.6 Hz, each 3H).

EXAMPLE 3(19)

N-[4-chloro-5-methyl-2-[4-(5-tetrazolyl)phenylmethyloxy]phenyl]-N-isobutyl-(4-methyl-2-thiazolyl)sulfonylamide

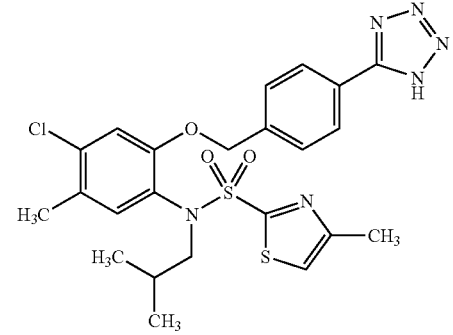

TLC: Rf 0.29 (chloroform:methanol:water=8:2:0.2); NMR(DMSO-d6): δ 8.05 (d, J=8.4 Hz, 2H), 7.52 (s, 1H), 7.45 (d, J=8.4 Hz, 2H), 7.26 (s, 1H), 7.25 (s, 1H), 5.25-4.73 (m, 2H), 3.62-3.40 (m, 2H), 2.26 (s, 3H), 2.22 (s, 3H), 1.66-1.50 (m, 1H), 0.88 (d, J=6.6 Hz, 6H).

EXAMPLE 3(20)

N-[4,5-dimethyl-2-[2-methoxy-4-(5-tetrazolyl)phenylmethyloxy]phenyl]-N-isopropyl-(4-methyl-2-thiazolyl)sulfonylamide

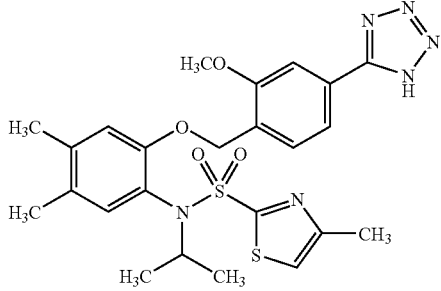

TLC: Rf 0.31 (chloroform:methanol=5:1); NMR (CDCl$_3$+1 drop of CD$_3$OD): δ 7.71 (d, J=7.5 Hz, 1H), 7.70 (d, J=1.5 Hz, 1H), 7.51 (dd, J=7.5, 1.5 Hz, 1H), 7.07 (d, J=0.9 Hz, 1H), 6.83 (s, 1H), 6.82 (s, 1H), 5.09 (d, J=13.8 Hz, 1H), 5.04 (d, J=13.8 Hz, 1H), 4.68 (m, 1H), 3.97 (s, 3H), 2.46 (d, J=0.9 Hz, 3H), 2.25 (s, 3H), 2.16 (s, 3H), 1.15 (d, J=6.6 Hz, 3H), 1.14 (d, J=6.6 Hz, 3H).

EXAMPLE 3(21)

N-[4-trifluoromethyl-2-[4-(5-tetrazolyl)phenylmethyloxy]phenyl]-N-isopropyl-3-pyridylsulfonylamide

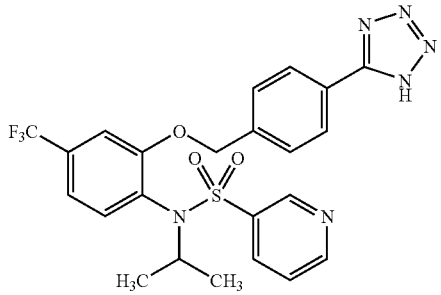

TLC: Rf 0.47 (chloroform:methanol=3:1); NMR(DMSO-d$_6$): δ 8.91 (dd, J=2.4, 0.6 Hz, 1H), 8.73 (dd, J=4.5, 1.8 Hz, 1H), 8.14 (ddd, J=8.4, 2.4, 1.8 Hz, 1H), 8.04 (d, J=8.4 Hz, 2H), 7.57 (s, 1H), 7.55 (d, J=8.4 Hz, 2H), 7.47 (ddd, J=8.4, 4.5, 0.6 Hz, 1H), 7.43-7.38 (m, 2H), 5.28 (d, J=12.3 Hz, 1H), 5.21 (d, J=12.3 Hz, 1H), 4.45-4.25 (m, 1H), 1.04 (d, J=6.6 Hz, 3H), 1.00 (d, J=6.6 Hz, 3H).

EXAMPLE 3(22)

N-[4-trifluoromethyl-2-[4-(5-tetrazolyl)phenylmethyloxy]phenyl]-N-isobutyl-3-pyridylsulfonylamide

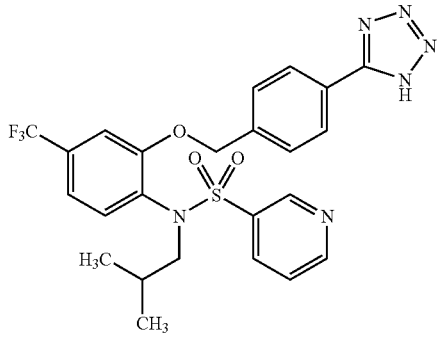

TLC: Rf 0.47 (chloroform:methanol=3:1); NMR: δ 8.89 (d, J=1.5 Hz, 1H), 8.46 (dd, J=4.8, 1.5 Hz, 1H), 8.00 (d, J=8.4 Hz, 2H), 7.83 (dt, J=8.1, 1.5 Hz, 1H), 7.59 (d, J=8.4 Hz, 1H), 7.35 (dd, J=8.4, 0.9 Hz, 1H), 7.26-7.20 (m, 1H), 7.19 (d, J=0.9 Hz, 1H), 7.14 (d, J=8.4 Hz, 2H), 4.95 (brs, 1H), 4.77 (brs, 1H), 3.56 (brs, 1H), 3.40 (brs, 1H), 1.70-1.60 (m, 1H), 0.94 (brs, 6H).

EXAMPLE 3(23)

N-[4-trifluoromethyl-2-[4-(5-tetrazolyl)phenylmethyloxy]phenyl]-N-isopropyl-2-pyridylsulfonylamide

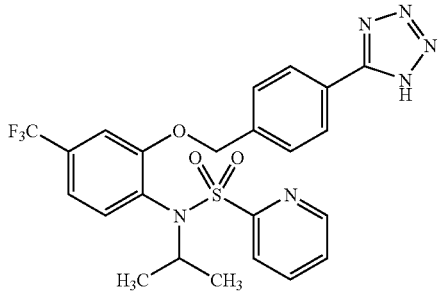

TLC: Rf 0.47 (chloroform:methanol=3:1); NMR: δ 8.69 (d, J=4.8 Hz, 1H), 8.02 (d, J=8.4 Hz, 2H), 7.92-7.76 (m, 2H), 7.52 (d, J=8.4 Hz, 2H), 7.46-7.38 (m, 1H), 7.30-7.26 (m, 3H), 5.08 (d, J=12.0 Hz, 1H), 5.01 (d, J=12.0 Hz, 1H), 4.75-4.55 (m, 1H), 1.11 (d, J=7.5 Hz, 3H), 1.08 (d, J=7.5 Hz, 3H).

EXAMPLE 3(24)

N-[4-trifluoromethyl-2-[4-(5-tetrazolyl)phenylmethyloxy]phenyl]-N-isobutyl-2-pyridylsulfonylamide

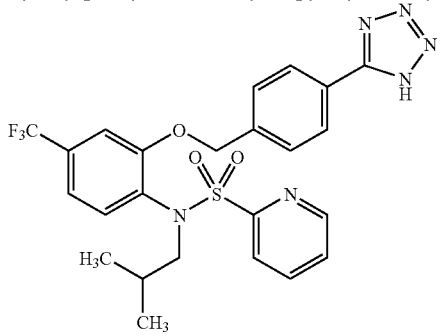

TLC: Rf 0.38 (chloroform:methanol=3:1); NMR: δ 8.60-8.45 (m, 1H), 8.10 (d, J=8.4 Hz, 2H), 7.80-7.70 (m, 2H), 7.49 (d, J=8.1 Hz, 1H), 7.38 (d, J=8.4 Hz, 2H), 7.38-7.31 (m, 1H), 7.30-7.20 (m, 1H), 7.14 (d, J=1.8 Hz, 1H), 4.91 (brs, 2H), 3.63 (brd, J=6.3 Hz, 2H), 1.70-1.55 (m, 1H), 0.89 (d, J=6.6 Hz, 6H).

EXAMPLE 3(25)

N-[4-trifluoromethyl-2-[2-methyl-4-(5-tetrazolyl)phenylmethyloxy]phenyl]-N-isopropyl-2-pyridylsulfonylamide

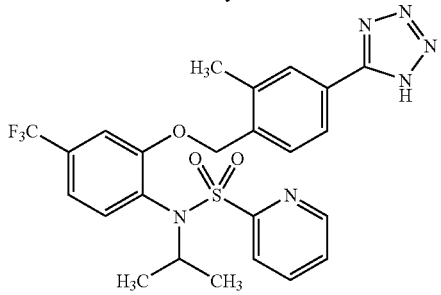

TLC: Rf 0.24 (chloroform:methanol=3:1); NMR: δ 8.69 (d, J=4.8 Hz, 1H), 7.92-7.75 (m, 4H), 7.58 (d, J=7.8 Hz, 1H), 7.48-7.39 (m, 1H), 7.31-7.18 (m, 3H), 5.03 (s, 2H), 4.72-4.58 (m, 1H), 2.37 (s, 3H), 1.11 and 1.09 (each d, J=6.6 Hz, each 3H).

EXAMPLE 3(26)

N-[4,5-dimethyl-2-[2-methyl-4-(5-tetrazolyl)phenylmethyloxy]phenyl]-N-isobutyl-2-pyridylsulfonylamide

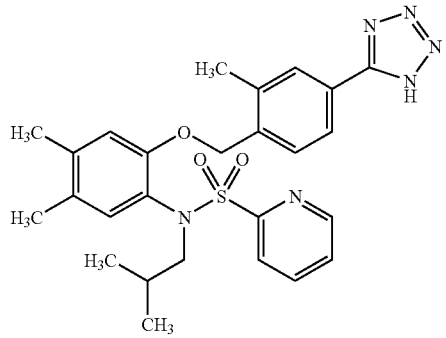

TLC: Rf 0.40 (chloroform:methanol:water=8:2:0.2); MS (FAB, Pos.): 507 (M+H)$^+$.

EXAMPLE 3(27)

N-[4,5-dimethyl-2-[2-methyl-4-(5-tetrazolyl)phenylmethyloxy]phenyl]-N-isobutyl-3-pyridylsulfonylamide

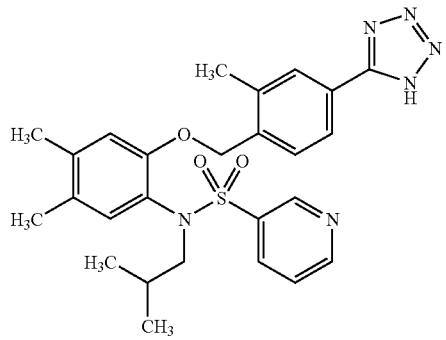

TLC: Rf 0.44 (chloroform:methanol:water 8:2:0.2); MS (FAB, Pos.): 507 (M+H)$^+$.

EXAMPLE 3(28)

N-[4-chloro-5-methyl-2-[4-(5-tetrazolyl)phenylmethyloxy]phenyl]-N-isobutyl-3-pyridylsulfonylamide

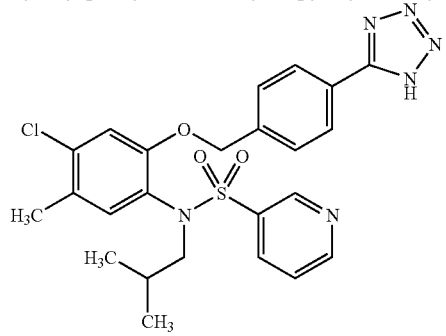

TLC: Rf 0.28 (chloroform:methanol:water=8:2:0.2); NMR(DMSO-d$_6$): δ 8.69 (d, J=1.8 Hz, 1H), 8.64 (dd, J=4.8, 1.8 Hz, 1H), 8.00 (d, J=8.1 Hz, 2H), 7.98-7.92 (m, 1H), 7.40 (dd, J=8.1, 4.8 Hz, 1H), 7.30 (d, J=8.4 Hz, 2H), 7.27 (s, 1H), 7.24 (s, 1H), 5.17-4.68 (m, 2H), 3.46-3.16 (m, 2H), 2.28 (s, 3H), 1.60-1.42 (m, 1H), 1.00-0.73 (m, 6H).

EXAMPLE 3(29)

N-[4,5-dimethyl-2-[2-chloro-4-(5-tetrazolyl)phenylmethyloxy]phenyl]-N-isobutyl-2-pyridylsulfonylamide

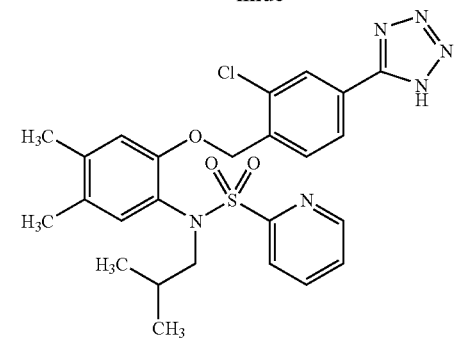

TLC: Rf 0.22 (chloroform:methanol:water=40:10:1); NMR: δ 8.52 (d, J=4.5 Hz, 1H), 8.20 (d, J=1.5 Hz, 1H), 7.98 (d, J=7.8 Hz, 1H), 7.79 (dt, J=1.5, 8.1 Hz, 1H), 7.71 (d, J=8.1 Hz, 1H), 7.47 (d, J=7.8 Hz, 1H), 7.35-7.30 (m, 1H), 7.04 (s, 1H), 6.63 (s, 1H), 4.90 (br, 1H), 4.64 (br, 1H), 3.67 (br, 1H), 3.57 (br, 1H), 2.21 (s, 3H), 2.15 (s, 3H), 1.80-1.60 (m, 1H), 0.91 (br, 6H).

EXAMPLE 3(30)

N-[4,5-dimethyl-2-[2-chloro-4-(5-tetrazolyl)phenylmethyloxy]phenyl]-N-isopropyl-3-pyridylsulfonylamide

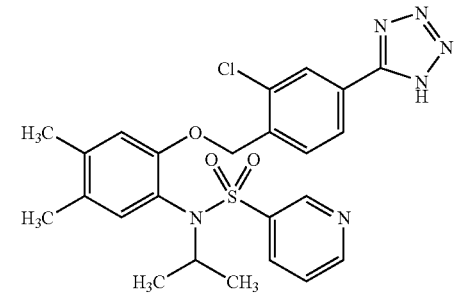

TLC: Rf 0.22 (chloroform:methanol:water=40:10:1); NMR: δ 9.11 (d, J=1.8 Hz, 1H), 8.61 (dd, J=4.8, 1.5 Hz, 1H), 8.20-8.10 (m, 2H), 7.88 (dd, J=7.8, 1.5 Hz, 1H), 7.42 (dd, J=8.1, 4.8 Hz, 1H), 7.33 (d, J=7.8 Hz, 1H), 7.01 (s, 1H), 6.79 (s, 1H), 4.96 (d, J=13.5 Hz, 1H), 4.93 (d, J=13.5 Hz, 1H), 4.60-4.45 (m, 1H), 2.29 (s, 3H), 2.23 (s, 3H), 1.25 (d, J=6.6 Hz, 3H), 1.11 (d, J=6.6 Hz, 3H).

EXAMPLE 3(31)

N-[4,5-dimethyl-2-[2-chloro-4-(5-tetrazolyl)phenylmethyloxy]phenyl]-N-isobutyl-3-pyridylsulfonylamide

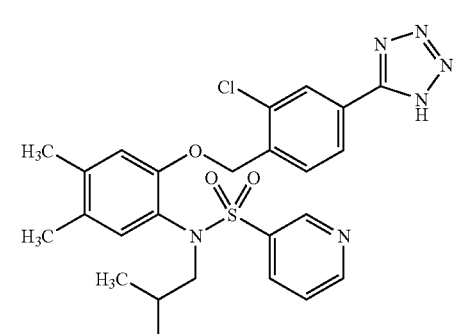

TLC: Rf 0.22 (chloroform:methanol:water=40:10:1); NMR: δ 8.97 (d, J=1.8 Hz, 1H), 8.55-8.45 (m, 1H), 8.15 (d, J=1.5 Hz, 1H), 7.89 (d, J=7.8 Hz, 1H), 7.83 (dt, J=8.1, 1.8 Hz, 1H), 7.31 (dd, J=8.1, 4.8 Hz, 1H), 7.24 (s, 1H), 7.07 (d, J=7.8 Hz, 1H), 6.75 (s, 1H), 4.89 (d, J=12.5 Hz, 1H), 4.63 (d, J=12.5 Hz, 1H), 3.70-3.60 (m, 1H), 3.45-3.30 (m, 1H), 2.30 (s, 3H), 2.26 (s, 3H), 1.80-1.60 (m, 1H), J=6.6 Hz, 3H), 0.93 (d, J=6.6 Hz, 3H).

EXAMPLE 3(32)

N-[4,5-dimethyl-2-[4-(5-tetrazolyl)phenylmethyloxy]phenyl]-N-isopropyl-2-pyridylsulfonylamide

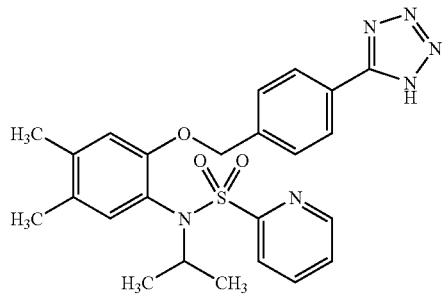

TLC: Rf 0.23 (chloroform:methanol=5:1); MS (APCI, Neg. 20V): 477 (M-H)⁻.

EXAMPLE 3(33)

N-[4,5-dimethyl-2-[4-(5-tetrazolyl)phenylmethyloxy]phenyl]-N-isobutyl-2-pyridylsulfonylamide

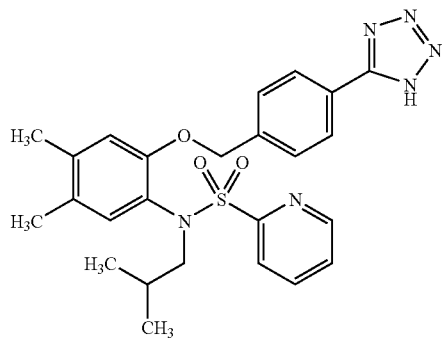

TLC: Rf 0.23 (chloroform:methanol=5:1); MS (APCI, Neg. 20V): 491 (M-H)⁻.

EXAMPLE 3(34)

N-[4,5-dimethyl-2-[4-(5-tetrazolyl)phenylmethyloxy]phenyl]-N-isobutyl-3-pyridylsulfonylamide

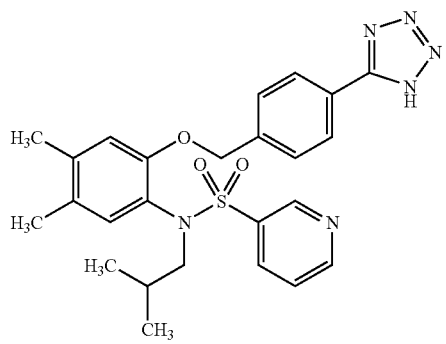

TLC: Rf 0.23 (chloroform:methanol=5:1); MS (APCI, Neg. 20V): 491 (M-H)⁻.

EXAMPLE 3(35)

N-[4-chloro-5-methyl-2-[2-methyl-4-(5-tetrazolyl)phenylmethyloxy]phenyl]-N-isopropyl-2-pyridylsulfonylamide

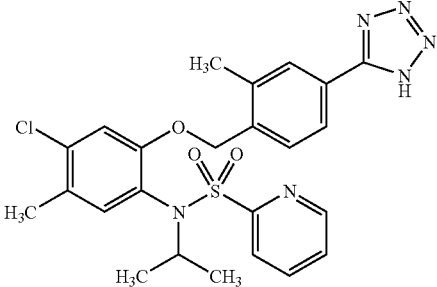

TLC: Rf 0.30 (chloroform:methanol:water=8:2:0.2); NMR(DMSO-d₆): δ 8.67 (d, J=3.6 Hz, 1H), 7.98-7.88 (m, 2H), 7.85-7.78 (m, 2H), 7.55-7.48 (m, 2H), 7.37 (s, 1H), 7.04 (s, 1H), 5.10 (ABd, J=13.2 Hz) and 5.04 (ABd, J=13.2 Hz) total 2H, 4.49 (sept, J=6.9 Hz, 1H), 2.36 (s, 3H), 2.23 (s, 3H), 1.02 (d, J=6.9 Hz) and 0.99 (d, J=6.9 Hz) total 6H.

EXAMPLE 3(36)

N-[4-chloro-5-methyl-2-[2-methyl-4-(5-tetrazolyl)phenylmethyloxy]phenyl]-N-isobutyl-2-pyridylsulfonylamide

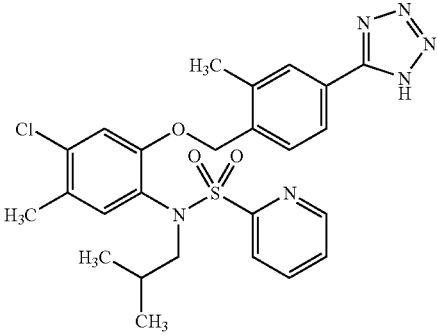

TLC: Rf 0.26 (chloroform:methanol:water=8:2:0.2); NMR(DMSO-d₆): δ 8.48 (m, 1H), 7.93-7.85 (m) and 7.90 (dd, J=7.8, 1.8 Hz) total 2H, 7.81 (d, J=8.1 Hz, 1H), 7.68 (d, J=8.1 Hz, 1H), 7.44 (ddd, J=7.8, 4.8, 1.2 Hz, 1H), 7.29 (s) and 7.27 (d, J=7.8 Hz) total 2H, 7.20 (s, 1H), 4.92 (m, 2H), 3.47 (m, 2H), 2.31 (s, 3H), 2.23 (s, 3H), 1.50 (m, 1H), 0.81 (d, J=6.6 Hz, 6H).

EXAMPLE 3(37)

N-[4,5-dimethyl-2-[2-methoxy-4-(5-tetrazolyl)phenylmethyloxy]phenyl]-N-isobutyl-2-pyridylsulfonylamide

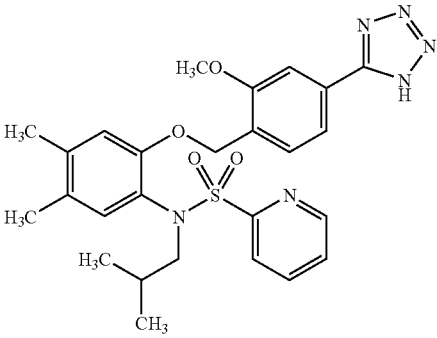

TLC: Rf 0.23 (dichloromethane:methanol=10:1); MS (FAB, Pos.): 523 (M+H)⁺.

EXAMPLE 3(38)

N-[4,5-dimethyl-2-[2-methoxy-4-(5-tetrazolyl)phenylmethyloxy]phenyl]-N-isopropyl-2-pyridylsulfonylamide

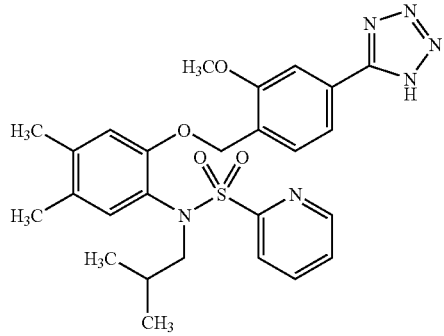

TLC: Rf 0.23 (chloroform:methanol=10:1).

REFERENCE EXAMPLE 5

N-[4,5-dimethyl-2-[2-methyl-4-(N-hydroxyamidino)phenylmethyloxy]phenyl]-N-isobutyl-(5-methyl-2-furyl)sulfonylamide

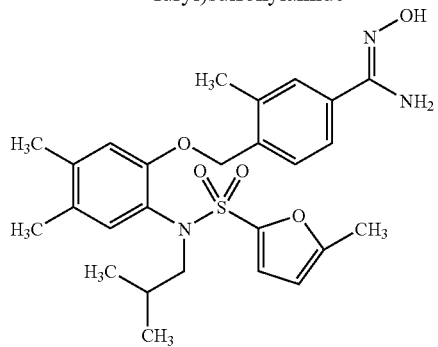

To a solution of N-[4,5-dimethyl-2-(2-methyl-4-cyanophenylmethyloxy)phenyl]-N-isobutyl-(5-methyl-2-furyl)sulfonylamide prepared in reference example 4 (70 mg) in ethanol (2 ml), triethylamine (42 μl) and hydroxylamine hydrogen chloride salt (21 mg) were added at room temperature, then mixture was refluxed for 5 hours. After termination of reaction, the reaction mixture was poured into ethyl acetate-water. The organic layer was washed, dried and concentrated under reduced pressure to give the title compound (80 mg) having the following physical data.

TLC: Rf 0.38 (n-hexane:ethyl acetate=2:3).

EXAMPLE 4

N-[4,5-dimethyl-2-[2-methyl-4-(5-oxo-1,2,4-oxadiazol-3-yl)phenylmethyloxy]phenyl]-N-isobutyl-(5-methyl-2-furyl)sulfonylamide

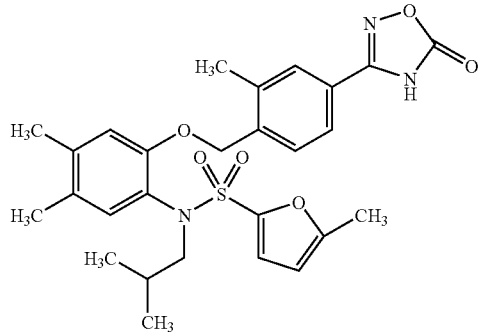

To a solution of N-[4,5-dimethyl-2-[2-methyl-4-(N-hydroxyamidino)phenylmethyloxy]phenyl]-N-isobutyl-(5-methyl-2-furyl)sulfonylamide prepared in reference example 5 (78 mg) in N,N-dimethylformamide (1 ml), pyridine (16 μl) and chloro formic acid 2-ethylhexyl ester (30 μl) were added and the mixture was stirred for 1 hour at 0° C. After termination of reaction, the reaction mixture was poured into ethyl acetate-water. The organic layer was washed, dried and concentrated under reduced pressure. To the residue, xylene (2 ml) was added, and the mixture was refluxed for 6 hours at 140° C. After termination of reaction, the reaction mixture was concentrated under reduced pressure. The residue was purified by column chromatography on silica gel (hexane-ethyl acetate) to give the title compound (42 mg) having the following physical data.

TLC: Rf 0.43 (chloroform:methanol=19:1); NMR: δ 10.69 (br, 1H), 7.62 (s, 1H), 7.59 (d, J=8.1 Hz, 1H), 7.54 (d, J=8.1 Hz, 1H), 6.97 (s, 1H), 6.78 (d, J=3.3 Hz, 1H), 6.71 (s, 1H), 6.00 (d, J=3.3 Hz, 1H), 4.94 (br, 2H), 3.46 (d, J=7.5 Hz, 2H), 2.39 (s, 3H), 2.24 (s, 3H), 2.19 (s, 3H), 2.18 (s, 3H), 1.70-1.55 (m, 1H), 0.89 (d, J=6.6 Hz, 6H).

EXAMPLE 4(1)~EXAMPLE 4(22)

By the same procedures as described in reference examples 1-5 and example 4, the compounds having the following physical data were obtained.

EXAMPLE 4(1)

N-[4-chloro-5-methyl-2-[4-(5-oxo-1,2,4-oxadiazol-3-yl)phenylmethyloxy]phenyl]-N-isopropyl-(5-methyl-2-furyl)sulfonylamide

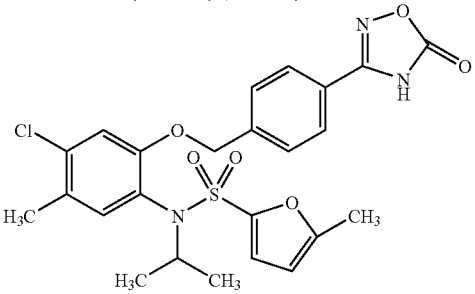

TLC: Rf 0.40 (chloroform:methanol=19:1); NMR: δ 10.81 (br, 1H), 7.79 (d, J=8.3 Hz, 2H), 7.63 (d, J=8.3 Hz, 2H), 6.97 (s, 1H), 6.92 (s, 1H), 6.84 (d, J=3.3 Hz, 1H), 6.10-6.00 (m, 1H), 5.07 (s, 2H), 4.55-4.35 (m, 1H), 2.34 (s, 3H), 2.28 (s, 3H), 1.10 (d, J=6.6 Hz, 3H), 1.07 (d, J=6.6 Hz, 3H).

EXAMPLE 4(2)

N-[4-chloro-5-methyl-2-[4-(5-oxo-1,2,4-oxadiazol-3-yl)phenylmethyloxy]phenyl]-N-isobutyl-(5-methyl-2-furyl)sulfonylamide

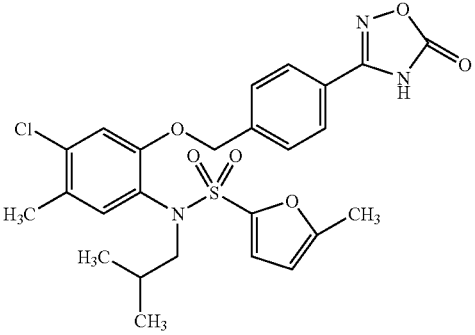

TLC: Rf 0.38 (chloroform:methanol=19:1); NMR: δ 11.01 (br, 1H), 7.80 (d, J=8.3 Hz, 2H), 7.52 (d, J=8.3 Hz, 2H), 7.10 (s, 1H), 6.92 (s, 1H), 6.78 (d, J=3.3 Hz, 1H), 6.05-5.95 (m, 1H), 5.02 (br, 2H), 3.45 (d, J=7.2 Hz, 2H), 2.29 (s, 3H), 2.20 (s, 3H), 1.70-1.55 (m, 1H), 0.90 (d, J=6.9 Hz, 6H).

EXAMPLE 4(3)

N-[4,5-dimethyl-2-[2-methyl-4-(5-oxo-1,2,4-oxadiazol-3-yl)phenylmethyloxy]phenyl]-N-isopropyl-(5-methyl-2-furyl)sulfonylamide

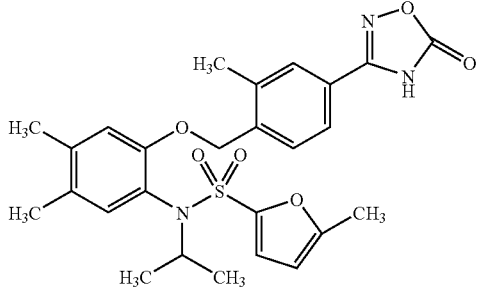

TLC: Rf 0.43 (chloroform:methanol=19:1); NMR: δ 10.34 (br, 1H), 7.71 (d, J=8.1 Hz, 1H), 7.65-7.55 (m, 2H), 6.86 (d, J=3.3 Hz, 1H), 6.79 (s, 1H), 6.74 (s, 1H), 6.10-6.05 (m, 1H), 4.93 (s, 2H), 4.50-4.40 (m, 1H), 2.37 (s, 3H), 2.34 (s, 3H), 2.26 (s, 3H), 2.17 (s, 3H), 1.09 (d, J=6.6 Hz, 3H), 1.07 (d, J=6.6 Hz, 3H).

EXAMPLE 4(4)

N-[4,5-dimethyl-2-[4-(5-oxo-1,2,4-oxadiazol-3-yl)phenylmethyloxy]phenyl]-N-isobutyl-(5-methyl-2-furyl)sulfonylamide

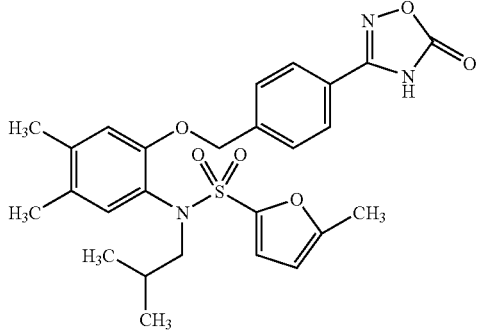

TLC: Rf 0.53 (chloroform:methanol=9:1); NMR: δ 11.10-10.50 (br, 1H, NH), 7.78 (d, J=8.7 Hz, 2H), 7.52 (d, J=8.7 Hz, 2H), 6.97 (s, 1H), 6.78 (d, J=3.3 Hz, 1H), 6.69 (s, 1H), 6.01-5.98 (m, 1H), 5.15-4.85 (m, 2H), 3.46 (d, J=7.2 Hz, 2H), 2.22 (s, 3H), 2.20 (s, 3H), 2.17 (s, 3H), 1.73-1.60 (m, 1H), 0.90 (d, J=6.9 Hz, 6H).

EXAMPLE 4(5)

N-[4,5-dimethyl-2-[2-methoxy-4-(5-oxo-1,2,4-oxadiazol-3-yl)phenylmethyloxy]phenyl]-N-isobutyl-(5-methyl-2-furyl)sulfonylamide

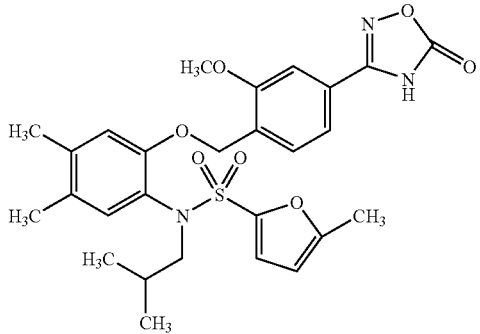

TLC: Rf 0.46 (dichloromethane:methanol=10:1); MS (FAB, Pos.): 542 (M+H)$^+$.

EXAMPLE 4(6)

N-[4,5-dimethyl-2-[2-methoxy-4-(5-oxo-1,2,4-oxadiazol-3-yl)phenylmethyloxy]phenyl]-N-isopropyl-(5-methyl-2-furyl)sulfonylamide

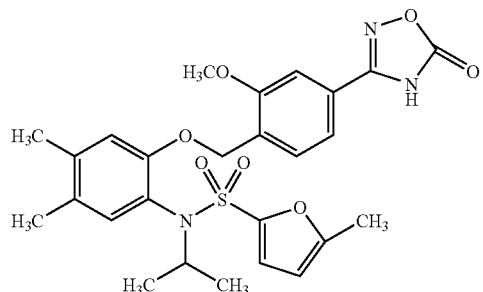

TLC: Rf 0.44 (dichloromethane:methanol=19:1); NMR: δ 7.68 (d, J=8.1 Hz, 1H), 7.35 (dd, J=8.1, 1.5 Hz, 1H), 7.24 (d, J=1.5 Hz, 1H), 6.91 (d, J=3.3 Hz, 1H), 6.77 (s, 1H), 6.72 (s, 1H), 6.11 (dd, J=3.3, 0.6 Hz, 1H), 4.92 (d, J=14.7 Hz, 1H), 4.83 (d, J=14.7 Hz, 1H), 4.49 (m, 1H), 3.93 (s, 3H), 2.37 (s, 3H), 2.25 (s, 3H), 2.17 (s, 3H), 1.09 (d, J=6.9 Hz, 3H), 1.07 (d, J=6.9 Hz, 3H).

EXAMPLE 4(7)

N-[4-trifluoromethyl-2-[4-(5-oxo-1,2,4-oxadiazol-3-yl)phenylmethyloxy]phenyl]-N-isopropyl-2-thiazolylsulfonylamide

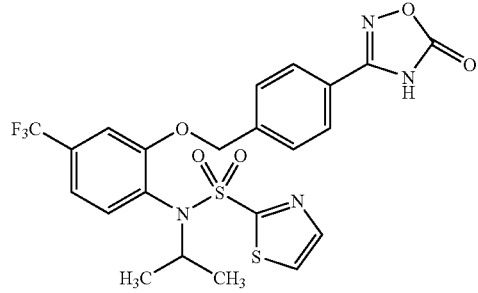

TLC: Rf 0.23 (n-hexane:ethyl acetate=1:1); NMR: δ 7.96 (d, J=3.3 Hz, 1H), 7.82 (d, J=8.4 Hz, 2H), 7.65 (d, J=8.4 Hz, 2H), 7.57 (d, J=3.3 Hz, 1H), 7.34-7.22 (m, 3H), 5.19 (s, 2H), 4.68 (sept, J=6.6 Hz, 1H), 1.15 and 1.14 (each d, J=6.6 Hz, each 3H).

EXAMPLE 4(8)

N-[4-trifluoromethyl-2-[4-(5-oxo-1,2,4-oxadiazol-3-yl)phenylmethyloxy]phenyl]-N-isopropyl-(4-methyl-2-thiazolyl)sulfonylamide

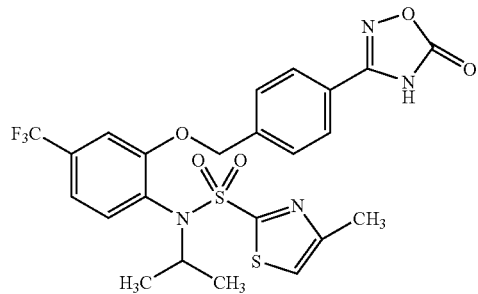

TLC: Rf 0.60 (chloroform:methanol:water=8:2:0.2); NMR: δ 7.82 (d, J=8.4 Hz, 2H), 7.64 (d, J=8.4 Hz, 2H), 7.32-7.24 (m, 3H), 7.11 (d, J=0.9 Hz, 1H), 5.19 (s, 2H), 4.68 (quint, J=6.6 Hz, 1H), 2.51 (d, J=0.9 Hz, 3H), 1.14 (d, J=6.6 Hz, 6H).

EXAMPLE 4(9)

N-[4-trifluoromethyl-2-[4-(5-oxo-1,2,4-oxadiazol-3-yl)phenylmethyloxy]phenyl]-N-isobutyl-(4-methyl-2-thiazolyl)sulfonylamide

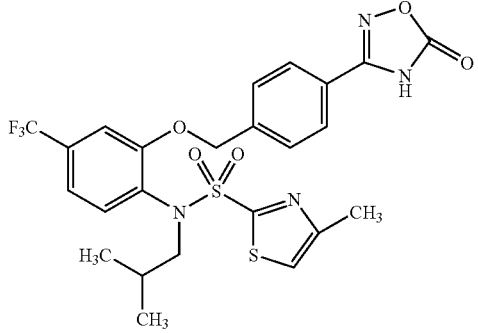

TLC: Rf 0.60 (chloroform:methanol:water=8:2:0.2); NMR: δ 7.83 (d, J=8.4 Hz, 2H), 7.48 (d, J=8.4 Hz, 2H), 7.45 (d, J=7.8 Hz, 1H), 7.27 (m, 1H), 7.18 (d, J=1.5 Hz, 1H), 7.04 (d, J=0.6 Hz, 1H), 5.05 (br, 2H), 3.60 (d, J=6.9 Hz, 2H), 2.38 (d, J=0.6 Hz, 3H), 1.66 (sep, J=6.9 Hz, 1H), 0.92 (d, J=6.9 Hz, 6H).

EXAMPLE 4(10)

N-[4-chloro-5-methyl-2-[4-(5-oxo-1,2,4-oxadiazol-3-yl)phenylmethyloxy]phenyl]-N-isobutyl-(4-methyl-2-thiazolyl)sulfonylamide

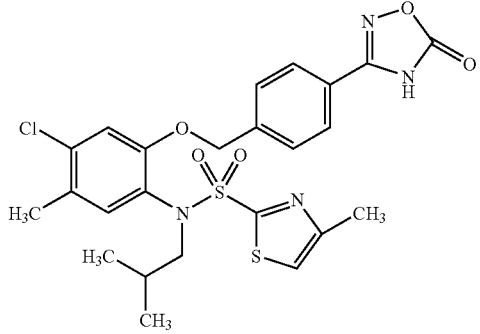

TLC: Rf 0.37 (chloroform:methanol=19:1); NMR: δ 10.89 (br, 1H), 7.79 (d, J=8.4 Hz, 2H), 7.44 (d, J=8.4 Hz, 2H), 7.17 (s, 1H), 7.01 (s, 1H), 6.92 (s, 1H), 4.99 (br, 1H), 4.87 (br, 1H), 3.57 (br, 2H), 2.36 (s, 3H), 2.27 (s, 3H), 1.80-1.60 (m, 1H), 0.93 (d, J=6.6 Hz, 6H).

EXAMPLE 4(11)

N-[4-chloro-5-methyl-2-[2-methyl-4-(5-oxo-1,2,4-oxadiazol-3-yl)phenylmethyloxy]phenyl]-N-isobutyl-(4-methyl-2-thiazolyl)sulfonylamide

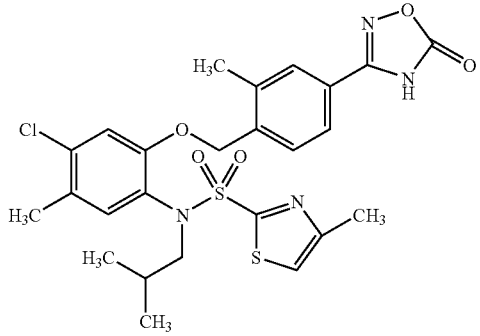

TLC: Rf 0.43 (ethyl acetate); NMR(DMSO-d₆): δ 7.67 (s, 1H), 7.64 (d, J=8.1 Hz, 1H), 7.50 (s, 1H), 7.34 (s, 1H), 7.32 (d, J=8.1 Hz, 1H), 7.21 (s, 1H), 5.06 (brs, 1H), 4.87 (brs, 1H), 3.45 (brs, 2H), 2.33 (s, 3H), 2.27 (s, 3H), 2.22 (s, 3H), 1.70-1.50 (m, 1H), 0.86 (brd, J=6.3 Hz, 6H).

EXAMPLE 4(12)

N-[4,5-dimethyl-2-[2-methyl-4-(5-oxo-1,2,4-oxadiazol-3-yl)phenylmethyloxy]phenyl]-N-isopropyl-(4-methyl-2-thiazolyl)sulfonylamide

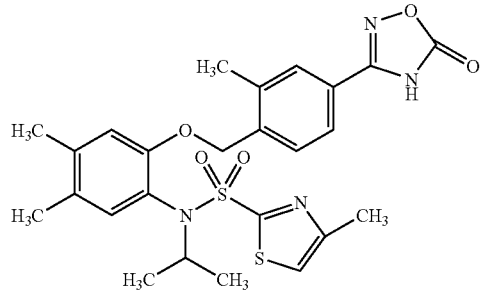

TLC: Rf 0.45 (chloroform:methanol=19:1); NMR: δ 10.56 (br, 1H), 7.64 (d, J=8.1 Hz, 1H), 7.62 (s, 1H), 7.57 (dd, J=8.1, 1.8 Hz, 1H), 7.07 (s, 1H), 6.83 (s, 1H), 6.77 (s, 1H), 4.98 (s, 2H), 4.75-4.60 (m, 1H), 2.49 (s, 3H), 2.39 (s, 3H), 2.25 (s, 3H), 2.16 (s, 3H), 1.14 (d, J=6.6 Hz, 3H), 1.13 (d, J=6.6 Hz, 3H).

EXAMPLE 4(13)

N-[4,5-dimethyl-2-[2-methyl-4-(5-oxo-1,2,4-oxadiazol-3-yl)phenylmethyloxy]phenyl]-N-isobutyl-(4-methyl-2-thiazolyl)sulfonylamide

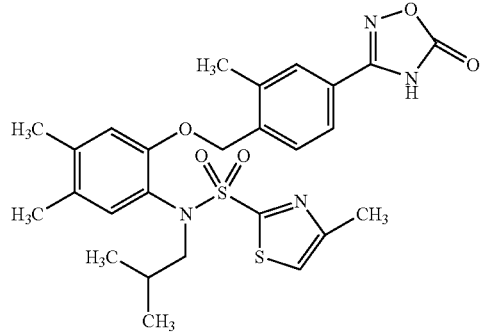

TLC: Rf 0.45 (chloroform:methanol=19:1); NMR: δ 10.95 (br, 1H), 7.62 (s, 1H), 7.59 (d, J=8.1 Hz, 1H), 7.40 (d, J=8.1 Hz, 1H), 7.03 (s, 1H), 6.99 (s, 1H), 6.71 (s, 1H), 4.91 (br, 1H), 4.82 (br, 1H), 3.57 (br, 2H), 2.37 (s, 3H), 2.34 (s, 3H), 2.24 (s, 3H), 2.17 (s, 3H), 1.80-1.60 (m, 1H), 0.93 (br, 6H).

EXAMPLE 4(14)

N-[4,5-dimethyl-2-[4-(5-oxo-1,2,4-oxadiazol-3-yl)phenylmethyloxy]phenyl]-N-isopropyl-(4-methyl-2-thiazolyl)sulfonylamide

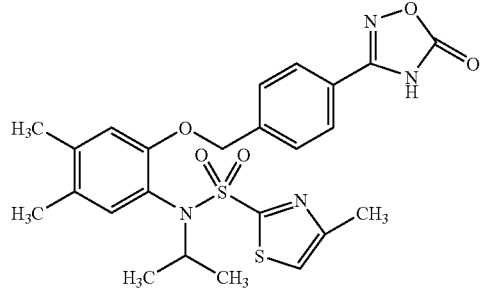

TLC: Rf 0.42 (chloroform:methanol=10:1); NMR: δ 7.77 (d, J=8.4 Hz, 2H), 7.57 (d, J=8.4 Hz, 2H), 7.06 (d, J=0.9 Hz, 1H), 6.83 (s, 1H), 6.74 (s, 1H), 5.05 (d, J=12.9 Hz, 1H), 5.00 (d, J=12.9 Hz, 1H), 4.68 (m, 1H), 2.49 (d, J=0.9 Hz, 3H), 2.24 (s, 3H), 2.15 (s, 3H), 1.15 (d, J=6.6 Hz, 3H), 1.13 (d, J=6.6 Hz, 3H).

EXAMPLE 4(15)

N-[4,5-dimethyl-2-[4-(5-oxo-1,2,4-oxadiazol-3-yl)phenylmethyloxy]phenyl]-N-isobutyl-(4-methyl-2-thiazolyl)sulfonylamide

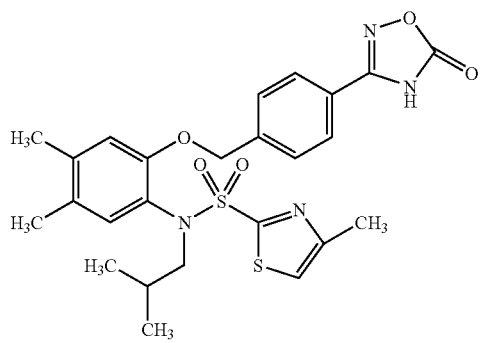

TLC: Rf 0.39 (chloroform:methanol=10:1); NMR: δ 7.78 (d, J=8.4 Hz, 2H), 7.43 (d, J=8.4 Hz, 2H), 7.03 (s, 1H), 6.97 (d, J=0.9 Hz, 1H), 6.68 (s, 1H), 5.12-4.68 (m, 2H), 3.73-3.42 (m, 2H), 2.35 (d, J=0.9 Hz, 3H), 2.23 (s, 3H), 2.17 (s, 3H), 1.69 (m, 1H), 1.03-0.86 (m, 6H).

EXAMPLE 4(16)

N-[4,5-dimethyl-2-[2-methoxy-4-(5-oxo-1,2,4-oxadiazol-3-yl)phenylmethyloxy]phenyl]-N-isopropyl-(4-methyl-2-thiazolyl)sulfonylamide

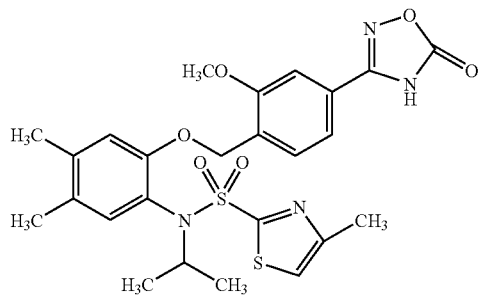

TLC: Rf 0.37 (dichloromethane:methanol=19:1); NMR: δ 7.63 (d, J=7.8 Hz, 1H), 7.33 (dd, J=7.8, 1.5 Hz, 1H), 7.30 (d, J=1.5 Hz, 1H), 7.08 (brs, 1H), 6.83 (s, 1H), 6.76 (s, 1H), 5.02 (d, J=14.4 Hz, 1H), 4.93 (d, J=14.4 Hz, 1H), 4.69 (m, 1H), 3.93 (s, 3H), 2.49 (d, J=1.2 Hz, 3H), 2.25 (s, 3H), 2.16 (s, 3H), 1.14 (d, J=6.9 Hz, 3H), 1.13 (d, J=6.9 Hz, 3H).

EXAMPLE 4(17)

N-[4-trifluoromethyl-2-[4-(5-oxo-1,2,4-thiadiazol-3-yl)phenylmethyloxy]phenyl]-N-isopropyl-2-thiazolylsulfonylamide

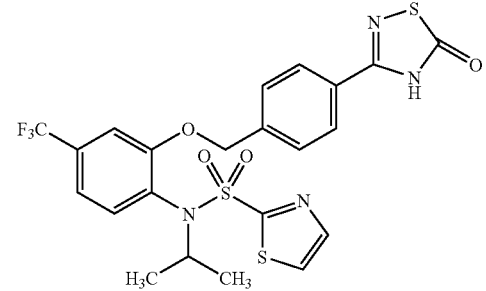

TLC: Rf 0.44 (n-hexane:ethyl acetate=1:1); NMR: δ 11.41 (brs, 1H), 7.94 (d, J=8.4 Hz, 2H), 7.94 (d, J=3.0 Hz, 1H), 7.60 (d, J=8.4 Hz, 2H), 7.54 (d, J=3.0 Hz, 1H), 7.34-7.20 (m, 3H), 5.16 (s, 2H), 4.69 (sept, J=6.6 Hz, 1H), 1.15 (d, J=6.6 Hz, 6H).

EXAMPLE 4(18)

N-[4-trifluoromethyl-2-[4-(5-oxo-1,2,4-oxadiazol-3-yl)phenylmethyloxy]phenyl]-N-isobutyl-2-pyridylsulfonylamide

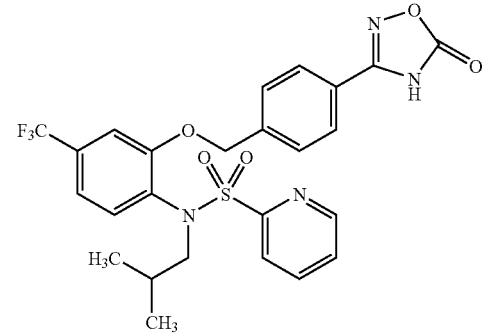

TLC: Rf 0.46 (chloroform:methanol=9:1); NMR(DMSO-d$_6$): δ 8.60-8.50 (m, 1H), 7.90 (dt, J=1.8, 7.8 Hz, 1H), 7.81 (d, J=8.4 Hz, 2H), 7.72 (d, J=7.5 Hz, 1H), 7.55-7.35 (m, 6H), 5.08 (brs, 2H), 3.52 (brd, J=7.5 Hz, 2H), 1.60-1.40 (m, 1H), 0.83 (d, J=6.6 Hz, 6H).

EXAMPLE 4(19)

N-[4,5-dimethyl-2-[2-methyl-4-(5-oxo-1,2,4-oxadiazol-3-yl)phenylmethyloxy]phenyl]-N-isopropyl-2-pyridylsulfonylamid

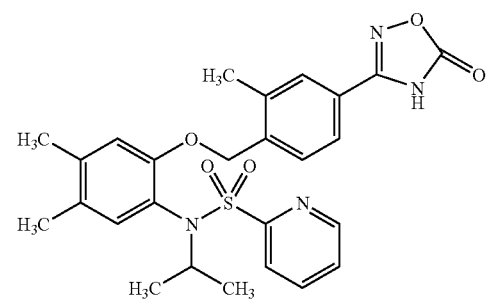

TLC: Rf 0.33 (chloroform:methanol=19:1); NMR: δ 10.41 (br, 1H), 8.75-8.70 (m, 1H), 7.90 (dd, J=7.8, 0.9 Hz, 1H), 7.80 (dt, J=0.9, 7.8 Hz, 1H), 7.65-7.50 (m, 3H), 7.41 (ddd, J=7.8, 4.8, 0.9 Hz, 1H), 6.78 (s, 1H), 6.72 (s, 1H), 4.87 (d, J=13.4 Hz, 1H), 4.83 (d, J=13.4 Hz, 1H), 4.75-4.60 (m, 1H), 2.34 (s, 3H), 2.25 (s, 3H), 2.13 (s, 3H), 1.10 (d, J=6.6 Hz, 6H).

EXAMPLE 4(20)

N-[4,5-dimethyl-2-[2-methyl-4-(5-oxo-1,2,4-oxadiazol-3-yl)phenylmethyloxy]phenyl]-N-isobutyl-3-pyridylsulfonylamide

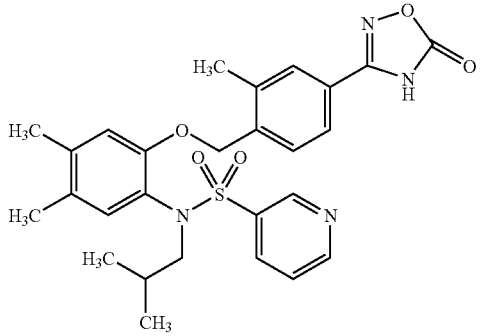

TLC: Rf 0.30 (chloroform:methanol=19:1); NMR: δ 11.28 (br, 1H), 8.84 (d, J=1.8 Hz, 1H), 8.49 (dd, J=4.8, 1.8 Hz, 1H), 7.87 (dt, J=8.1, 1.8 Hz, 1H), 7.62 (s, 1H), 7.47 (d, J=7.8 Hz, 1H), 7.19 (dd, J=8.1, 4.8 Hz, 1H), 7.15 (s, 1H), 6.97 (d, J=7.8 Hz, 1H), 6.69 (s, 1H), 4.82 (br, 1H), 4.62 (br, 1H), 3.53 (br, 1H), 3.34 (br, 1H), 2.30 (s, 3H), 2.27 (s, 3H), 2.22 (s, 3H), 1.80-1.60 (m, 1H), 1.00 (br, 3H), 0.87 (br, 3H).

EXAMPLE 4(21)

N-[4,5-dimethyl-2-[2-methoxy-4-(5-oxo-1,2,4-oxadiazol-3-yl)phenylmethyloxy]phenyl]-N-isobutyl-2-pyridylsulfonylamid

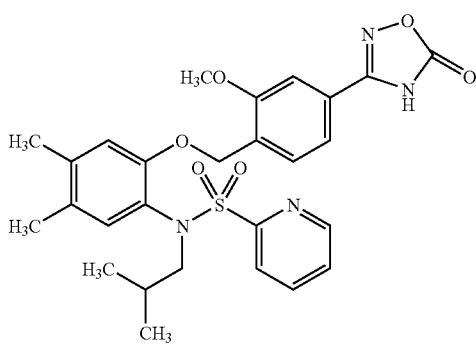

TLC: Rf 0.36 (dichloromethane:methanol=10:1); MS (FAB, Pos.): 539 (M+H)$^+$.

EXAMPLE 4(22)

N-[4,5-dimethyl-2-[2-methoxy-4-(5-oxo-1,2,4-oxadiazol-3-yl)phenylmethyloxy]phenyl]-N-isopropyl-2-pyridylsulfonylamide

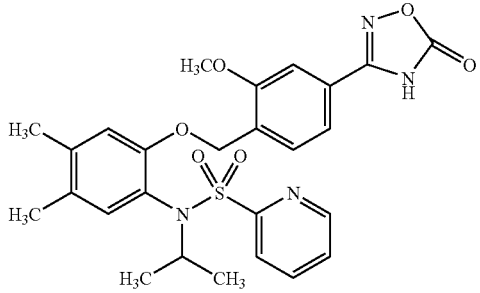

TLC: Rf 0.37 (dichloromethane:methanol=19:1); NMR: δ 8.73 (ddd, J=4.8, 1.5, 0.9 Hz, 1H), 7.91 (ddd, J=7.8, 1.2, 0.9 Hz, 1H), 7.82 (ddd, J=7.8, 7.8, 1.5 Hz, 1H), 7.57 (d, J=7.8 Hz, 1H), 7.43 (ddd, J=7.8, 4.8, 1.2 Hz, 1H), 7.32 (dd, J=7.8, 1.5 Hz, 1H), 7.26 (m, 1H), 6.76 (s, 1H), 6.72 (s, 1H), 4.88 (d, J=14.1 Hz, 1H), 4.78 (d, J=14.1 Hz, 1H), 4.71 (m, 1H), 3.91 (s, 3H), 2.24 (s, 3H), 2.13 (s, 3H), 1.10 (d, J=6.6 Hz, 3H), 1.09 (d, J=6.6 Hz, 3H).

EXAMPLE 5(1)~EXAMPLE 5(63)

By the same procedure as described in reference examples 1~3 and example 2, the compounds of the present invention having the following physical data were obtained.

EXAMPLE 5(1)

3,5-dimethyl-4-[2-[N-isobutyl-N-(5-methyl-2-furylsulfonyl)amino]-5-trifluoromethylphenoxymethyl]benzoic acid

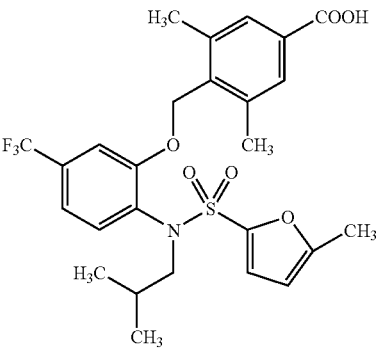

TLC: Rf 0.49 (chloroform:methanol=10:1); NMR: δ 7.82 (s, 2H), 7.40-7.20 (m, 3H), 6.70 (d, J=3.3 Hz, 1H), 6.00-5.95 (m, 1H), 5.07 (s, 2H), 3.35 (d, J=7.5 Hz, 2H), 2.43 (s, 6H), 2.19 (s, 3H), 1.60-1.45 (m, 1H), 0.79 (d, J=6.6 Hz, 6H).

EXAMPLE 5(2)

3-methyl-4-[6-[N-(5-methyl-2-furylsulfonyl)-N-(2-methyl-2-propenyl)amino]indan-5-yloxymethyl]benzoic acid

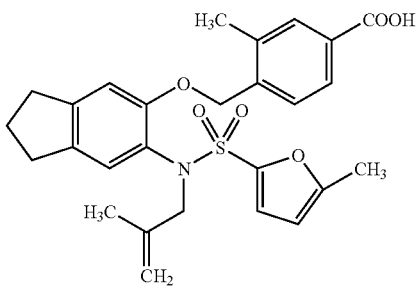

TLC: Rf 0.54 (chloroform:methanol=9:1); NMR(DMSO-d$_6$): δ 7.80-7.70 (m, 2H), 7.37 (d, J=7.8 Hz, 1H), 7.05 (s, 1H), 6.99 (s, 1H), 6.87 (d, J=3.3 Hz, 1H), 6.17 (d, J=3.3 Hz, 1H), 4.99 (br, 2H), 4.72 (s, 2H), 4.13 (br, 2H), 2.83 (t, J=7.4 Hz, 2H), 2.77 (t, J=7.4 Hz, 2H), 2.32 (s, 3H), 2.08 (s, 3H), 2.05-1.90 (m, 2H), 1.65 (s, 3H).

EXAMPLE 5(3)

4-[6-[N-cyclopropylmethyl-N-(5-methyl-2-furylsulfonyl)amino]indan-5-yloxymethyl]-3-methylbenzoic acid

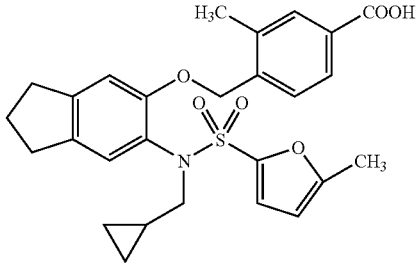

TLC: Rf 0.54 (chloroform:methanol=9:1); NMR(DMSO-d$_6$): δ 7.77 (s, 1H), 7.74 (d, J=8.1 Hz, 1H), 7.38 (d, J=8.1 Hz, 1H), 7.09 (s, 1H), 7.02 (s, 1H), 6.85 (d, J=3.3 Hz, 1H), 6.20-6.15 (m, 1H), 5.01 (br, 2H), 3.41 (br, 2H), 2.86 (t, J=7.4 Hz, 2H), 2.79 (t, J=7.4 Hz, 2H), 2.32 (s, 3H), 2.10 (s, 3H), 2.10-1.95 (m, 2H), 0.90-0.70 (m, 1H), 0.35-0.25 (m, 2H), 0.05-(−0.05) (m, 2H).

EXAMPLE 5(4)

4-[3-[N-isobutyl-N-(4-methyl-2-thiazolylsulfonyl)amino]naphthalen-2-yloxymethyl]benzoic acid

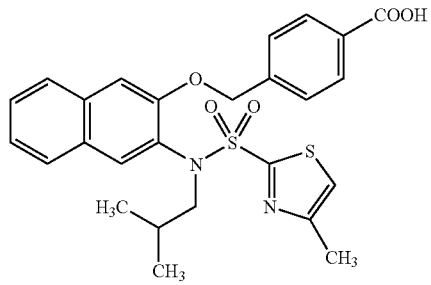

TLC: Rf 0.55 (ethyl acetate:methanol=9:1); NMR: δ 8.14 (d, J=8.4 Hz, 2H), 7.85 (s, 1H), 7.78 (d, J=8.1 Hz, 1H), 7.70 (d, J=8.1 Hz, 1H), 7.51-7.37 (m, 4H), 7.18 (s, 1H), 6.93 (s, 1H), 5.17 and 4.96 (each br-m, total 2H), 3.85-3.62 (br-m, 2H), 2.34 (s, 3H), 1.82-1.69 (m, 1H), 0.97 (br-s, 6H).

EXAMPLE 5(5)

4-[3-[N-isopropyl-N-(4-methyl-2-thiazolylsulfonyl)amino]naphthalen-2-yloxymethyl]benzoic acid

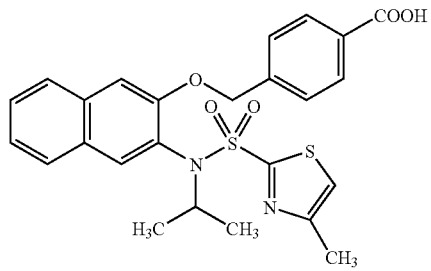

TLC: Rf 0.55 (ethyl acetate:methanol=9:1); NMR: δ 8.15 (d, J=8.4 Hz, 2H), 7.72 (d, J=9.0 Hz, 2H), 7.61 (s, 1H), 7.60 (d, J=9.0 Hz, 2H), 7.51-7.46 (m, 1H), 7.44-7.35 (m, 1H), 7.24 (s, 1H), 7.03 (s, 1H), 5.24 (s, 2H), 4.84-4.75 (m, 1H), 2.52 (s, 3H), 1.26 (d, J=6.6 Hz, 3H), 1.17 (d, J=6.6 Hz, 3H).

EXAMPLE 5(6)

4-[3-[N-isobutyl-N-(4-methyl-2-thiazolylsulfonyl)amino]naphthalen-2-yloxymethyl]-3-methylbenzoic acid

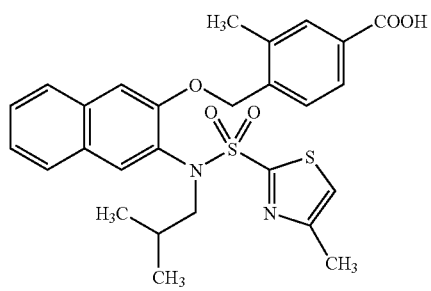

TLC: Rf 0.63 (ethyl acetate:methanol=9:1); NMR: δ 7.98-7.96 (m, 2H), 7.84 (s, 1H), 7.78 (d, J=8.1 Hz, 1H), 7.72 (d, J=8.1 Hz, 1H), 7.52-7.47 (m, 1H), 7.42-7.37 (m, 2H), 7.21 (s, 1H), 6.95 (s, 1H), 5.10 and 4.96 (each br-m, total 2H), 3.84-3.60 (br-m, 2H), 2.41 (s, 3H), 2.34 (s, 3H), 1.82-1.68 (m, 1H), 0.96 (br-s, 6H).

EXAMPLE 5(7)

4-[3-[N-isopropyl-N-[2-(4-methylthiazolyl)sulfonyl]amino]naphthalen-2-yloxymethyl]-3-methylbenzoic acid

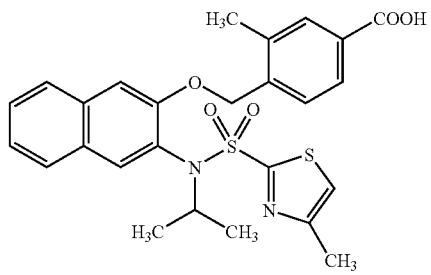

TLC: Rf 0.56 (ethyl acetate:methanol=9:1); NMR: δ 8.00-7.97 (m, 2H), 7.76-7.65 (m, 3H), 7.61 (s, 1H), 7.52-7.47 (m, 1H), 7.40-7.35 (m, 1H), 7.26 (s, 1H), 7.04 (s, 1H), 5.22 (d, J=15.0 Hz, 1H), 5.17 (d, J=15.0 Hz, 1H), 4.83-4.73 (m, 1H), 2.53 (s, 3H), 2.46 (s, 3H), 1.25 (d, J=6.6 Hz, 3H), 1.16 (d, J=6.6 Hz, 3H).

EXAMPLE 5(8)

4-[3-[N-isobutyl-N-(4-methyl-2-thiazolylsulfonyl)amino]naphthalen-2-yloxymethyl]cinnamic acid

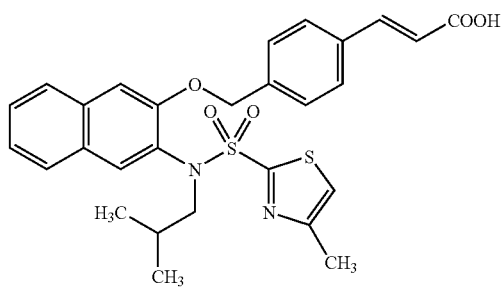

TLC: Rf 0.67 (ethyl acetate:methanol=9:1); NMR: δ 7.84-7.69 (m, 4H), 7.58 (d, J=8.1 Hz, 2H), 7.51-7.45 (m, 1H), 7.41-7.35 (m, 3H), 7.18 (s, 1H), 6.93 (s, 1H), 6.49 (d, J=16.2 Hz, 1H), 5.02 and 4.91 (each br-m, total 2H), 3.84-3.62 (br-m, 2H), 2.33 (s, 3H), 1.82-1.68 (m, 1H), 0.91 (br-s, 6H).

EXAMPLE 5(9)

4-[3-[N-isopropyl-N-(4-methyl-2-thiazolylsulfonyl)amino]naphthalen-2-yloxymethyl]cinnamic acid

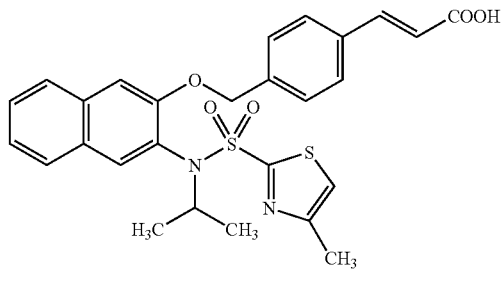

TLC: Rf 0.61 (ethyl acetate:methanol=9:1); NMR: δ 7.80 (d, J=16.9 Hz, 1H), 7.71 (d, J=8.7 Hz, 2H), 7.61-7.46 (m, 6H), 7.39-7.34 (m, 1H), 7.24 (s, 1H), 7.03 (s, 1H), 6.48 (d, J=16.9 Hz, 1H), 5.19 (s, 2H), 4.85-4.72 (m, 1H), 2.51 (s, 3H), 1.25 (d, J=6.6 Hz, 3H), 1.16 (d, J=6.6 Hz, 3H).

EXAMPLE 5(10)

3-methyl-4-[6-[N-methyl-N-(5-methyl-2-furylsulfonyl)amino]indan-5-yloxymethyl]benzoic acid

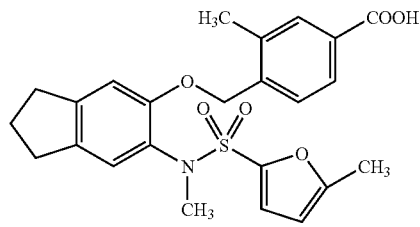

TLC: Rf 0.58 (chloroform:methanol=9:1); NMR(DMSO-$d_6$): δ 7.77 (s, 1H), 7.74 (d, J=7.8 Hz, 1H), 7.36 (d, J=7.8 Hz, 1H), 7.09 (s, 1H), 6.99 (s, 1H), 6.90 (d, J=3.3 Hz, 1H), 6.25-6.15 (m, 1H), 5.02 (s, 2H), 3.15 (s, 3H), 2.84 (t, J=7.4 Hz, 2H), 2.78 (t, J=7.4 Hz, 2H), 2.32 (s, 3H), 2.12 (s, 3H), 2.10-1.95 (m, 2H).

EXAMPLE 5(11)

4-[6-[N-ethyl-N-(5-methyl-2-furylsulfonyl)amino]indan-5-yloxymethyl]-3-methylbenzoic acid

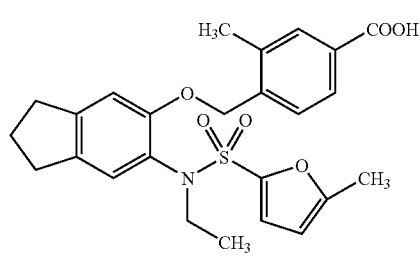

TLC: Rf 0.59 (chloroform:methanol=9:1); NMR(DMSO-$d_6$): δ 7.77 (s, 1H), 7.74 (d, J=7.8 Hz, 1H), 7.38 (d, J=7.8 Hz, 1H), 7.10 (s, 1H), 6.95 (s, 1H), 6.86 (d, J=3.3 Hz, 1H), 6.16 (d, J=3.3 Hz, 1H), 5.01 (br, 2H), 3.58 (br, 2H), 2.86 (t, J=7.4 Hz, 2H), 2.79 (t, J=7.4 Hz, 2H), 2.32 (s, 3H), 2.10 (s, 3H), 2.10-1.95 (m, 2H), 0.99 (t, J=7.2 Hz, 3H).

EXAMPLE 5(12)

4-[6-[N-methyl-N-(5-methyl-2-furylsulfonyl)amino]indan-5-yloxymethyl]cinnamic acid

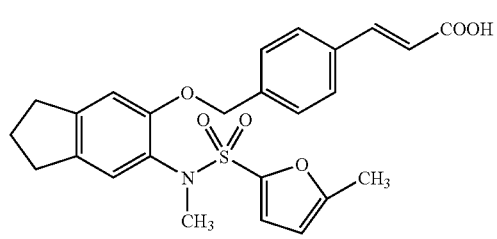

TLC: Rf 0.53 (chloroform:methanol=9:1); NMR: δ 7.77 (d, J=15.9 Hz, 1H), 7.55 (d, J=8.4 Hz, 2H), 7.37 (d, J=8.4 Hz, 2H), 7.14 (s, 1H), 6.80 (s, 1H), 6.79 (d, J=3.6 Hz, 1H), 6.47 (d, J=15.9 Hz, 1H), 5.97 (d, J=3.6 Hz, 1H), 4.98 (s, 2H), 3.31 (s, 3H), 2.90-2.80 (m, 4H), 2.17 (s, 3H), 2.08 (quint, J=7.5 Hz, 2H).

EXAMPLE 5(13)

4-[6-[N-ethyl-N-(5-methyl-2-furylsulfonyl)amino]indan-5-yloxymethyl]cinnamic acid

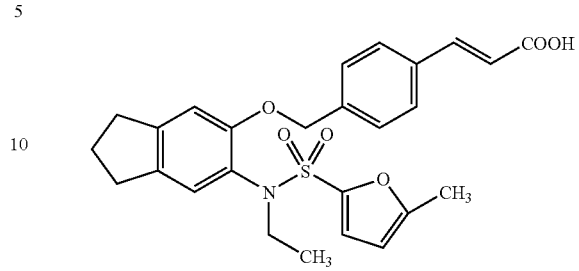

TLC: Rf 0.53 (chloroform:methanol=9:1); NMR: δ 7.77 (d, J=16.2 Hz, 1H), 7.55 (d, J=8.4 Hz, 2H), 7.37 (d, J=8.4 Hz, 2H), 7.08 (s, 1H), 6.80 (s, 1H), 6.75 (d, J=3.3 Hz, 1H), 6.47 (d, J=16.2 Hz, 1H), 5.94 (d, J=3.3 Hz, 1H), 4.97 (s, 2H), 3.82-3.65 (m, 2H), 2.90-2.80 (m, 4H), 2.15 (s, 3H), 2.08 (quint, J=7.2 Hz, 2H), 1.14 (t, J=7.2 Hz, 3H).

EXAMPLE 5(14)

4-[6-[N-(5-methyl-2-furylsulfonyl)-N-propylamino]indan-5-yloxymethyl]cinnamic acid

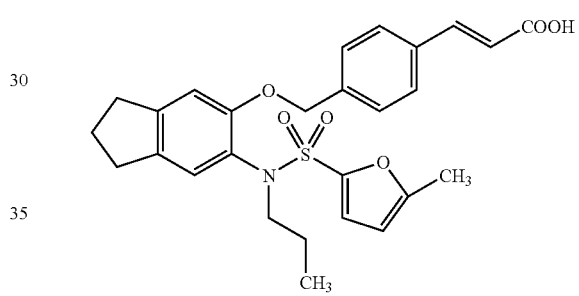

TLC: Rf 0.54 (chloroform:methanol=9:1); NMR: δ 7.78 (d, J=15.9 Hz, 1H), 7.55 (d, J=8.1 Hz, 2H), 7.37 (d, J=8.1 Hz, 2H), 7.08 (s, 1H), 6.79 (s, 1H), 6.74 (d, J=3.3 Hz, 1H), 6.46 (d, J=15.9 Hz, 1H), 5.94 (brd, J=3.3 Hz, 1H), 4.97 (br s, 2H), 3.65-3.61 (m, 2H), 2.90-2.80 (m, 4H), 2.15 (s, 3H), 2.08 (quint, J=7.5 Hz, 2H), 1.53 (sext, J=7.2 Hz, 2H), 0.89 (t, J=7.2 Hz, 3H).

EXAMPLE 5(15)

4-[4,5-dimethyl-2-[N-(5-methyl-2-furylsulfonyl)-N-(2-methyl-2-propenyl)amino]phenoxy methyl]-3-methylbenzoic acid

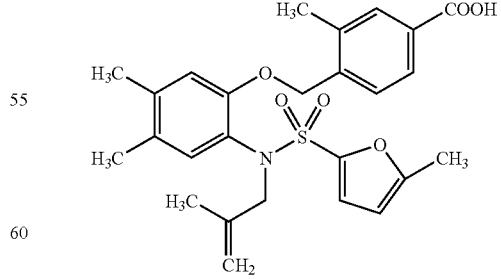

TLC: Rf 0.45 (chloroform:methanol=9:1); NMR: δ 8.00-7.93 (m, 2H), 7.44 (d, J=8.1 Hz, 1H), 7.02 (s, 1H), 6.75 (d, J=3.3 Hz, 1H), 6.69 (s, 1H), 5.96 (m, 1H), 4.94 (s, 2H), 4.77 (s, 2H), 4.27 (s, 2H), 2.38 (s, 3H), 2.22 (s, 3H), 2.18 (s, 3H), 2.12 (s, 3H), 1.78 (s, 3H).

EXAMPLE 5(16)

4-[6-[N-(5-methyl-2-furylsulfonyl)-N-(2-methyl-2-propenyl)amino]indan-5-yloxymethyl]cinnamic acid

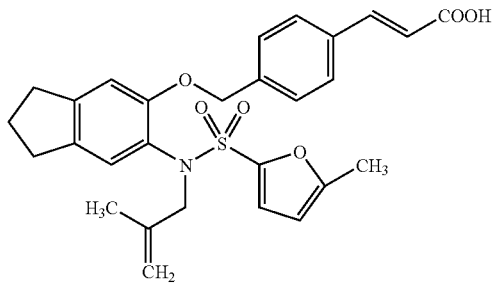

TLC: Rf 0.61 (chloroform:methanol=9:1); NMR: δ 7.78 (d, J=15.9 Hz, 1H), 7.56 (d, J=8.4 Hz, 2H), 7.36 (d, J=8.4 Hz, 2H), 7.09 (s, 1H), 6.76 (s, 1H), 6.74 (d, J=3.0 Hz, 1H), 6.47 (d, J=15.9 Hz, 1H), 5.94 (d, J=3.0 Hz, 1H), 4.95 (brs, 2H), 4.77 (s, 2H), 4.38-4.18 (m, 2H), 2.90-2.75 (m, 4H), 2.14 (s, 3H), 2.07 (quint, J=7.5 Hz, 2H), 1.78 (s, 3H).

EXAMPLE 5(17)

4-[6-[N-cyclopropylmethyl-N-(5-methyl-2-furylsulfonyl)amino]indan-5-yloxymethyl]cinnamic acid

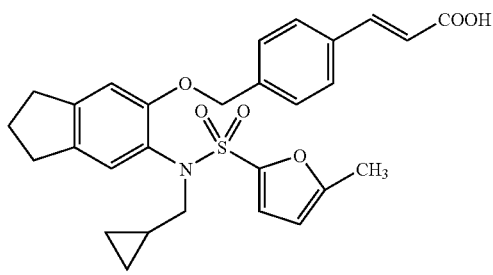

TLC: Rf 0.51 (chloroform:methanol=9:1); NMR: δ 7.79 (d, J=15.9 Hz, 1H), 7.55 (d, J=8.4 Hz, 2H), 7.38 (d, J=8.4 Hz, 2H), 7.15 (s, 1H), 6.79 (s, 1H), 6.74 (d, J=3.3 Hz, 1H), 6.47 (d, J=15.9 Hz, 1H), 5.94 (d, J=3.3 Hz, 1H), 4.97 (brs, 2H), 3.65-3.50 (m, 2H), 2.92-2.70 (m, 4H), 2.15 (s, 3H), 2.08 (quint, J=7.5 Hz, 2H), 1.00-0.85 (m, 1H), 0.45-0.36 (m, 2H), 0.20-0.05 (m, 2H).

EXAMPLE 5(18)

4-[6-[N-(5-methyl-2-furylsulfonyl)-N-(2-propenyl)amino]indan-5-yloxymethyl]cinnamic acid

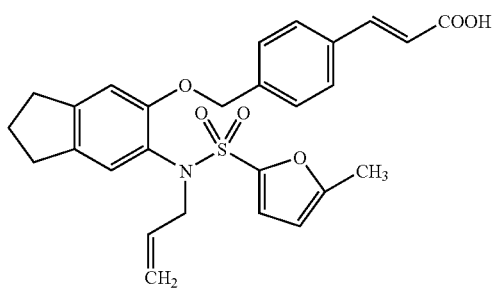

TLC: Rf 0.57 (chloroform:methanol=9:1); NMR: δ 7.79 (d, J=15.9 Hz, 1H), 7.56 (d, J=8.4 Hz, 2H), 7.38 (d, J=8.4 Hz, 2H), 7.07 (s, 1H), 6.78 (s, 1H), 6.76 (d, J=3.3 Hz, 1H), 6.47 (d, J=15.9 Hz, 1H), 5.96 (d, J=3.3 Hz, 1H), 5.96-5.77 (m, 1H), 5.13-5.03 (m, 2H), 4.97 (s, 2H), 4.42-4.20 (m, 2H), 2.90-2.80 (m, 4H), 2.16 (s, 3H), 2.07 (quint, J=7.5 Hz, 2H).

EXAMPLE 5(19)

3-methyl-4-[6-[N-(5-methyl-2-furylsulfonyl)-N-propylamino]indan-5-yloxymethyl]benzoic acid

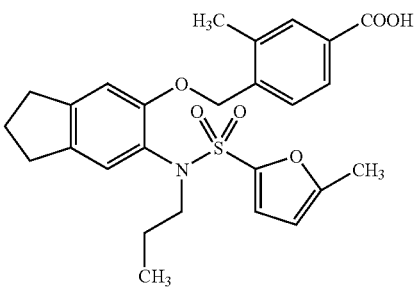

TLC: Rf 0.40 (chloroform:methanol=10:1); NMR: δ 7.95 (d, J=7.8 Hz, 1H), 7.93 (s, 1H), 7.46 (d, J=7.8 Hz, 1H), 7.10 (s, 1H), 6.81 (s, 1H), 6.75 (d, J=3.3 Hz, 1H), 5.95 (dd, J=3.3, 0.9 Hz, 1H), 4.96 (s, 2H), 3.76-3.47 (m, 2H), 2.92-2.82 (m, 4H), 2.37 (s, 3H), 2.13 (s, 3H), 2.15-2.03 (m, 2H), 1.60-1.47 (m, 2H), 0.89 (t, J=7.5 Hz, 3H).

EXAMPLE 5(20)

3-methyl-4-[6-[N-(5-methyl-2-furylsulfonyl)-N-(2-propenyl)amino]indan-5-yloxymethyl]benzoic acid

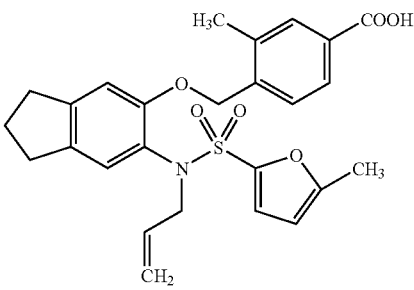

TLC: Rf 0.41 (chloroform:methanol=10:1); NMR: δ 7.95 (d, J=7.8 Hz, 1H), 7.94 (s, 1H), 7.47 (d, J=7.8 Hz, 1H), 7.08 (s, 1H), 6.80 (s, 1H), 6.78 (d, J=3.3 Hz, 1H), 5.97 (d, J=3.3 Hz, 1H), 5.85 (m, 1H), 5.10 (dd, J=16.8, 1.2 Hz, 1H), 5.05 (dd, J=9.9, 1.2 Hz, 1H), 4.97 (s, 2H), 4.43-4.18 (m, 2H), 2.91-2.81 (m, 4H), 2.37 (s, 3H), 2.15 (s, 3H), 2.13-2.03 (m, 2H).

EXAMPLE 5(21)

4-[4,5-dimethyl-2-[N-methyl-N-(4-methyl-2-thiazolylsulfonyl)amino]phenoxymethyl]-3-methylbenzoic acid

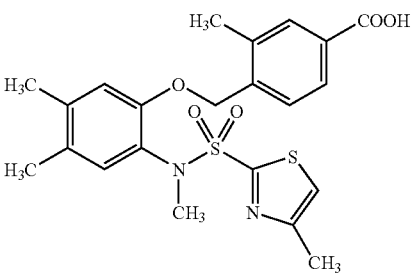

TLC: Rf 0.49 (dichloromethane:methanol=10:1); NMR: δ 7.94-7.90 (m, 2H), 7.31 (d, J=9.0 Hz, 1H), 7.13 (s, 1H), 6.94 (m, 1H), 6.73 (s, 1H), 4.88 (s, 2H), 3.42 (s, 3H), 2.35 (s, 3H), 2.34 (d, J=0.9 Hz, 3H), 2.24 (s, 3H), 2.19 (s, 3H).

EXAMPLE 5(22)

4-[4,5-dimethyl-2-[N-ethyl-N-(4-methyl-2-thiazolyl-sulfonyl)amino]phenoxymethyl]-3-methylbenzoic acid

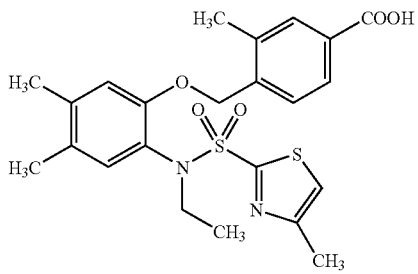

TLC: Rf 0.49 (dichloromethane:methanol=10:1); NMR: δ 7.96-7.90 (m, 2H), 7.32 (d, J=8.1 Hz, 1H), 7.06 (s, 1H), 6.90 (m, 1H), 6.74 (s, 1H), 4.87 (brs, 2H), 3.85 (br, 2H), 2.34 (s, 3H), 2.32 (d, J=0.9 Hz, 3H), 2.25 (s, 3H), 2.19 (s, 3H), 1.18 (t, J=7.2 Hz, 3H).

EXAMPLE 5(23)

4-[4,5-dimethyl-2-[N-(4-methyl-2-thiazolylsulfo-nyl)-N-propylamino]phenoxymethyl]-3-methylben-zoic acid

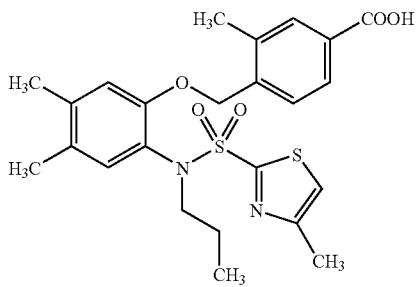

TLC: Rf 0.49 (dichloromethane:methanol=10:1); NMR (DMSO-$d_6$): δ 12.88 (s, 1H), 7.78-7.72 (m, 2H), 7.49 (m, 1H), 7.25 (d, J=7.8 Hz, 1H), 7.03 (s, 1H), 6.95 (s, 1H), 4.88 (br, 2H), 3.59 (br, 2H), 2.28 (s, 3H), 2.22 (s, 3H), 2.18 (s, 3H), 2.13 (s, 3H), 1.44-1.35 (m, 2H), 0.81 (t, J=7.2 Hz, 3H).

EXAMPLE 5(24)

4-[4,5-dimethyl-2-[N-(4-methyl-2-thiazolylsulfo-nyl)-N-(2-propenyl)amino]phenoxymethyl]3-meth-ylbenzoic acid

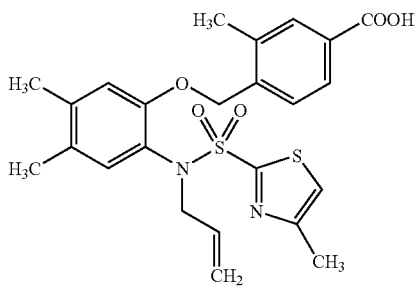

TLC: Rf 0.49 (dichloromethane:methanol=10:1); NMR (DMSO-$d_6$): δ 12.88 (s, 1H), 7.78-7.72 (m, 2H), 7.50 (s, 1H), 7.26 (d, J=7.5 Hz, 1H), 7.01 (s, 1H), 6.95 (s, 1H), 5.74 (m, 1H), 5.09 (d, J=17.1 Hz, 1H), 5.04 (d, J=9.9 Hz, 1H), 4.89 (br, 2H), 4.27 (br, 2H), 2.29 (s, 3H), 2.21 (s, 3H), 2.18 (s, 3H), 2.12 (s, 3H).

EXAMPLE 5(25)

4-[2-[N-cyclopropylmethyl-N-(4-methyl-2-thiazolyl-sulfonyl)amino-4,5-dimethyl]phenoxymethyl]-3-methylbenzoic acid

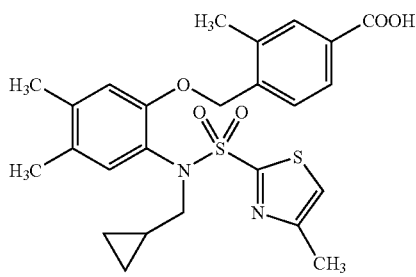

TLC: Rf 0.49 (dichloromethane:methanol=10:1); NMR (DMSO-$d_6$): δ 12.87 (br, 1H), 7.78-7.72 (m, 2H), 7.48 (s, 1H), 7.25 (d, J=7.5 Hz, 1H), 7.03 (s, 1H), 7.00 (s, 1H), 4.90 (br, 2H), 3.45 (br, 2H), 2.27 (s, 3H), 2.23 (s, 3H), 2.17 (s, 3H), 2.14 (s, 3H), 0.82 (m, 1H), 0.38-0.30 (m, 2H), 0.10-0.02 (m, 2H).

EXAMPLE 5(26)

4-[4,5-dimethyl-2-[N-(2-hydroxy-2-methylpropyl)-N-(4-methyl-2-thiazolylsulfonyl)amino]phenoxym-ethyl]-3-methylbenzoic acid

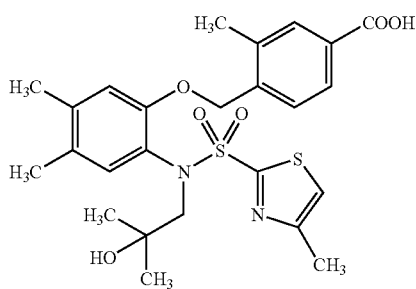

TLC: Rf 0.49 (dichloromethane:methanol=10:1); NMR: δ 7.99-7.94 (m, 2H), 7.47 (d, J=8.1 Hz, 1H), 7.04 (m, 1H), 6.79 (s, 1H), 6.77 (s, 1H), 5.06 (d, J=12.3 Hz, 1H), 4.95 (d, J=12.3 Hz, 1H), 3.95 (d, J=15.3 Hz, 1H), 3.73 (d, J=15.3 Hz, 1H), 2.420 (s, 3H), 2.417 (s, 3H), 2.23 (s, 3H), 2.11 (s, 3H), 1.25 (s, 3H), 1.21 (s, 3H).

EXAMPLE 5(27)

4-[4,5-dimethyl-2-[N-methyl-N-(5-methyl-2-furyl-sulfonyl)amino]phenoxymethyl]benzoic acid

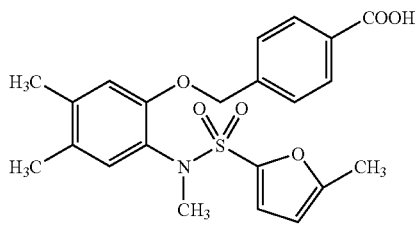

TLC: Rf 0.46 (chloroform:methanol=9:1); NMR: δ 8.11 (d, J=8.4 Hz, 2H), 7.42 (d, J=8.4 Hz, 2H), 7.08 (s, 1H), 6.79 (d, J=3.3 Hz, 1H), 6.71 (s, 1H), 5.99-5.95 (m, 1H), 5.03 (s, 2H), 3.31 (s, 3H), 2.22 (s, 3H), 2.18 (s, 3H), 2.16 (s, 3H).

EXAMPLE 5(28)

4-[4,5-dimethyl-2-[N-ethyl-N-(5-methyl-2-furylsulfonyl)amino]phenoxymethyl]benzoic acid

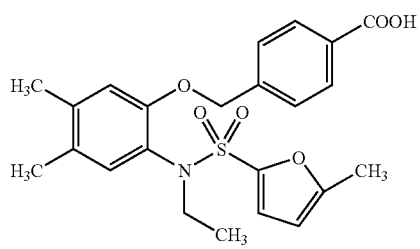

TLC: Rf 0.41 (chloroform:methanol=9:1); NMR: δ 8.10 (d, J=8.4 Hz, 2H), 7.43 (d, J=8.4 Hz, 2H), 7.01 (s, 1H), 6.76 (d, J=3.3 Hz, 1H), 6.71 (s, 1H), 5.96-5.93 (m, 1H), 5.02 (s, 2H), 3.83-3.65 (m, 2H), 2.23 (s, 3H), 2.18 (s, 3H), 2.14 (s, 3H), 1.14 (t, J=7.2 Hz, 3H).

EXAMPLE 5(29)

4-[4,5-dimethyl-2-[N-(5-methyl-2-furylsulfonyl)-N-propylamino]phenoxymethyl]benzoic acid

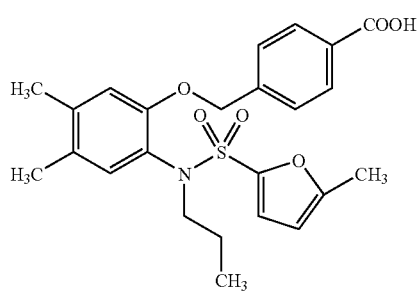

TLC: Rf 0.43 (chloroform:methanol=9:1); NMR: δ 8.11 (d, J=8.4 Hz, 2H), 7.43 (d, J=8.4 Hz, 2H), 7.02 (s, 1H), 6.74 (d, J=3.0 Hz, 1H), 6.70 (s, 1H), 5.96-5.93 (m, 1H), 5.01 (s, 2H), 3.75-3.53 (m, 2H), 2.22 (s, 3H), 2.18 (s, 3H), 2.14 (s, 3H), 1.60-1.46 (m, 2H), 0.90 (t, J=7.2 Hz, 3H).

EXAMPLE 5(30)

4-[6-[N-(2-methyl-2-propenyl)-N-(4-methyl-2-thiazolylsulfonyl)amino]indan-5-yloxymethyl]benzoic acid

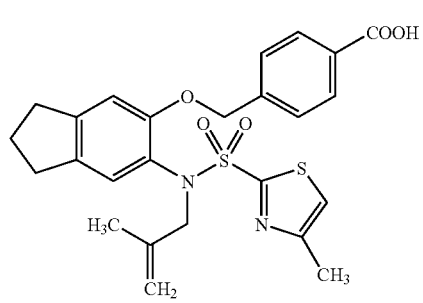

TLC: Rf 0.36 (dichloromethane:methanol=19:1); NMR: δ 8.11 (d, J=8.7 Hz, 2H), 7.35 (d, J=8.7 Hz, 2H), 7.14 (s, 1H), 6.92 (brs, 1H), 6.74 (s, 1H), 5.10-4.70 (brs, 2H), 4.80 (brs, 2H), 4.60-4.20 (brs, 2H), 2.88-2.82 (m, 4H), 2.32 (d, J=0.9 Hz, 3H), 2.07 (m, 2H), 1.83 (s, 3H).

EXAMPLE 5(31)

4-[6-[N-(4-methyl-2-thiazolylsulfonyl)-N-(2-propenyl)amino]indan-5-yloxymethyl]benzoic acid

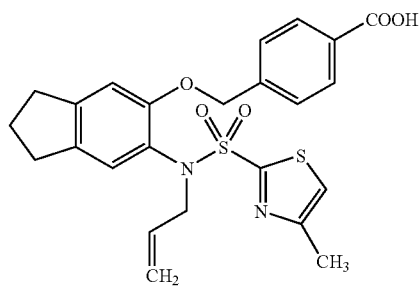

TLC: Rf 0.34 (dichloromethane:methanol=19:1); NMR: δ 8.11 (d, J=8.7 Hz, 2H), 7.35 (d, J=8.7 Hz, 2H), 7.13 (s, 1H), 6.93 (brs, 1H), 6.76 (s, 1H), 5.89 (ddt, J=17.1, 10.2, 6.3 Hz, 1H), 5.17-5.06 (m, 2H), 4.92 (brs, 2H), 4.70-4.10 (brs, 2H), 2.89-2.83 (m, 4H), 2.34 (d, J=0.9 Hz, 3H), 2.08 (m, 2H).

EXAMPLE 5(32)

4-[6-[N-cyclopropylmethyl-N-(4-methyl-2-thiazolylsulfonyl)amino]indan-5-yloxymethyl]benzoic acid

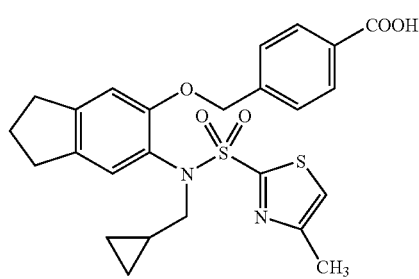

TLC: Rf 0.36 (dichloromethane:methanol=19:1); NMR: δ 8.10 (d, J=8.7 Hz, 2H), 7.35 (d, J=8.7 Hz, 2H), 7.22 (s, 1H), 6.89 (brs, 1H), 6.78 (s, 1H), 5.10-4.70 (m, 2H), 3.90-3.50 (m, 2H), 2.90-2.85 (m, 4H), 2.32 (d, J=0.9 Hz, 3H), 2.09 (m, 2H), 1.00 (m, 1H), 0.43 (m, 2H), 0.20 (brs, 2H).

EXAMPLE 5(33)

4-[3-[N-isopropyl-N-(5-methyl-2-furylsulfonyl)amino]naphthalen-2-yloxymethyl]-3-methylbenzoic acid

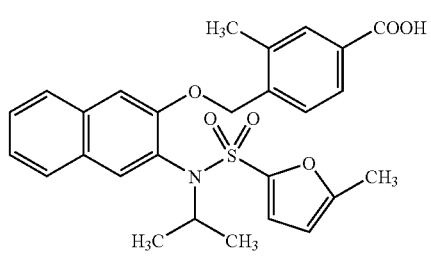

TLC: Rf 0.52 (chloroform:methanol=9:1); NMR(DMSO-d$_6$): δ 7.92-7.80 (m, 3H), 7.77 (d, J=8.1 Hz, 1H), 7.69 (d, J=8.1 Hz, 1H), 7.63 (s, 1H), 7.60 (s, 1H), 7.57-7.50 (m, 1H), 7.45-7.36 (m, 1H), 6.95 (d, J=3.3 Hz, 1H), 6.29 (d, J=3.3 Hz, 1H), 5.26 and 5.24 (each d, J=13.5 Hz, each 1H), 4.34 (sept, J=6.6 Hz, 1H), 2.42 (s, 3H), 2.34 (s, 3H), 1.06 and 1.00 (each d, J=6.6 Hz, each 3H).

EXAMPLE 5(34)

4-[3-[N-isobutyl-N-(5-methyl-2-furylsulfonyl)amino]naphthalen-2-yloxymethyl]-3-methylbenzoic acid

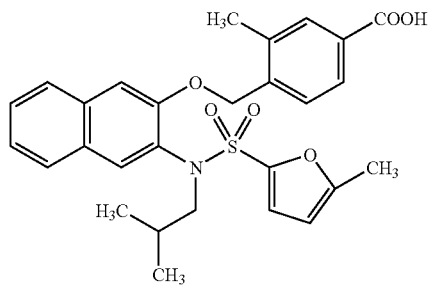

TLC: Rf 0.50 (chloroform:methanol=9:1); NMR(DMSO-d$_6$): δ 7.88 (d, J=7.8 Hz, 1H), 7.86-7.74 (m, 4H), 7.59 (s, 1H), 7.56-7.36 (m, 3H), 6.86 (d, J=3.3 Hz, 1H), 6.19 (d, J=3.3 Hz, 1H), 5.40-4.90 (br, 2H), 3.47 (brd, J=6.9 Hz, 2H), 2.39 (s, 3H), 2.12 (s, 3H), 1.65-1.50 (m, 1H), 0.83 (brd, J=6.3 Hz, 6H).

EXAMPLE 5(35)

4-[3-[N-isopropyl-N-(5-methyl-2-furylsulfonyl)amino]naphthalen-2-yloxymethyl]cinnamic acid

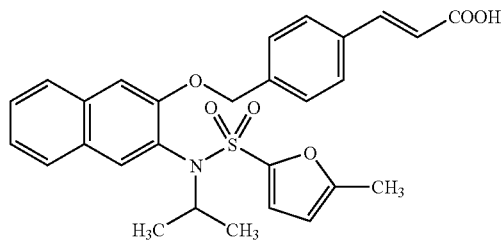

TLC: Rf 0.45 (chloroform:methanol=9:1); NMR(DMSO-d$_6$): δ 7.87 (d, J=7.8 Hz, 1H), 7.82 (d, J=7.8 Hz, 1H), 7.73 (d, J=8.4 Hz, 2H), 7.67-7.46 (m, 6H), 7.44-7.34 (m, 1H), 6.94 (d, J=3.3 Hz, 1H), 6.56 (d, J=15.9 Hz, 1H), 6.28 (d, J=3.3 Hz, 1H), 5.27 and 5.21 (each d, J=13.2 Hz, each 1H), 4.36 (sept, J=6.6 Hz, 1H), 2.33 (s, 3H), 1.08 and 1.03 (each d, J=6.6 Hz, each 3H).

EXAMPLE 5(36)

4-[3-[N-isobutyl-N-(5-methyl-2-furylsulfonyl)amino]naphthalen-2-yloxymethyl]cinnamic acid

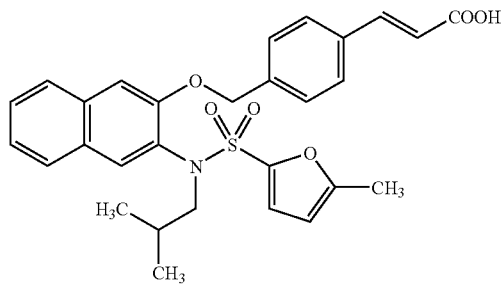

TLC: Rf 0.45 (chloroform:methanol=9:1); NMR(DMSO-d$_6$): δ 7.88 (d, J=8.4 Hz, 1H), 7.81 (s, 1H), 7.80 (d, J=8.1 Hz, 1H), 7.72 (d, J=7.8 Hz, 2H), 7.61 (s, 1H), 7.55-7.34 (m, 2H), 7.50 (s, 1H), 7.44 (d, J=7.8 Hz, 1H), 6.82 (d, J=3.6 Hz, 1H), 6.56 (d, J=15.9 Hz, 1H), 6.16 (d, J=3.6 Hz, 1H), 5.40-4.90 (br, 2H), 3.49 (d, J=6.6 Hz, 2H), 2.13 (s, 3H), 1.64-1.48 (m, 1H), 0.85 (d, J=6.6 Hz, 6H).

EXAMPLE 5(37)

4-[3-[N-isopropyl-N-(5-methyl-2-furylsulfonyl)amino]naphthalen-2-yloxymethyl]-3-methylcinnamic acid

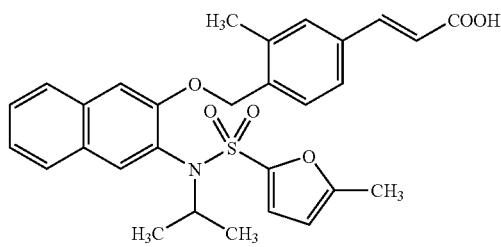

TLC: Rf 0.46 (chloroform:methanol=9:1); NMR(DMSO-d$_6$): δ 7.87 (d, J=8.1 Hz, 1H), 7.86 (d, J=8.4 Hz, 1H), 7.64-7.48 (m, 7H), 7.44-7.36 (m, 1H), 6.93 (d, J=3.6 Hz, 1H), 6.54 (d, J=15.9 Hz, 1H), 6.29 (d, J=3.6 Hz, 1H), 5.23 and 5.18 (each d, J=14.4 Hz, each 1H), 4.33 (sept, J=6.6 Hz, 1H), 2.39 (s, 3H), 2.34 (8, 3H), 1.06 and 1.00 (each d, J=6.6 Hz, each 3H).

EXAMPLE 5(38)

4-[3-[N-isobutyl-N-(5-methyl-2-furylsulfonyl)amino]naphthalen-2-yloxymethyl]-3-methylcinnamic acid

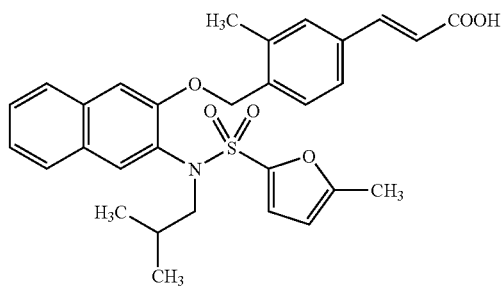

TLC: Rf 0.46 (chloroform:methanol=9:1); NMR(DMSO-d$_6$): δ 7.88 (d, J=8.1 Hz, 1H), 7.84 (d, J=8.4 Hz, 1H), 7.78 (s, 1H), 7.62-7.47 (m, 5H), 7.44-7.35 (m, 2H), 6.84 (d, J=3.6 Hz, 1H), 6.54 (d, J=16.2 Hz, 1H), 6.20 (d, J=3.6 Hz, 1H), 5.35-4.90 (br, 2H), 3.47 (d, J=7.2 Hz, 2H), 2.35 (s, 3H), 2.14 (s, 3H), 1.63-1.49 (m, 1H), 0.83 (d, J=6.3 Hz, 6H).

EXAMPLE 5(39)

4-[3-[N-isobutyl-N-[2-(4-methylthiazolyl)sulfonyl]amino]naphthalen-2-yloxymethyl]-3-methylbenzoic acid

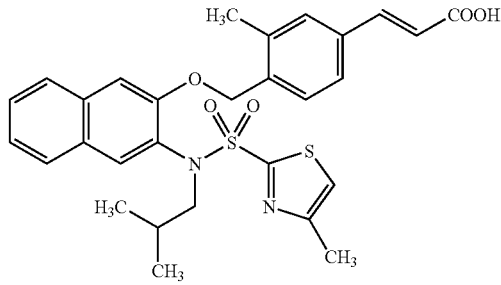

TLC: Rf 0.71 (ethyl acetate:methanol=9:1); NMR: δ 7.82-7.71 (m, 4H), 7.51-7.46 (m, 1H), 7.43-7.32 (m, 4H), 7.21 (s, 1H), 6.95 (s, 1H), 6.48 (d, J=16.2 Hz, 1H), 5.04 and 4.91 (each br-m, total 2H), 3.83-3.60 (br-m, 2H), 2.38 (s, 3H), 2.34 (s, 3H), 1.81-1.67 (m, 1H), 0.95 (br-s, 6H).

EXAMPLE 5(40)

4-[3-[N-isopropyl-N-(4-methyl-2-thiazolylsulfonyl)amino]naphthalen-2-yloxymethyl]-3-methylbenzoic acid

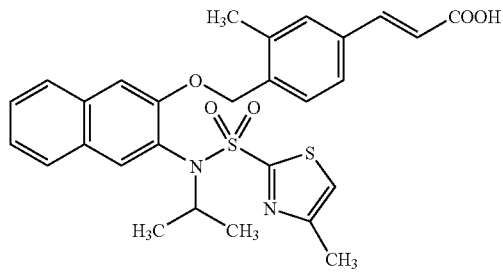

TLC: Rf 0.71 (ethyl acetate:methanol=9:1); NMR (DMSO-d$_6$): δ 7.88-7.83 (m, 2H), 7.65-7.47 (m, 8H), 7.42-7.37 (m, 1H), 6.55 (d, J=15.9 Hz, 1H), 5.16 (s, 2H), 4.62-4.49 (m, 1H), 2.42 (s, 3H), 2.36 (s, 3H), 1.13 (d, J=6.6 Hz, 3H), 1.03 (d, J=6.6 Hz, 3H).

EXAMPLE 5(41)

4-[6-[N-ethyl-N-(4-methyl-2-thiazolylsulfonyl)amino]indan-5-yloxymethyl]benzoic acid

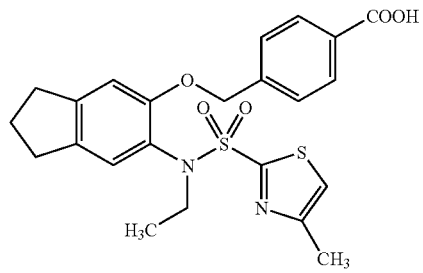

TLC: Rf 0.34 (dichloromethane:methanol=19:1); NMR: δ 8.10 (d, J=8.4 Hz, 2H), 7.35 (d, J=8.4 Hz, 2H), 7.14 (s, 1H), 6.90 (brs, 1H), 6.79 (s, 1H), 4.92 (m, 2H), 4.20-3.60 (m, 2H), 2.90-2.83 (m, 4H), 2.33 (s, 3H), 2.09 (m, 2H), 1.20 (t, J=7.2 Hz, 3H).

EXAMPLE 5(42)

4-[6-[N-(4-methyl-2-thiazolylsulfonyl)-N-propylamino]indan-5-yloxymethyl]benzoic acid

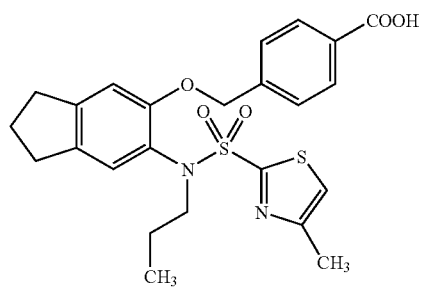

TLC: Rf 0.34 (dichloromethane:methanol=19:1); NMR: δ 8.11 (d, J=8.4 Hz, 2H), 7.35 (d, J=8.4 Hz, 2H), 7.15 (s, 1H), 6.90 (brs, 1H), 6.78 (s, 1H), 5.10-4.70 (m, 2H), 4.00-3.50 (m, 2H), 2.90-2.84 (m, 4H), 2.32 (s, 3H), 2.09 (m, 2H), 1.58 (m, 2H), 0.93 (t, J=7.5 Hz, 3H).

EXAMPLE 5(43)

4-[4,5-dimethyl-2-[N-(5-methyl-2-furylsulfonyl)-N-(2-propenyl)amino]phenoxymethyl]benzoic acid

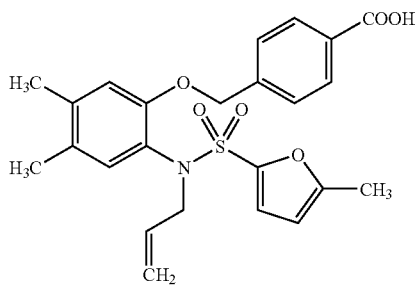

TLC: Rf 0.44 (chloroform:methanol=9:1); NMR: δ 8.12 (d, J=8.4 Hz, 2H), 7.43 (d, J=8.4 Hz, 2H), 7.01 (s, 1H), 6.77 (d, J=3.0 Hz, 1H), 6.68 (s, 1H), 5.99-5.94 (m, 1H), 5.92-5.75 (m, 1H), 5.16-5.03 (m, 2H), 5.02 (s, 2H), 4.42-4.20 (m, 2H), 2.21 (s, 3H), 2.17 (s, 3H), 2.15 (s, 3H).

EXAMPLE 5(44)

4-[4,5-dimethyl-2-[N-methyl-N-(5-methyl-2-furylsulfonyl)amino]phenoxymethyl]-3-methylbenzoic acid

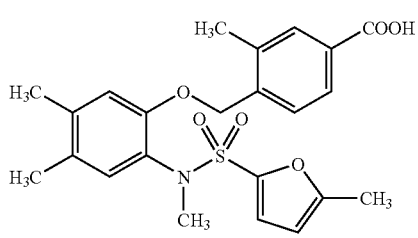

TLC: Rf 0.42 (chloroform:methanol=9:1); NMR: δ 7.98-7.91 (m, 2H), 7.43 (d, J=8.7 Hz, 1H), 7.08 (s, 1H), 6.79 (d, J=3.3 Hz, 1H), 6.74 (s, 1H), 5.98 (m, 1H), 4.98 (s, 2H), 3.30 (s, 3H), 2.38 (s, 3H), 2.24 (s, 3H), 2.19 (s, 3H), 2.15 (s, 3H).

EXAMPLE 5(45)

4-[4,5-dimethyl-2-[N-ethyl-N-(5-methyl-2-furylsulfonyl)amino]phenoxymethyl]-3-methylbenzoic acid

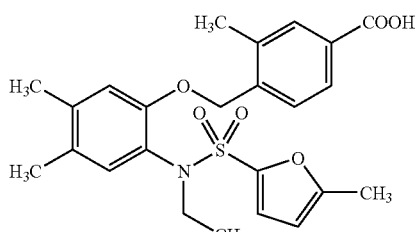

TLC: Rf 0.42 (chloroform:methanol=9:1); NMR: δ 7.97-7.90 (m, 2H), 7.45 (d, J=8.1 Hz, 1H), 7.01 (s, 1H), 6.76 (s, 1H), 6.75 (d, J=3.3 Hz, 1H), 5.95 (m, 1H), 4.96 (s, 2H), 3.82-3.66 (br, 2H), 2.37 (s, 3H), 2.25 (s, 3H), 2.19 (s, 3H), 2.13 (s, 3H), 1.14 (t, J=7.2 Hz, 3H).

EXAMPLE 5(46)

4-[4,5-dimethyl-2-[N-(5-methyl-2-furylsulfonyl)-N-propylamino]phenoxymethyl]-3-methylbenzoic acid

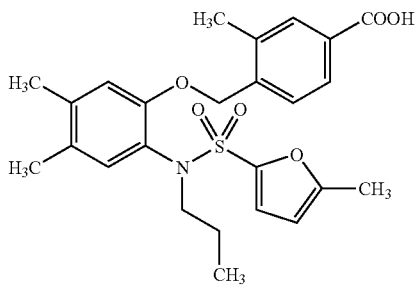

TLC: Rf 0.42 (chloroform:methanol=9:1); NMR: δ 7.98-7.90 (m, 2H), 7.45 (d, J=8.1 Hz, 1H), 7.02 (s, 1H), 6.78-6.70 (m, 2H), 5.95 (m, 1H), 4.95 (s, 2H), 3.71-3.55 (br, 2H), 2.37 (s, 3H), 2.24 (s, 3H), 2.19 (s, 3H), 2.12 (s, 3H), 1.60-1.44 (m, 2H), 0.88 (t, J=7.5 Hz, 3H).

EXAMPLE 5(47)

4-[4,5-dimethyl-2-[N-(5-methyl-2-furylsulfonyl)-N-(2-propenyl)amino]phenoxymethyl]-3-methylbenzoic acid

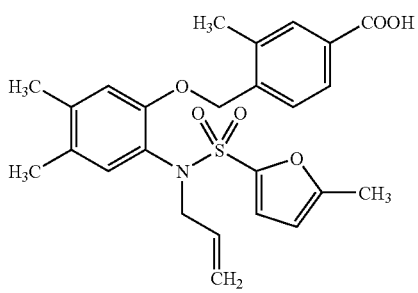

TLC: Rf 0.45 (chloroform:methanol=9:1); NMR: δ 7.98-7.90 (m, 2H), 7.45 (d, J=8.1 Hz, 1H), 7.01 (s, 1H), 6.77 (d, J=3.3 Hz, 1H), 6.71 (s, 1H), 5.96 (m, 1H), 5.83 (m, 1H), 5.15-5.00 (m, 2H), 4.96 (s, 2H), 4.40-4.20 (br, 2H), 2.38 (s, 3H), 2.23 (s, 3H), 2.18 (s, 3H), 2.14 (s, 3H).

EXAMPLE 5(48)

4-[4,5-dimethyl-2-[N-(2-hydroxy-2-methylpropyl)-N-(5-methyl-2-furylsulfonyl)amino]phenoxymethyl]-3-methylbenzoic acid

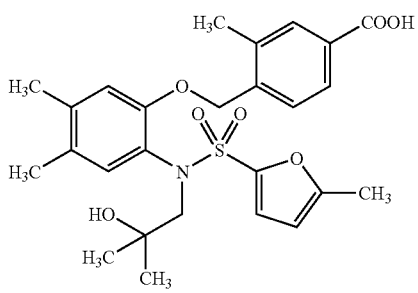

TLC: Rf 0.41 (chloroform:methanol=9:1); NMR: δ 8.00-7.94 (m, 2H), 7.53 (d, J=7.8 Hz, 1H), 6.80 (s, 1H), 6.77 (s, 1H), 6.75 (d, J=3.3 Hz, 1H), 6.01 (m, 1H), 5.08 (d, J=12.3 Hz, 1H), 5.00 (d, J=12.3 Hz, 1H), 3.84 (d, J=14.4 Hz, 1H), 3.56 (d, J=14.4 Hz, 1H), 2.42 (s, 3H), 2.23 (s, 3H), 2.21 (s, 3H), 2.14 (s, 3H), 1.25 (s, 3H), 1.18 (s, 3H).

EXAMPLE 5(49)

4-[6-[N-methyl-N-(4-methyl-2-thiazolylsulfonyl)amino]indan-5-yloxymethyl]benzoic acid

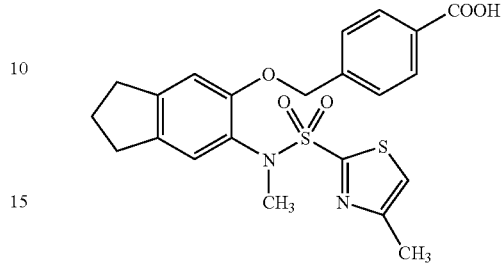

TLC: Rf 0.34 (dichloromethane:methanol=19:1); NMR: δ 8.11 (d, J=8.7 Hz, 2H), 7.35 (d, J=8.7 Hz, 2H), 7.20 (s, 1H), 6.94 (brs, 1H), 6.78 (s, 1H), 4.92 (brs, 2H), 3.44 (s, 3H), 2.89-2.83 (m, 4H), 2.35 (d, J=0.9 Hz, 3H), 2.08 (m, 2H).

EXAMPLE 5(50)

4-[6-[N-(2-hydroxy-2-methylpropyl)-N-(5-methyl-2-furylsulfonyl)amino]indan-5-yloxymethyl]-3-methylbenzoic acid

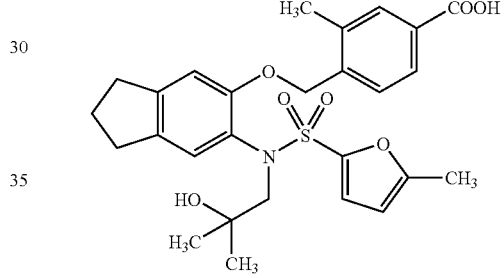

TLC: Rf 0.32 (chloroform:methanol=10:1); NMR: δ 7.97 (d, J=7.8 Hz, 1H), 7.95 (s, 1H), 7.53 (d, J=7.8 Hz, 1H), 6.89 (s, 1H), 6.86 (s, 1H), 6.75 (d, J=3.3 Hz, 1H), 6.01 (dd, J=3.3, 0.9 Hz, 1H), 5.08 (d, J=12.9 Hz, 1H), 5.02 (d, J=12.9 Hz, 1H), 3.85 (d, J=14.7 Hz, 1H), 3.58 (d, J=14.7 Hz, 1H), 2.90-2.78 (m, 4H), 2.42 (s, 3H), 2.21 (s, 3H), 2.13-2.01 (m, 2H), 1.25 (s, 3H), 1.18 (s, 3H).

EXAMPLE 5(51)

3-methyl-4-[6-[N-methyl-N-(4-methyl-2-thiazolylsulfonyl)amino]indan-5-yloxymethyl]cinnamic acid

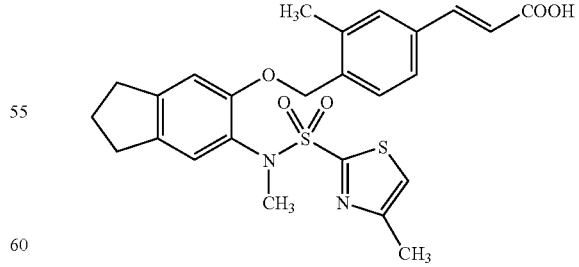

TLC: Rf 0.45 (chloroform:methanol=9:1); NMR(DMSO-d$_6$): δ 7.60-7.50 (m, 3H), 7.49 (d, J=8.1 Hz, 1H), 7.20 (d, J=8.1 Hz, 1H), 7.09 (s, 1H), 7.04 (s, 1H), 6.53 (d, J=15.9 Hz, 1H), 4.87 (br, 2H), 3.24 (s, 3H), 2.85 (t, J=7.4 Hz, 2H), 2.77 (t, J=7.4 Hz, 2H), 2.25 (s, 3H), 2.23 (s, 3H), 2.10-1.95 (m, 2H).

EXAMPLE 5(52)

4-[6-[N-ethyl-N-(4-methyl-2-thiazolylsulfonyl)amino]indan-5-yloxymethyl]-3-methylcinnamic acid

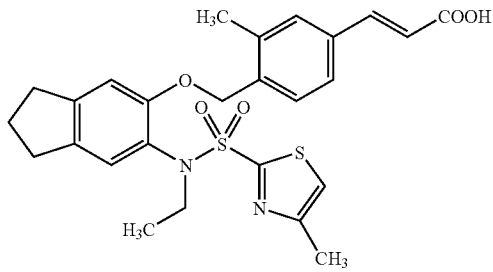

TLC: Rf 0.44 (chloroform:methanol=9:1); NMR(DMSO-$d_6$): δ 7.55 (d, J=16.0 Hz, 1H), 7.50-7.40 (m, 3H), 7.19 (d, J=8.1 Hz, 1H), 7.09 (s, 1H), 6.98 (s, 1H), 6.52 (d, J=16.0 Hz, 1H), 4.84 (br, 2H), 3.66 (br, 2H), 2.85 (t, J=7.4 Hz, 2H), 2.77 (t, J=7.4 Hz, 2H), 2.23 (s, 3H), 2.19 (s, 3H), 2.10-1.90 (m, 2H), 1.01 (t, J=7.0 Hz, 3H).

EXAMPLE 5(53)

4-[2-[N-cyclopropylmethyl-N-(5-methyl-2-furylsulfonyl)amino]-4,5-dimethylphenoxymethyl]benzoic acid

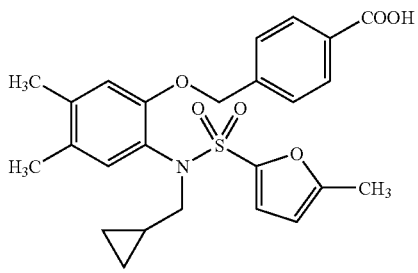

TLC: Rf 0.41 (chloroform:methanol=9:1); NMR: δ 8.11 (d, J=8.4 Hz, 2H), 7.43 (d, J=8.4 Hz, 2H), 7.09 (s, 1H), 6.74 (d, J=3.0 Hz, 1H), 6.70 (s, 1H), 5.96-5.92 (m, 1H), 5.02 (brs, 2H), 3.68-3.40 (m, 2H), 2.23 (s, 3H), 2.19 (s, 3H), 2.14 (s, 3H), 1.03-0.86 (m, 1H), 0.46-0.35 (m, 2H), 0.21-0.06 (m, 2H).

EXAMPLE 5(54)

4-[4,5-dimethyl-2-[N-(2-hydroxy-2-methylpropyl)-N-(5-methyl-2-furylsulfonyl)amino]phenoxymethyl]benzoic acid

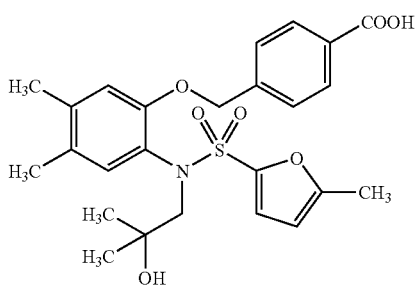

TLC: Rf 0.34 (chloroform:methanol=9:1); NMR: δ 8.13 (d, J=8.4 Hz, 2H), 7.52 (d, J=8.4 Hz, 2H), 6.81 (s, 1H), 6.75 (s, 1H), 6.74 (d, J=3.0 Hz, 1H), 6.03-5.98 (m, 1H), 5.22-4.96 (m, 2H), 3.92-3.76 and 3.64-3.48 (each m, total 2H), 2.21 (s, 6H), 2.13 (s, 3H), 1.28 and 1.19 (each brs, each 3H).

EXAMPLE 5(55)

3-methyl-4-[6-[N-(2-methyl-2-propeny-N-(4-methyl-2-thiazolylsulfonyl)amino]indan-5-yloxymethyl]cinnamic acid

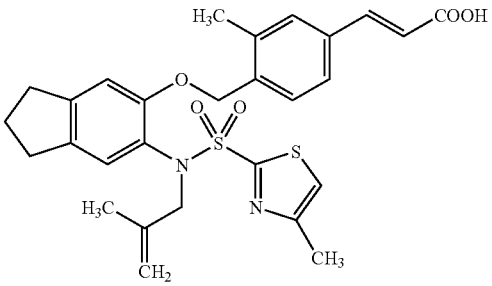

TLC: Rf 0.60 (chloroform:methanol=9:1); NMR: δ 7.76 (d, J=15.9 Hz, 1H), 7.42-7.34 (m, 2H), 7.27-7.22 (m, 1H), 7.12 (s, 1H), 6.92 (d, J=0.9 Hz, 1H), 6.78 (s, 1H), 6.47 (d, J=15.9 Hz, 1H), 4.90-4.72 (m, 4H), 4.50-4.14 (m, 2H), 2.92-2.80 (m, 4H), 2.31 (s, 6H), 2.18-2.00 (m, 2H), 1.81 (s, 3H).

EXAMPLE 5(56)

4-[6-[N-cyclopropylmethyl-N-(4-methyl-2-thiazolylsulfonyl)amino]indan-5-yloxymethyl]-3-methylcinnamic acid

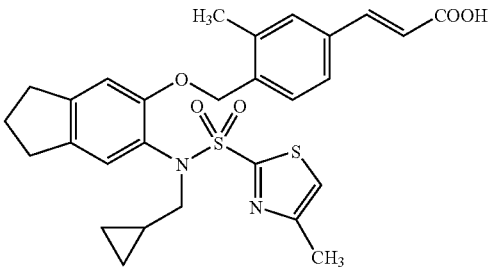

TLC: Rf 0.60 (chloroform:methanol=9:1); NMR: δ 7.77 (d, J=15.9 Hz, 1H), 7.42-7.38 (m, 2H), 7.30-7.25 (m, 1H), 7.21 (s, 1H), 6.89 (d, J=0.9 Hz, 1H), 6.82 (s, 1H), 6.46 (d, J=15.9 Hz, 1H), 4.92-4.64 (m, 2H), 3.84-3.42 (m, 2H), 2.95-2.76 (m, 4H), 2.31 (s, 3H), 2.31 (s, 3H), 2.18-2.02 (m, 2H), 1.08-0.90 (m, 1H), 0.46-0.40 (m, 2H), 0.26-0.08 (m, 2H).

EXAMPLE 5(57)

4-[6-[N-(2-hydroxy-2-methylpropyl)-N-(5-methyl-2-furylsulfonyl)amino]indan-5-yloxymethyl]cinnamic acid

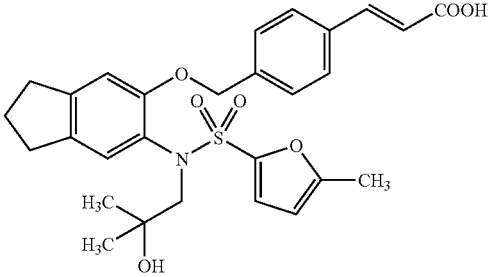

TLC: Rf 0.46 (chloroform:methanol=9:1); NMR: δ 7.78 (d, J=15.9 Hz, 1H), 7.58 (d, J=8.1 Hz, 2H), 7.47 (d, J=8.1 Hz, 2H), 6.85 (d, J=3.6 Hz, 2H), 6.74 (d, J=3.6 Hz, 1H), 6.47 (d, J=15.9 Hz, 1H), 6.01 (d, J=2.1 Hz, 1H), 5.10 (d, J=12.0 Hz, 1H), 4.99 (d, J=12.0 Hz, 1H), 3.85 (d, J=14.1 Hz, 1H), 3.53 (d, J=14.1 Hz, 1H), 2.90-2.77 (m, 4H), 2.23 (s, 3H), 2.07 (m, 2H), 1.27 (s, 3H), 1.16 (s, 3H).

EXAMPLE 5(58)

3-methyl-4-[6-[N-(4-methyl-2-thiazolylsulfonyl)-N-(2-propenyl)amino]indan-5-yloxymethyl]cinnamic acid

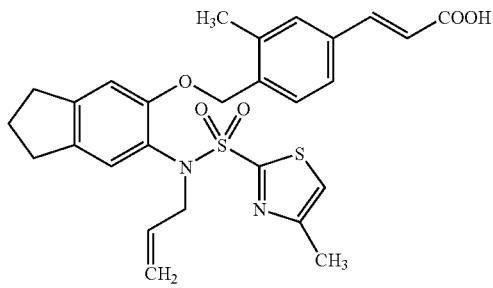

TLC: Rf 0.42 (dichloromethane:methanol=10:1); NMR: δ 7.76 (d, J=15.9 Hz, 1H), 7.42-7.36 (m, 2H), 7.28 (m, 1H), 7.11 (s, 1H), 6.92 (m, 1H), 6.80 (s, 1H), 6.47 (d, J=15.9 Hz, 1H), 5.87 (m, 1H), 5.11 (dd, J=17.1, 1.5 Hz, 1H), 5.07 (dd, J=8.7, 1.5 Hz, 1H), 4.83 (br, 2H), 4.32 (br, 2H), 2.92-2.82 (m, 4H), 2.33 (d, J=0.6 Hz, 3H), 2.32 (s, 3H), 2.16-2.04 (m, 2H).

EXAMPLE 5(59)

4-[6-[N-(2-hydroxy-2-methylpropyl)-N-(4-methyl-2-thiazolylsulfonyl)amino]indan-5-yloxymethyl]-3-methylcinnamic acid

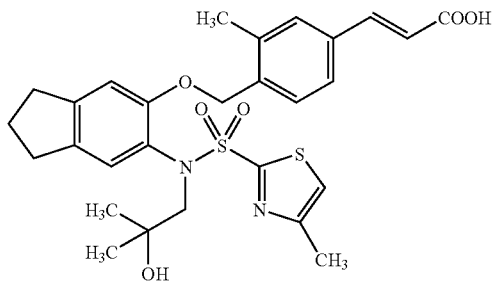

TLC: Rf 0.42 (dichloromethane:methanol=10:1); NMR: δ 7.76 (d, J=15.9 Hz, 1H), 7.44-7.38 (m, 3H), 7.05 (m, 1H), 6.88 (s, 1H), 6.82 (s, 1H), 6.46 (d, J=15.9 Hz, 1H), 5.03 (d, J=12.0 Hz, 1H), 4.93 (d, J=12.0 Hz, 1H), 3.96 (d, J=14.4 Hz, 1H), 3.69 (d, J=14.4 Hz, 1H), 2.87 (t, J=7.5 Hz, 2H), 2.77 (t, J=7.5 Hz, 2H), 2.43 (s, 3H), 2.40 (s, 3H), 2.13-2.00 (m, 2H), 1.23 (s, 3H), 1.18 (s, 3H).

EXAMPLE 5(60)

4-[4,5-dimethyl-2-[N-cyclopropylmethyl-N-(5-methyl-2-furylsulfonyl)amino]phenoxymethyl]-3-methylbenzoic acid

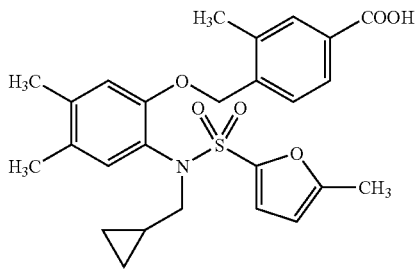

TLC: Rf 0.45 (chloroform:methanol=9:1); NMR: δ 8.00-7.92 (m, 2H), 7.47 (d, J=7.8 Hz, 1H), 7.09 (s, 1H), 6.78-6.71 (m, 2H), 5.94 (m, 1H), 4.96 (s, 2H), 3.63-3.45 (br, 2H), 2.37 (s, 3H), 2.25 (s, 3H), 2.19 (s, 3H), 2.13 (s, 3H), 0.95 (m, 1H), 0.44-0.35 (m, 2H), 0.15-0.22 (m, 2H).

EXAMPLE 5(61)

3-methyl-4-[6-[N-(4-methyl-2-thiazolylsulfonyl)-N-propylamino]indan-5-yloxymethyl]cinnamic acid

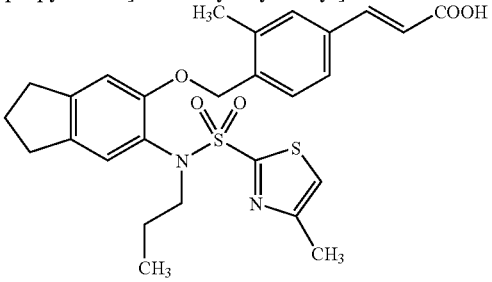

TLC: Rf 0.41 (chloroform:methanol=9:1); NMR: δ 7.76 (d, J=16.2 Hz, 1H), 7.44-7.34 (m, 2H), 7.32-7.20 (m, 1H), 7.13 (s, 1H), 6.90 (s, 1H), 6.82 (s, 1H), 6.46 (d, J=16.2 Hz, 1H), 4.90-4.70 (m, 2H), 3.90-3.50 (m, 2H), 2.89 (t, J=7.5 Hz) and 2.86 (t, J=7.5 Hz) total 4H, 2.31 (s) and 2.30 (s) total 6H, 2.09 (quint, J=7.5 Hz, 2H), 1.58 (m, 2H), 0.91 (t, J=7.5 Hz, 3H).

EXAMPLE 5(62)

4-[6-[N-(2-hydroxy-2-methylpropyl)-N-(4-methyl-2-thiazolylsulfonyl)amino]indan-5-yloxymethyl]benzoic acid

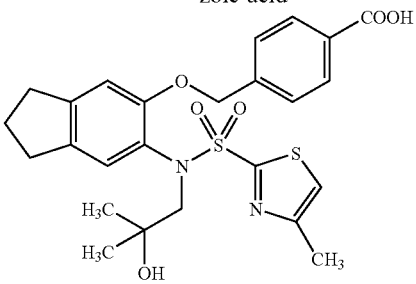

TLC: Rf 0.29 (dichloromethane:methanol=19:1); NMR: δ 8.13 (d, J=7.8 Hz, 2H), 7.48 (d, J=7.8 Hz, 2H), 7.02 (brs, 1H), 6.90 (s, 1H), 6.83 (s, 1H), 5.12 (d, J=12.6 Hz, 1H), 4.95 (d, J=12.6 Hz, 1H), 3.96 (d, J=15.0 Hz, 1H), 3.77 (d, J=15.0 Hz, 1H), 2.88-2.75 (m, 4H), 2.42 (s, 3H), 2.06 (m, 2H), 1.29 (s, 3H), 1.22 (s, 3H).

EXAMPLE 6

3-methyl-4-[6-[N-isobutyl-N-(4-methyl-2-thiazolylsulfonyl)amino]indan-5-yloxymethyl]cinnamic acid sodium salt

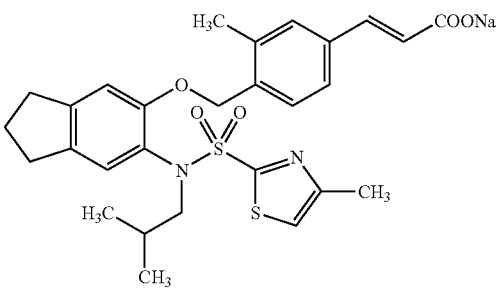

To a suspension of the compound prepared in example 2(74) (213 g) in ethanol (2 L), 5N aqueous solution of sodium hydroxide (74.7 ml) was added. The mixture was stirred for 0.5 hour at 80° C. The reaction solution was filtered under heating to remove the insolubles, then the mixture was cooled, and the precipitate was collected. The mother liquor was concentrated and the residue was dissolved in ethanol (500 ml) and water (25 ml) under heating. The mixture was filtered under heating to remove the insolubles, then the mixture was colled, and the precipitate was collected. Under heating, all collected solids were dried under reduced pressure to give the compound of the present invention (165 g) having the following physical data.

TLC: Rf 0.52 (chloroform:methanol=9:1); NMR(DMSO-$d_6$): δ 7.49 (s, 1H), 7.29 (s, 1H), 7.26 (d, J=8.1 Hz, 1H), 7.10-7.00 (m, 4H), 6.38 (d, J=15.9 Hz, 1H), 4.89 (br-d, J=10.5 Hz, 1H), 4.63 (br-d, J=10.5 Hz, 1H), 3.55-3.25 (m, 2H), 2.85 (t, J=7.2 Hz, 2H), 2.78 (t, J=7.2 Hz, 2H), 2.21 (s, 3H), 2.18 (s, 3H), 2.10-1.90 (m, 2H), 1.60-1.45 (m, 1H), 1.00-0.70 (m, 6H).

EXAMPLE 6(1)

4-[2-[N-isopropyl-N-(5-methyl-2-furylsulfonyl)amino]-5-trifluoromethylphenoxymethyl]benzoic acid sodium salt

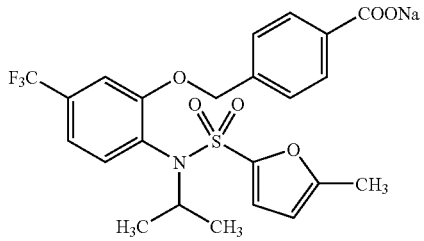

TLC: Rf 0.50 (chloroform:methanol=9:1); NMR: δ 7.84 (d, J=8.1 Hz, 2H), 7.20-6.95 (m, 5H), 6.65 (d, J=3.3 Hz, 1H), 5.84 (d, J=3.3 Hz, 1H), 4.75 (brs, 2H), 4.30-4.10 (m, 1H), 2.12 (s, 3H), 0.86 (brd, J=3.9 Hz, 6H).

EXAMPLE 6(2)

4-[2-[N-isobutyl-N-(5-methyl-2-furylsulfonyl)amino]-4,5-dimethylphenoxymethyl]benzoic acid sodium salt

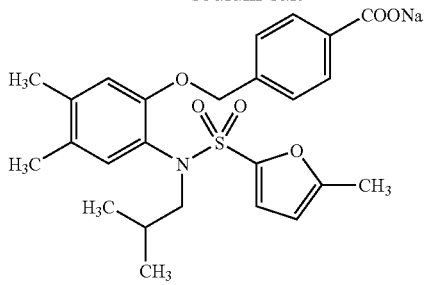

TLC: Rf 0.40 (chloroform:methanol=9:1); NMR: δ 7.83 (d, J=8.1 Hz, 2H), 7.00 (d, J=8.1 Hz, 2H), 6.88 (s, 1H), 6.59 (s, 1H), 6.54 (d, J=3.0 Hz, 1H), 5.74 (s, 1H), 4.90-4.50 (m, 2H), 3.33 (brd, J=6.3 Hz, 2H), 2.09 (s, 3H), 2.05 (s, 3H), 1.93 (s, 3H), 1.60-1.40 (m, 1H), 0.73 (d, J=6.3 Hz, 6H).

EXAMPLE 6(3)

3-methyl-4-[2-[N-isobutyl-N-(5-methyl-2-furylsulfonyl)amino]-4,5-dimethylphenoxymethyl]benzoic acid sodium salt

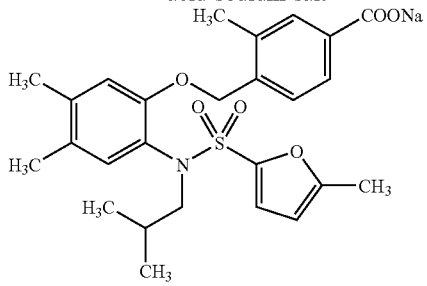

TLC: Rf 0.41 (chloroform:methanol=9:1) NMR(DMSO-$d_6$): δ 7.70 (s, 1H), 7.66 (d, J=7.8 Hz, 1H), 7.13 (d, J=7.8 Hz, 1H), 6.99 (s, 1H), 6.91 (s, 1H), 6.76 (d, J=3.3 Hz, 1H), 6.14 (d, J=3.3 Hz, 1H), 4.88 (brs, 2H), 3.36 (d, J=6.9 Hz, 2H), 2.26 (s, 3H), 2.14 (s, 3H), 2.10 (s, 3H), 1.60-1.45 (m, 1H), 0.81 (brd, J=6.3 Hz, 6H).

EXAMPLE 6(4)

4-[6-[N-isobutyl-N-(4-methyl-2-thiazolylsulfonyl)amino]indan-5-yloxymethyl]benzoic acid sodium salt

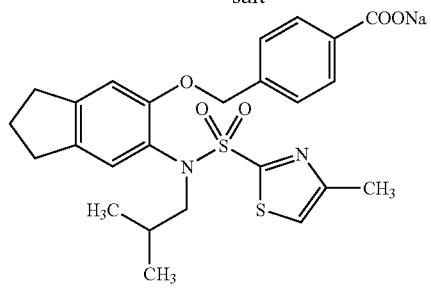

TLC: Rf 0.40 (chloroform:methanol=9:1); NMR (CD$_3$OD): δ 7.91 (d, J=8.1 Hz, 2H), 7.19 (s, 1H), 7.18 (d, J=8.1 Hz, 2H), 7.13 (s, 1H), 6.93 (s, 1H), 5.00-4.80 (m, 1H), 3.65-3.48 (m, 2H), 2.95-2.80 (m, 4H), 2.21 (d, J=0.9 Hz, 3H), 2.09 (quint, J=7.5 Hz, 2H), 1.66 (m, 1H), 1.03-0.85 (m, 6H).

EXAMPLE 6(5)

4-[6-[N-isobutyl-N-(4-methyl-2-thiazolysulfonyl)amino]indan-5-yloxymethyl]benzoic acid potassium salt

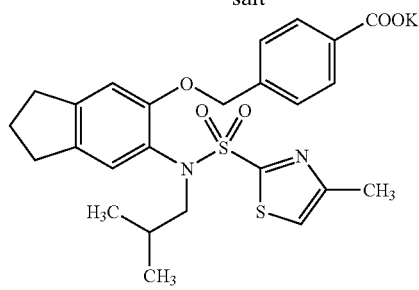

TLC: Rf 0.37 (chloroform:methanol=9:1); NMR(DMSO-$d_6$): δ 7.81 (d, J=8.0 Hz, 2H), 7.47 (q, J=0.4 Hz, 1H), 7.06 (d, J=8.0 Hz, 1H), 7.03 (s, 2H), 6.95 (s, 1H), 5.10-4.80 (m, 1H), 4.80-4.50 (m, 1H), 3.43 (brs, 2H), 2.80 (q, J=7.0 Hz, 4H), 2.23 (d, J=0.4 Hz, 3H), 2.01 (1n, J=7.0 Hz, 2H), 1.53 (sept, J=6.6 Hz, 1H), 0.85 (brs, 6H).

EXAMPLE 6(6)

4-[6-[N-isobutyl-N-(5-methyl-2-furylsulfonyl)amino]indan-5-yloxymethyl]cinnamic acid sodium salt

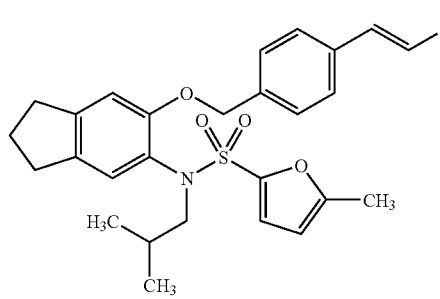

TLC: Rf 0.51 (chloroform:methanol=9:1); NMR: δ 7.37 (d, J=15.9 Hz, 1H), 7.17 (d, J=7.5 Hz, 2H), 7.10-6.90 (m, 3H), 6.67 (s, 1H), 6.55 (s, 1H), 6.45 (d, J=15.9 Hz, 1H), 5.74

(s, 1H), 4.80-4.45 (m, 2H), 3.35 (d, J=6.3 Hz, 2H), 2.85-2.55 (m, 4H), 2.10-1.80 (m, 5H), 1.65-1.40 (m, 1H), 0.74 (brs, 6H).

EXAMPLE 6(7)

3-methyl-4-[6-[N-isobutyl-N-(5-methyl-2-furylsulfonyl)amino]indan-5-yloxymethyl]benzoic acid sodium salt

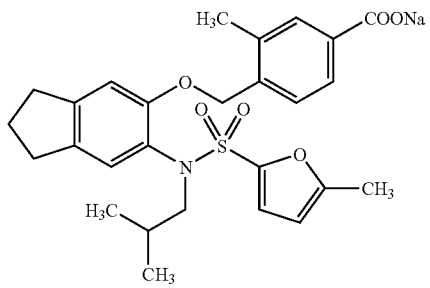

TLC: Rf 0.60 (chloroform:methanol=9:1); NMR (CD$_3$OD): δ 7.78 (s) and 7.75 (d, J=8.1 Hz) total 2H, 7.24 (d, J=8.1 Hz, 1H), 7.07 (s, 1H), 6.97 (s, 1H), 6.64 (d, J=3.3 Hz, 1H), 6.03 (dd, J=3.3, 0.9 Hz, 1H), 5.08-4.75 (m, 2H), 3.48 (d, J=7.5 Hz, 2H), 2.94-2.80 (m, 4H), 2.32 (s, 3H), 2.15-2.00 (m) and 2.04 (s) total 5H, 1.87 (m, 1H), 0.98-0.80 (m, 6H).

EXAMPLE 6(8)

4-[6-[N-isopropyl-N-(4-methyl-2-thiazolylsulfonyl)amino]indan-5-yloxymethyl]cinnamic acid potassium salt

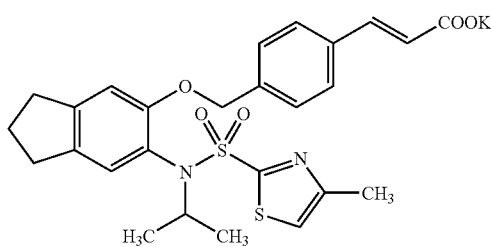

TLC: Rf 0.36 (chloroform:methanol=9:1); NMR: δ 7.27 (d, J=15.9 Hz, 1H), 7.21 (d, J=7.5 Hz, 2H), 6.98 (d, J=7.5 Hz, 2H), 6.84 (s, 1H), 6.78 (s, 1H), 6.70 (s, 1H), 6.41 (d, J=15.9 Hz, 1H), 4.70-4.40 (m, 3H), 2.85-2.60 (m, 4H), 2.24 (s, 3H), 2.05-1.90 (m, 2H), 1.01 (d, J=6.6 Hz, 3H), 0.95 (d, J=6.6 Hz, 3H).

EXAMPLE 6(9)

4-[2-[N-isobutyl-N-(2-thiazolylsulfonyl)amino]-4,5-dimethylphenoxymethyl]benzoic acid potassium salt

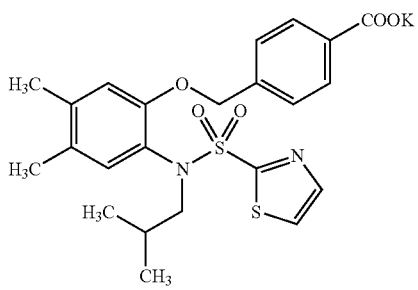

TLC: Rf 0.32 (chloroform:methanol=9:1); NMR: δ 7.82 (d, J=8.1 Hz, 2H), 7.33 (d, J=3.0 Hz, 1H), 7.15 (d, J=3.0 Hz, 1H), 6.94 (s, 1H), 6.89 (d, J=8.1 Hz, 2H), 6.56 (s, 1H), 4.70-4.55 (m, 1H), 4.45-4.25 (m, 1H), 3.60-3.30 (m, 2H), 2.09 (s, 6H), 1.60-1.45 (m, 1H), 0.78 (brs, 3H), 0.72 (brs, 3H).

EXAMPLE 6(10)

3-methyl-4-[2-[N-isobutyl-N-(2-thiazolylsulfonyl)amino]-4,5-dimethylphenoxymethyl]benzoic acid sodium salt

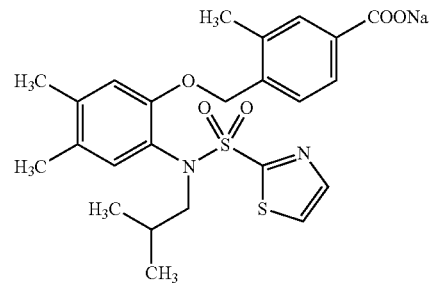

TLC: Rf 0.37 (chloroform:methanol=10:1); NMR (DMSO-d$_6$): δ 7.98 (d, J=3.0 Hz, 1H), 7.82 (d, J=3.0 Hz, 1H), 7.64 (s, 1H), 7.60 (d, J=7.8 Hz, 1H), 6.99 (d, J=7.8 Hz, 1H), 6.97 (s, 1H), 6.91 (s, 1H), 5.00-4.54 (m, 2H), 3.42 (d, J=6.3 Hz, 2H), 2.20 (s, 3H), 2.20 (s, 3H), 2.11 (s, 3H), 1.50 (m, 1H), 0.90-0.73 (m, 6H).

EXAMPLE 7

4-[5-trifluoromethyl-2-[N-(5-methyl-2-furylcarbonyl)-N-isopropylamino]phenoxymethyl]cinnamic acid

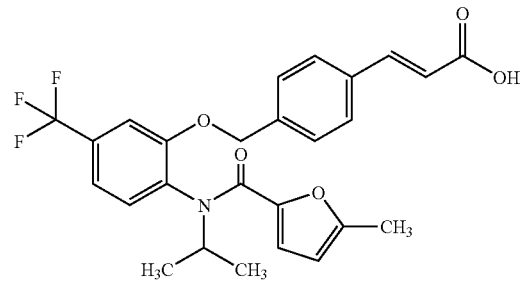

By the same procedures as described in specification of WO 98/27053 as Example 59(2) using the corresponding compound, the title compound having the following physical data was obtained.

TLC: Rf 0.38 (chloroform:methanol=10:1); NMR: δ 7.75 (d, J=15.9 Hz, 1H), 7.50 (d, J=8.1 Hz, 2H), 7.37-7.16 (m, 5H), 6.45 (d, J=15.9 Hz, 1H), 5.98 (m, 1H), 5.81 (d, J=3.3 Hz, 1H), 5.12-4.90 (m, 3H), 2.05 (s, 3H), 1.33-0396 (m, 6H).

FORMULATION EXAMPLE 1

Preparation of Capsules

The following components were admixed and granulated in conventional method, and then they were filled in second hard capsules to obtain 100 capsules each containing 100 mg of active ingredient.

| | |
|---|---|
| The compound A | 10.0 g |
| Lactose | 6.09 g |
| Microcrystalline cellulose | 2.61 g |
| Low-substituted hydroxypropylcellulose | 2.0 g |
| Hydroxypropylcellulose | 1.0 g |
| light silicic anhydride | 0.1 g |
| Magnesium stearate | 0.2 g |

FORMULATION EXAMPLE 2

Preparation of Tablets

The following components were admixed, granulated and punched out in conventional method and then they were coated to obtain film-coated 100 tablets each containing 100 mg of active ingredient.

| | |
|---|---|
| The compound B | 10.0 g |
| Lactose | 5.88 g |
| Corn Starch | 2.52 g |
| Low-substituted hydroxypropylcellulose | 1.00 g |
| Hydroxypropylcellulose | 0.60 g |
| Magnesium stearate | 0.20 g |
| Coating Composition | |
| Hydroxypropylmethylcellulose | 0.3 g |
| Polyethyleneglycole | 0.03 g |
| Titanium oxide | 0.10 g |

The invention claimed is:

1. A method for the treatment of depression, comprising administering to a subject in need thereof an effective amount of $EP_1$ antagonist, wherein $EP_1$ antagonist is N-arylsulfonylamide compound of formula (IK)

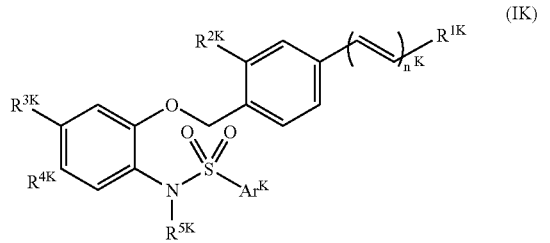

wherein $R^{1K}$ is COOH, hydroxymethyl, 5-tetrazolyl, 5-oxo-1,2,4-oxadiazolyl or 5-oxo-1,2,4-thiadiazolyl, $R^{2K}$ is hydrogen, methyl, methoxy or chloro, $R^{3K}$ and $R^{4K}$ are a combination of (1) methyl and methyl, (2) methyl and chloro, (3) chloro and methyl, or (4) trifluoromethyl and hydrogen; or $R^3$ and $R^4$ are taken together with the carbon to which $R^3$ and $R^4$ are attached to form (5) cyclopentene, (6) cyclohexene or (7) benzene ring, $R^{5K}$ is isopropyl, isobutyl, 2-methyl-2-propenyl, cyclopropylmethyl, methyl, ethyl, propyl, 2-propenyl or 2-hydroxy-2-methylpropyl, $Ar^k$ is thiazolyl optionally substituted with methyl, pyridyl or 5-methyl-2-furyl, $n^K$ is 0 or 1, with the proviso that n is 0 when $R^{1K}$ is 5-tetrazolyl, 5-oxo-1,2,4-oxadiazolyl or 5-oxo-1,2,4-thiadiazolyl, an alkyl ester thereof or a non-toxic salt thereof.

2. The method according to claim 1, wherein $EP_1$ antagonist is (1) 4-[2-[N-isopropyl-N-(5-methyl-2-furylsulfonyl)amino]-5-trifluoromethylphenoxymethyl]benzoic acid, (2) 4-[2-[N-isopropyl-N-(5-methyl-2-furylsulfonyl)amino]-4,5-dimethylphenoxymethyl]benzoic acid, (3) 3-methyl-4-[2-[N-isobutyl-N-(5-methyl-2-furylsulfonyl)amino]-4,5-dimethylphenoxymethyl]benzoic acid, (4) 4-[6-[N-isobutyl-N-(5-methyl-2-furylsulfonyl)amino]indan-5-yloxymethyl]cinnamic acid, (5) 3-methyl-4-[6-[N-isobutyl-N-(4-methyl-2-thiazolylsulfonyl)amino]indan-5-yloxymethyl]cinnamic acid, (6) 4-[4,5-dimethyl-2-[N-methyl-N-(5-methyl-2-furylsulfonyl)-N-propylamino]phenoxymethyl]benzoic acid, (7) 4-[6-[N-isobutyl-N-(4-methyl-2-thiazolylsulfonyl)amino]indan-5-yloxymethyl]benzoic acid, or (8) 3-methyl-4-[6-[N-isobutyl-N-(2-thiazolylsulfonyl)amino]indan-5-yloxymethyl]benzoic acid, a non-toxic salt thereof, or ester thereof.

* * * * *